US009498404B2

(12) United States Patent
Murison

(10) Patent No.: US 9,498,404 B2
(45) Date of Patent: Nov. 22, 2016

(54) FLUIDIC METHODS AND DEVICES

(71) Applicant: Obotics Inc., North Gower (CA)

(72) Inventor: Bruce Murison, North Gower (CA)

(73) Assignee: Obotics Inc., North Gower (CA)

( * ) Notice: Subject to any disclaimer, the term of this patent is extended or adjusted under 35 U.S.C. 154(b) by 450 days.

(21) Appl. No.: 14/037,581

(22) Filed: Sep. 26, 2013

(65) Prior Publication Data

US 2014/0088351 A1 Mar. 27, 2014

Related U.S. Application Data

(60) Provisional application No. 61/705,809, filed on Sep. 26, 2012.

(51) Int. Cl.

*A61F 5/00* (2006.01)
*A61H 19/00* (2006.01)
(Continued)

(52) U.S. Cl.

CPC ............ *A61H 19/40* (2013.01); *A61H 9/0057* (2013.01); *A61H 9/0078* (2013.01); *A61H 19/32* (2013.01); *A61H 23/00* (2013.01); *A61H 23/0218* (2013.01); *A61H 23/0263* (2013.01); *A61H 23/04* (2013.01); *F04B 3/00* (2013.01); *F04B 11/0008* (2013.01); *F04B 11/0033* (2013.01);
(Continued)

(58) Field of Classification Search

CPC .................... A61H 19/00; A61H 19/30; A61H 19/40
USPC ............ 600/38–41; 601/46, 55, 76, 148–152
See application file for complete search history.

(56) References Cited

U.S. PATENT DOCUMENTS

| | | | |
|---|---|---|---|
| 3,327,633 | A | 6/1967 | Gossel |
| 3,740,171 | A | 6/1973 | Farkos |

(Continued)

FOREIGN PATENT DOCUMENTS

| | | |
|---|---|---|
| DE | 10227659 | 12/2004 |
| DE | 102010009152 | 8/2011 |

(Continued)

OTHER PUBLICATIONS

Astratini-Enache et al., "Moving Magnet Type Actuator with Ring Magnets", Journal of Electrical Engineering, 2010, pp. 144-147, vol. 61, No. 7/s, Slovak University of Technology in Bratislava, Slovakia.

(Continued)

*Primary Examiner* — John Lacyk
(74) *Attorney, Agent, or Firm* — The Law Office of Michael E. Kondoudis

(57) ABSTRACT

A device for use by an individual for sexual pleasure varying in form, i.e. shape, during its use and allowing for the user to select multiple variations of form either discretely or in combination and for these dynamic variations to be controllable simultaneously and interchangeably while being transparent to the normal use of the device, including the ability to insert, withdraw, rotate, and actuate the variable features manually or remotely. According to embodiments of the invention localized and global variations of devices are implemented using fluidics and electromagnetic pumps/valves wherein a fluid is employed such that controlling the pressure of the fluid results in the movement of an element within the device or the expansion/contraction of an element within the device.

12 Claims, 64 Drawing Sheets

(51) Int. Cl.

| | |
|---|---|
| ***A61H 9/00*** | (2006.01) |
| ***A61H 23/00*** | (2006.01) |
| ***A61H 23/04*** | (2006.01) |
| ***F04B 3/00*** | (2006.01) |
| ***F04B 11/00*** | (2006.01) |
| ***F04B 17/04*** | (2006.01) |
| ***A61H 23/02*** | (2006.01) |

(52) U.S. Cl.

CPC ............ *F04B 17/04* (2013.01); *F04B 17/044* (2013.01); *A61H 2201/0153* (2013.01); *A61H 2201/1238* (2013.01); *A61H 2201/1246* (2013.01); *A61H 2201/1409* (2013.01); *A61H 2201/5002* (2013.01); *A61H 2201/5064* (2013.01); *A61H 2201/5071* (2013.01); *Y10T 137/85978* (2015.04)

(56) References Cited

U.S. PATENT DOCUMENTS

| | | | |
|---|---|---|---|
| 3,862,629 | A | 1/1975 | Rotta |
| 3,910,262 | A | 10/1975 | Stoughton |
| 4,407,275 | A | 10/1983 | Schroeder |
| 4,722,327 | A | 2/1988 | Harvey |
| 4,790,296 | A | 12/1988 | Segal |
| 5,076,261 | A | 12/1991 | Black |
| 5,501,650 | A | 3/1996 | Gellert |
| 5,573,499 | A | 11/1996 | McAllister |
| 5,690,603 | A | 11/1997 | Kain |
| 5,690,604 | A | 11/1997 | Barnett |
| 5,725,473 | A | 3/1998 | Taylor |
| 5,833,440 | A | 11/1998 | Berling |
| 5,851,175 | A | 12/1998 | Nickell |
| 5,853,362 | A | 12/1998 | Jacobs |
| 6,142,929 | A | 11/2000 | Padgett |
| 6,203,491 | B1 | 3/2001 | Uribe |
| 6,436,029 | B1 | 8/2002 | Benderev |
| 6,533,718 | B1 | 3/2003 | Ritchie et al. |
| 6,599,236 | B1 | 7/2003 | Castro |
| 6,749,557 | B2 | 6/2004 | Garland |
| 6,866,645 | B2 | 3/2005 | Lee |
| 6,870,454 | B1 | 3/2005 | Vladmirescu |
| 6,899,671 | B1 | 5/2005 | Fontenot |
| 6,902,525 | B1 | 6/2005 | Jewell |
| 6,991,599 | B2 | 1/2006 | Hudson |
| 6,997,888 | B2 | 2/2006 | Rehrig |
| 7,108,668 | B2 | 9/2006 | Fang |
| 7,166,072 | B2 | 1/2007 | Smith |
| 7,438,681 | B2 | 10/2008 | Kobashikawa |
| 7,452,326 | B2 | 11/2008 | Fladl |
| 7,513,868 | B1 | 4/2009 | Fontenot |
| 7,524,283 | B1 | 4/2009 | Johnstone |
| 7,530,944 | B1 | 5/2009 | Kain |
| 7,534,203 | B2 | 5/2009 | Gil |
| 7,604,587 | B2 | 10/2009 | Manska |
| D605,779 | S | 12/2009 | Murison |
| 7,670,280 | B2 | 3/2010 | Gloth |
| 7,857,005 | B2 | 12/2010 | Rich |
| 7,871,386 | B2 | 1/2011 | Nan |
| 7,931,605 | B2 | 4/2011 | Murison |
| 7,967,740 | B2 | 6/2011 | Mertens |
| 7,998,057 | B2 | 8/2011 | Kain |
| D652,942 | S | 1/2012 | Murison |
| 8,109,869 | B2 | 2/2012 | Beaulieu |
| 2002/0103415 | A1 | 8/2002 | Manska |
| 2003/0073881 | A1 | 4/2003 | Levy |
| 2003/0195441 | A1 | 10/2003 | Firouzgar |
| 2004/0034315 | A1 | 2/2004 | Chen |
| 2004/0082831 | A1 | 4/2004 | Kobashikawa |
| 2004/0127766 | A1 | 7/2004 | Chen |
| 2004/0147858 | A1 | 7/2004 | Lee |
| 2005/0033112 | A1 | 2/2005 | Bruton |
| 2005/0049453 | A1 | 3/2005 | Faulkner |
| 2005/0234292 | A1 | 10/2005 | Faulkner |
| 2006/0041210 | A1 | 2/2006 | Regey |
| 2006/0074273 | A1 | 4/2006 | Smith |
| 2006/0106327 | A1 | 5/2006 | Thielen |
| 2006/0210410 | A1 | 9/2006 | Mokler |
| 2006/0247493 | A1 | 11/2006 | Chen |
| 2007/0055096 | A1 | 3/2007 | Berry |
| 2007/0232967 | A1 | 10/2007 | Driscoll |
| 2007/0244418 | A1 | 10/2007 | Harkness |
| 2008/0071138 | A1 | 3/2008 | Mertens |
| 2008/0082028 | A1 | 4/2008 | Blevins |
| 2008/0119767 | A1 | 5/2008 | Berry |
| 2008/0139980 | A1 | 6/2008 | Fladl |
| 2008/0213106 | A1 | 9/2008 | Schmidt |
| 2009/0318755 | A1 | 12/2009 | Adams |
| 2010/0087703 | A1 | 4/2010 | Gabrielidis |
| 2010/0204542 | A1 | 8/2010 | Hodge |
| 2010/0292531 | A1 | 11/2010 | Beaulieu |
| 2011/0009693 | A1 | 1/2011 | Borrero |
| 2011/0021870 | A1 | 1/2011 | Lee |
| 2011/0034837 | A1 | 2/2011 | Lee |
| 2011/0082332 | A1 | 4/2011 | Lee |
| 2011/0082333 | A1 | 4/2011 | Wilson |
| 2011/0105837 | A1 | 5/2011 | Lee |
| 2011/0124959 | A1 | 5/2011 | Murison |
| 2011/0166415 | A1 | 7/2011 | Zamar |
| 2011/0218395 | A1 | 9/2011 | Stout |
| 2011/0319707 | A1 | 12/2011 | Mertens |
| 2012/0118296 | A1 | 5/2012 | Oeltjen |
| 2012/0123199 | A1 | 5/2012 | Topolev |
| 2012/0136205 | A1 | 5/2012 | Galeote |
| 2012/0143001 | A1 | 6/2012 | Case |
| 2012/0179077 | A1 | 7/2012 | Tuck |
| 2012/0184884 | A1 | 7/2012 | Dyer |
| 2012/0197072 | A1 | 8/2012 | Cordle |
| 2014/0088468 | A1* | 3/2014 | Murison ............ A61H 23/0218 601/46 |

FOREIGN PATENT DOCUMENTS

| | | |
|---|---|---|
| EP | 0511124 | 10/1992 |
| WO | WO 0147434 | 7/2001 |
| WO | WO 2010042045 | 4/2010 |

OTHER PUBLICATIONS

Leu et al., "Characteristics and Optimal Design of Variable Airgap Linear Force Motors", IEE Proceedings, Nov. 1988, pp. 340-345, vol. 135, Pt. B, No. 6, Scholars' Mine.

Petrescu et al., "Study of a Mini-Actuator with Permanent Magnets", Advances in Electrical and Computer Engineering, 2009, pp. 3-6, vol. 9, No. 3, Faculty of Electrical Engineering and Computer Science—Stefan cel Mare University of Suceava, Romania.

Ibrahim et al., "Design and Optimization of a Moving-Iron Linear Permanent Magnet Motor for Reciprocating Compressors using Finite Element Analysis", International Journal of Electrical & Computer Sciences IJECS-IJENS, Apr. 2010, pp. 78-84, vol. 10, No. 02, The International Journals of Engineering and Sciences, Pakistan.

Evans et al., "Permanent-Magnet Linear Actuator for Static and Reciprocating Short-Stroke Electromechanical Systems", IEEE/ASME Transactions on Mechatronics, Mar. 2001, pp. 36-42, vol. 6, No. 1, Institute of Electrical and Electronics Engineers, United States.

Hertanu et al., "A Novel Minipump ActuateJournald by Magnetic Piston", Journal of Electrical Engineering, 2010, pp. 148-151, vol. 61, No. 7/s, Slovak University of Technology in Bratislava, Slovakia.

Ibrahim et al., "Analysis of a Short-Stroke, Single-Phase Tubular Permanent Magnet Actuator for Reciprocating Compressors", International Symposium on Linear Drives for Industrial Applications, LDIA, 2007, France.

Ibrahim et al., "Analysis of a Single-Phase, Quasi-Halbach Magnetised Tubular Permanent Magnet Motor with Non-Ferromagnetic Support Tube", 4th IET Conference on Power Electronics,

(56) References Cited

OTHER PUBLICATIONS

Machines and Drives, Apr. 2-4, 2008, pp. 762-766, Institution of Engineering and Technology, United Kingdom.
Lee et al., “Linear Compression for Air Conditioner”, International Compressor Engineering Conference at Perdue, Jul. 12-15, 2004, Paper 1667, Purdue University, United States.

* cited by examiner

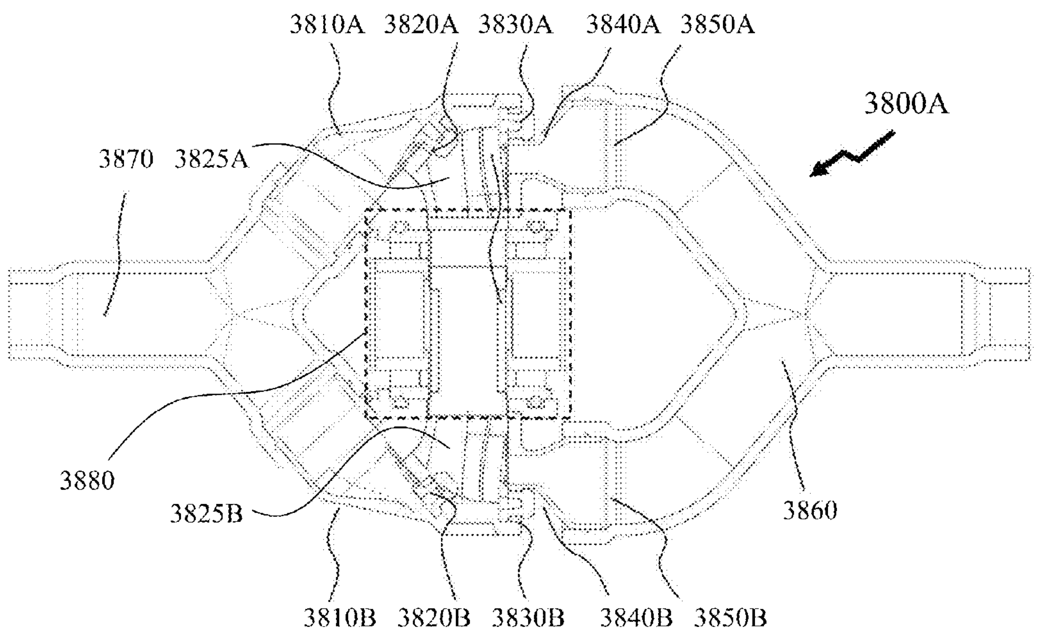
Figure 38
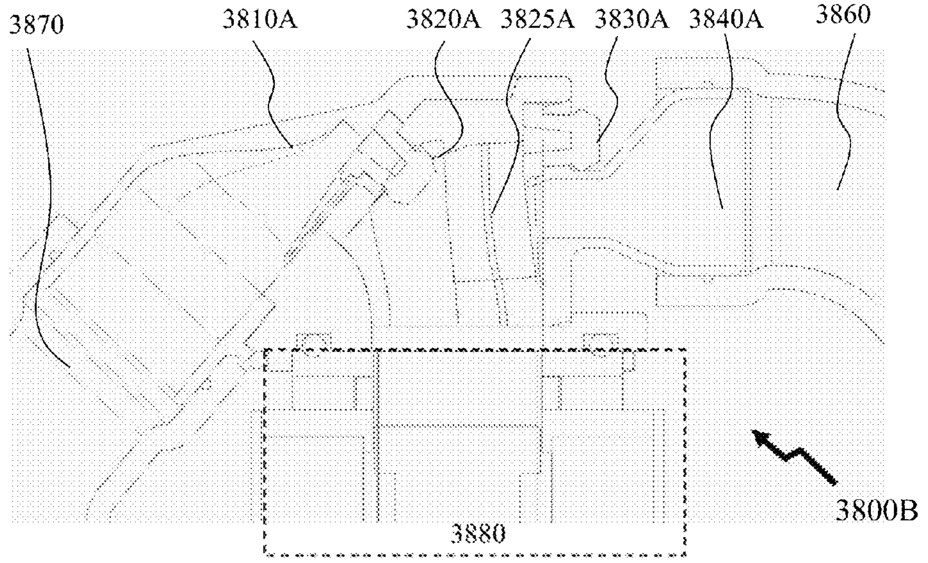

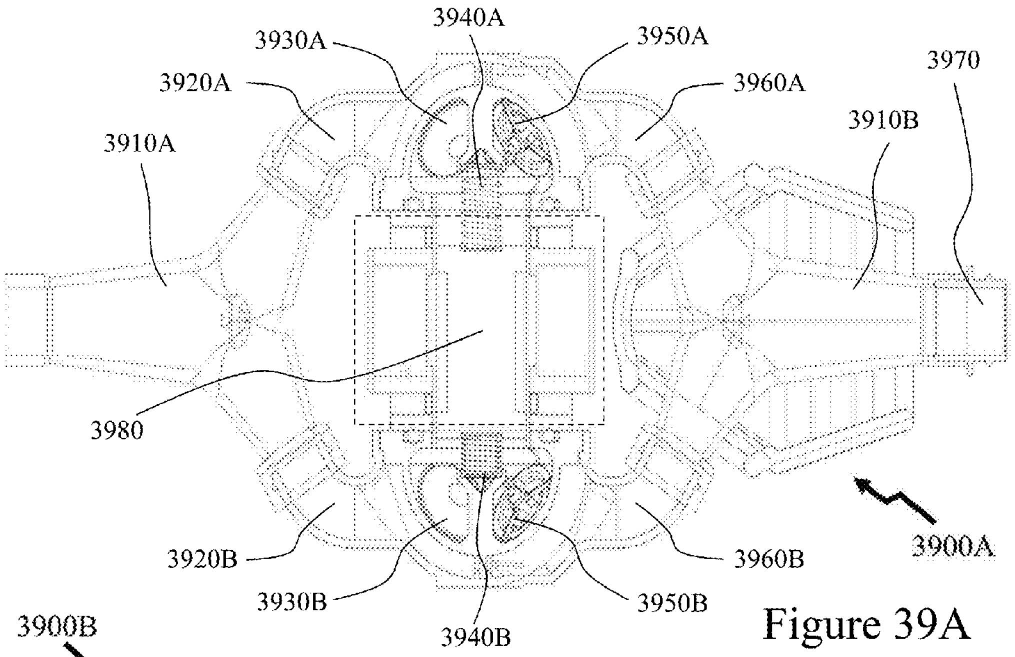
Figure 39A
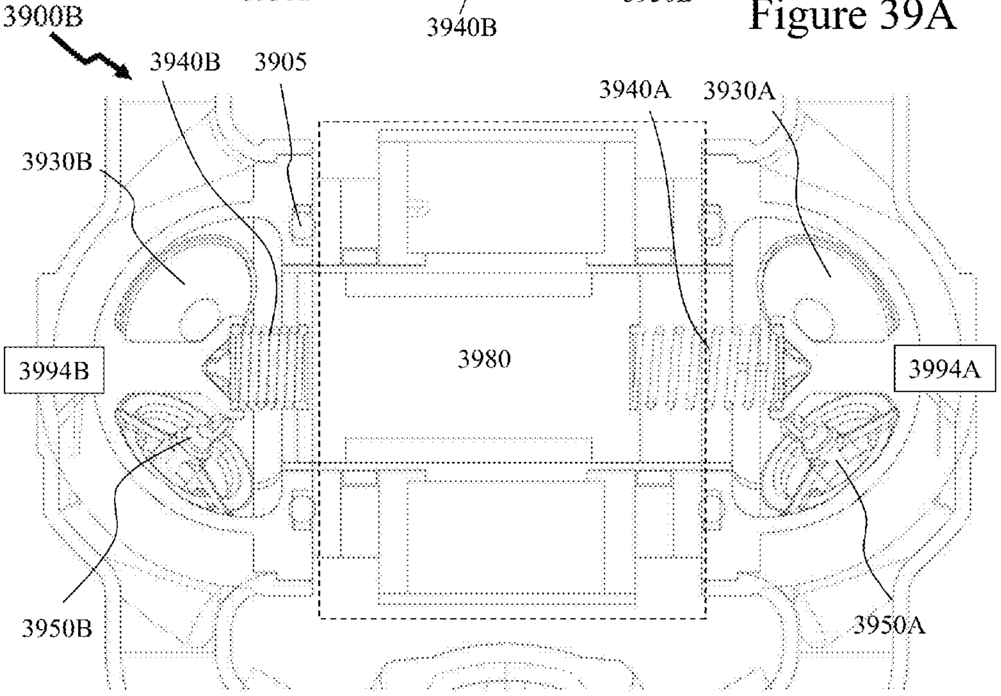

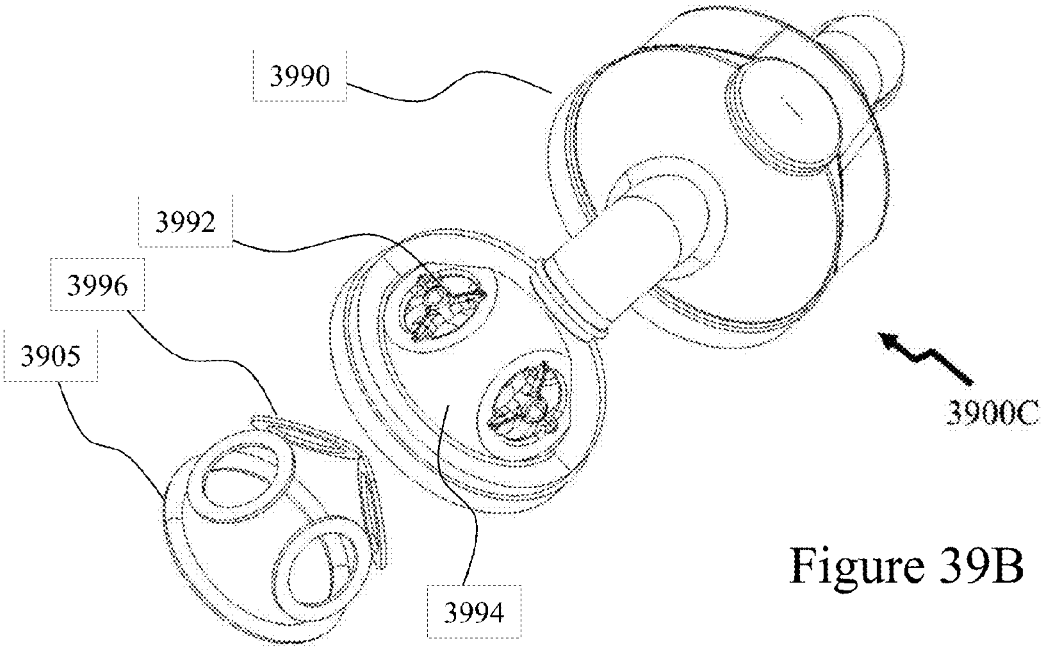
Figure 39B
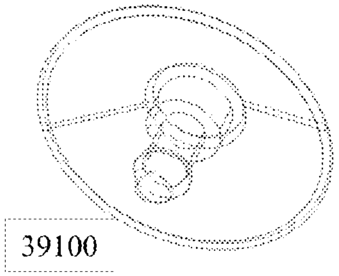
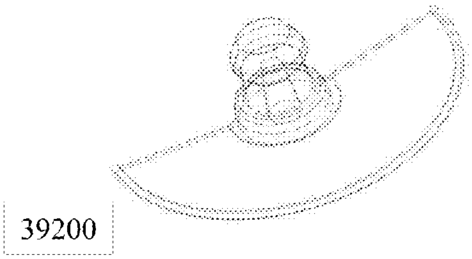
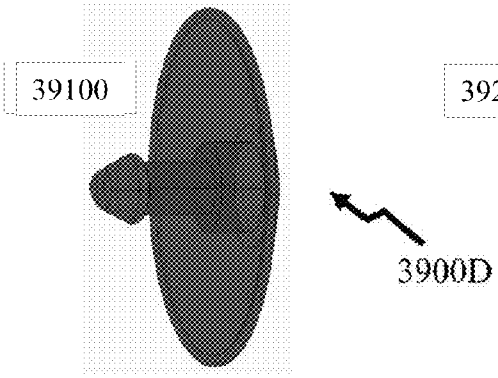
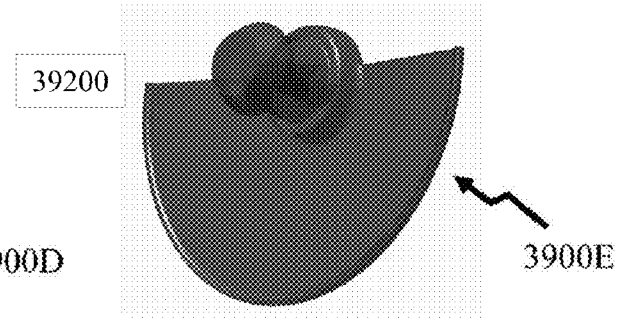

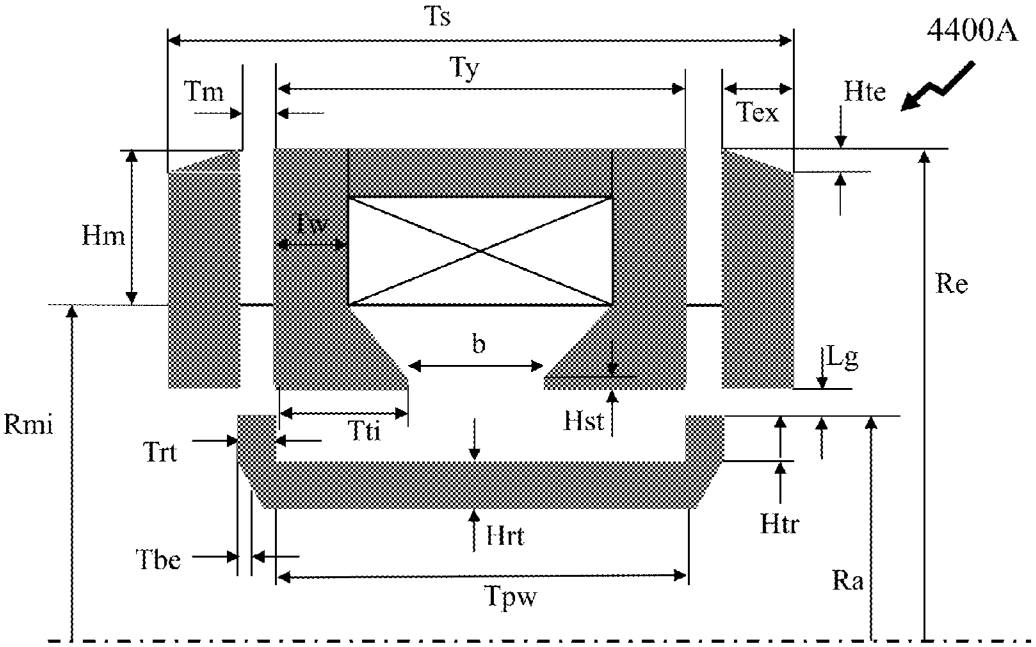
4400A
Figure 44
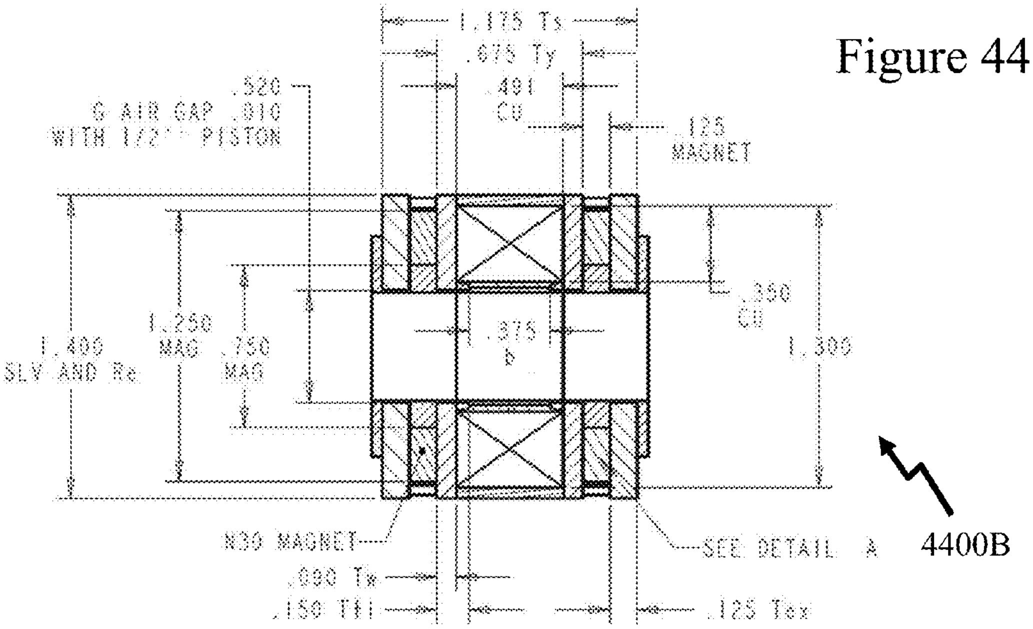
4400B

Flow-Rate Fluctuations vs Pump Frequency $10^2$
$10^0$
$10^{-2}$
ΔQ/Q
$P_0$
$P_1$
$P_2$
$P_3$
0
10
20
30
40
50
Pump Frequency (Hz)

Mean Cylinder Pressure vs Pump Frequency 12
11
10
9
8
7
Mean Cylinder Pressure (psi)
$P_0$
$P_1$
$P_2$
$P_3$
0
10
20
30
40
50
Pump Frequency (Hz)

6020
6000A
6010
6000B
6040
6050
6040
6050
6000C

FLUIDIC METHODS AND DEVICES

CROSS-REFERENCE TO RELATED APPLICATIONS

This patent application claims the benefit of U.S. Provisional Patent Application 61/705,809 filed on Sep. 26, 2012 entitled "Methods and Devices for Fluid Driven Adult Devices."

FIELD OF THE INVENTION

The present invention relates to devices for sexual pleasure and more particularly to devices exploiting fluidic control in conjunction with vibratory and non-vibratory function and movement.

BACKGROUND OF THE INVENTION

The sexual revolution, also known as a time of "sexual liberation", was a social movement that challenged traditional codes of behavior related to sexuality and interpersonal relationships throughout the Western world from the 1890s to the 1980s. However, its roots may be traced back further to the Enlightenment and the Victorian era in the Western world and even further in the Eastern world. Sexual liberation included increased acceptance of sex outside of traditional heterosexual, monogamous relationships (primarily marriage) as well as contraception and the pill, public nudity, the normalization of homosexuality and alternative forms of sexuality, and the legalization of abortion.

At the same time the growing acceptance of sexuality and masturbation resulted in the growth of a market for sexual devices, also known as sex toys, and then with technology evolution the concepts of "cyber-sex," "phone sex" and "webcam sex." A sex toy is an object or device that is primarily used to facilitate human sexual pleasure and typically are designed to resemble human genitals and may be vibrating or non-vibrating. Prior to this shift there had been a plethora of devices sold for sexual pleasure, although primarily under euphemistic names and a pretense of providing "massage" although their history extends back through ancient Greece to the Upper Paleolithic period before 30,000 BC. Modern devices fall broadly into two classes: mechanized and non-mechanized, and in fact the American company Hamilton Beach in 1902 patented the first electric vibrator available for retail sale, making the vibrator the fifth domestic appliance to be electrified. Mechanized devices typically vibrate, although there are examples that rotate, thrust, and even circulate small beads within an elastomeric shell. Non-mechanized devices are made from a solid mass of rigid or semi-rigid material in a variety of shapes.

Examples of such non-mechanized devices which require their motion to be induced either by the individual user themselves or a partner within the prior art include U.S. Pat. Nos. 5,853,362; 5,690,603; 5,853,362; 6,436,029; 6,599,236; 6,533,718; 6,997,888; 7,513,868; 7,530,944 as well as U.S. Patent Applications 2003/0,023,139; 2005/0,228,218; 2007/0,106,109; 2010/0,087,703; 2010/0,204,542; 2011/0,021,870; 2012/0,123,199; 2012/0,136,205 and 2012/0,143,001. Other associated prior art relates to how such devices may be "worn" by a partner either with or without the need of straps or belts or used by an individual including U.S. Pat. Nos. 5,725,473; 6,203,491; and 6,991,599 as well as U.S. Patent Applications 2010/0,087,703; 2011/0,082,333; and 2012/0,118,296.

Not surprisingly many early mechanized devices within the prior art were primarily intended to automate the motion of penetrative intercourse. Such prior art includes for example U.S. Pat. Nos. 4,722,327; 4,790,296; 5,076,261; 5,690,604; 5,851,175; 6,142,929; 6,866,645; 6,899,671; 6,902,525; 7,524,283 and U.S. Patent Application 2004/0,147,858. In contrast to these mechanized devices producing repeated penetrative action, vibrators are used to excite the nerve endings in the pelvic region, amongst others, of the user such as those same regions of the vagina that respond to touch. For many users the level of stimulation that a vibrator provides is inimitable. They can be used for masturbation or as part of sexual activities with a partner. Vibrators may be used upon the clitoris, inside the vagina, inserted into the rectum, and against nipples either discretely or in some instances in combination through multiple vibratory elements within the same vibrator or through using multiple vibrators.

Vibrators typically operate through the operation of an electric motor wherein a small weight attached off-axis to the motor results in vibration of the motor and hence the body of the portion of the vibrator coupled to the electric motor. They may be powered from connection to an electrical mains socket but typically such vibrators are battery driven which places emphasis on efficiency to derive not only an effective vibration but one over an extended period of time without the user feeling that the vibrator consumes batteries at a high rate. For example, typical vibrators employ 2 or 4 AA batteries, which if of alkaline construction, each have a nominal voltage of 1.5V and a capacity of 1800 mAh to 2600 mAh under 500 mA drain. As such, each battery under such a nominal drain can provide 0.75 W of power for 3 to 5 hours such that a vibrator with 2 AA batteries providing such lifetime of use must consume only 1.5 W in contrast to less than 3 W for one with 4 AA batteries. More batteries consume more space within devices which are generally within a relatively narrow range of physical sizes approximating that of the average penis in penetrative length and have an external portion easily gripped by the user thereby complicating the design. Typically, toys that are large due to power requirements are not as successful as more compact toys.

Example of such vibrators within the prior art include U.S. Pat. Nos. 5,573,499; 6,902,525; 7,108,668; 7,166,072; 7,438,681; 7,452,326; 7,604,587; 7,871,386; 7,967,740 and U.S. Patent Applications 2002/0,103,415; 2003/0,195,441 (Wireless); 2004/0,082,831; 2005/0,033,112; 2006/0,074,273; 2006/0,106,327; 2006/0,247,493; 2007/0,055,096; 2007/0,232,967; 2007/0,244,418; 2008/0,071,138; 2008/0,082,028; 2008/0,119,767; 2008/0,139,980; 2009/0,093,673; 2008/0,228,114; 2009/0,099,413; 2009/0,105,528; 2009/0,318,753; 2009/0,318,755; 2010/0,292,531; 2011/0,009,693; 2011/0,034,837; 2011/0,082,332; 2011/0,105,837; 2011/0,166,415; 2011/0,218,395; 2011/0,319,707; 2012/0,179,077; 2012/0,184,884; and 2012/0,197,072.

However, such electric motors with off-axis weights cannot easily operate at low frequencies when seeking to induce excitation to the user in a manner that mimics physical intercourse and stimulation where for example stimulation would be very low or low frequency and high or very high amplitude. Such low frequency, high amplitude vibrations are desirable to users but are not achieved with the vibrators of the prior art. For example providing operation below 40 Hz, below 10 Hz, below 4 Hz, below 1 Hz cannot be provided where small DC motors cannot produce much torque at low revolutions per minute (RPM) and therefore cannot move the large heavy weight to produce high amplitude variations. Typically, several thousand RPM is required in this scenario. Accordingly, reducing the weight to reduce torque required leads to reduced vibrations. It is this mode that vibrators operate within through high frequency low amplitude vibrations. It would be beneficial for an alternative drive means to allow low and very low frequency operation discretely or in combination with higher frequency operation and provide user settable high amplitude stimulation as well as offering reduced amplitudes.

Within these prior art embodiments of vibrators different approaches have been described to provide different stimulation mechanisms other than simple vibration. Some of these, such as rotating rows or arrays of balls, typically metal, have been commercially successful. However, others have not been commercially successful to date including, for example, the use of linear screw drive mechanisms to provide devices that adjust in length. Another common approach has been to include a rotary motor with a profiled metal rod to either impact the device's outer body or provide rotary motion of the device head.

It would be evident from consideration of the prior art and devices described above that these devices are primarily driven to stimulation of the female clitoris, vagina and rectum as well as the male rectum. Whilst vibrators such as described supra may be used for stimulating the male penis, and in some instances such as the "Cobra Libre" vibrator designed specifically for attachment to the penis there has been relatively little prior art and development towards stimulating the male penis through simulation of intercourse above and beyond manual devices. One exception being Gellert in U.S. Pat. No. 5,501,650 that provides a variable speed motor powering a crankshaft driven sealed assembly producing pneumatically induced reciprocating motion against the penis when inserted.

Accordingly, today, a wide range of vibrators are offered commercially to users but most of them fall into several broad categories including:

Clitoral: The clitoral vibrator is a sex toy used to provide sexual pleasure and to enhance orgasm by stimulating the clitoris. Although most of the vibrators available can be used as clitoral vibrators, those designed specifically as clitoral vibrators typically have special designs that do not resemble a vibrator and are generally not phallic shaped. For example, the most common type of clitoral vibrators are small, egg-shaped devices attached to a multi-speed battery pack by a cord. Common variations on the basic design include narrower, bullet-shaped vibrators and those resembling an animal. In other instances, the clitoral vibrator forms part of a vibrator with a second portion to be inserted into the vagina wherein they often have a small animal, such as a rabbit, bear, or dolphin perched near the base of the penetrative vibrator and facing forward to provide clitoral stimulation at the same time with vaginal stimulation. Prior art for clitoral stimulators includes U.S. Pat. Nos. 7,670,280 and 8,109,869 as well as U.S. Patent Application 2011/0,124,959.

In some instances, such as the We-Vibe™, the clitoral vibrator forms part of a vibrator wherein another section is designed to contact the "G-spot." Prior art for such combined vibrators includes U.S. Pat. No. 7,931,605, U.S. Design Pat. Nos. 605,779 and 652,942, and U.S. Patent Application 2011/0,124,959.

Dildo-Shaped: Typically these devices are approximately penis-shaped and can be made of plastic, silicone, rubber, vinyl, or latex. Dildo is the common name used to define a phallus-like sex toy, which does not, however, provide any type of vibrations. But as vibrators have commonly the shape of a penis, there are many models and designs of vibrating dildos available including those designed for both individual usage, with a partner, for vaginal and anal penetration as well as for oral penetration, and some may be double-ended.

Rabbit: As described above these comprise two vibrators of different sizes. One, a phallus-like shaped vibrator intended to be inserted in the user's vagina, and a second smaller clitoral stimulator placed to engage the clitoris when the first is inserted. The rabbit vibrator was named after the shape of the clitoral stimulator, which resembles a pair of rabbit ears.

G-Spot: These devices are generally curved, often with a soft jelly-like coating intended to make it easier to use to stimulate the g-spot or prostate. These vibrators are typically more curved towards the tip and made of materials such as silicone or acrylic.

Egg: Generally small smooth vibrators designed to be used for stimulation of the clitoris or insertion. They are considered discreet sex toys as they do not measure more than 3 inches in length and approximately ¾ inches to 1¼ inches in width allowing them to be used discretely, essentially at any time.

Anal: Vibrators designed for anal use typically have either a flared base or a long handle to grip, to prevent them from slipping inside and becoming lodged in the rectum. Anal vibrators come in different shapes but they are commonly butt plugs or phallus-like vibrators. They are recommended to be used with a significant amount of lubricant and to be inserted gently and carefully to prevent any potential damage to the rectal lining Cock Ring: Typically a vibrator inserted in or attached to a cock ring primarily intended to enhance clitoral stimulation during sexual intercourse.

Pocket Rocket (also known as Bullet): Generally cylindrical in shape one of its ends has some vibrating bulges and is primarily intended to stimulate the clitoris or nipples, and not for insertion. Typically, a "pocket rocket" is a mini-vibrator that is typically about three to five inches long and which resembles a small, travel-sized flashlight providing for a discreet sex toy that can be carried around in a purse, pouch, etc. of the user. Due to its small dimension, it is typically powered by a single battery and usually has limited controls; some may have only one speed.

Butterfly: Generally describing a vibrator with straps for the legs and waist allowing for hands-free clitoral stimulation during sexual intercourse. Typically, these are offered in three variations, traditional, remote control, and with anal and/or vaginal stimulators, and are generally made of flexible materials such as silicone, soft plastic, latex, or jelly.

In addition to the above general categories there are variants including, but not limited to:

- Dual vibrators which are designed to stimulate two erogenous zones simultaneously or independently, the most common being both clitoral and vaginal stimulators within the same vibrator;
- Triple vibrators which are designed to stimulate three erogenous zones simultaneously or independently;
- Multispeed vibrators which allow users to adjust how fast the vibrator's pulsing or massaging movements occur and generally provide a series of discrete speed settings selectable through a button, slider etc. or pseudo-continuously variable through a rotary control;
- Double ended devices for use by two users together, usually doubled ended dildo or double ended vibrator, for vaginal-vaginal, vaginal-anal, or anal-anal stimulation;

Nipple stimulators which are designed to stimulate the nipples and/or areola through vibration, suction, and clamping;

Electrostimulators which are designed to apply electrical stimulation to the nerves of the body, with particular emphasis on the genitals;

"Flapping" stimulators which have multiple flexible projections upon a "Ferris-wheel" assembly to simulate oral stimulation; and Male stimulators which are typically soft silicone sleeves to surround the penis and stimulate it through rhythmic movement by the user.

Naturally, there are other common forms including, but not limited to, so-called "alarm clock vibrators" wherein a vibrator is combined with a clock or a timer and worn in or against the genitals such that the user is woken with a gentle vibration and then with increasing power. "Undercover" vibrators are discreetly shaped as everyday objects, such as lipstick tubes, cell phones, or art pieces and typically only one speed and are powered by a single battery. By virtue of being an exact copy of the shape and design of the object they are intended to be mistaken as they are very discreet for users.

The prior art devices described above exploit mechanical actions arising from linear and/or rotary motors in order to achieve the desired physical stimulation. However, motion and pressure may be achieved also through the use of fluidics wherein a fluid is employed such that controlling the pressure of the fluid results in the movement of an element within a structure or the expansion/contraction of an element. However, to date the commercial deployment of sex toys exploiting fluidics has been limited to the provisioning of lubricating oils or gels during use of the device to reduce friction and subsequent pain/irritation either through extended use of the device or from low natural lubrication of the user upon whom the device is used. Examples of prior art for such lubricating devices include, but is not limited to, U.S. Pat. Nos. 6,749,557 and 7,534,203 and U.S. Patent Applications 2004/0,034,315; and 2004/0,127,766.

When considering users of the prior art devices described above these present several limitations and drawbacks in terms of providing enhanced functionality, dynamic device adaptability during use, and user specific configuration for example.

As noted supra, the commercial deployment of devices exploiting fluidics has been limited to lubricant release during device use despite several prior art references to using fluidics including, for example, those described below.

Stoughton in U.S. Pat. No. 3,910,262 entitled "Therapeutic Apparatus" teaches the use of a piston under electric motor control coupled to a massaging sleeve designed to fit around a penis such that the piston provides cyclic suction and pressure to the user's penis. The system taught is bulky and complex requiring set-up through needle valves to set the volumes of air adjusted within the massaging sleeve during the suction and injection phases.

Schroeder in U.S. Pat. No. 4,407,275 entitled "Artificial Erection Device" teaches a semi-rigid annular ring having individual expandable chambers on the internal wall that are distended separately by fluid pressure. Fluid pressure supplied either manually by a bulb or electrically by a pump allowing the chambers to expand and contract in a linear sequence.

Kain in U.S. Pat. No. 5,690,603 entitled "Erogenic Stimulator" teaches a dildo for use by two partners wherein one end of the dildo is intended to be retained by one partner within an orifice whilst the other end is used to penetrate an orifice of the other partner. Within an embodiment of the invention a fluid is disposed within an internally sealed fluidic assembly wherein muscular activity of one partner will displace the fluid within the internally sealed fluidic assembly towards the other end of the device and hence adjust the end used by the other partner. Kain does not teach dimensional adjustment but rather the fluid causing a pressure sensation.

Kain in U.S. Pat. No. 7,998,057 entitled "Erogenic Stimulator with Expandable Bulbous End" teaches similar dildos but wherein a fluidic chamber within one end of the device is coupled to a hand operated pump, internal or external to the device, allowing the dimension of the end of the device with the fluidic chamber to be inflated/deflated. However, Kain does not teach the use of such motion for stimulation purposes but rather to allow for adjustment of that end of the device to accommodate different users allowing, for example, insertion, inflation and hence retention of that device end.

Levy in U.S. Patent Application 2003/0,073,881 entitled "Sexual Stimulation" teaches a predominantly solid, phallus-shaped, semi-rigid device that includes mechanisms that expand designated surface regions outwardly to change the shape of the device. A fluid filled reservoir located at one end of the device expresses fluid through internal channels, causing resilient expansion at specified surface regions due to a locally reduced cross section. As taught by Levy, a single fluid reservoir is coupled to one or more internal channels and the reservoir expresses the fluid into the channel(s) under manual control of an individual.

Faulkner in U.S. Patent Application 2005/0,049,453 and 2005/0,234,292, each of which is entitled "Hydraulically Driven Vibrating Massagers," teaches devices with means to vibrate and/or rhythmically deform elements within the device. Faulkner teaches a hydraulic actuator to move hydraulic fluid into and out of the device to sequentially and repeatedly inflate and deflate an elastomeric element within the device. Faulkner teaches simple hydraulic drivers, such as cylinders, which are moved by an eccentric gear attached to a rotating shaft, thus injecting and removing hydraulic fluid in a pattern where deformation and flow are sine waves. Also taught, are more complicated hydraulic drivers using cams or computer-controlled drivers wherein cyclic deformations that are not simple sine waves can be created. A preferred embodiment taught by Faulkner is a voice-coil driver, which comprises a solenoid type coil directly coupled to the shaft of a piston which is in turn coupled to a spring, which provides a base level of pressure. Accordingly, a low frequency alternating current is applied to the coil, which in turn drives the shaft, thereby driving the piston such that hydraulic fluid is driven into and out of the piston, thereby moving the elastomeric stimulator. Faulkner further teaches a second fluid immersed driver, such as an electrical coil-driven diaphragm or piezoelectric crystal, which is used to add higher frequency pressure variations to the low frequency cyclic pressure variation from the primary piston based hydraulic oscillator. Accordingly, Faulkner teaches generating a cyclic motion of an element or elements of the device through the cyclic first hydraulic oscillator and applying a vibratory element through a second fluid immersed hydraulic oscillator.

Regey in U.S. Patent Application 2006/0,041,210 entitled "Portable Sealed Water Jet Female Stimulator" teaches to a water pump that directs a jet or focused stream of water at a waterproof flexible membrane thereby imparting pressure to that part of the user where the membrane is located upon.

The water, re-circulating in a closed system inside a casing, may be heated, pulsed, swirled, or directed in a steady stream.

Gil in U.S. Pat. No. 7,534,203 entitled "Vibrator Device with Inflatable, Alterable Accessories" teaches detachable "accessories" which are attached to predetermined locations on the outer surface of a device and couple to pneumatic passageways coupled to an accessory pump. The accessories may be selected by an individual for size and surface texture for example to adjust the degree of friction or material wherein thinner softer materials for the accessory provide increased inflation relative to accessories made from harder, thicker materials. Accordingly, these accessories are discrete inflatable elements that replace the discrete solid projections, commonly referred to as nubbies that are disposed on the outer body of many dildo and vibrator devices. However, Gil teaches that vibratory action of the device is provided by a conventional electric motor with off-axis weight.

It is evident therefore to one skilled in the art that the hydraulic driven devices as taught by Faulkner, Gil, Kain, Levy, Schroeder, and Stoughton do not provide devices with the desirable and beneficial features described above which are lacking within known devices of the conventional mechanical activation with electrical motors. Further in considering fluidic pumps that may be employed as part of hydraulic devices then within the prior art there are naturally several designs of pumps. However, to date as discussed supra hydraulic devices have not been developed or commercially deployed despite the prior art fluidic concepts identified above in respect of fluidic devices and these prior art pumps. This is likely due to the fact that fluidic pumps are bulky, have low efficiency, and do not operate in the modes required for such devices, such as, for example, low frequency, variable duration, and pulsed for those providing primary pumps for dimensional adjustments or for example high frequency operation for those providing secondary pumps for vibration and other types of motion/excitation. For example, a conventional rotary pump offers poor pressure at low revolutions per minute (rpm), has a complicated motor and separate pump, multiple moving parts, relatively large and expensive even with small impeller, and low effective flow rate from a small impeller.

Within the prior art there are examples of electromechanical actuators which may provide alternative pumps to those described below in respect of embodiments of the invention in FIGS. 25 through 31 but with varying limitations and drawbacks. For example so-called voice-coil linear vibrating motors whilst compatible with modification to fluid pumping do not exert a strong force relative to a solenoids closing force but can provide an increased linearity of force over distance. Examples include long coil—short gap with magnetization along axis of motor, short coil motor with magnetization perpendicular to motor axis. Solenoids whilst offering larger force than voice coil motors have a poor ability to exert a steady force on a long stroke piston, typically a few millimeters, and where constant force solenoids are implemented these tend to be short stroke with increased complexity in the design of the coil, body and shape of the cross-section of the plunger. An example of such prior art solenoids based actuators are the FFA and MMA series of actuators from Magnetic Innovations (www.magneticinnovations.com). However, such actuators are primarily designed for long stroke, large load displacement, and as replacements for pneumatic cylinders.

Other prior art moving magnet motor is that described by Astratini-Enache et al. in "Moving Magnet Type Actuator with Ring Magnets" (J. Elect. Eng., Vol. 61, pp. 144-147) and Leu et al. in "Characteristics and Optimal Design of Variable Airgap Linear Force Motors" (IEEE Proc. Pt B, Vol. 135, pp. 341-345) but exploit neodymium and samarium-cobalt rare-earth magnets in order to miniaturize the motor dimensions. Petrescu et al. in "Study of a Mini-Actuator with Permanent Magnets" (Adv. Elect. & Comp. Eng., Vol. 9, pp. 3-6) adds fixed magnets to either end of a moving magnet actuator in order to define the moving magnet position when no activation is provided due to the requirements of robotics and defined zero activation positions for actuators as well as adjusting the force versus displacement characteristic of the actuator. Vladimirescu et al. in U.S. Pat. No. 6,870,454 entitled "Linear Switch Actuator" teach to a latching actuator for a microwave switch application wherein the actuator comprises an armature rod with permanent magnets at either end such that as one or other permanent magnet moves outside the coils the structure latches.

In contrast to moving magnet motors moving iron motors have been reported within the prior art as an alternative, see for example Ibrahim et al. in "Design and Optimization of a Moving Iron Linear Permanent Magnet Motor for Reciprocating Compressors using Finite Element Analysis" (Int. J. Elect. & Comp. Sci. IJECS-IJENS, Vol. 10, pp. 84-90). As taught by Ibrahim the design of Evans et al. in "Permanent Magnet Linear Actuator for Static and Reciprocating Short Stroke Electromechanical Systems" (IEEE/ASME Trans. Mechatronics, Vol. 6, pp. 36-42) which employs rare earth magnets is adapted to employ lower cost magnets which also remove Eddy current issues which required magnet segmentation in prior art moving magnet linear motors. Ibrahim adjusts the resulting reduction in force from the reduced strength magnets by increasing dimensions, magnetic loading and electrical loading whilst optimizing the design for 50 Hz electrical mains operation. The resulting motor at 100 mm (4 inches) long and 55 mm (2.2 inches) diameter, is larger than many of the devices within the prior art and the device dimensions sought for the devices targeted for implementation using these fluidic actuators.

Likewise, Berling in U.S. Pat. No. 5,833,440 entitled "Linear Motor Arrangement for a Reciprocating Pump System" describes a moving magnet actuator exploiting a pole piece pair magnetically soft material abutting a permanent magnet to conduct the magnetic flux in two different magnetic circuit pathways. In one pathway the armature is attracted to the pole pieces resulting in coil driven motion. However, in the second pathway whilst the armature is not attracted to the pole pieces there is no repulsive force and accordingly a compression spring is used to push the armature away from the pole pieces. Likewise Cedrat Technologies with their Moving Iron Controllable Actuator (MICA) exploit a pair of soft magnetic pole pieces within a magnetic field wherein the magnetic force is intrinsically quadratic meaning that only attraction forces can be produced and accordingly to achieve a return a return spring is added, leading to one fixed position at rest.

Mokler in U.S. Patent Application 2006/0,210,410 describes a pump comprising a pair of electromagnets disposed around a tubular member wherein associated with each is a magnet. Disposed between the two electromagnets is a pair of permanent magnets as well as permanent magnets at each outer end of the electromagnets. Accordingly, the permanent magnets limit the movement of the magnets under action of the electromagnets. Hertanu et al. in "A Novel Minipump Actuated by Magnetic Piston" (J. Elec. Eng., Vol. 61, pp. 148-151) similarly exploits permanent magnets at either end to limit the motion of the moving magnet and define the initial position. However, Hertanu also employs ferrofluidic rings at either end of the moving magnet wherein the ferrofluid conforms to the channel shape providing very good seal and can be controlled by external magnetic fields.

Ibrahim in "Analysis of a Short Stroke, Single Phase Tubular Permanent Magnet Actuator for Reciprocating Compressors" (6th Int. Symposium on Linear Drives for Industrial Applications, LDIA2007, 2007) describes a moving magnet actuator wherein the central moving magnet is formed from a series of radially and axially magnetized trapezoidal ring magnets stacked together with varying magnetic field directions. Accordingly, the resulting magnet is complicated and expensive and whilst Ibrahim in "T. Ibrahim, J. Wang, and D. Howe, "Analysis of a Single-Phase, Quasi-Halbach Magnetised Tubular Permanent Magnet Motor with Non-Ferromagnetic Support Tube" (14th IET Int. Conf. on Power Electronics, Machines and Drives, Vol. 1, pp. 762-766) adjusted the magnetized ring magnet design it still requires multiple rings stacked together with different field orientations, they are simply rectangular rather than trapezoidal. Another variant is taught by Lee et al. in "Linear Compression for Air Conditioner" (International Compressor Engineering Conference 2004, Paper C047) wherein whilst the magnet again surrounds an inner core and is a single element the compressor exploits a resonant spring assembly and a controller that controls the excitation frequency for maximizing the linear motor efficiency by using system resonance follow-up algorithm.

Accordingly, it would be desirable to provide pumps and valves that allow for multiple ranges of motion of the device both in terms of overall configuration and dimensions as well as localized variations and multiple moving elements may be implemented using fluidics wherein a fluid is employed such that controlling the pressure and/or flow of the fluid results in the movement of an element(s) within the device or the expansion/contraction of an element(s) within the device. As noted supra, the commercial deployment of sexual stimulation devices or devices for sexual pleasure exploiting fluidics has been limited to lubricant release during device use despite several prior art references to using fluidics including, for example, those described below. Accordingly, there remains a need for methods and devices that provide these desirable and beneficial features. It would be particularly beneficial to provide fluidic devices having all of the functions described supra in respect of prior art devices but also have the ability to provide these within a deformable device and/or a device having deformable element(s). Further, it would be beneficial to provide devices that employ fluidic actuators, which are essentially non-mechanical and, consequently, are not susceptible to wear-out such as, by stripping drive gears, etc., thereby increasing their reliability and reducing noise. Fluidic devices allow for high efficiency, high power to size ratio, low cost, limited or single moving part(s) and allow for mechanical springless designs as well as functional reduction by providing a piston which is both pump and vibrator.

Other aspects and features of the present invention will become apparent to those ordinarily skilled in the art upon review of the following description of specific embodiments of the invention in conjunction with the accompanying figures.

SUMMARY OF THE INVENTION

It is an object of the present invention to mitigate limitations within the prior art relating to devices for sexual pleasure and more particularly to devices exploiting fluidic control with vibratory and non-vibratory functions.

In accordance with an embodiment of the invention there is provided a device comprising:

an electromagnetically driven pump for pumping a fluid from an inlet port to an outlet port; and a fluidic capacitor coupled at one end to the electromagnetically driven pump at other end to a fluidic system; wherein the fluidic capacitor comprises a first predetermined portion having a first predetermined elasticity and a second predetermined portion having a second predetermined elasticity lower than the first predetermined elasticity wherein the second predetermined portion deforms under activation of the electromagnetically driven pump in a manner such that the electromagnetically driven pump is not at least one of drawing upon or pumping into the complete fluidic system according to whether the fluidic capacitor is on the inlet side or the outlet side port of the electromagnetically driven pump.

In accordance with an embodiment of the invention there is provided a method comprising:

an electromagnetically driven pump for pumping a fluid upon both forward and backward piston strokes;

first and second valve assemblies coupled to each end of the electromagnetically driven pump, each valve assembly comprising an inlet non-return valve, an outlet non-return valve, and a valve body having a port fluidically coupled to the electromagnetically driven pump, a port coupled to the inlet non-return valve, and a port coupled to the output non-return valve; and a first fluidic capacitor disposed at least one of prior to an inlet non-return valve and after an outlet non-return valve; wherein the first fluidic capacitor comprises a first predetermined portion having a first predetermined elasticity and a second predetermined portion having a second predetermined elasticity lower than the first predetermined elasticity wherein the second predetermined portion deforms under activation of the electromagnetically driven pump in a manner such that the electromagnetically driven pump is not at least one of drawing upon or pumping into fluidic system to which the electromagnetically driven pump is connected according to whether the fluidic capacitor is on the inlet side or the outlet side port of the electromagnetically driven pump.

In accordance with an embodiment of the invention there is provided a device comprising:

providing an electrical coil wound upon a bobbin having an inner tubular opening with a minimum diameter determined in dependence upon at least the piston and having a predetermined taper profile at either end of the bobbin providing an increasing diameter towards each end of the bobbin to a predetermined maximum diameter, the predetermined taper profile determined in dependence upon the target performance of an electromagnetically driven device;

providing a pair of thin electrically insulating washers for assembly directly to either side of the coil, each thin electrically insulating washer having an inner diameter at least equal to the predetermined maximum diameter of the bobbin;

providing a pair of inner washers disposed either side of the coil with each adjacent one of the thin electrically insulating washers, each inner washer comprising a disc of predetermined thickness and a projection on the inner edge of the washer matching the predetermined taper profile on the bobbin;

providing a pair of magnets disposed either side of the coil with each adjacent one of the inner washers;

providing a pair of outer washers disposed either side of the coil with each adjacent one of magnets;

assembling the electrical coil, the pair of thin electrically insulating washers, the pair of inner washers, the pair of magnets, and the pair of outer washers in their correct order within a jig, the jig comprising a central circular rod defining a minimum barrel diameter which is less than the minimum diameter of the bobbin by a predetermined amount;

potting the assembled components within the jig; and disassembling the potted assembly for subsequent insertion of a piston of predetermined dimensions within the barrel formed within the potting material to provide the electromagnetically driven device under appropriate electrical control.

In accordance with an embodiment of the invention there is provided a method:

providing an electromagnetically driven device comprising at least a piston, the piston having a predetermined outer diameter profile along its length and a predetermined gaps and tolerances with respect to a barrel formed within the electromagnetically driven motor within which the piston moves; wherein the piston outer diameter profile is determined in dependence upon at least characteristics of the piston stroke within the electromagnetically driven device and a fluid the piston is moving within such that above a predetermined minimum piston speed sufficient hydrodynamic pressure can be generated to generate sufficient lift forces on the piston to offset magnetic attraction forces from off-axis positioning and preventing surface-surface contact between outer surface of the piston and the inner surface of the barrel.

In accordance with an embodiment of the invention there is provided a method comprising:

simulating the piston dynamics of a piston moving within a fluid within an electromagnetically driven device with at least current induced force as an input, the simulation determining piston position, fluid pressure, and piston velocity as a function of time;

establishing a force signal curve that imparts energy over the entire stroke and permits the piston to traverse the entire desired stroke length;

evolving the force signal curve using a optimization method where the mean current from a particular force curve was minimized;

translating the resulting evolved force signal curve to an applied electrical drive signal curve to provide the signal control current profile for an electrical control circuit to provide to drive the electromagnetically driven device.

In accordance with an embodiment of the invention there is provided a device comprising:

an electromagnetically driven device comprising:

a piston of predetermined shape with a plurality of slots machined along its axis, the plurality of slots penetrating to a predetermined depth;

a pair of washer-magnet-washer assemblies, each assembly disposed on either side of an electromagnetic coil of the electromagnetically driven device where each washer has a slot cut through its thickness from the inner edge to the other edge; wherein the slots formed within the piston and washer reduce the formation of radial or circular Eddy currents within the respective one of the piston and washer.

In accordance with an embodiment of the invention there is provided a device comprising:

an electromagnetically driven device;

a fluidic capacitor which acts as a low pass fluidic filter in combination with other elements of the fluidic system to smooth pressure fluctuations arising from the operation of the electromagnetically driven device over a first predetermined frequency range; and a control circuit providing a first signal for driving the electromagnetically driven device at a frequency within the first predetermined frequency range and a second signal for driving the electromagnetically driven device with an oscillatory signal above the low pass cut-off frequency of the low pass fluidic filter; wherein the pulsed fluidic output generated by the second signal is coupled to the fluidic system but the pulsed fluidic output generated by the first signal is filtered to provide a constant fluidic flow from the electromagnetically driven device with predetermined ripple.

In accordance with an embodiment of the invention there is provided a device comprising:

a pressure valve wherein the pressure valve opens when an applied fluidic pressure exceeds a predetermined value such that a spring force from a spring coupled to a ball bearing seated within a seat sealing the an inlet within the pressure valve cannot keep the ball bearing in position within the seat;

a drive pin operable by an actuator between a first position preventing the ball bearing from moving and a second position allowing the ball bearing to move and having a profile at its end that re-positions the ball bearing back into seat when it transitions to the first position; and a control circuit for receiving an external control signal and controlling the actuator in dependence therein.

In accordance with an embodiment of the invention there is provided a method comprising:

a) providing a set-up procedure for an action relating to a functional element of a device to be personalized to an individual;

b) automatically varying an aspect of the action relating to the functional element of the device between a first predetermined value and a second predetermined value in a predetermined number of steps until an input is received from the individual; and c) terminating step (b) upon receiving the individual's input and storing the value relating to the aspect of the action when the individual provided the input within a profile of a plurality of profiles associated with the device.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 38 depicts a compact ECPUMP according to an embodiment of the invention exploiting the motor depicted in FIGS. 35 to 36B;

FIGS. 39A and 39B depict a compact ECPUMP according to an embodiment of the invention exploiting the motor depicted in FIGS. 35 to 36B;

FIG. 44 depicts a cross-section and dimensioned compact ECPUMP according to an embodiment of the invention exploiting the motor depicted in FIGS. 35 to 36B;

DETAILED DESCRIPTION

Figure 2:
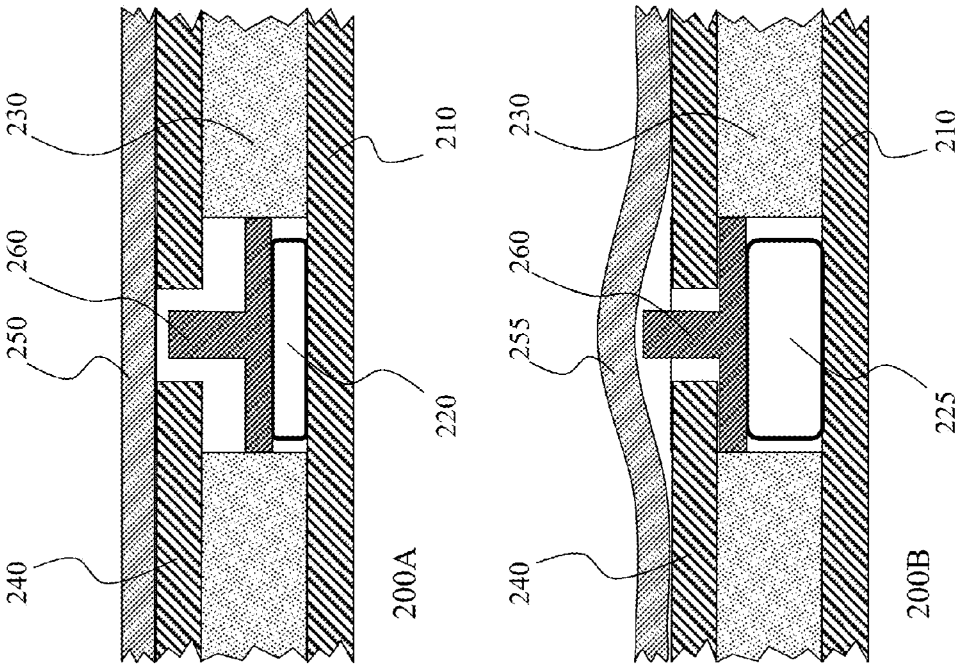
FIG. 2 depicts a fluidic actuator based pressure element according to an embodiment of the invention.

The present invention is directed to devices for sexual pleasure and more particularly to devices exploiting fluidic control with vibratory and non-vibratory function and movement.

The ensuing description provides representative embodiment(s) only, and is not intended to limit the scope, applicability or configuration of the disclosure. Rather, the ensuing description of the embodiment(s) will provide those skilled in the art with an enabling description for implementing an embodiment or embodiments of the invention. It being understood that various changes can be made in the function and arrangement of elements without departing from the spirit and scope as set forth in the appended claims. Accordingly, an embodiment is an example or implementation of the inventions and not the sole implementation. Various appearances of "one embodiment," "an embodiment" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention can also be implemented in a single embodiment or any combination of embodiments.

Reference in the specification to "one embodiment", "an embodiment", "some embodiments" or "other embodiments" means that a particular feature, structure, or characteristic described in connection with the embodiments is included in at least one embodiment, but not necessarily all embodiments, of the inventions. The phraseology and terminology employed herein is not to be construed as limiting but is for descriptive purpose only. It is to be understood that where the claims or specification refer to "a" or "an" element, such reference is not to be construed as there being only one of that element. It is to be understood that where the specification states that a component feature, structure, or characteristic "may", "might", "can" or "could" be included, that particular component, feature, structure, or characteristic is not required to be included.

Reference to terms such as "left", "right", "top", "bottom", "front" and "back" are intended for use in respect to the orientation of the particular feature, structure, or element within the figures depicting embodiments of the invention. It would be evident that such directional terminology with respect to the actual use of a device has no specific meaning as the device can be employed in a multiplicity of orientations by the user or users.

Reference to terms "including", "comprising", "consisting" and grammatical variants thereof do not preclude the addition of one or more components, features, steps, integers or groups thereof and that the terms are not to be construed as specifying components, features, steps or integers. Likewise the phrase "consisting essentially of", and grammatical variants thereof, when used herein is not to be construed as excluding additional components, steps, features integers or groups thereof but rather that the additional features, integers, steps, components or groups thereof do not materially alter the basic and novel characteristics of the claimed composition, device or method. If the specification or claims refer to "an additional" element, that does not preclude there being more than one of the additional element.

A "personal electronic device" (PED) as used herein and throughout this disclosure, refers to a wireless device used for communications and/or information transfer that requires a battery or other independent form of energy for power. This includes devices such as, but not limited to, a cellular telephone, smartphone, personal digital assistant (PDA), portable computer, pager, portable multimedia player, remote control, portable gaming console, laptop computer, tablet computer, and an electronic reader.

A "fixed electronic device" (FED) as used herein and throughout this disclosure, refers to a device that requires interfacing to a wired form of energy for power. However, the device can access one or more networks using wired and/or wireless interfaces. This includes, but is not limited to, a television, computer, laptop computer, gaming console, kiosk, terminal, and interactive display.

A "server" as used herein, and throughout this disclosure, refers to a physical computer running one or more services as a host to users of other computers, PEDs, FEDs, etc. to serve the client needs of these other users. This includes, but is not limited to, a database server, file server, mail server, print server, web server, gaming server, or virtual environment server.

A "user" as used herein, and throughout this disclosure, refers to an individual engaging a device according to embodiments of the invention wherein the engagement is a result of their personal use of the device or having another individual using the device upon them.

A "vibrator" as used herein, and throughout this disclosure, refers to an electronic sexual pleasure device intended for use by an individual or user themselves or in conjunction with activities with another individual or user wherein the vibrator provides a vibratory mechanical function for stimulating nerves or triggering physical sensations.

A "dildo" as used herein, and throughout this disclosure, refers to a sexual pleasure device intended for use by an individual or user themselves or in conjunction with activities with another individual or user wherein the dildo provides non-vibratory mechanical function for stimulating nerves or triggering physical sensations.

A "sexual pleasure device" as used herein, and throughout this disclosure, refers to a sexual pleasure device intended for use by an individual or user themselves or in conjunction with activities with another individual or user which can provide one or more functions including, but not limited to, those of a dildo and a vibrator. The sexual pleasure device/toy can be designed to have these functions in combination with design features that are intended to be penetrative or non-penetrative and provide vibratory and non-vibratory mechanical functions. Such sexual pleasure devices can be designed for use with one or more regions of the male and female bodies including but not limited to, the clitoris, the clitoral area (which is the area surrounding and including the clitoris), vagina, rectum, nipples, breasts, penis, testicles, prostate, and "G-spot." In one example a "male sexual pleasure device" is a sexual pleasure device configured to receive a user's penis within a cavity or recess. In another example, a "female sexual pleasure device" is a sexual pleasure device having at least a portion configured to be inserted in a user's vagina or rectum. It should be understood that the user of a female sexual pleasure device can be a male or a female when it is used for insertion in a user's rectum.

An "ECPUMP" as used herein, and throughout this disclosure, refers to an electrically controlled pump.

A "profile" as used herein, and throughout this disclosure, refers to a computer and/or microprocessor readable data file comprising data relating to settings and/or limits of a sexual pleasure device. Such profiles may be established by a manufacturer of the sexual pleasure device or established by an individual through a user interface to the sexual pleasure device or a PED/FED in communication with the sexual pleasure device.

A "nubby" or "nubbies" as used herein, and throughout this disclosure, refers to a projection or projections upon the surface of a sexual pleasure device intended to provide additional physical interaction. A nubby can be permanently part of the sexual pleasure device or it can be replaceable or interchangeable to provide additional variation to the sexual pleasure device.

An "accessory" or "accessories" as used herein, and throughout this disclosure, refers to one or more objects that can be affixed to or otherwise appended to the body of a sexual pleasure device in order to enhance and/or adjust the sensation(s) provided. Such accessories can be passive, such as nubbies or a dildo, or active, such as a vibrator.

A "balloon" as used herein, and throughout this disclosure, refers to an element intended to adjust its physical geometry upon the injection of a fluid within it. Such balloons can be formed from a variety of elastic and non-elastic materials and be of varying non-inflated and inflated profiles, including for example spherical, elongated, wide, thin, etc. A balloon may also be used to transmit pressure or pressure fluctuations to the sexual pleasure device surface and user where there is an inappreciable, or very low, change in the volume of the balloon.

When considering users of the prior art sexual pleasure devices described above these present several limitations and drawbacks in terms of providing enhanced functionality, dynamic sexual pleasure device adaptability during use, and user specific configuration for example. For example, it would be desirable for a single sexual pleasure device to support variations in size during use both in length and radial diameter to simulate intercourse even with the sexual pleasure device held static by the user as well as adapting to the user of the sexual pleasure device or the individual upon whom the sexual pleasure device is being used.

It would be further beneficial for a sexual pleasure device to vary in form, i.e. shape, during its use. It would be yet further desirable for this variation to be integral to the traditional operation of the sexual pleasure device. It would be yet further desirable to provide variable sized and shaped features in an asymmetric fashion on the sexual pleasure device so that the sexual pleasure device provides a further level of sensation control. Such variable sized and shaped features, such as bumps, undulations, knobs, and ridges, may beneficially appear and disappear during use discretely or in conjunction with one or more other motions. In some instances, it may be desirable to provide a radial increase along selected portions of the length of the sexual pleasure device to accommodate specific predilections as well as curvature. In some sexual pleasure device embodiments it would be desirable to have a protrusion at the tip of a sexual pleasure device that extends and retracts while inside the body, providing an internal "tickling"/"stroking" effect, or for use against the clitoris for external "tickling"/"stroking" effect. It would further be desirable to omit radial increase (i.e., provide a constant and unchanging radius) along selected portions of the length of the shaft to accommodate specific predilections whilst the length of the sexual pleasure device changes.

In some sexual pleasure device embodiments it would be desirable for the outer surface or "skin" of the sexual pleasure device to move within the plane of the skin so that one or more areas of the skin relative to the majority of the outer skin of the sexual pleasure device to provide a capability of friction to the user. Optionally, these regions may also move perpendicular to the plane of the skin surface at the same time. In addition to these various effects it would also be beneficial to separately vary characteristics such as frequency and amplitude over wide ranges as well as being able to control the pulse shape for variable acceleration of initial contact and subsequent physical action as well as being able to simulate/provide more natural physical sensations. For example, a predefined "impact" motion at low frequency may be modified for vibration at the end of the cycle.

It would be desirable for these dynamic variations to be controllable simultaneously and interchangeably while being transparent to the normal use of the sexual pleasure device, including the ability to insert, withdraw, rotate, and actuate the variable features either with one hand, without readjusting or re-orienting the hand, with two hands, or hands free. In some embodiments of the sexual pleasure device it would be desirable to provide two, perhaps more, independently controllable ranges of shape changes within the same sexual pleasure device, so that in one configuration a first range of overall shapes, vibrations, undulations, motions etc. is available and a second range is available in a second configuration. These configurations may be provided sequentially or in different sessions. Within another embodiment of the invention these configurations may be stored remotely and recalled either by an individual to an existing sexual pleasure device, a new sexual pleasure device, or another sexual pleasure device as part of an encounter with another individual who possesses another sexual pleasure device. Optionally, such profile storage and transfer may also provide for a remote user to control a sexual pleasure device of an individual.

Accordingly, the desirable multiple ranges of motion of the sexual pleasure device both in terms of overall configuration and dimensions as well as localized variations and movement may be implemented using fluidics wherein a fluid is employed such that controlling the pressure of the fluid results in the movement of an element within the sexual pleasure device or the expansion/contraction of an element within the sexual pleasure device. Embodiments of the invention allow for large amplitude variations of the toy as well as providing operation over a ranges of frequencies from near-DC to frequencies of hundreds of Hertz. Further embodiments of the invention provide for efficient continuous flow/pressure as well as more power hungry pulsed actuations. Further embodiments of the invention provide for designs with no seals or sealing rings on the piston.

Fluidic Actuator Systems

Figure 1:
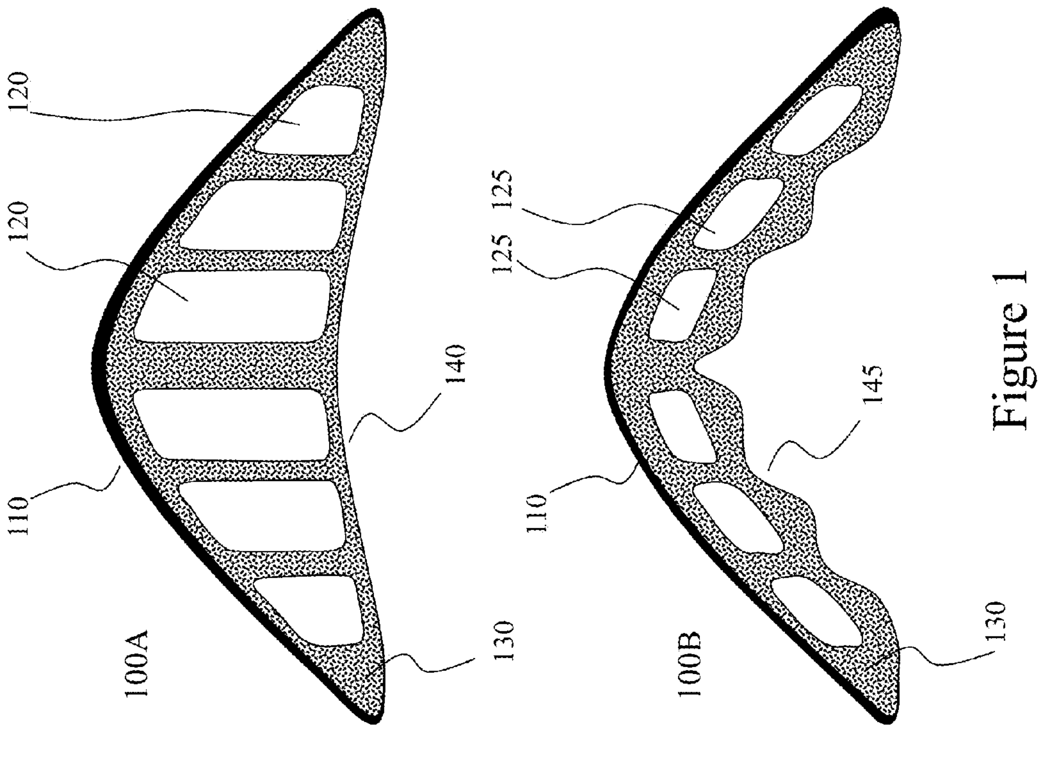
FIG. 1 depicts a fluidic actuator based suction element according to an embodiment of the invention.

Fluidic Actuator based Suction: Referring to FIG. 1 there is depicted a fluidic actuator based suction element in first and second states 100A and 100B respectively according to an embodiment of the invention. As depicted within first state 100A the fluidic actuator based suction element comprises a shaped resilient frame 110 and an elastic body 130 within which are disposed a plurality of expanded fluidic chambers 120 controlled dependently or independently. The side of the elastic body 130 opposite the shaped resilient frame 110 defining a first contour 140 in the first state 100A. In second state 100B the expanded chambers 120 have been collapsed to form reduced fluidic chamber(s) 125 wherein the elastic body 130 has now relaxed back towards the shaped resilient frame 110 such that the side of the elastic body 130, opposite the shaped resilient frame 110, defines a second contour 145 in the second state 100B. Accordingly, the fluidic actuator suction element can be transitioned from first state 100A to second state 100B by the removal of fluid from the expanded chambers 135 to compress them or conversely the fluidic actuator suction element can be transitioned from second state 100B to first state 100A by the injection of fluid into the compressed chambers 135. Optionally the chambers can be expanded/reduced in various configurations together or separately to apply varying sensations to the user. For example, if attached to the areola and nipple of the user these can be stimulated simultaneously, discretely, sequentially, or in any order by adjustment in the electronic controller program controlling the fluidic system to which the fluidic actuator is connected.

Depending on the overall design of the fluidic actuation system coupled to the fluidic chambers within the fluidic actuator based suction element, the power off state can be either first state 100A, second state 100B, or an intermediate state between first state 100A and second state 100B. In operation, therefore, the fluidic actuator based suction element when placed against a region of a user provides a suction effect as it transitions from the first state 100A to second state 100B and a pressure effect as it transitions from second state 100B to first state 100A. Accordingly, as the pressure within the chambers within the elastic body 130 is varied the user experiences varying suction/pressure. For example, the region of user can be a user's clitoral area, nipples, penis or testicles. The size and shape of the shaped resilient frame 110 can be adjusted within different sexual pleasure devices according to the intended functionality, product type, and user preference. Optionally, multiple fluidic actuators can be disposed on the same resilient frame.

Fluidic Actuator based Pressure: Now referring to FIG. 2 there is depicted a fluidic actuator based pressure element according to an embodiment of the invention depicted between a first withdrawn state 200A and second extended state 200B. As depicted in first withdrawn state 200A a resilient base element 210 and first shell layer 240 encase a filler 230 wherein a gap within the filler 230 has disposed within it reduced fluidic chamber 220 and pressure element 260. Disposed atop the first shell layer 240 is elastic layer 250. Accordingly, as depicted in first withdrawn state 200A the dimensions of the fluidic chamber 220 are such that the top of the pressure element 260 is flush or below that of the top of the first shell layer 240. In second extended state 200B the fluidic chamber is expanded fluidic chamber 225 such that the top of the pressure element 260 is above the top of the first shell layer 240 distorting the elastic layer 250 to deformed form 255.

Depending upon the overall design of the fluidic actuation system coupled to the chambers within the fluidic actuator based pressure element the power off state can be either first withdrawn state 200A, second extended state 200B, or an intermediate state between first withdrawn state 200A and second extended state 200B. In operation, therefore the fluidic actuator based pressure element when placed against a region of a user provides a pressure against the user as it transitions from the first withdrawn state 200A to second extended state 200B. Accordingly, as the pressure within the fluidic chamber varies the pressure element 260 provides a varying pressure and/or tissue displacement on the user. It would be evident that the size and shape of the pressure element 260 as well as the travel range determined by the fluidic chamber can be adjusted in different sexual pleasure devices according to the intended functionality, product type, and user preference. It would be evident to one skilled in the art that the area of extension of the fluidic actuator relative to the surface area of the fluidic actuator can provide some effective amplification of the force applied to the user's body relative to the pressure of the fluid within the fluidic actuator.

Additionally, it would be evident that multiple pressure elements as well as pressure elements on opposite sides of a sexual pleasure device can be controlled via a single fluidic chamber. Optionally, first and second shell layers 240 and 250 as depicted within first withdrawn state 200A are single piece-part where the region associated with the pressure element 260 is thinned relative to the remainder of the layers. Likewise resilient base element 210 and filler 230 can be formed from the same single piece-part wherein a recess is formed within to accept the fluidic chamber and pressure element 260. Optionally, the elastic layer 250 may engage directly a balloon style fluidic actuator without the additional elements 250 or alternatively the elastic layer 250 may be a thinned region of an outer body of the sexual pleasure device which is otherwise presenting a "hard" surface to the user but these thinned regions provide for the stimulation through pressure.

Figure 3:
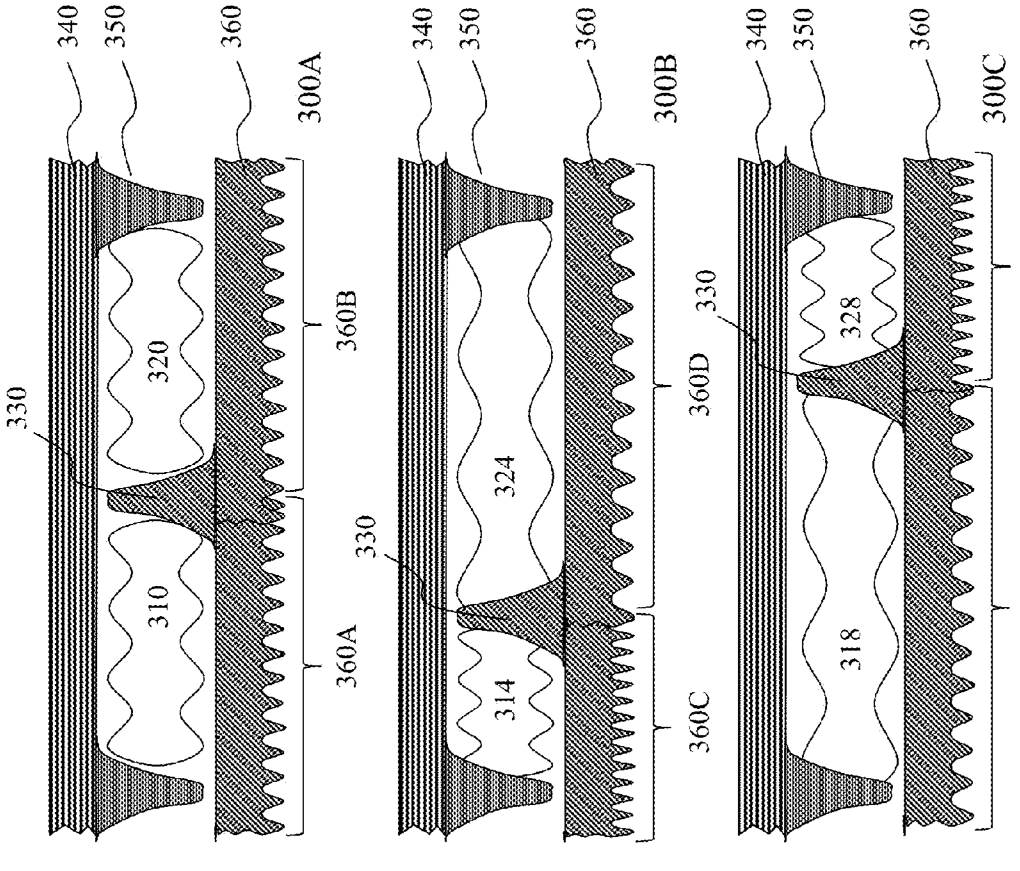
FIG. 3 depicts a fluidic actuator based surface friction element according to an embodiment of the invention.

Fluidic Actuator based Friction: Referring to FIG. 3 there is depicted a fluidic actuator based surface friction element according to an embodiment of the invention in first to third states 300A through 300C respectively. As depicted in FIG. 3, the fluidic actuator based surface friction element comprises an upper layer 340 upon which are disposed first projections 350 defining a recess therebetween on the lower surface of the upper layer 340. Disposed below and spaced apart from upper layer 340 is flexible layer 360, which has on its upper surface a second projection 330, which extends into the recess formed between a pair of first projections 350 and is positioned between the pair of first projections 350. Disposed to the left of second projection 330 between flexible layer 360 and upper layer 340 is first fluidic chamber 310 whilst to the right of second projection 330 between the flexible layer 360 and upper layer 340 is second fluidic chamber 320. As depicted in first state 300A the first and second fluidic chambers 310 and 320, respectively, have approximately the same dimensions such that the flexible layer 360 is defined as having first left and right regions 360A and 360B respectively which are similar as evident from the lower contour profile of the textured surface of the flexible layer 360.

Now referring to second state 300B the right fluidic chamber has expanded to become expanded right fluidic chamber 324 whilst the left fluidic chamber has reduced to become reduced left fluidic chamber 314. Accordingly, the resulting motion of the second projection 330 results in the flexible layer now being defined by second left and right regions 360C and 360D respectively wherein the textured surface now differs to the left and right. Now referring to third state 300C the left fluidic chamber has expanded to become expanded left fluidic chamber 318 whilst the right fluidic chamber has reduced to become reduced right fluidic chamber 328. Accordingly, the resulting motion of the second projection 330 results in the flexible layer now being defined by third left and right regions 360E and 360F respectively wherein the textured surface now differs to the left and right. Accordingly, based upon the overall design of the fluidic actuation system coupled to the left and right fluidic chambers within the sexual pleasure device of which the fluidic actuator based surface friction element forms part then fluid can be pumped into and out of the first and second fluidic chambers 310 and 320 in a predetermined manner such that the lower surface of the elastic layer 360 moves back and forth wherein when placed against the user's skin the motion in combination with the surface texture of the elastic layer 360 causes friction thereby imparting sensations according to the region of the user the elastic layer 360 contacts. It would be evident that first projections 350 and upper layer 340 can be formed from the same single piece-part as can second projection 330 and elastic layer 360. In contrast to mechanical coupled systems it would be evident that fluidic systems allow for user manual manipulation of the sexual pleasure device shape to be easily accomplished/accommodated without significant additional complexity by provisioning flexible or semi-flexible tubing in such regions rather than complex mechanical joints etc.

Figure 4:
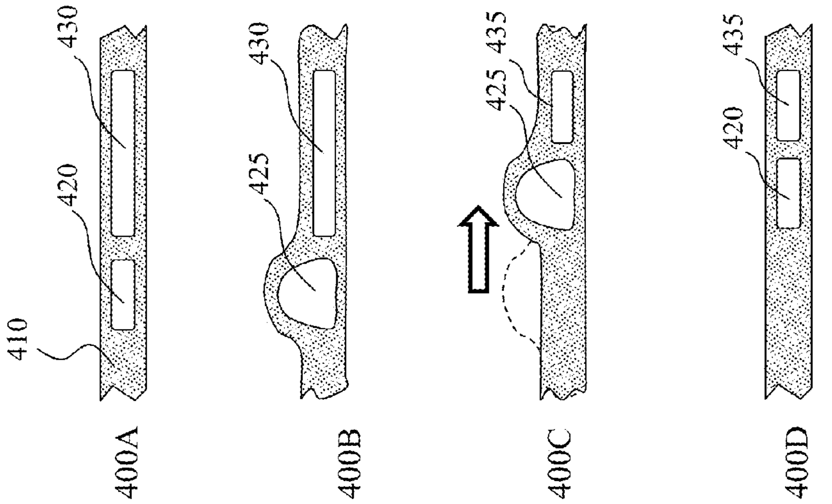
FIG. 4 depicts a fluidic actuator based translational pressure element according to an embodiment of the invention.

Fluidic Actuator based Translational Pressure: Now referring to FIG. 4 there is depicted a fluidic actuator based translational pressure element according to an embodiment of the invention in its first to fourth states 400A through 400D, respectively. As depicted a layer 410 has disposed within two fluidic chambers, which are "expanded" or "contracted" according to a predetermined sequence. Accordingly, in first state 400A these are first contracted fluidic chamber 420 and second expanded fluidic chamber 430 whilst in second state 400B these are first expanded fluidic chamber 425 and second expanded fluidic chamber 430. Third state 400C now has first expanded fluidic chamber 425 and second contracted fluidic chamber 435 whilst fourth state 400D has first and second fluidic chambers contracted 420 and 435 respectively. Based upon the design of the fluidic chamber(s) the expansion may be in one or more directions according to the design of the fluidic chamber(s)

Accordingly, based on the overall design of the fluidic actuation system coupled to the first and second fluidic chambers within the sexual pleasure device of which the fluidic actuator based surface translational element forms part then fluid can be pumped into and out of the first and second fluidic chambers in a predetermined sequence to cycle through first to fourth states 400A through 400D in order and subsequently repeating wherein the result is that the first fluidic chamber expanded 425 is moved against in a cyclic manner. It would be evident to one skilled in the art that combining an elastic film with thickness variations and anisotropic reinforcing elements can provide for a single piece part construction. It would also be evident that multiple fluidic actuators based translational pressure elements can be combined within a sexual pleasure device.

Figure 5B:
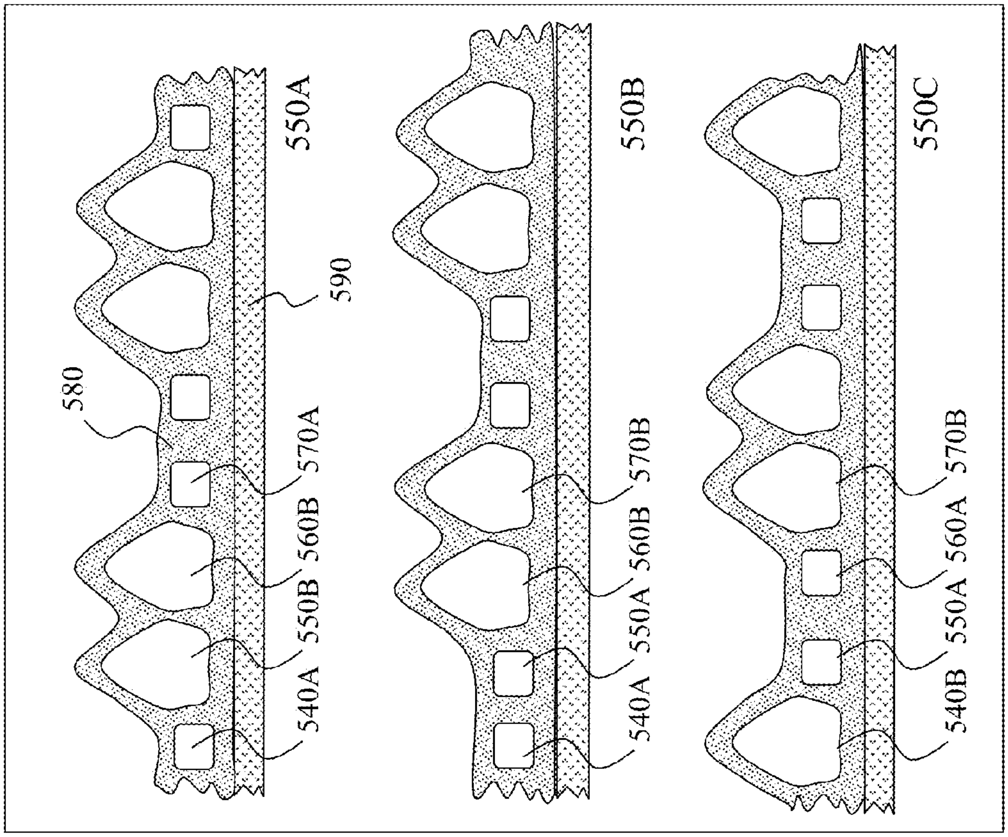
FIGS. 5A and 5B depict fluidic actuator based evolving location pressure elements according to embodiments of the invention.
Figure 5A:
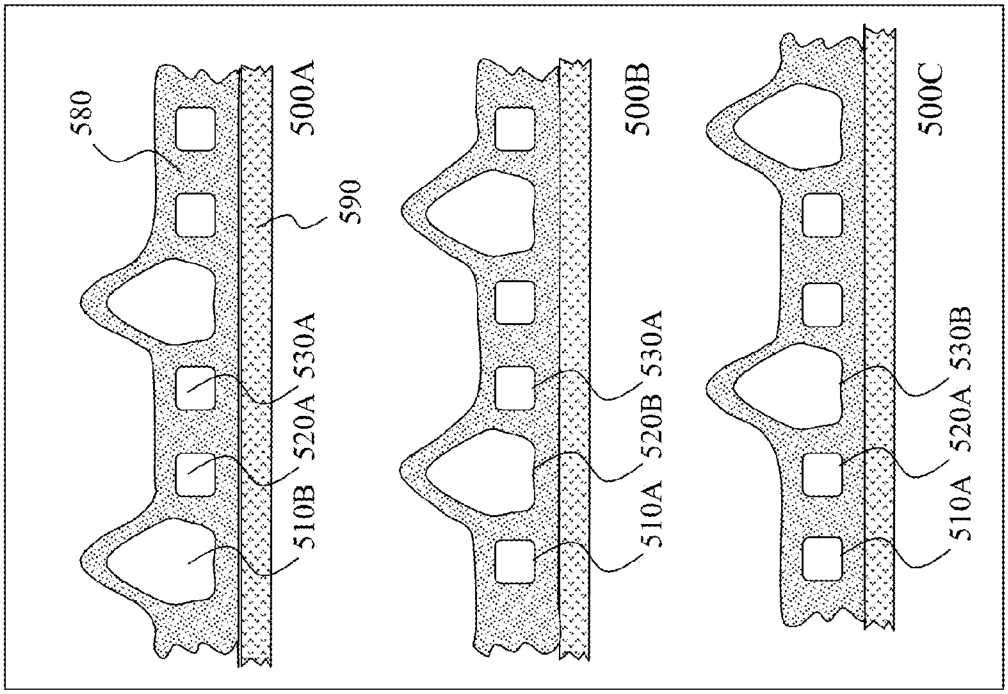

Fluidic Actuator based Evolving Location Pressure: Referring to FIGS. 5A and 5B there are depicted first and second fluidic actuator based evolving location pressure elements according to embodiments of the invention. First fluidic actuator based evolving location pressure element is depicted in its first to third states 500A through 500C, respectively, in FIG. 5A. Second fluidic actuator based evolving location pressure element is depicted in its fourth to sixth states 550A through 550C, respectively, in FIG. 5B. Within each of first and second fluidic actuator based evolving location pressure elements a plurality of fluidic chambers are disposed within an elastic layer 580 disposed above a resilient layer 590 in a repeating pattern of 3 and 4 elements. Accordingly, inflation of the fluidic chambers results in expansion locally due to the thinning of the elastic layer 580 in conjunction with the resilient layer 590. Accordingly, as depicted in FIG. 5A with first to third states 500A through 500C the first to third fluidic chambers 510 through 530 respectively are cycled between compressed state "A" and expanded state "B" such that overall the user feels a pressure moving along the length of the sexual pleasure device. While only two repeats of the sequence of first to third fluidic chambers 510 through 530, respectively, are depicted it would be evident to one skilled in the art that one, two, three or more sets can be employed in sequence as well as in multiple positions on the sexual pleasure device.

Likewise referring to FIG. 5B with fourth to sixth states 550A through 550C respectively then fourth to sixth fluidic chambers 540 through 570 respectively are cycled between compressed state "A" and expanded state "B" such that overall the user feels a pressure moving along the length of the sexual pleasure device. While only two repeats of the sequence of fourth to sixth fluidic chambers 540 through 570, respectively, are depicted it would be evident to one skilled in the art that one, two, three or more sets can be employed in sequence as well as in multiple positions on the sexual pleasure device.

Figure 6A:
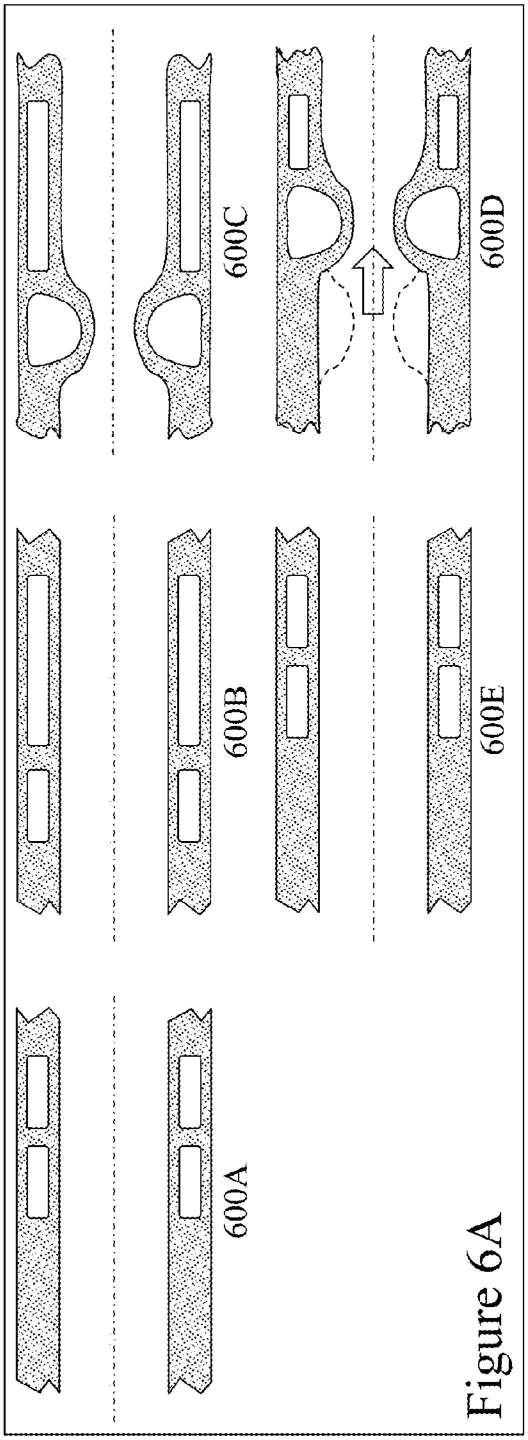
FIGS. 6A and 6B depict fluidic actuator based translational pressure structures for male and female users according to embodiments of the invention.
Figure 6B:
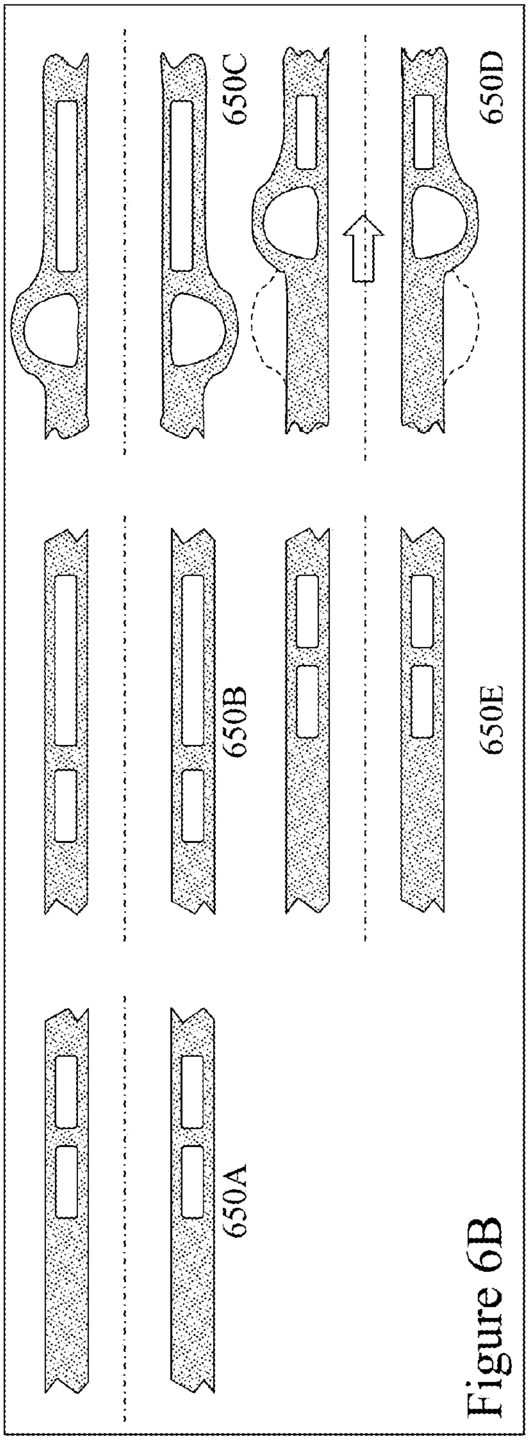

Fluidic Actuator based Translation Pressure for Male and Female Sexual pleasure devices: Referring to FIGS. 6A and 6B there are depicted fluidic actuator based translational pressure structures for male and female sexual pleasure devices, respectively, according to embodiments of the invention exploiting fluidic actuator based translational pressure elements similar to those described above in respect of FIG. 4. In FIG. 6A a pair of fluidic actuator based translational pressure elements are depicted facing towards one another, such as can be employed within a male sexual pleasure device, such that the movement and pressure of the fluidic actuator based translational pressure elements is applied to the user's penis when inserted along the axis of the sexual pleasure device. In FIG. 6B the pair of fluidic actuator based translational pressure elements are depicted on the outside of the sexual pleasure device such as can be employed wherein the movement and pressure of the fluidic actuator based translational pressure elements is to be applied to the user's body when the sexual pleasure device is inserted or pushed against them (e.g., when the pressure is to be applied to the user's vaginal walls following insertion of the sexual pleasure device or a portion of the sexual pleasure device into the user's vagina).

Figure 7A:
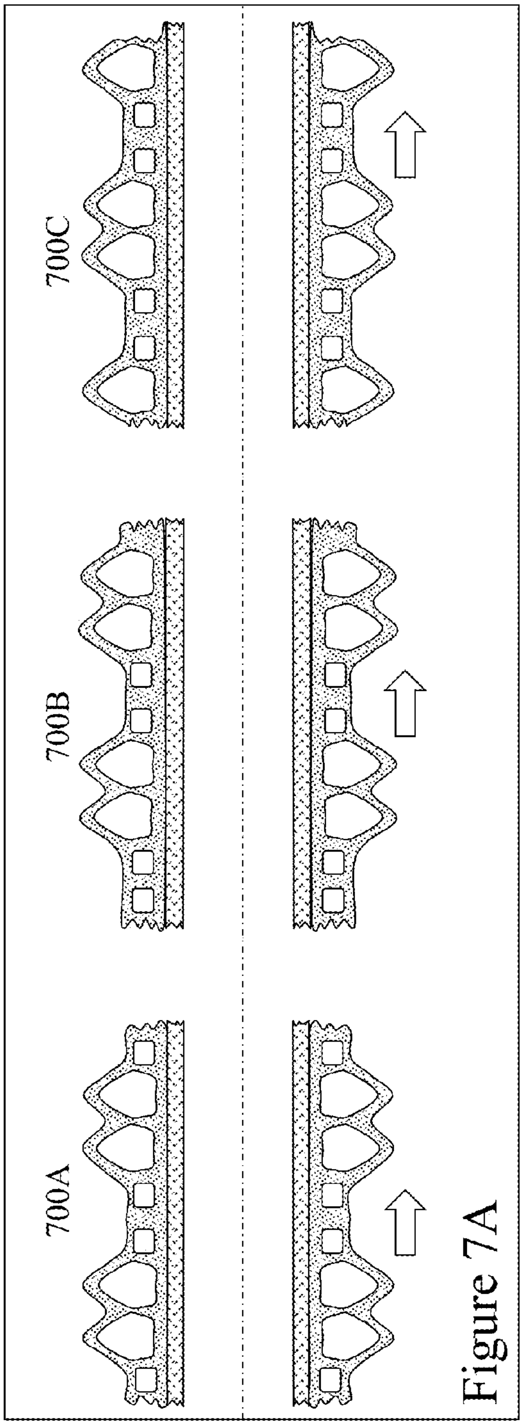
FIGS. 7A and 7B depict fluidic actuator based evolving location pressure structures for male and female users according to embodiments of the invention.
Figure 7B:
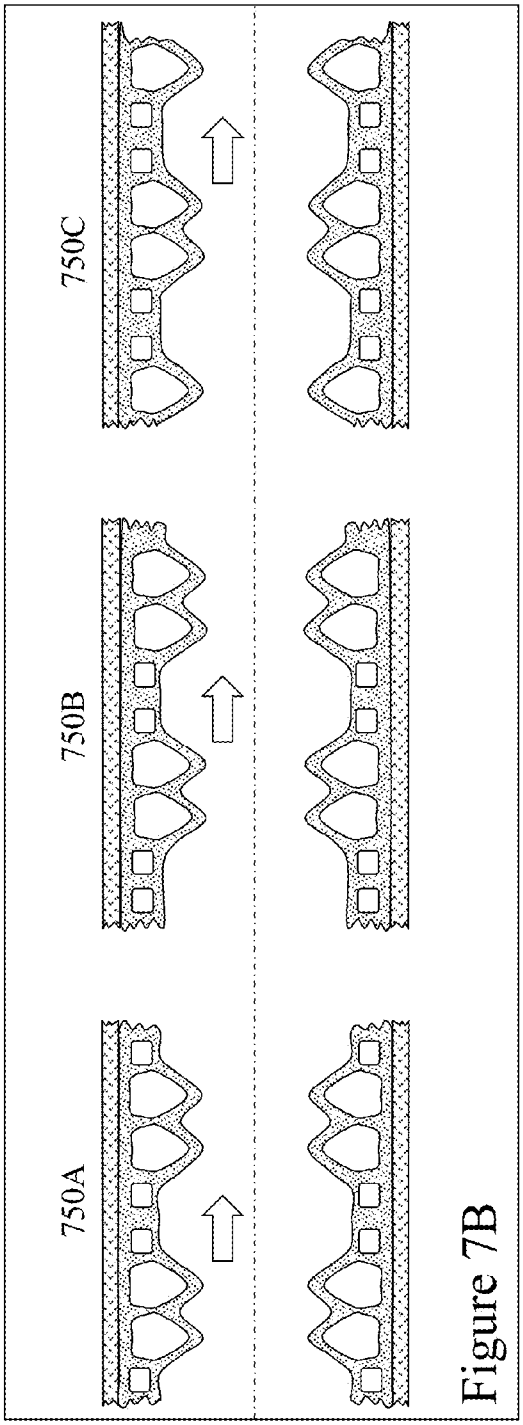

FIGS. 7A and 7B depict fluidic actuator based evolving location pressure structures for male and female sexual pleasure devices according to embodiments of the invention in similar manner to those depicted in FIGS. 6A and 6B but wherein the fluidic actuator based translational pressure elements according to an embodiment of the invention as described above in respect of FIG. 4 are replaced with fluidic actuator based translational pressure elements according to an embodiment of the invention as described above in respect of FIG. 5. In each instance of embodiments of the invention in FIGS. 6A through 7B a controller within the overall fluidic control system interfaced to the fluidic actuator based translational pressure elements can provide for user or pre-programmed control of the characteristics of the pressure such as, for example, frequency, pressure, and/or duration. Optionally, different fluidic actuator based translational pressure elements within different regions of the sexual pleasure device can be controlled separately with respect to these characteristics. The physical effects of fluidic actuator systems such as described supra in respect of FIGS. 5 through 7B can be likened to fluidic equivalents of mechanical inchworm drives.

Figure 8:
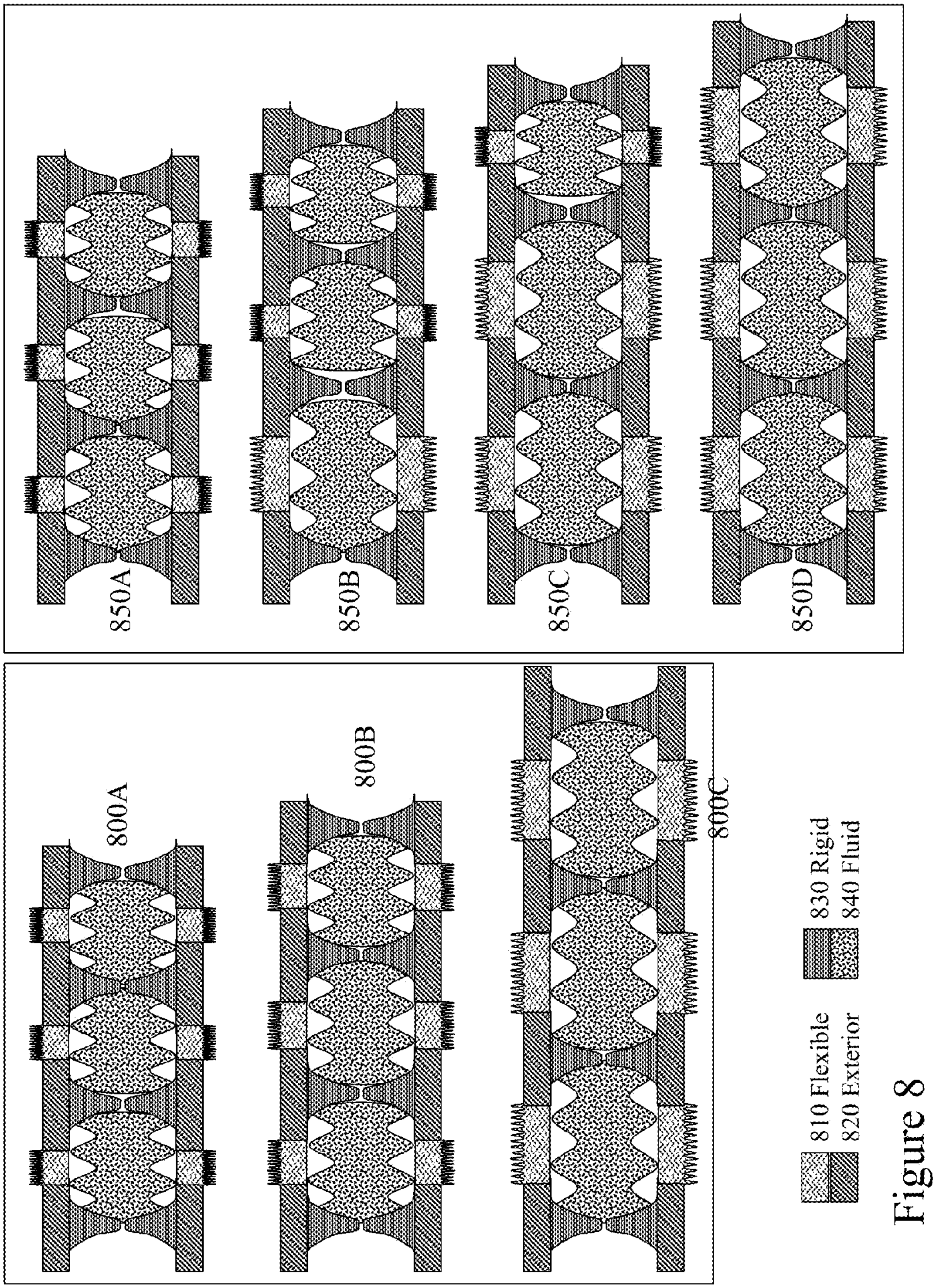
FIG. 8 depicts linear expansion fluidic actuator based elements according to embodiments of the invention.

Fluidic Actuator based Linear Expansion: Now referring to FIG. 8 there are depicted first and second linear expansion fluidic actuator based elements according to embodiments of the invention in first and second state sequences 800A to 800C and 850A to 850D, respectively. In each instance a portion of the sexual pleasure device comprises an outer body comprising exterior regions 820 with flexible sections 810 disposed between exterior regions 820. Disposed internally in association with each exterior region 820 are rigid projections 830. In between sequential rigid projections 830 there are fluidic chambers 840, which can be increased/decreased in dimension under control of an overall fluidic control system by adding/removing fluid from one or more fluidic chambers 840.

As depicted in respect of first linear expansion fluidic actuator based elements according to an embodiment of the invention in first state sequence 800A to 800C respectively all fluidic chambers 840 are expanded simultaneously. In contrast the second linear expansion fluidic actuator based element according to an embodiment of the invention in second state sequence 850A to 850D respectively is operated wherein each fluidic chamber 840 is expanded individually in sequence. It would be evident that with respect to first linear expansion fluidic actuator based element that the multiple fluidic chambers 840 can be connected in parallel to a fluid source as they operate in concert whilst in second linear expansion fluidic actuator based element the multiple fluidic chambers 840 can be connected individually to a fluid source via valves controlling the flow of fluid to each fluidic chamber 840 independently or that they can be connected in series with fluid regulators between each fluidic chamber 840 that limit flow to a subsequent fluidic chamber 840 until a predetermined pressure is reached. Where the multiple fluidic chambers 840 are connected individually to a fluid source via valves controlling the flow of fluid to each fluidic chamber 840 then it would be evident that in addition to a basic extension/retraction that more complex motions are possible whereby predetermined portions of the sexual pleasure device expand as others contract and vice-versa.

Figures 9A, 9B:
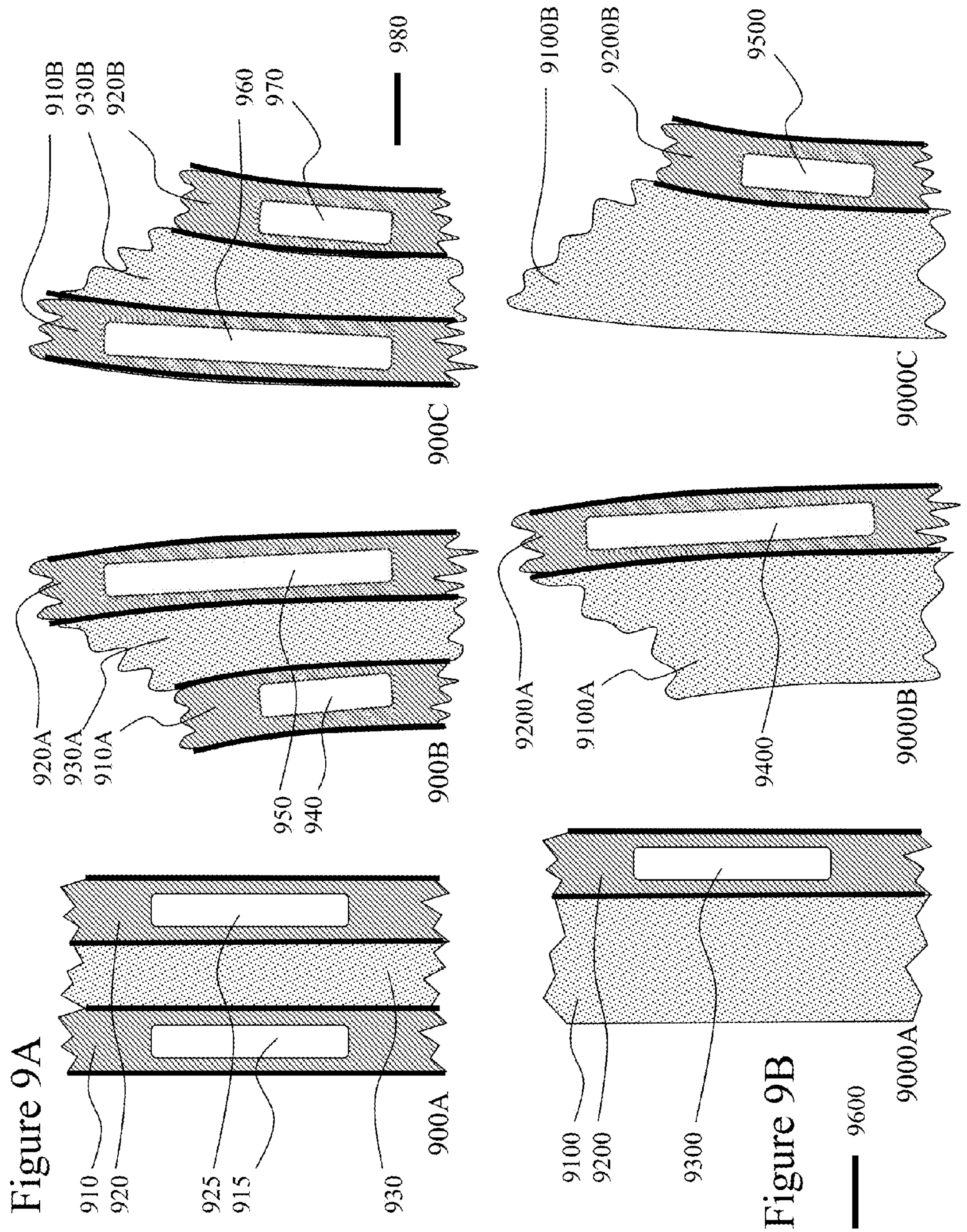
FIGS. 9A and 9B depict flexural fluidic actuator based elements according to embodiments of the invention.

Fluidic Actuator based Flexation: Referring to FIGS. 9A and 9B there are depicted portions of a sexual pleasure device comprising flexural fluidic actuator based elements according to embodiments of the invention. In FIG. 9A in first to third states 900A through 900C, respectively, a dual chamber flexural fluidic actuator is depicted. As depicted, the sexual pleasure device in first state 900A comprises core 930, which has disposed on either side thereof first and second elastic elements 910 and 920, respectively. First and second elastic elements 910 and 920 contain first and second fluidic chambers 915 and 925, respectively. Also disposed within the sexual pleasure device, on either side of the different elements are resilient walls or elements 980 that surround the fluidic chambers and limit lateral expansion of the fluidic chambers without limiting expansion in the plane of resilient elements 980. As a result, as a fluidic chamber expands, the respective elastic element lengthens but does not widen.

As first and second fluidic chambers 915 and 925 are comparable in size the elastic stresses are balanced and the sexual pleasure device orientated linearly. In second state 900B the first fluidic chamber 915 has been reduced in size to third reduced fluidic chamber 940 and the second fluidic chamber 925 increased to fourth expanded fluidic chamber 950 such that the resulting action upon the sexual pleasure device is to bend the sexual pleasure device to the left resulting in left bent core 930A and left bent sides 910A and 920A respectively. In third state 900C the first fluidic chamber 915 has been increased in size to fifth expanded fluidic chamber 960 and the second fluidic chamber 925 reduced to sixth reduced fluidic chamber 970 such that the resulting action upon the sexual pleasure device is to bend the sexual pleasure device to the right resulting in right bent core 930B and right bent sides 910B and 920B respectively. Optionally, the resilient elements 980 are omitted. In particular, if core 930 is sufficiently rigid and/or if the fluid chambers are configured to only permit axial, or approximately axial, expansion/retraction, then resilient elements 980 may not be necessary.

Figure 10:
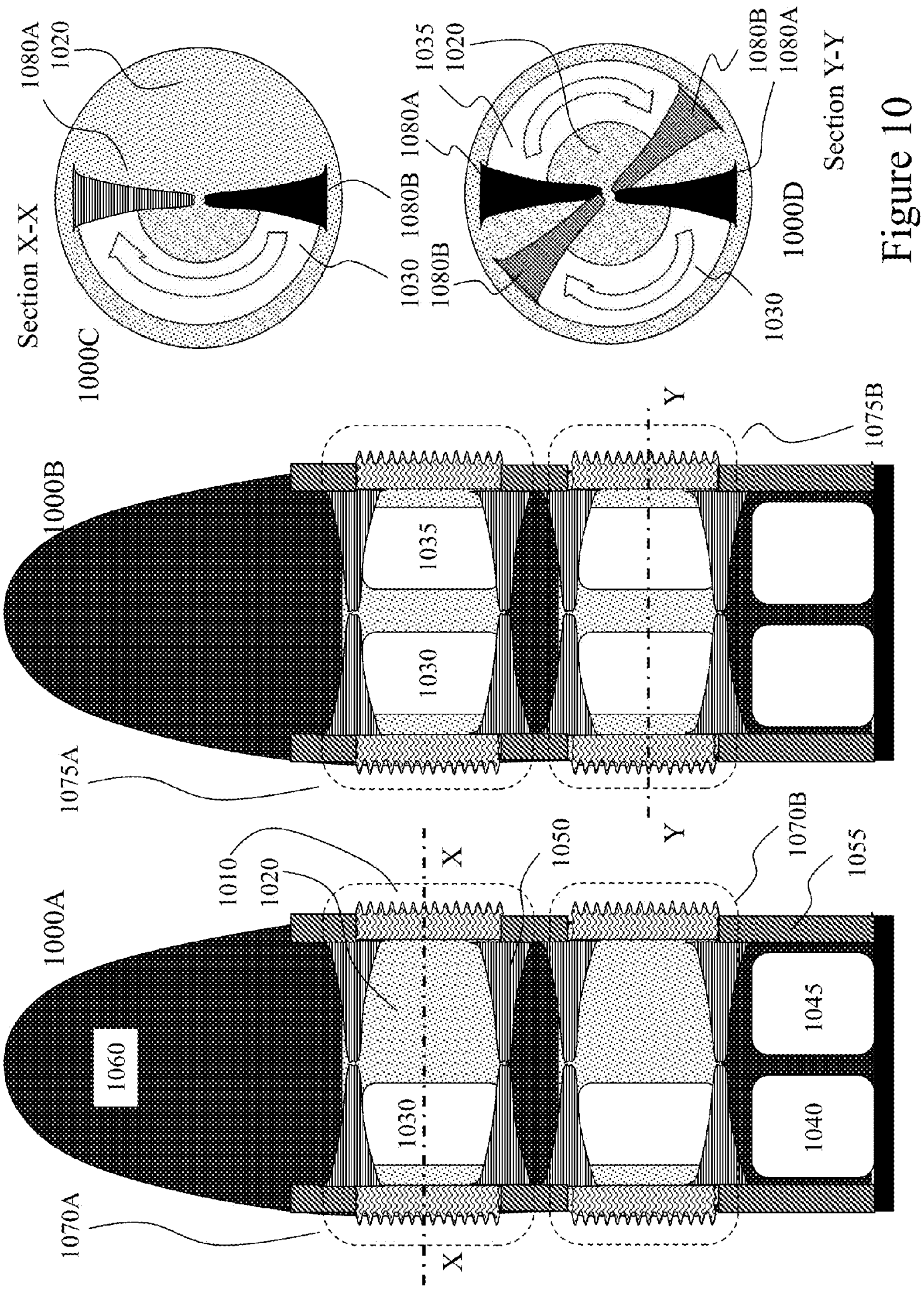
FIG. 10 depicts a device providing rotational motion using fluidic actuator based elements according to an embodiment of the invention.

Fluidic Actuator based Rotation Motion: Now referring to FIG. 10 there are depicted first and second sexual pleasure devices 1000A and 1000B, respectively, which provide rotational motion using fluidic actuator based elements according to an embodiment of the invention. As depicted, first sexual pleasure device 1000A comprises a body 1060 within which is disposed first and second fluidic rotational elements 1070A and 1070B, wherein each fluidic element is disposed between upper and lower end projections 1050 coupled to outer body element 1055. Each of the first and second fluidic rotational elements 1070A and 1070B comprises an outer ring 1010 and inner filler 1020 within which is disposed a fluidic chamber 1030. Disposed at the bottom of the body 1060 are first and second fluidic chambers 1040 and 1045, respectively, which house the fluidic control circuit. The fluidic control circuit comprises, for example, pump, valves, and reservoir, and electrical control circuit. The electrical control circuit provides, for example, on/off selector, power, power management, and processor to control the fluidic control circuit.

Second sexual pleasure device 1000B has essentially identical construction except that in addition to fluidic chamber 1030 a second fluidic chamber 1035 is provided. The result being third and fourth fluidic rotational elements 1075A and 1075B. Now referring to first and second cross-sections 1000C and 1000D, which represent Section X-X through first sexual pleasure device 1000A and Section Y-Y through second sexual pleasure device 1000B, respectively. As evident in first cross-section 1000C the fluidic chamber 1030 extends between movable projection 1080A and restrained projection 1080B in extended state. In reduced state fluidic chamber 1030 is reduced back towards the restrained projection 1080B such that movable projection 1080A has rotated back due to the elasticity of the inner filler 1020. Movable projection 1080A is attached to outer ring 1010 so that expansion/contraction of fluidic chamber 1030 translates into motion of movable projection 1080A and hence outer ring 1010.

Second cross-section 1000D depicts Section Y-Y wherein fluidic chamber 1030 and second fluidic chamber 1035 each engage at one end restrained projections 1080A and movable projections 1080B. Accordingly, expansion/contraction of fluidic chamber 1030 and second fluidic chamber 1035 translates into motion of movable projection 1080A and hence outer ring 1030. Accordingly, each of first and second sexual pleasure devices 1000A and 1000B provides for rotational motion of portions of the body of a sexual pleasure device under control of the electrical control circuit, which is executing either a predetermined program or sequence established by the user.

Figure 11:
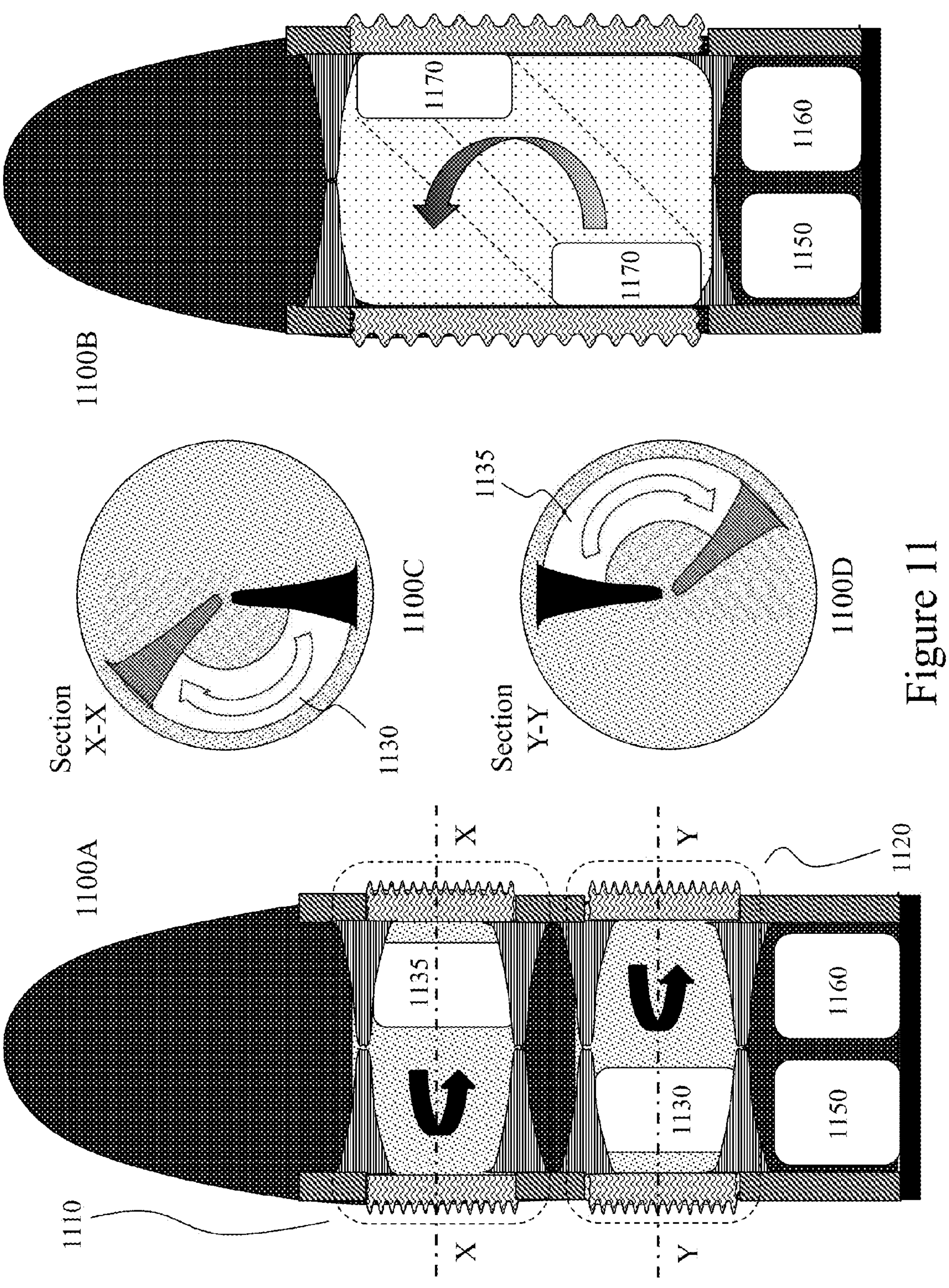
FIG. 11 depicts devices with twisting motion using fluidic actuator based elements according to embodiments of the invention.

Fluidic Actuator based Twisting Motion: Now referring to FIG. 11 there are depicted first and second sexual pleasure devices 1100A and 1100B, respectively, providing twisting motion using fluidic actuator based elements according to embodiments of the invention. First sexual pleasure device 1100A has a similar construction to that of first sexual pleasure device 1000A in FIG. 10 with first and second fluidic rotational elements 1110 and 1120 comprising first and second fluidic chambers 1135 and 1130, respectively. However, as evident from first and second cross-sections 1100C and 1100D first and second fluidic rotational elements 1110 and 1120 are offset from one another and unlike first sexual pleasure device 1000A in FIG. 10 first fluidic rotational element 1110 is coupled at its base to the top of second fluidic rotational element 1120. Accordingly, simultaneous expansion of first and second fluidic chambers 1135 and 1130, respectively, within first and second fluidic rotational elements 1110 and 1120 results in second fluidic rotational element 1120 rotating by an angle of $\alpha\Delta$, and the first fluidic rotational element 1110 rotating by an angle of $2\alpha$ relative to its position when first and second fluidic chambers 1135 and 1130 are collapsed. Accordingly, this motion mimics a twisting action of the sexual pleasure device. It would be evident that additional fluidic rotational elements can either be used to increase the overall rotation induced or provide for multiple twisting elements within the sexual pleasure device. Optionally, an electronically controlled link can be provided between vertically stacked elements such that they operate in either rotational mode, twisting mode, or multiple twisting mode according to the settings of the links. Such links can be, for example, electromagnetically activated pins engaging holes in adjacent elements.

Fluidic Actuator Configuration: Now referring to FIG. 12 there are depicted parallel and serial element actuation schematics 1200A and 1200B, respectively, exploiting fluidic elements in conjunction with fluidic pump, reservoir and valves according to embodiments of the invention. Within parallel actuation schematic 1200A first to third fluidic actuators 1230A through 1230C are depicted coupled to first pump 1220A on one side via first to third inlet valves 1240A through 1240C, respectively, and to second pump 1220B on the other side via first to third outlet valves 1250A through 1250C, respectively. First and second pumps 1220A and 1220B being coupled on their other end to reservoir 1210 such that, for example, first pump 1220A pumps fluid towards first to third fluidic actuators 1230A through 1230C respectively and second pump 1220B pumps fluid away from them to the reservoir. Accordingly, each of first to third fluidic actuators 1230A through 1230C, respectively, can be pumped with fluid by opening their respective inlet valve, thereby increasing internal pressure and triggering the motion according to their design such as described above in respect of FIGS. 1 through 11 or other means as FIGS. 1 to 11 are merely exemplary embodiments of the invention. Each of first to third fluidic actuators 1230A through 1230C, respectively, can be held at increased pressure until their respective outlet valve is opened and second pump 1220B removes fluid from the actuator. Accordingly, first to third fluidic actuators 1230A through 1230C can be individually controlled in pressure profile through the valves and pumps.

In contrast serial actuation schematic 1200B first to third fluidic actuators 1280A through 1280C are depicted coupled to first pump 1270A on one side and to second pump 1270B on the other side. First and second pumps 1270A and 1270B being coupled on their other end to reservoir 1260 such that, for example, first pump 1270A pumps fluid towards first to third fluidic actuators 1280A through 1280C, respectively, and second pump 1270B pumps fluid away from them to the reservoir. However, in serial actuation schematic 1200B first pump 1270A is connected only to first reservoir 1280A wherein operation of first pump 1270A will increase pressure within first reservoir 1280A if first valve 1290A is closed, second reservoir 1280B if first valve 1290A is open and second valve 1290B closed, or third reservoir 1280C if first and second valves 1290A and 1290B, respectively, are open and third valve 1290C closed. Accordingly, by control of first to third valves 1290A through 1290C, respectively, the first to third fluidic actuators 1280A through 1280C, respectively, can be pressurized although some sequences of actuator pressurization and intermediate pressurization available in the parallel actuation schematic 1200A are not available although these limitations are counter-balanced by reduced complexity in that fewer valves are required. It would be apparent to one skilled in the art that parallel and serial element actuation schematics 1200A and 1200B respectively exploiting fluidic elements in conjunction with fluidic pump, reservoir and valves according to embodiments of the invention can be employed together within the same sexual pleasure device either through the use of multiple pump or single pump configurations. In a single pump configuration an additional valve prior to first actuator 1280A can be provided to isolate the actuator from the pump when the pump is driving other fluidic actuated elements.

Figure 12:
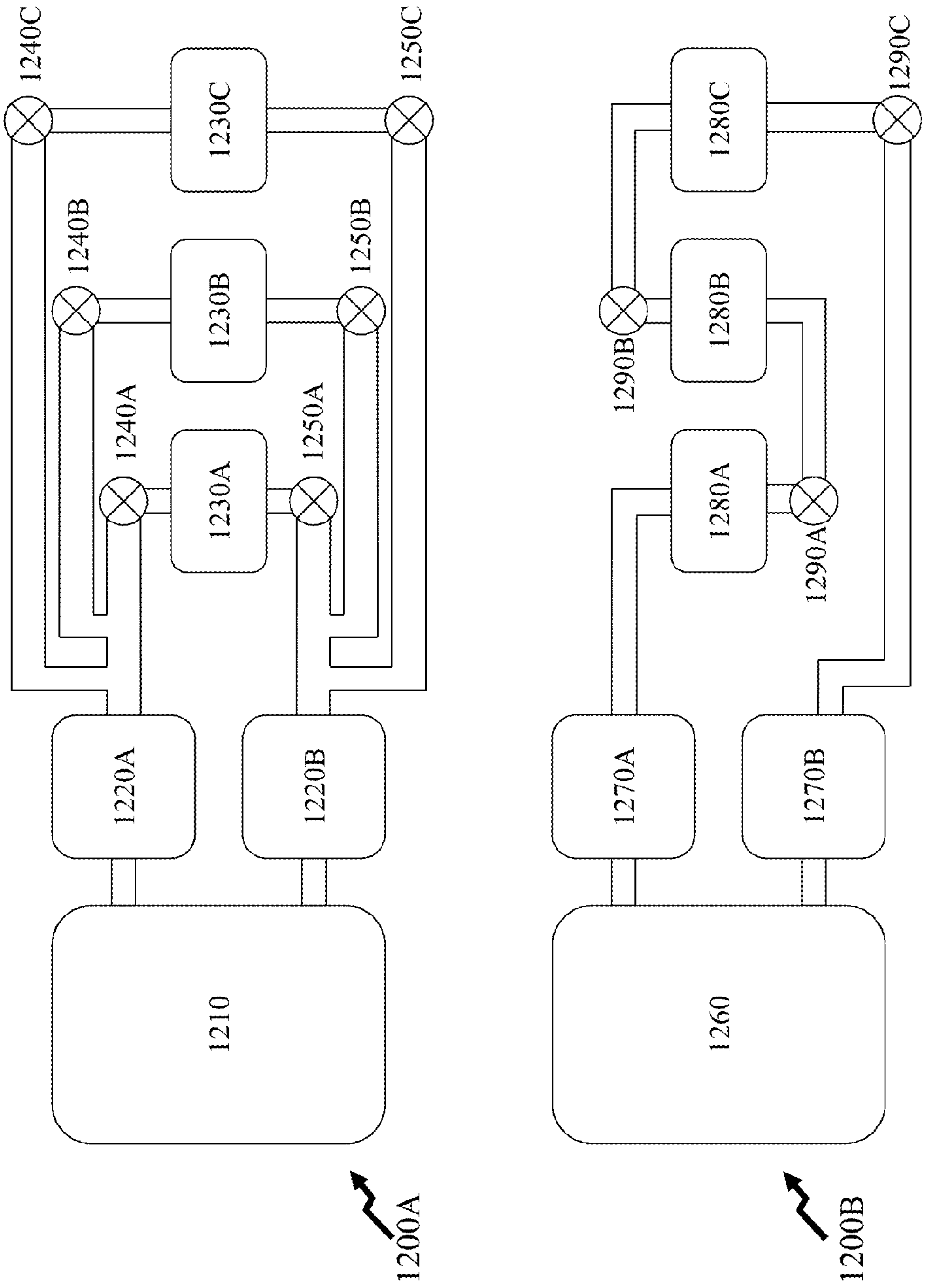
FIG. 12 depicts parallel and serial element actuation exploiting fluidic elements in conjunction with fluidic pump, reservoir and valves according to embodiments of the invention.
Figure 13:
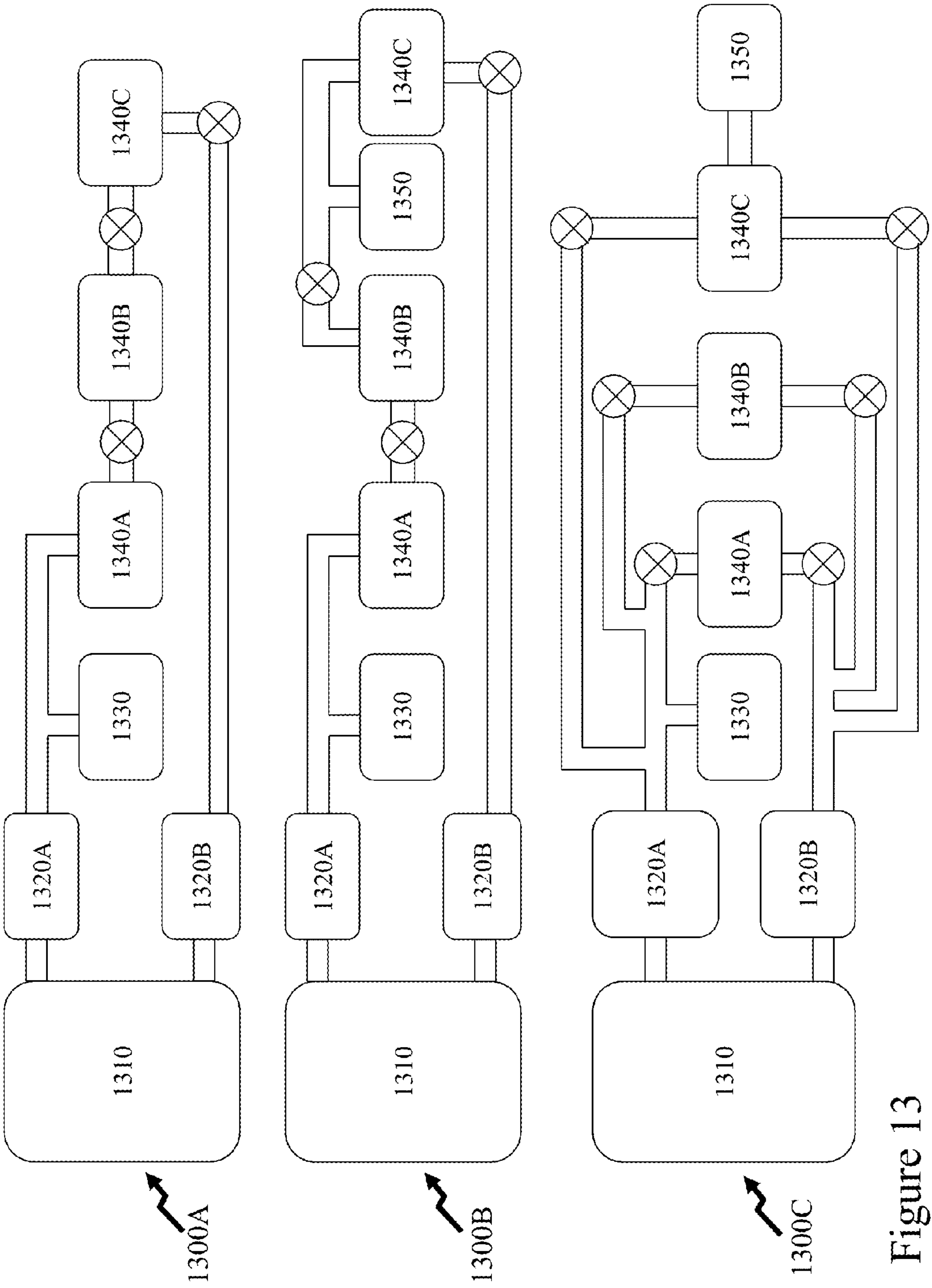
FIG. 13 depicts serial element constructions exploiting secondary fluidic pumps and fluidic elements in conjunction with primary fluidic pump, reservoir and valves according to embodiments of the invention.

Now referring to FIG. 13 there are depicted first and second serially activated schematics 1300A through 1300B respectively wherein secondary fluidic pumps and fluidic elements are employed in conjunction with first and second primary fluidic pumps 1320A and 1320B, reservoir 1310 and valves according to embodiments of the invention. In first serially activated schematic 1300A first to third fluidic actuators 1340A through 1340C are disposed in similar configuration as serial actuation schematic 1200B in FIG. 12. However, a secondary fluidic pump 1330 is disposed between the first primary fluidic pump 1320A and first fluidic actuator 1340A. Accordingly, the secondary fluidic pump 1330 can provide additional fluidic motion above and beyond that provided through the pressurization of fluidic actuators by first primary fluidic pump 1320A. Such additional fluidic motion can be, for example, the application of a periodic pulse to a linear or sinusoidal pressurization wherein the periodic pulse can be at a higher frequency than the pressurization. For example, the first primary fluidic pump 1320A can be programmed to drive sequentially first to third fluidic actuators 1340A through 1340C to extend the sexual pleasure device length over a period of 1 second before the second primary pump 1320B sequentially withdraws fluid over a similar period of 1 second such that the sexual pleasure device has a linear expansion frequency of 0.5 Hz. However, the secondary fluidic pump 1330 provides a continuous 10 Hz sinusoidal pressure atop this overall ramp and reduction thereby acting as a vibration overlap to a piston motion of the sexual pleasure device. According to embodiments of the invention the primary pump can provide operation to a few Hz or tens of Hz, whereas secondary pump can provide operation from similar ranges as primary pump to hundreds of Hz and tens of kHz.

Second serially activated schematic 1300B depicts a variant wherein first and second secondary fluidic pumps 1330 and 1350 are employed within the fluidic circuit before the first and third fluidic actuators 1340A and 1340C, respectively such that each of the first and second secondary fluidic pumps 1330 and 1350 can apply different overlay pressure signals to the overall pressurization of the sexual pleasure device from first primary pump 1320A. Accordingly, using the example supra, first fluidic pump 1330 can apply a 10 Hz oscillatory signal to the overall 0.5 Hz expansion of the sexual pleasure device but when third fluidic actuator 1340C is engaged with the opening of the valve between it and second fluidic actuator 1340B the second fluidic pump 1350 applies a 2 Hz spike to the third fluidic actuator 1340C wherein the user senses a "kick" or "sharp push" in addition to the linear expansion and vibration. Second fluidic pump 1350 can be activated only when the valve between the second and third fluidic actuators 1340B and 1340C is open and fluid is being pumped by the first primary pump 1320A.

Also depicted in FIG. 13 is parallel activated schematic 1300C wherein a circuit similar that of parallel actuation schematic 1200A in FIG. 12 is shown. However, now a first fluidic pump 1330 is disposed prior to the fluidic flow separating to first and second fluidic actuators 1340A and 1340B respectively and a second fluidic pump 1350 is coupled to the third fluidic actuator 1340C. Accordingly, using the same example as that of second serially activated schematic 1300B supra first primary pump 1320A provides an overall 0.5 Hz pressure increase which drives first and second fluidic actuators 1340A and 1340B when their valves are opened as well as third fluidic actuator 1340C. First fluidic pump 1330 provides a 10 Hz oscillatory signal to the first and second fluidic actuators 1340A and 1340B whilst second fluidic pump 5 Hz oscillatory signal to third fluidic actuator 1340C. As will be evident from discussion of some embodiments of sexual pleasure devices below in respect of FIGS. 14 through 19 first and second fluidic actuators 1340A and 1340B can be associated with a penetrative element of the sexual pleasure device whilst the third fluidic actuator 1340C is associated with a clitoral stimulator element of the sexual pleasure device. Optionally, first and second fluidic pumps, or one of first and second fluidic pumps, are combined serially in order to provide higher pressure within the fluidic system or they are combined serially such that they provide different fluidic pulse profiles that either can provide individually.

Sexual Pleasure Devices

Figure 14:
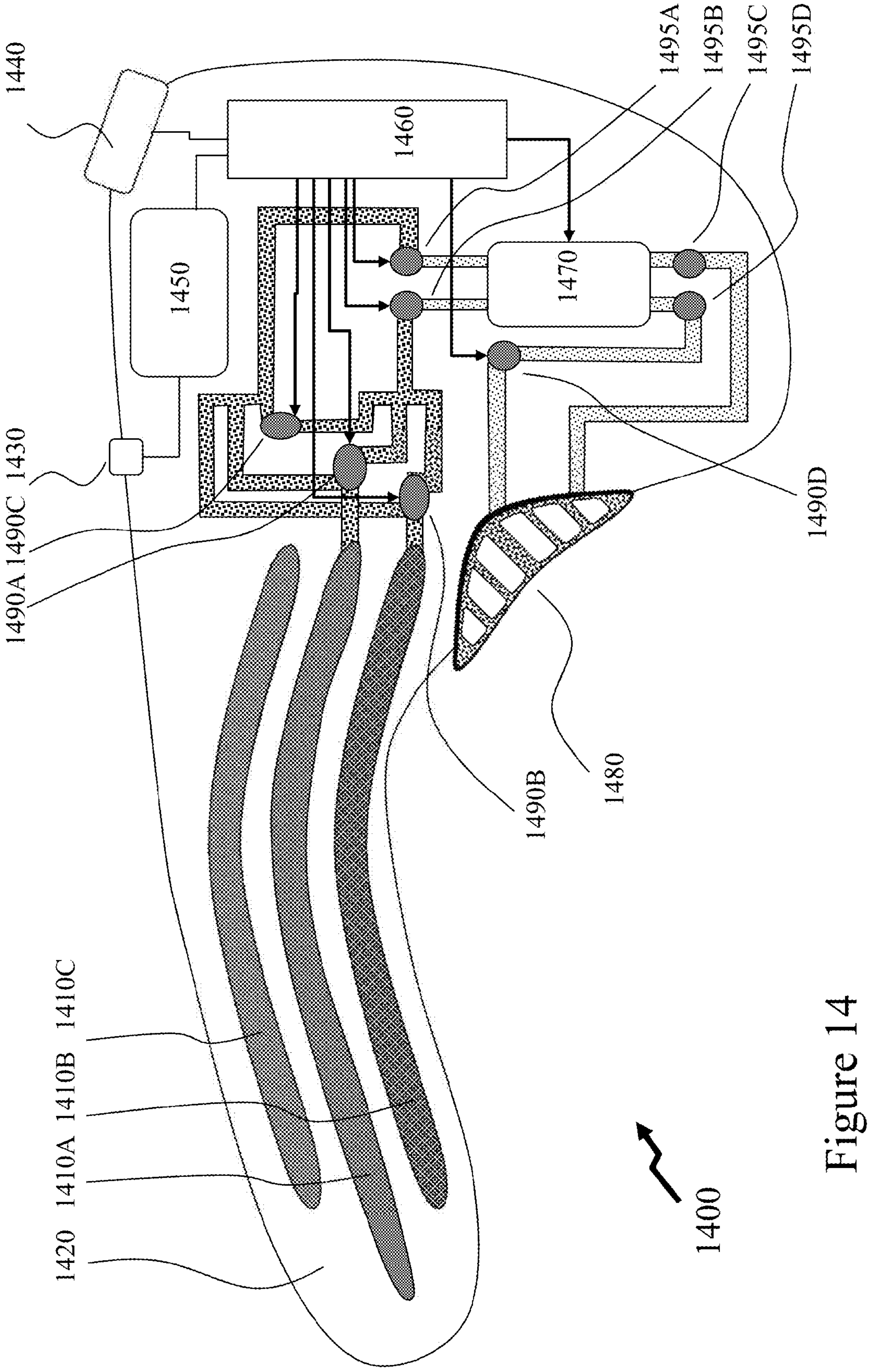
FIG. 14 depicts a device according to an embodiment of the invention exploiting fluidic elements to adjust aspects of the device during use.

Now referring to FIG. 14 there is depicted a sexual pleasure device 1400 according to an embodiment of the invention exploiting fluidic elements to adjust aspects of the sexual pleasure device 1400 during use. As depicted in FIG. 14, sexual pleasure device 1400 comprises extension 1420 within which are disposed first to third fluidic actuators 1410A through 1410C that are coupled to first to third valves 1490A through 1490C, respectively. As depicted one side of each of first to third valves 1490A through 1490C respectively are coupled via pump module 1470 via second capacitor 1495B and on the other side to pump module 1470 via first capacitor 1495A. Also forming part of the sexual pleasure device is fluidic suction element 1480 which is coupled to the pump module 1470 via third and fourth capacitors 1495C and 1495D and fourth valve 1490D. First to fourth valves 1490A through 1490D, respectively, and pump module 1470 are coupled to electronic controller 1460 that provides the necessary control signals to these elements to sequence the fluidic pumping of the first to third fluidic actuators 1410A through 1410C and fluidic suction element 1480 either in response to a program selected by the user installed within the electronic controller 1460 at purchase, a program downloaded by the user to the sexual pleasure device, or a program established by the user.

Also coupled to the electronic controller 1460 are rechargeable battery 1450, charger socket 1430, and control selector 1440 which provides control inputs to the electronic controller 1460. Control selector 1440 can for example include at least one of a control knob, a push-button selector, LEDs for setting information to the user, electronic connector for connection to remote electronic sexual pleasure device for program transfer to/from the sexual pleasure device 1400 and a wireless interface circuit, such as one operating according to the Bluetooth protocol for example. As depicted, sexual pleasure device 1400, therefore, can provide a penetrative vibrator via extension 1420 and clitoral stimulator via fluidic suction element 1480. Accordingly, first to third fluidic actuators 1410A through 1410C can for example comprise one or more fluidic actuators such as described above in respect of FIGS. 1 through 11 as well as a simple radial variant element wherein the pressure expands an element of the sexual pleasure device directly in a radial direction. In other embodiments of the invention a plurality of linear fluidic actuators such as first to third fluidic actuators 1410A through 1410C can be arranged radially and operated simultaneously, sequentially in order, sequentially in random order, non-sequentially in predetermined order, at fixed rate and/or variable rate.

Figure 15A:
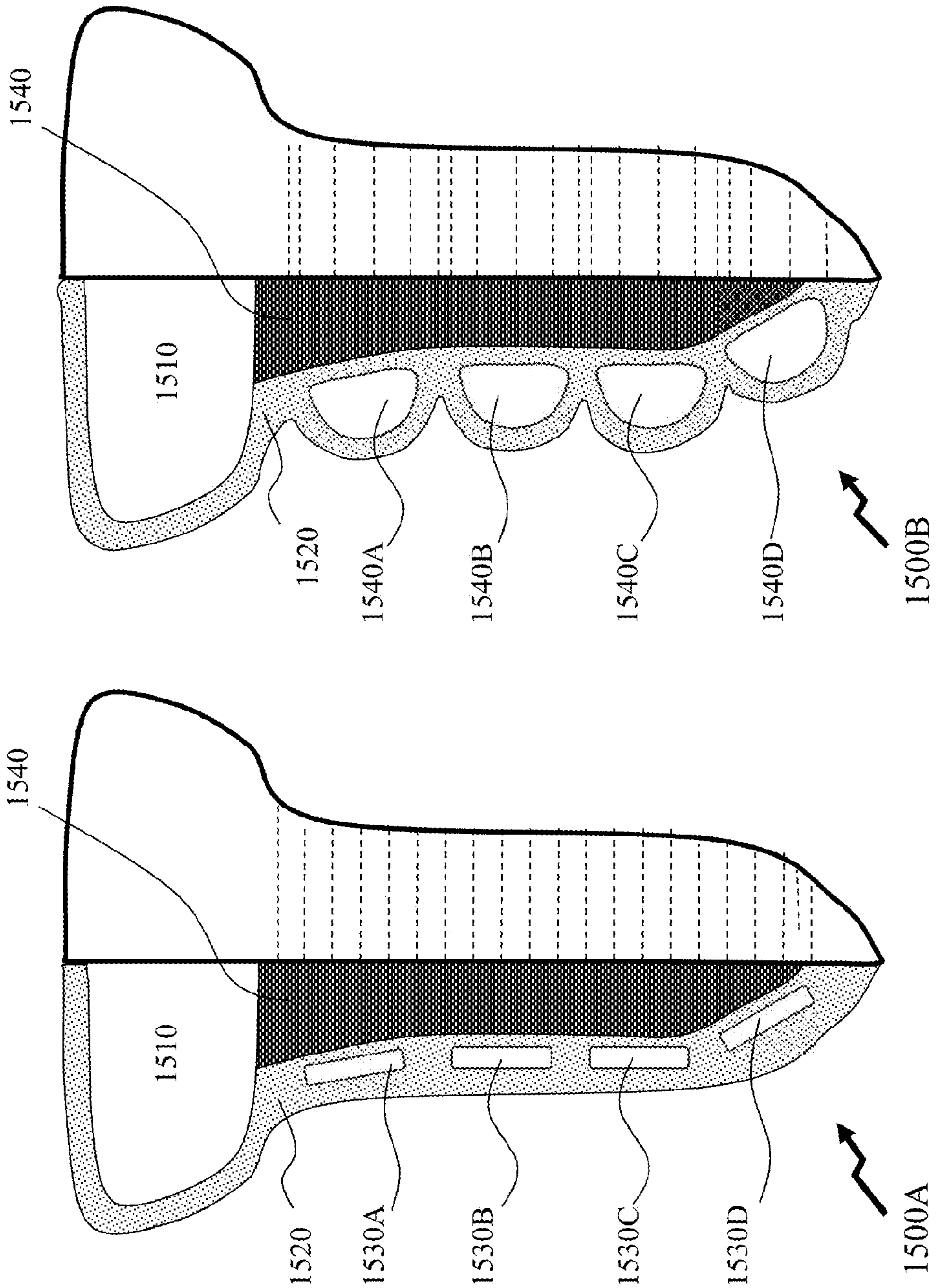
FIG. 15A depicts a device according to an embodiment of the invention exploiting expanding fluidic elements to adjust aspects of the device during use.

Now referring to FIG. 15A there is depicted a sexual pleasure device in first and second states 1500A and 1500B according to an embodiment of the invention exploiting expanding fluidic elements to adjust aspects of the sexual pleasure device during use. As depicted in first state 1500A the sexual pleasure device comprises a core 1540 surrounding which is an elastic layer 1520 within which are disposed first to fourth fluidic chambers 1530A through 1530D respectively. At the base of the sexual pleasure device is compartment 1510 within which is disposed the fluidic pump, reservoir, valves etc. necessary to control the fluidic flow to first to fourth fluidic chambers 1530A through 1530D respectively as well as the electronic control circuit to provide the required control signals to these fluidic control elements. As depicted in second state 1500B each of the first to fourth fluidic chambers 1540A through 1540D has been pressurized from the fluidic pump expanding the first to fourth fluidic chambers 1540A through 1540D and their surrounding elastic layer 1520. According to the control sequence provided by the electronic control circuit with the compartment 1510 the first to fourth fluidic chambers 1540A through 1540D can execute for variety simultaneous expansion, sequential expansion from one end of the sexual pleasure device to another, random expansion, and rippling expansion such as described above in respect of FIGS. 5A and 5B for example.

Figure 15B:
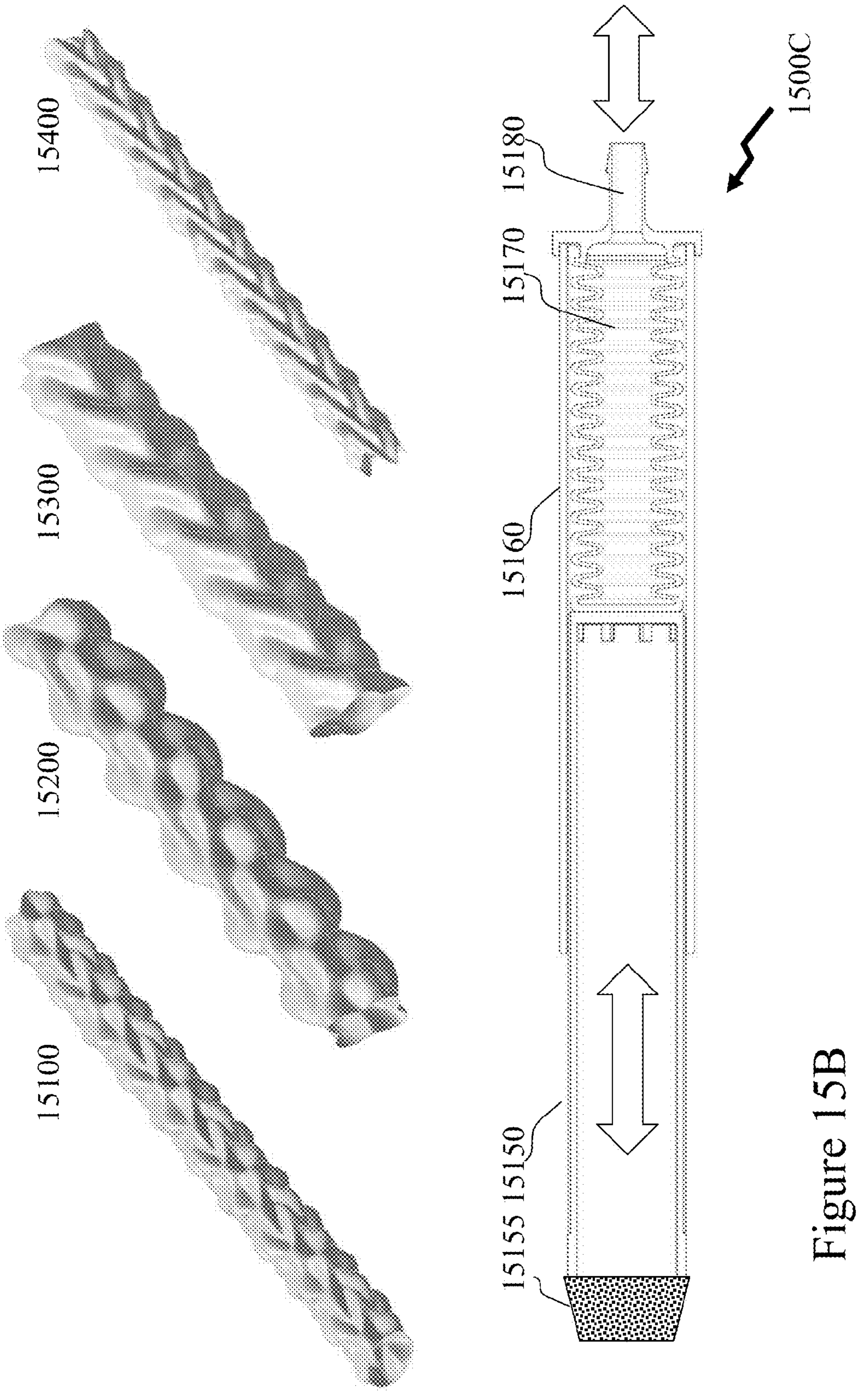
FIG. 15B depicts low resistance expansion fluidic actuators and a linear piston fluidic actuator according to embodiments of the invention.

Referring to FIG. 15B there are depicted first to fourth low resistance expansion fluidic actuators 15100 through 15400, respectively, together with a linear piston fluidic actuator 1500C according to embodiments of the invention. First to fourth low resistance expansion fluidic actuators 15100 through 15400, respectively, are formed from a resilient sheet material which may or may not have elastic characteristics. Previously employed elastic balloons require a certain pressure be exceeded to overcome the elastic force of the balloon material before it starts its inflation, which then typically begins close to the end of the balloon and progresses away from the source of the fluid applied to pressurize it. In contrast a low resistance fluidic actuator, such as first to fourth low resistance expansion fluidic actuators 15100 through 15400, respectively, begins to inflate immediately as fluid is pumped into it. Further, by virtue of the contouring the inventors have established that appropriate contouring also results in rapid fluid evolution along the length of the "balloons" of the invention which consequently expand with an increased uniformity in comparison to the prior art. Accordingly, a user of a sexual pleasure device with such a balloon would experience a more uniform pressure as the balloon "inflates" towards its final geometry. It would be evident to one skilled in the art that such contouring can be applied to portions of the surface of a tubular material or to the entire surface of the tubular material. In the instance that it is applied partially then the regions between can form "passive" sections whilst those with contouring form "active" sections. Filling of first to fourth low resistance expansion fluidic actuators 15100 through 15400, respectively, can be thought more of flattening and filling rather than expanding thereby minimizing energy requirements for expanding and fluid volume for same physical effect.

Also depicted in FIG. 15B is linear piston fluidic actuator 1500C comprising inlet/outlet 15180, fluidic actuator 15170, outer shell 15160, and piston 15150. It would be evident that fluid injection into the fluidic actuator 15170, which is constrained by outer shell 15160, via inlet/outlet 15180 results in expansion of the fluidic actuator 15170 such that piston 15150 either moves linearly thereby increasing its length and hence an aspect of the sexual pleasure device within which it forms part or that piston 15150 applies pressure to a part of a user's body. Accordingly, if linear piston fluidic actuator 1500C forms a substantial part of the main body of a sexual pleasure device the user can experience a sexual pleasure device that increases and decreases in length under direction of a controller during use or that expands to an initial length and is maintained during their use before when powered down the sexual pleasure device reduces back to a more compact profile. Alternatively, the linear piston fluidic actuator 1500C may be within another portion of the sexual pleasure device, such as the handle. Piston 15150 can therefore itself comprise additional fluidic actuators and/or other actuators to provide physical stimulation to the user according to different designs described supra in respect of FIGS. 1 through 15A and 16 to 19. Expansion to an initial length can, for example, be part of a user personalization such as described below in respect of FIGS. 21A through 23 respectively. Within other embodiments of the invention linear piston fluidic actuator 1500C can be dimensioned to project from the surface of the sexual pleasure device either discretely or in combination with other linear piston fluidic actuators 1500C such that the end 15155 engages the user's body. End 15155 can, therefore, be a fluidically controlled nubby. Optionally, the fluidic actuator 15170 can be formed with rigid radial members along its length so that the fluidic actuator 15170 does not expand radially when fluid fills it so that the requirements of the outer shell 15160 are relaxed or removed.

Figure 16:
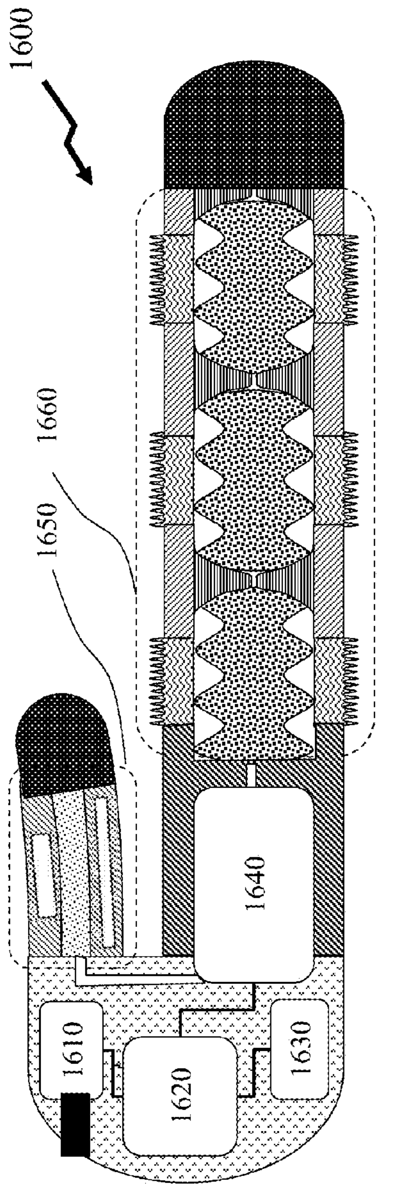
FIG. 16 depicts a device according to an embodiment of the invention exploiting fluidic elements to adjust aspects of primary and secondary elements of the device during use.

Now referring to FIG. 16 there is depicted a sexual pleasure device 1600 according to an embodiment of the invention exploiting fluidic elements to adjust aspects of primary and secondary elements 1660 and 1650 respectively of the sexual pleasure device 1600 during use. Primary element 1660 comprises an expansion element such as described supra in respect of FIG. 8 whilst secondary element 1650 comprises a flexure element such as described supra in respect of FIG. 9. Each of the primary and secondary elements 1660 and 1650 are coupled to pump module 1640, which is controlled via electronic controller 1620 that is interfaced to wireless module 1630 and battery 1610. Accordingly, sexual pleasure device 1600 represents a sexual pleasure device comprising a penetrative element, primary element 1660, and vibratory clitoral stimulator element, secondary element 1650. Optionally, as described above a second pump can be provided within the pump module 1640 or discretely to provide a vibratory function within the penetrative element, primary element 1660, as well as the expansion/contraction. Optionally, another pump can be provided within the pump module 1640 or discretely to provide a vibratory function in combination with the flexural motion of the secondary element 1650.

Figure 17:
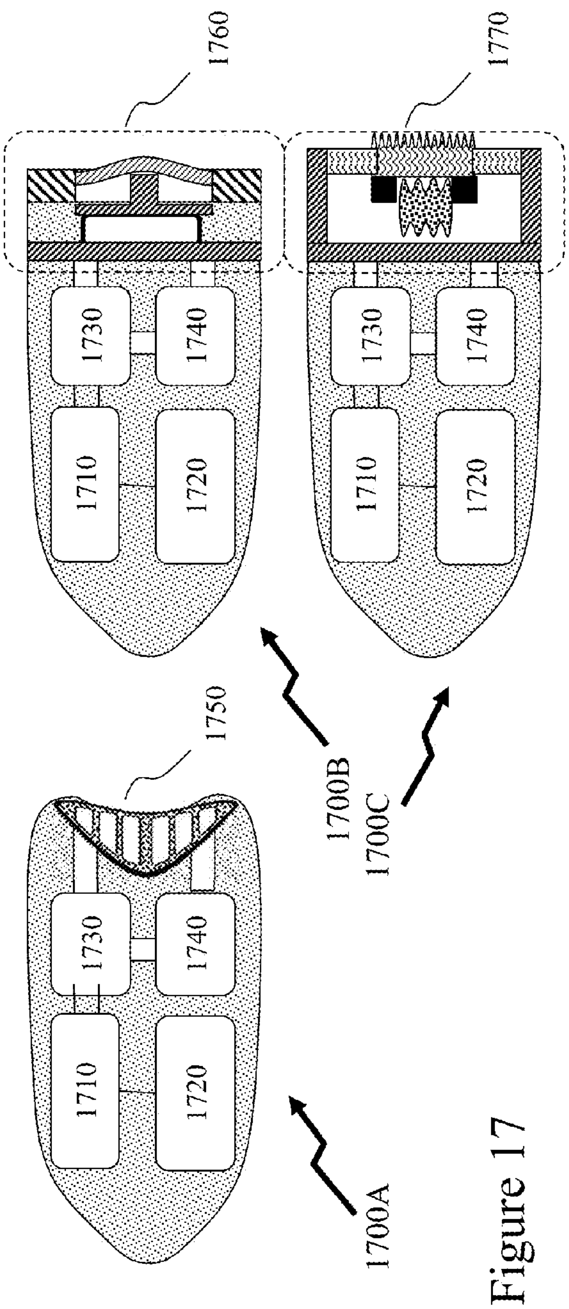
FIG. 17 depicts devices according to embodiments of the invention exploiting fluidic elements to provide suction, vibration, or motion sensations.

Now referring to FIG. 17 there are depicted first to third sexual pleasure devices 1700A through 1700C according to embodiments of the invention exploiting fluidic elements to provide suction and vibration sensations and mimicking an "egg" type vibrator of the prior art. Within each of first to third sexual pleasure devices 1700A through 1700C there are battery 1720, controller 1710, pump 1730 and reservoir 1740. However, in each of first to third sexual pleasure devices 1700A through 1700C the active element is respectively a suction element 1750 such as described supra in respect of FIG. 1, a pressure element 1760 such as described supra in respect of FIG. 2, and a friction element 1770 such as described supra in respect of FIG. 3. Optionally, the pump 1730 comprises primary and secondary fluidic pump elements to provide low frequency and high frequency motion to the body part to which the first to third sexual pleasure devices 1700A through 1700C are engaged upon.

Figure 18B:
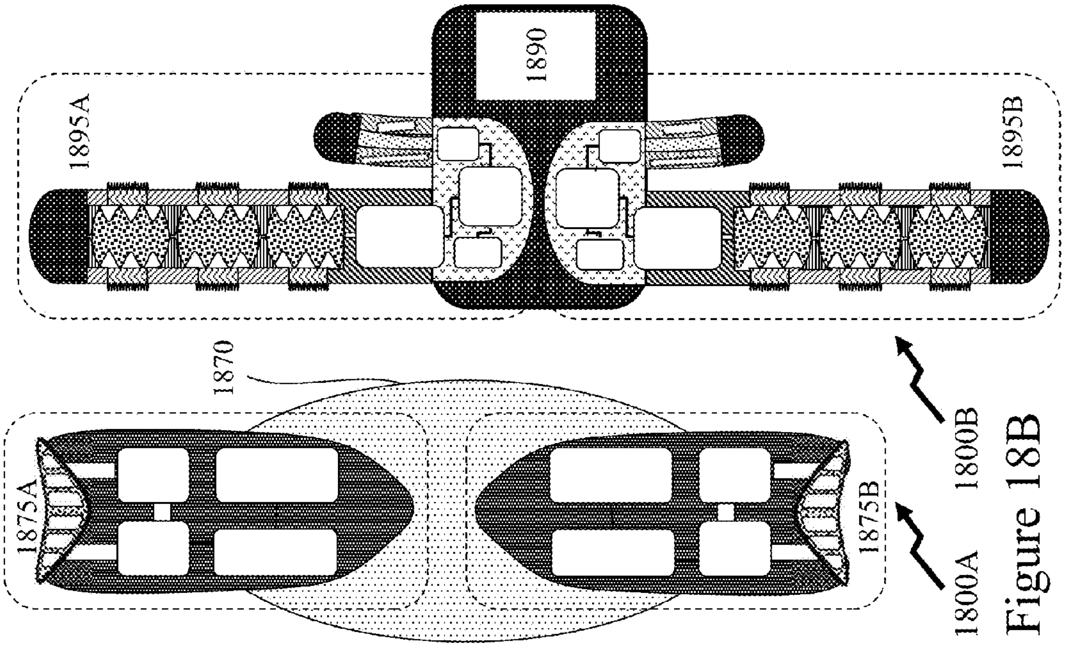
FIG. 18B depicts double ended devices according to an embodiment of the invention exploiting fluidic elements with each end of the device allowing different device performance to be provided to each user.
Figure 18A:
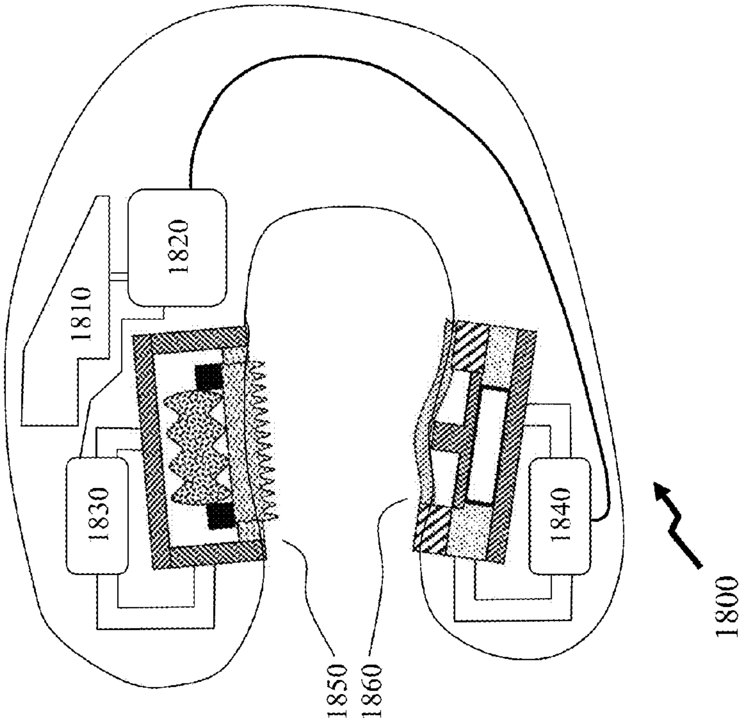
FIG. 18A depicts a device according to an embodiment of the invention exploiting fluidic elements to adjust aspects of primary and secondary elements of the device for the user during use.

Referring to FIG. 18A there is depicted a sexual pleasure device 1800 according to an embodiment of the invention exploiting fluidic elements to adjust aspects of primary and secondary elements of the sexual pleasure device for the user during use. In common with other sexual pleasure device embodiments the sexual pleasure device 1800 comprises battery 1810 coupled to electronic controller 1820, which is interfaced to first and second pumps 1830 and 1840 respectively. First pump 1830 provides fluidic actuation of first actuator 1850 such as a friction element as described supra in respect of FIG. 3. Second pump 1840 provides fluidic actuation of second actuator 1860 such as a pressure element as described supra in respect of FIG. 2. Optionally, either of first and second actuators can be implemented using a fluidic actuator according to the embodiments of the invention described above in respect of FIGS. 1 through 11 as well as others exploiting the concepts of these embodiments.

Referring to FIG. 18B there are depicted first and second double-ended sexual pleasure devices 1800A and 1800B respectively according to an embodiment of the invention exploiting fluidic elements within each end of the sexual pleasure device but allowing different sexual pleasure device performance to be provided to each user. First double ended sexual pleasure device 1800A comprises first and second sexual pleasure devices 1875A and 1875B respectively housed within flexible joint 1870 which retains each of the first and second sexual pleasure devices 1875A and 1875B respectively but allowing essentially independent orientation over a predetermined range for each as the users move during their activities with the first double ended sexual pleasure device 1800A. Second double ended sexual pleasure device 1800B comprises third and fourth sexual pleasure devices 1895A and 1895B respectively housed within flexible joint 1890 which retains each of the third and fourth sexual pleasure devices 1895A and 1895B respectively but allowing essentially independent orientation over a predetermined range for each as the users move during their activities with the second double ended sexual pleasure device 1800B. Each of the first and second sexual pleasure devices 1875A and 1875B respectively as well as third and fourth sexual pleasure devices 1895A and 1895B, respectively, comprise an electronic controller circuit controlling the respective sexual pleasure device discretely. Accordingly, the different ends of the double sided sexual pleasure devices can be independently controlled either through user selection of programs installed within the sexual pleasure devices at purchase, downloaded from a remote PED/FED based upon selections of one or other or both users, or stored based upon user preferences such as described below in respect of FIGS. 20 through 23.

However, as evident from the subsequent descriptions of ECPUMPs according to embodiments of the invention, in fact, the first and second pumps can be the same ECPUMP with appropriate electrical control signals applied to it. Optionally, a single pump controller can be employed to control both ends of a double-ended sexual pleasure device or dual controllers can be provided. Optionally, a single reservoir can be employed for all pumps whilst in other embodiments fluid from one end of the double-ended sexual pleasure device can be provided to the other sexual pleasure device but some features may not be available simultaneously or may be provided out of phase.

Within the description supra in FIGS. 1 to 18B in respect of sexual pleasure devices exploiting fluidic actuators discreetly or in combination with other mechanisms, e.g., off-axis weight based vibrators, conventional motors, etc. A variety of other sexual pleasure devices can be implemented without departing from the scope of the invention by combining functions described above in other combinations or exploiting other fluidic actuators. Further, even a specific sexual pleasure device can be designed in multiple variants according to a variety of factors including, but not limited, the intended market demographic and user preferences. For example, a sexual pleasure device initially designed for anal use can be varied according to such demographics, such that, for example, it can be configured for:

- heterosexual and homosexual male users for prostate interactions;
- heterosexual and homosexual female users to be worn during vaginal sex;
- heterosexual and homosexual users to be worn during non-vaginal sex with fixed outside dimensions;
- heterosexual and homosexual users to be worn during non-vaginal sex with expanding outside dimensions.

Whilst embodiments of the invention are described supra in respect of sexual pleasure device/device functions and designs it would be evident that other combination sexual pleasure devices can be provided using these elements and others exploiting the underlying fluidic actuation principles as well as other mechanical functionalities. For example, FIGS. 16, 18A and 18B depict combination (vaginal/clitoral) sexual pleasure devices. However, other combinations can be considered including, but not limited to, (anal/vaginal). (anal/vaginal/clitoral), (anal/clitoral), (anal/testicle), and (anal/penile). Such combinations can be provided as single user sexual pleasure devices (see FIGS. 16 and 18A) or dual user sexual pleasure devices (see FIG. 18B). It would also be evident that dual user sexual pleasure devices can be male-male, male-female, and female-female with different combinations for each user. Also as discussed below in respect of FIG. 20 multiple discrete sexual pleasure devices can be "virtually" combined through a remote controller such that a user can, for example, be presented with different functionality/options when using a sexual pleasure device depending upon the association of the sexual pleasure device with the remote controller and the other sexual pleasure devices or functionality/options can be identical but operation of the sexual pleasure devices are synchronous to each other, plesiochronous, or asynchronous. It would also be evident that male masturbators exploiting actuators such as described supra in respect of FIGS. 3 through 7B can be established for penile stimulation in contrast to prior art manual solutions.

Within the embodiments of the invention described supra the focus has been to closed loop fluidic systems, sexual pleasure devices and actuators. However, it would be evident that the ability to adjust dimensions of a sexual pleasure device may provide structures with fluidic actuators which suck/compress other chambers or portions of the sexual pleasure device such that a second fluid is manipulated. For example, a small fluidic actuator assembly may allow a chamber on the external surface of the sexual pleasure device to expand/collapse such that, for example, this chamber with a small external opening may provide the sensation of blowing air onto the user's skin. Alternatively, the chamber may provide for the ability for the sexual pleasure device to act upon a second fluid such as water, a lubricant, and a cream for example which is stored within a second reservoir or in the case of water is a fluid surrounding the sexual pleasure device in use within a bath tub for example. Accordingly, the sexual pleasure device may "inhale" water and through the fluidic actuators pumps it up to a higher pressure with or without nozzles to focus the water jet(s). Alternatively, the sexual pleasure device may suck in/blow out from the same end of the toy via non-return valves. In others, the sexual pleasure device may pump lubricant to the surface of the sexual pleasure device or simulate the sensations of ejaculation to a user such that the sexual pleasure device in addition to physically mimic a human action extends this to other sensations.

Figure 19:
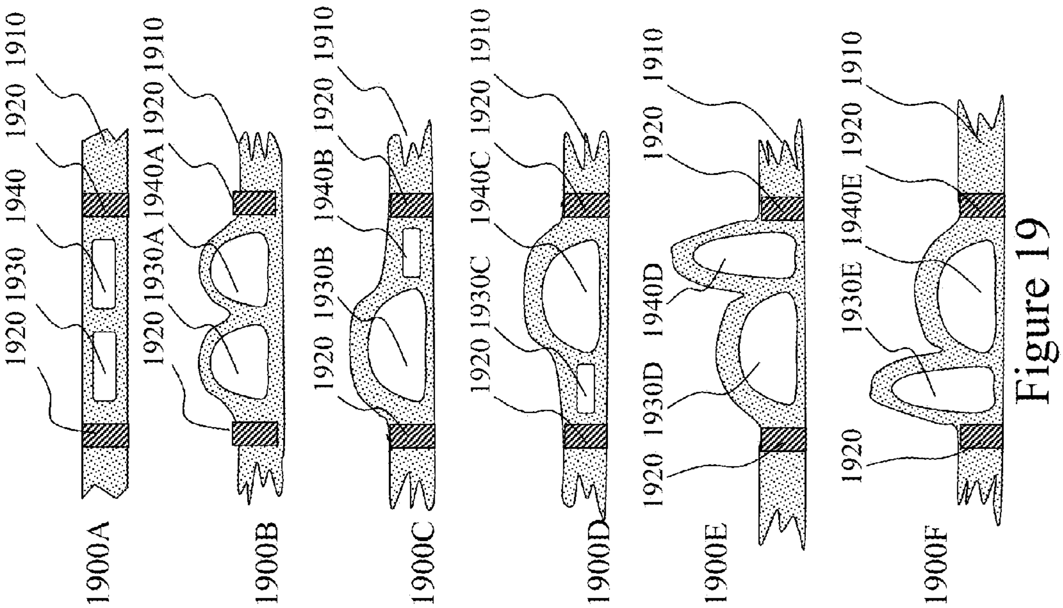
FIG. 19 depicts an embodiment of the invention wherein the action of a fluidic actuator is adjusted in dependence of the state of other fluidic actuators.

Now referring to FIG. 19 there is depicted an embodiment of the invention wherein the action of a fluidic actuator is adjusted independent of the state of other fluidic actuators as depicted in first to sixth states 1900A through 1900F respectively. As depicted in first state 1900A first and second actuators 1930 and 1940 are disposed within an elastic body 1910 which also has disposed within it resilient members 1920 either side of the first and second actuators 1930 and 1940 respectively. As depicted in second state 1900B both of the actuators have been pressurized concurrently yielding actuators in first inflated states depicted by third and fourth actuators 1930A and 1940A respectively.

Alternatively, one or other actuator is pressurized such as depicted in third and fourth states 1900C and 1900D wherein the pressurized actuator expands to compress the other actuator resulting in expanded actuators 1930B and 1940C in the third and fourth states 1900C and 1900D respectively with compressed actuators 1940B and 1930C. However, pressurization of the other actuator now results in extenuated actuators 1940D and 1930E in fifth and sixth states wherein the other pressurized actuators 1930D and 1940E, from a prior step in the sexual pleasure device operating sequence, in conjunction with resilient member 1920 provide lateral resistance such that the extenuated actuators 1940D and 1930E distend the elastic body 1910 further than in the instance of a single actuator being pressurized.

Figure 20:
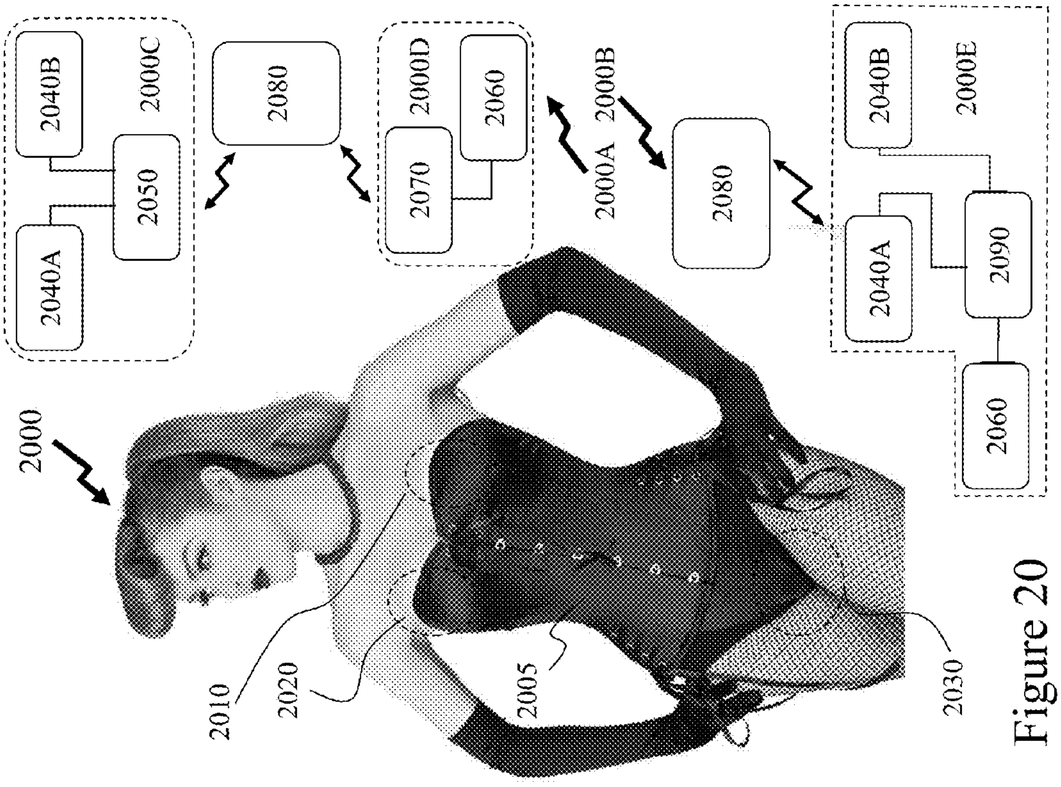
FIG. 20 depicts an embodiment of the invention relating to the inclusion of fluidic actuated devices within clothing.

Now referring to FIG. 20 there is depicted an embodiment of the invention relating to the inclusion of fluidic actuated sexual pleasure devices within clothing scenario 2000. Accordingly, as depicted in clothing scenario 2000 a user is wearing a corset 2005 wherein first to third regions 2010 through 2030 respectively have been fitted with sexual pleasure devices according to embodiments of the invention exploiting fluidic actuators such as described above in respect of FIGS. 1 to 18B and fluidic circuit elements such as described above in respect of FIGS. 24 through 60. As depicted first and second regions 2010 and 2020, respectively, can be provided with fluidic actuator based suction elements, for example, to provide stimulation to the nipple and areolae of the user and third region 2030 can be provided, for example, with a fluidic actuator based pressure element for clitoral stimulation. Based upon the design of the clothing the fluidic system can be distributed over a portion of the clothing such that the overall volume of the sexual pleasure device is not as evident to a third party either for discrete use by the user or such that the visual aesthetics of the clothing are significantly impacted. For example, a fluid reservoir can hold a reasonable volume but be thin and distributed over an area of the item or items of clothing. It would also be evident that combined functions can be provided for each of first to third regions 2010 to 2030 respectively. For example, first and second regions 2010 and 2020, respectively, can be a rubbing motion combined with a sucking effect whilst third region 2030 can be a sucking, vibration, or friction combination.

As depicted the clothing, such as depicted by corset 2005, can comprise first and second assemblies 2000C and 2000D, which are in communication with a remote electronic sexual pleasure device 2080. As depicted first assembly 2000C comprising first and second fluidic actuators 2040A and 2040B which are coupled to first fluidic assembly 2050, such that for example first and second fluidic actuators 2040A and 2040B are disposed at first and second locations 2010 and 2020 respectively. Second assembly 2000D comprises third fluidic actuator 2060 coupled to second fluidic assembly 2070 such that third fluidic actuator 2060 is associated with third region 2030. Alternatively, the first to third fluidic actuators 2040A, 2040B and 2060 respectively can be contained within a single assembly, second assembly 2000E, together with a third fluidic assembly 2090 which is similarly connected to remote electronic sexual pleasure device 2080.

It would be evident that additional fluidic actuators can be associated with each assembly and item of clothing according to the particular design and functions required. Optionally, remote electronic sexual pleasure device 2080 can be, for example, a PED of the user so that adjustments and control of the fluidic driven sexual pleasure devices within their clothing, additional to such clothing, or deployed individually can be performed discretely with their cellphone, PDA, etc. Alternative embodiments of the invention can exploit wired interfaces to controllers rather than wireless interfaces.

It would be evident to one skilled in the art that the sexual pleasure devices as described above in respect of FIGS. 1 through 20 can employ solely fluidic actuators to provide the desired characteristics for that particular sexual pleasure device or they can employ mechanical elements including, but not limited to, such as motors with off-axis weights, drive screws, crank shafts, levers, pulleys, cables etc. as well as piezoelectric elements etc. Some can employ additional electrical elements such as to support electrostimulation. For example, a fluidic actuator can be used in conjunction with a pulley assembly to provide motion of a cable which is attached at the other end to the sexual pleasure device such that retraction of the cable deforms the sexual pleasure device to provide variable curvature for example or simulate a finger motion such as exciting the female "G-spot" or male prostate. Most mechanical systems must convert high-speed rotation to low-speed linear motion through eccentric gears and gearboxes whilst fluidic actuators by default provide linear motion in 1, 2, or 3-axes according to the design of the actuator. Other embodiments of the invention may provide for user reconfiguration and/or adjustment. For example, a sexual pleasure device may comprise a base unit comprising pump, batteries, controller etc. and an active unit containing the fluidic actuators alone or in combination with other mechanical and non-mechanical elements. Accordingly, the active unit may be designed to slide relative to the active unit and be fixed at one or more predetermined offsets from an initial reduced state such that for example a user may adjust the length of the toy over, for example, 0, 1, and 2 inches whilst fluidic length adjustments are perhaps an inch maximum so that in combination the same sexual pleasure device provides length variations over 3 inches for example. It would also be evident that in other embodiments of the invention the core of the sexual pleasure device, e.g. a plug, may be manually pumped or expanded mechanically to different widths with subsequent fluidic diameter adjustments. Other variations would be evident combining fluidic actuated sexual pleasure devices with mechanical elements to provide wider variations to accommodate user physiology for example.

Personalized Control of Fluidic Actuators

Figure 21A:
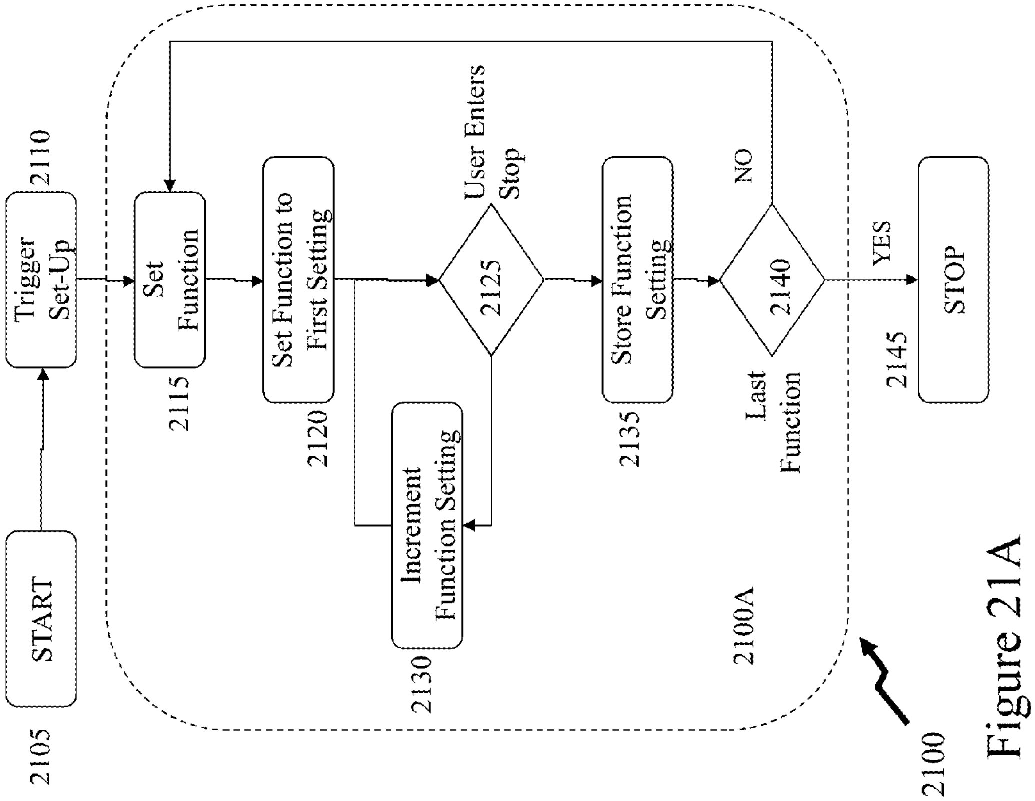
FIGS. 21A and 21B depict flow diagrams for process flows relating to setting a device exploiting fluidic elements with single and multiple functions according to embodiments of the invention according to the preference of a user of the device.
Figure 21B:
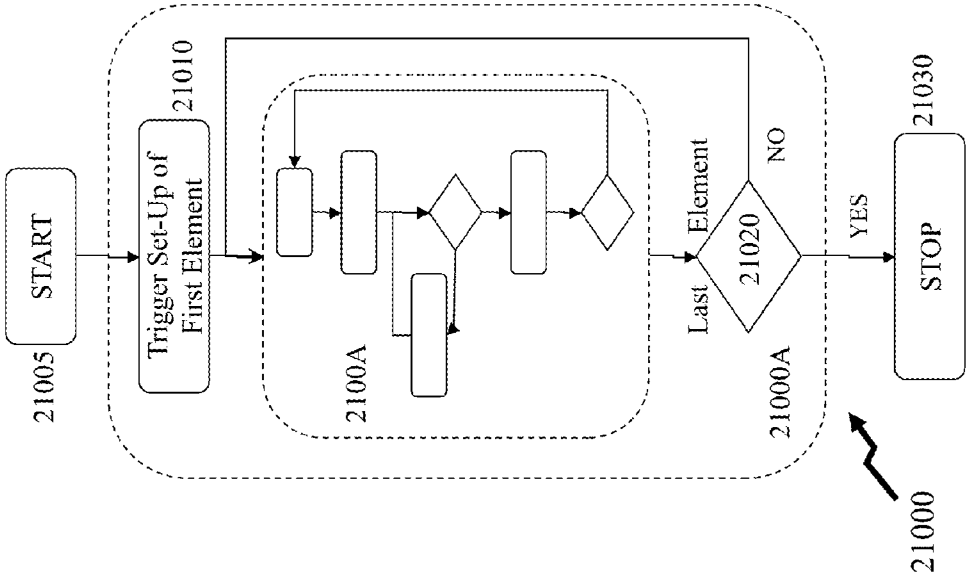

Referring to FIG. 21A there is depicted a flow diagram 2100 for a process flow relating to setting a sexual pleasure device exploiting fluidic elements according to embodiments of the invention according to the preference of a user of the sexual pleasure device. As depicted the process begins at step 2105 wherein the process starts and proceeds to step 2110 wherein the user triggers set-up of the sexual pleasure device. Next in step 2115 the user selects the function to be set wherein the process proceeds to step 2120 and the sexual pleasure device controller sets the sexual pleasure device to the first setting for that function. Next in step 2125 the sexual pleasure device checks for whether the user enters a stop command wherein if not the process proceeds to step 2130, increments the function setting, and returns to step 2125 for a repeat determination. If the user has entered a stop command the process proceeds to step 2135 wherein the setting for that function is stored into memory. Next in step 2140 the process determines whether the last function for the sexual pleasure device has been set-up wherein if not the process returns to step 2115 otherwise it proceeds to step 2145 and stops.

Accordingly, the process summarized in flow diagram 2100 allows a user to adjust the settings of a sexual pleasure device to their individual preferences. For example, such settings can include, but are not be limited to, the maximum radial expansion of the sexual pleasure device, the maximum linear expansion of the sexual pleasure device, frequency of vibration, amplitude of pressure elements, and frequency of expansion. Now referring to FIG. 21B there is depicted a flow diagram 21000 for a process flow relating to setting a sexual pleasure device exploiting fluidic elements with multiple functions according to embodiments of the invention according to the preference of a user of the sexual pleasure device. As depicted, the process begins at step 21005 and proceeds to step 21010 wherein the set-up of the first element of the sexual pleasure device, e.g. the penetrative element as described above in respect of primary element 1660 of sexual pleasure device 1600. Next the process proceeds to step 2100A which comprises steps 2015 through 2040 as depicted supra in respect of FIG. 21A. Upon completion of the first element the process determines in step 21020 whether the last element of the sexual pleasure device has been set-up. If not the process loops back to execute step 2100A again for the next element of the sexual pleasure device otherwise the process proceeds to step 21030 and stops.

For example, considering sexual pleasure device 1600 the process might loop back round based upon the user setting performance of the secondary element 1650 of sexual pleasure device 1600. In other instances, the user can elect to set-up only one of the elements of the sexual pleasure device, some elements or all elements of the sexual pleasure device. Optionally, the user can elect to set only some settings for one sexual pleasure device, and none or all for another sexual pleasure device. It would be evident to one skilled in the art that wherein process flow 21000 is employed with a double-ended sexual pleasure device, such as second double-ended sexual pleasure device 1900B, that the user making the setting determinations can change once one end of the sexual pleasure device has been set.

Figure 22:
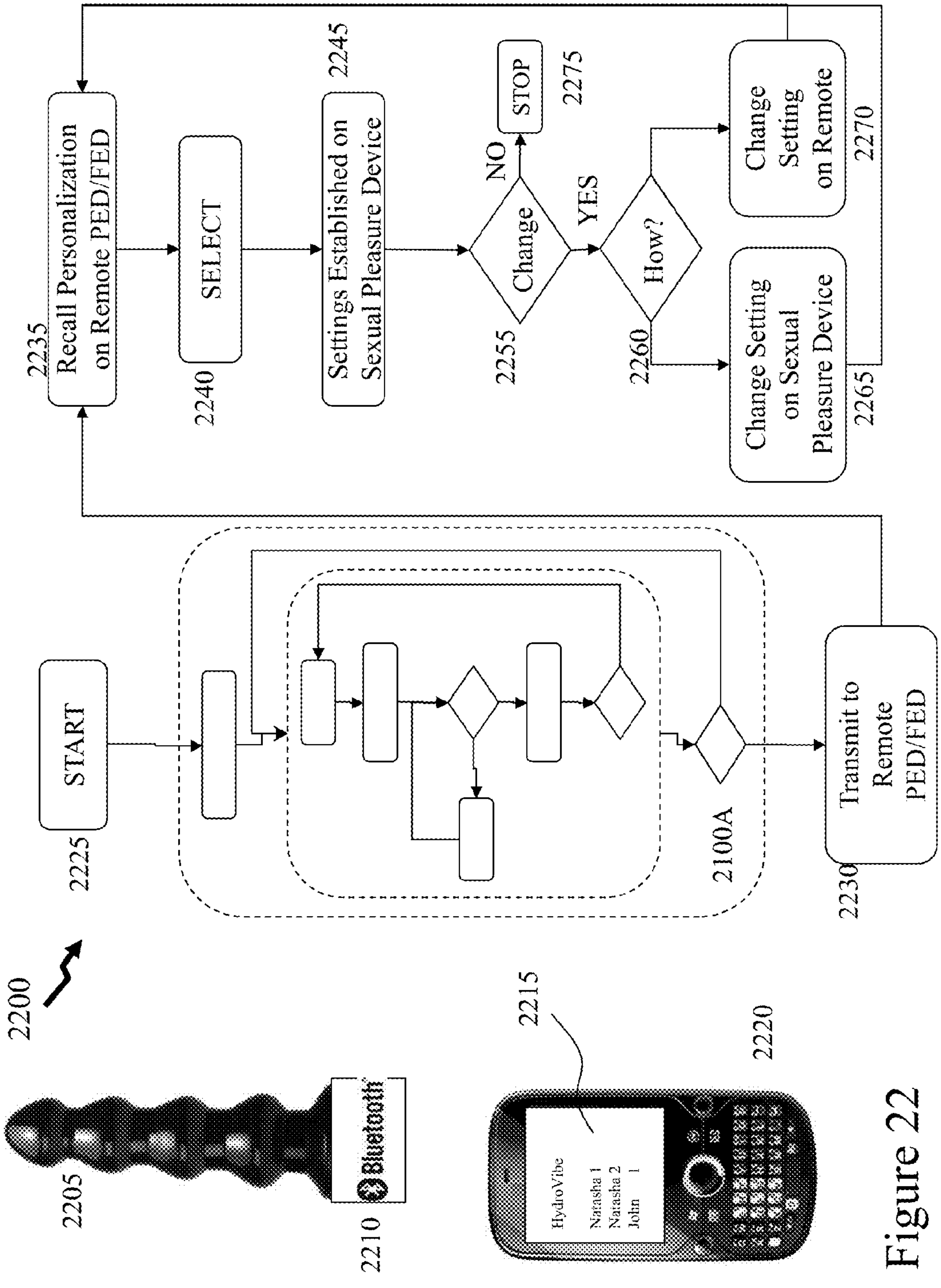
FIG. 22 depicts a flow diagram for a process flow relating to establishing a personalization setting for a device exploiting fluidic elements according to embodiments of the invention and its subsequent storage/retrieval from a remote location.

Now referring to FIG. 22 there is depicted a flow diagram 2200 for a process flow relating to establishing a personalization setting for a sexual pleasure device 2205 exploiting fluidic elements according to embodiments of the invention and its subsequent storage/retrieval from a remote location, for example, from a PED 2220. The flow diagram 2200 begins at step 2225 and proceeds to step 2100A, which comprises steps 2110, 2000A, and 2120 as described supra in respect of process flow 2100, wherein the user establishes their preferences for the sexual pleasure device. Upon completion of step 2100A the process proceeds to step 2230 and transmits the preferences of the user to a remote electronic device, such as a PED, and proceeds to step 2235 wherein the user can recall personalization settings on the remote electronic device and select one in step 2240. The selected setting is then transferred to the sexual pleasure device in step 2245 wherein the process then proceeds to offer the user the option in step 2255 to change the setting(s) selected. Based upon the determination in step 2255 the process either proceeds to step 2275 and stops wherein the setting previously selected is now used by the user or proceeds to step 2260 wherein the user is prompted with options on how to adjust the settings of the sexual pleasure device. These being for example changing settings on the sexual pleasure device or the remote wherein the process proceeds to steps 2265 and 2270 respectively on these determinations and proceeds back to step 2235.

Accordingly, as depicted in FIG. 22 a sexual pleasure device 2205 can comprise a wireless interface 2210, e.g., Bluetooth, allowing the sexual pleasure device to communicate with a remote electronic device, such as PED 2220 of the user. The remote electronic device 2220 stores settings of the user or users, for example, three are depicted in FIG. 22 entitled "Natasha 1", "Natasha 2", and "John 1." For example "Natasha 1" and "Natasha 2" can differ in speed of penetrative extension motion, radial extension, and length of extension and represent different settings for the user "Natasha", such as, for example solo use and couple use respectively or different moods of solo use.

In addition to these variations user programming can provide the ability to vary characteristics such as frequency and amplitude over wide ranges as well as being able to control the pulse shape for variable acceleration of initial contact and add other motions to better simulate/provide more natural physical sensations or provide increased sensations. For example, a user can be able to vary pulse width, repetition frequency, and amplitude for a predefined "impact" motion and then modify this to provide vibration over all or a portion of the "impact motion" as well as between "impact" pulses.

Figure 23:
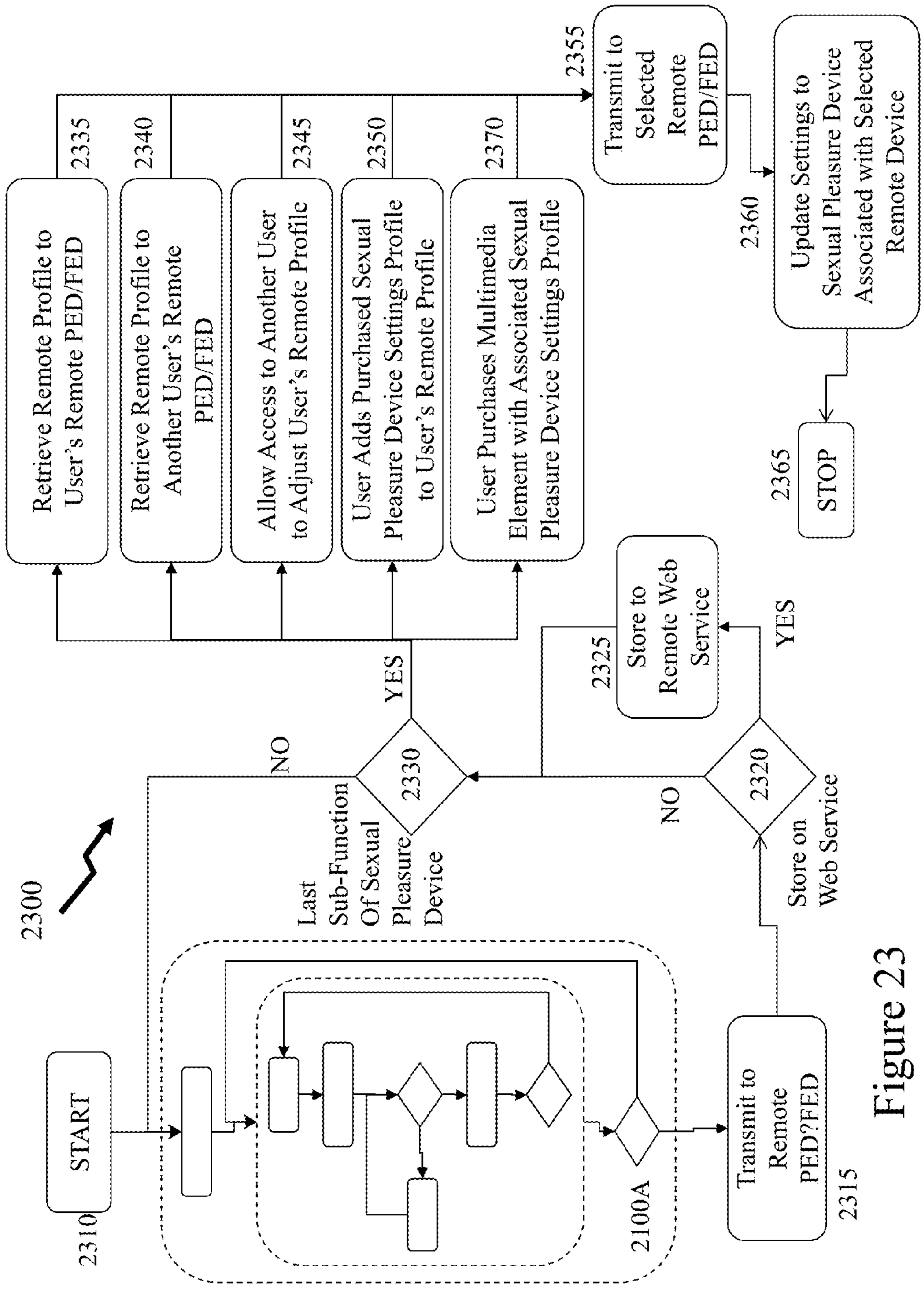
FIG. 23 depicts a flow diagram for a process flow relating to establishing a personalization setting for a device exploiting fluidic elements according to embodiments of the invention and its subsequent storage/retrieval from a remote location to the users device or another device.

Referring to FIG. 23 there is depicted a flow diagram 2300 for a process flow relating to establishing a personalization setting for a sexual pleasure device exploiting fluidic elements according to embodiments of the invention and its subsequent storage/retrieval from a remote location to the user's sexual pleasure device or another sexual pleasure device. Accordingly, the process begins at step 2310 and proceeds to step 2100A, which comprises steps 2110, 2000A, and 2120 as described supra in respect of process flow 2100, wherein the user establishes their preferences for the sexual pleasure device. Upon completion of step 2100A the process proceeds to step 2315 and transmits the preferences of the user to a remote electronic device and proceeds to step 2320 wherein the user selects whether or not to store the sexual pleasure device settings on a remote web service. A positive selection results in the process proceeding to step 2325 and storing the user preferences (settings) on the remote web service before proceeding to step 2330 otherwise the process proceeds directly to step 2330.

In step 2330 the process is notified as to whether all fluidic sub-assemblies of the device have been set-up. If not, the process proceeds to step 2100A, otherwise it proceeds to one of steps 2335 through 2350 based upon the selection of the user with regard to whether or not to store the user's preferences on the web service. These steps being:

- step 2335—retrieve remote profile for transmission to user's remote electronic device;
- step 2340—retrieve remote profile for transmission to another user's remote electronic device;
- step 2345—allow access for another user to adjust user's remote profile;
- step 2350—user adds purchased device setting profile to user's remote profiles; and
- step 2370—user purchases multimedia content with an associated user profile for a sexual pleasure device or sexual pleasure devices.

Next in step 2355 wherein a process step was selected requiring transmission of the user preferences to a remote electronic device and thence to the sexual pleasure device this is executed at this point prior to the settings of the sexual pleasure device being updated on the sexual pleasure device associated with the selected remote electronic device in step 2360 and the process proceeds to step 2365 and stops. Accordingly, in step 2335 a user can retrieve their own profile and select this for use on their sexual pleasure device, or a new sexual pleasure device they have purchased, whereas in step 2340 the user can associate the profile to another user's remote electronic device wherein it is subsequently downloaded to that remote electronic device and transferred to the device associated with that remote electronic device. Hence, a user can load a profile they have established and send it to a friend to use or a partner for loading to their sexual pleasure device either discretely or in combination with another profile associated with the partner. Accordingly a user can load their profile to one end of a double-end sexual pleasure device associated with another user as part of an activity with that other user or to a sexual pleasure device. Alternatively, in step 2345 the process allows for another user to control the profile allowing, for example, a remote user to control the sexual pleasure device through updated profiles whilst watching the user of the sexual pleasure device on a webcam whilst in step 2350 the process provides for a user to purchase a new profile from a sexual pleasure device manufacturer, a third party, or a friend/another user for their own use. An extension of step 2350 is wherein the process proceeds via step 2370 and the user purchases an item of multimedia content, such as for example an audio book, song, or video, which has associated with it a profile for a sexual pleasure device according to an embodiment of the invention such that as the user plays the item of multimedia content the profile is provided via a remote electronic device, e.g. the user's PED or Bluetooth enabled TV, to their sexual pleasure device and the profile executed in dependence of the replaying of the multimedia content and the profile set by the provider of the multimedia content. Optionally, the multimedia content can have multiple profiles or multiple modules to the profile such that the single item of multimedia content can be used with a variety of sexual pleasure devices with different functionalities and/or elements.

Within the process flows described above in respect of FIGS. 20 through 23 the user can be presented with different actuations patterns relating to different control parameters which can be provided in respect of a single fluidic actuator or multiple fluidic actuators. For example the user can be provided with varying frequency, varying pressure (relating to drive signal amplitude/power), varying pulse profiles, and slew rates. Within the embodiments of the invention described with respect of FIGS. 22 and 23 the sexual pleasure device communicates with a remote electronic device which can for example be the user's PED. Optionally, the sexual pleasure device can receive data other than a profile to use as part of the user experience including for example music or other audiovisual/multimedia data such that the electronic controller within the sexual pleasure device reproduces the audio portion directly or adjusts aspects of the sexual pleasure device in dependence upon the data received. An ECPUMP can be viewed as acting as a low-mid frequency actuator which can act in combination with a higher frequency actuator or by appropriate ECPUMP and electrical control provide full band coverage. Optionally, where multimedia content is coupled to the sexual pleasure device rather than the sexual pleasure device operating directly in response to the multimedia content the controller can apply the multimedia content raw or processed whilst maintaining the sexual pleasure device's operation within the user set preferences. Similarly, where multimedia content contains a profile which is provided to the sexual pleasure device and executed synchronously to the multimedia content then this profile can define actions which are then established as control profiles by the controller within the user set preferences. For example, an item of multimedia content relating to a woman being sexually stimulated can provide actions that mimic the multimedia content action for some sexual pleasure devices and provide alternate actions for other sexual pleasure devices but these are each synchronous or plesiochronous to the multimedia content.

Optionally, the user can elect to execute a personalization process, such as that depicted in FIG. 22 with respect to process flow 2200, upon initial purchase and use of a sexual pleasure device or subsequently upon another use of the sexual pleasure device. However, it would also be evident that the user can perform part or all of the personalization process whilst they are using the sexual pleasure device. For example, a user can be using a rabbit type sexual pleasure device and whilst in use characteristics such as maximum length extension and maximum radial extension of the sexual pleasure device can be limited to different values than previously whilst the inserted body and clitoral stimulator are vibrating. Due to the nature of the sensations felt by a user from such sexual pleasure devices it would also be evident that some personalization profile generating process flows can sub-divide the sexual pleasure device such that a sub-set of parameters can be set and adjusted in conjunction with one another prior to adjustment of other aspects. For example, length/diameter variations can be generally linked due to user physiology whilst vibrator amplitude and frequency, for example, can be varied over a wide range for a constant physical sexual pleasure device geometry.

Fluidic Assembly

The sexual pleasure devices described herein comprise a fluidic assembly that controls the expansion/reduction of the fluidic chamber(s) within the sexual pleasure devices. The fluidic assembly comprises a combination of fluidic channels, pumps and valves, together with the appropriate control systems. Examples of particular fluidic assemblies are described in detail below, however, it should be understood that alternative assemblies can be incorporated in the present sexual pleasure devices.

Figure 24:
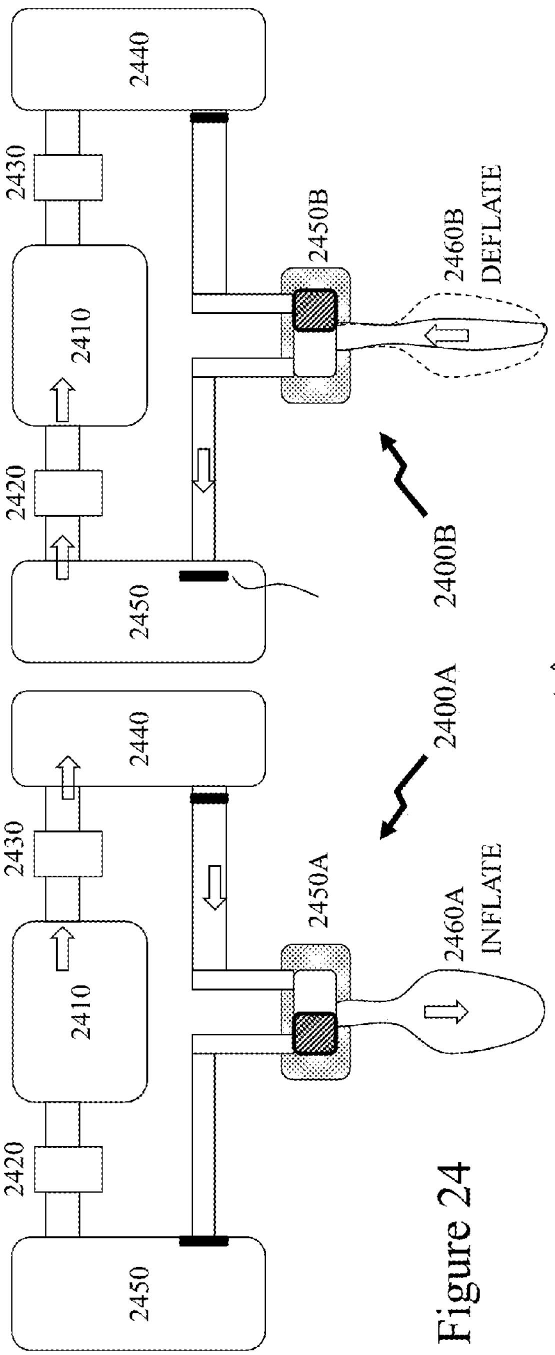
FIG. 24 depicts inflation/deflation of an element under fluidic control according to an embodiment of the invention with fluidic pump, reservoirs, non-return valves, and valves.

Within the sexual pleasure device embodiments of the invention described supra in respect of FIGS. 14 through 19 and the fluidic schematics of FIGS. 12 and 13 fluidic control system incorporating pumps and valves with interconnecting fluidic couplings have been described for providing pressure to a variety of fluidically controlled elements such as described above in respect of FIGS. 1 through 11. In FIG. 14 each of the first to third fluidic actuators 1410A through 1410C are coupled to the pump module 1470 via dual fluidic channels that meet at the associated one of the first to third valves 1490A through 1490C rather than the configurations depicted in FIGS. 12 and 13. Referring to FIG. 24 this inflation/deflation of an element under fluidic control according to an embodiment of the invention with a single valve is depicted in first and second states 2400A and 2400B respectively. As depicted, a fluidic pump 2410 is coupled to outlet and inlet reservoirs 2440 and 2450 respectively via outlet and inlet fluidic capacitors 2420 and 2430 respectively. Second ports on the outlet and inlet reservoirs 2440 and 2450 respectively are coupled via non-return valves to valve, which is depicted in first and second configurations 2450A and 2450B in first and second stated 2400A and 2400B respectively. In first configuration 2450A the valve couples the outlet of the pump via outlet reservoir 2440 to the fluidic actuator in inflate mode 2460A to increase pressure within the fluidic actuator. In second configuration 2450B the valve couples to the inlet of the pump via inlet reservoir 2450 from the fluidic actuator in deflate mode 2460B to decrease pressure within the fluidic actuator. Accordingly, the fluidic control circuit of FIG. 24 provides an alternative control methodology to those described supra in respect of FIGS. 12 and 13. Optionally, the non-return valves can be omitted.

Figure 25:
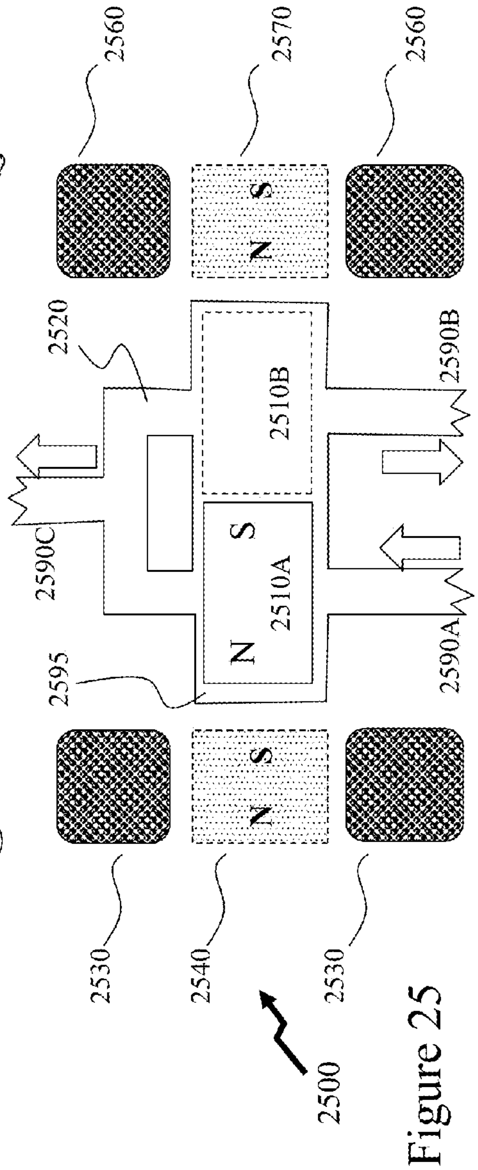
FIG. 25 depicts an electronically activated valve (EAV) or electronically activated switch for a fluidic system according to an embodiment of the invention.

Now referring to FIG. 25 there is depicted an electronically activated valve (EAV) 2500 for a fluidic system according to an embodiment of the invention such as described above in respect of FIG. 24, but which can also form the basis of valves for deployment within the fluidic control schematics described supra in respect of FIGS. 12 and 13. Accordingly, as shown a fluidic channel 2520 has an inlet port 2590A and first outlet port 2950B which are disposed on one side of a chamber 2595. On the other side of chamber 2595 are two ports that merge to second output port 2590C. Disposed within chamber 2595 is a magnetic valve core that can move from a first position 2510A blocking inlet port 2590A and associated chamber outlet to second position 2510B blocking first outlet port 2590B and associated chamber outlet. Disposed at one end of the chamber 2595 is first coil 2530 and at the other end second coil 2560. Accordingly in operation the magnetic valve core can be moved from one end of the chamber 2595 to the other end through the selected activation of the first and second coils 2530 and 2560 respectively thereby selectively blocking one or other of the fluidic channel from inlet port 2590A to second outlet port 2590C or first outlet port 2590B to second outlet port 2590C such as depicted and described in respect of FIG. 24 to provide selected inflation/deflation of the fluidic actuator through the injection/removal of fluid.

In operation with the magnetic pole orientation of the magnetic valve core depicted then to establish first position 2510A the North (N) pole is pulled left under operation of the first coil 2530 generating an effective South (S) pole towards the middle of the EAV 2500 and the S pole is pushed left under operation of the second coil 2560 generating an effective S pole towards the middle of the EAV 2500, i.e. the current within second coil 2560 is reversed relative to first coil 2530. Accordingly, to establish the second position 2510B the current within first coil 2530 is reversed relative to the preceding direction thereby generating an effective north pole towards the middle of the EAV 2500 generating a force pushing right and the S pole of the magnetic valve core is pulled right under operation of the second coil 2560 generating an effective N pole towards the middle of the EAV 2500. Optionally, according to the design of the control circuit and available power only one coil can be activated in each instance to generate the force moving the magnetic valve core. Further, it would be evident that in some embodiments of the invention only one electrical coil is provided.

Optionally, to make EAV 2500 latching and reduce power consumption on the basis that activation of the first or second coils 2530 and 2560 is only required to move the magnetic valve core between the first and second positions 2510A and 2510B first and second magnets 2540 and 2570 can be disposed at either end of the chamber with pole orientations to provide attraction to the magnetic valve core when at the associated end of the chamber 2595. Each of the first and second magnets 2540 and 2570 providing sufficient force to hold the magnetic valve core at each end once moved there under electromagnetic control of the first and/or second coils 2530 and 2560 respectively. Optionally, which of the piston/washers are magnetic can be inverted in other embodiments of the invention.

Optionally, these first and second magnets 2540 and 2570 can be pieces formed from a soft magnetic material such that they are magnetized based upon the excitation of the first and second coils 2530 and 2560 respectively. Alternatively first and second magnets 2540 and 2570 can be soft magnetic materials such that they conduct magnetic flux when in contact with the magnetic valve core and are essentially non-magnetised when the magnetic valve core is in the other valve position. It would be evident that variants of the electronically activated valve 2500 can be configured without departing from the scope of the invention including but not limited, non-latching designs, latching designs, single inlet/single outlet designs, single inlet/multiple outlet, multiple inlet/single outlet, as well as variants to the design of the chamber and inlet/outlet fluidic channels and joining to the chamber. Optionally, under no electrical activation the magnetic valve core can be disposed between first and second positions 2510A and 2510B and have a length relative to the valve positions such that multiple ports are "off" such as both of first and second outlet ports 2590B and 2590C respectively in FIG. 25.

Figure 26:
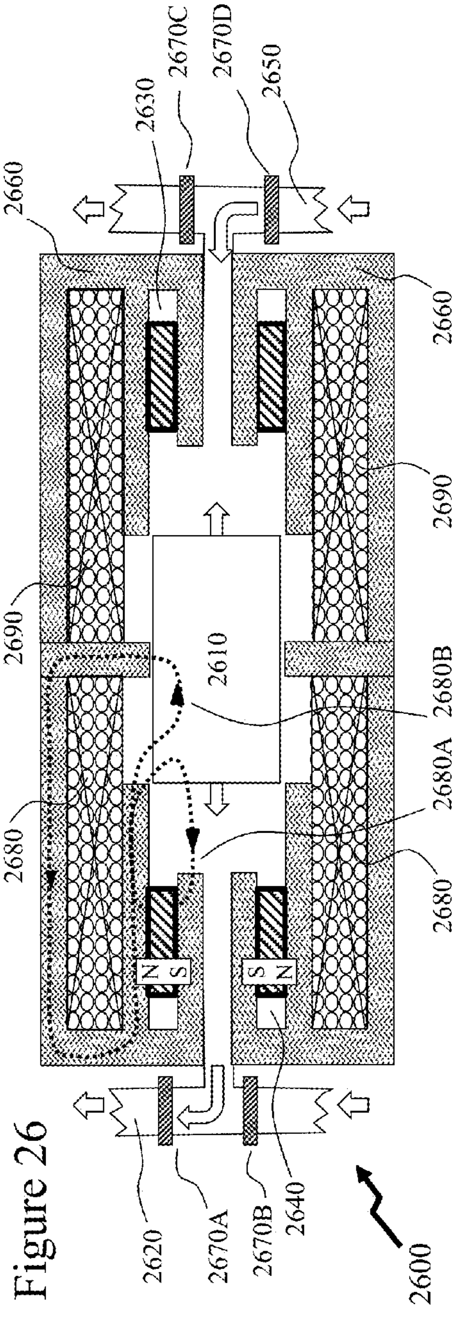
FIG. 26 depicts an electronically controlled pump for a fluidic system according to an embodiment of the invention.

Now referring to FIG. 26 there is depicted an electronically controlled pump (ECPUMP) 2600 for a fluidic system according to an embodiment of the invention. ECPUMP 2600 is depicted in cross-section view and comprises an outer body 2660 which houses at a first radius away from the axis first and second coils 2680 and 2690 respectively to the left and right hand sides. At a second smaller radius from the axis are first and second permanent magnets 2640 and 2630 respectively which as depicted are poled radially away from axis of the ECPUMP 2600 so that the North (N) pole is disposed towards the first and second coils 2680 and 2690 respectively whilst the South (S) pole is disposed towards the central axis. Disposed within the centre of the ECPUMP 2600 is magnetic piston 2610. Accordingly, alternate activation of the first and second coils 2680 and 2690 results in the magnetic piston 2610 moving along the axis of the ECPUMP 2600. Activation of first coil 2680, with no activation of second coil 2690, results in generation of electromagnetic flux path 2680B, which acts in conjunction with permanent magnet flux path 2680A to pull the magnetic piston 2610 to the left. Subsequently, de-activation of the first coil 2680 and activation of the second coil results in a new electromagnetic flux path being generated from second coil 2690 to magnetic piston 2610, not shown for clarity, and removal of electromagnetic flux paths 2680A and 2680B thereby pulling the magnetic piston 2610 to the right. Accordingly, motion of the magnetic piston 2610 to the left draws fluid from second fluidic channel 2650 past fourth check valve 2670D and subsequent motion to the right pushes fluid past third check valve 2670C. At the same time motion of the magnetic piston 2610 to the left pushes fluid past third check valve 2670A into first fluidic channel 2620 and subsequent motion to the right draws fluid from the first fluidic channel 2620 past second check valve 2670B. Optionally, only a single fluidic channel is provided to the ECPUMP 2600.

Figure 27:
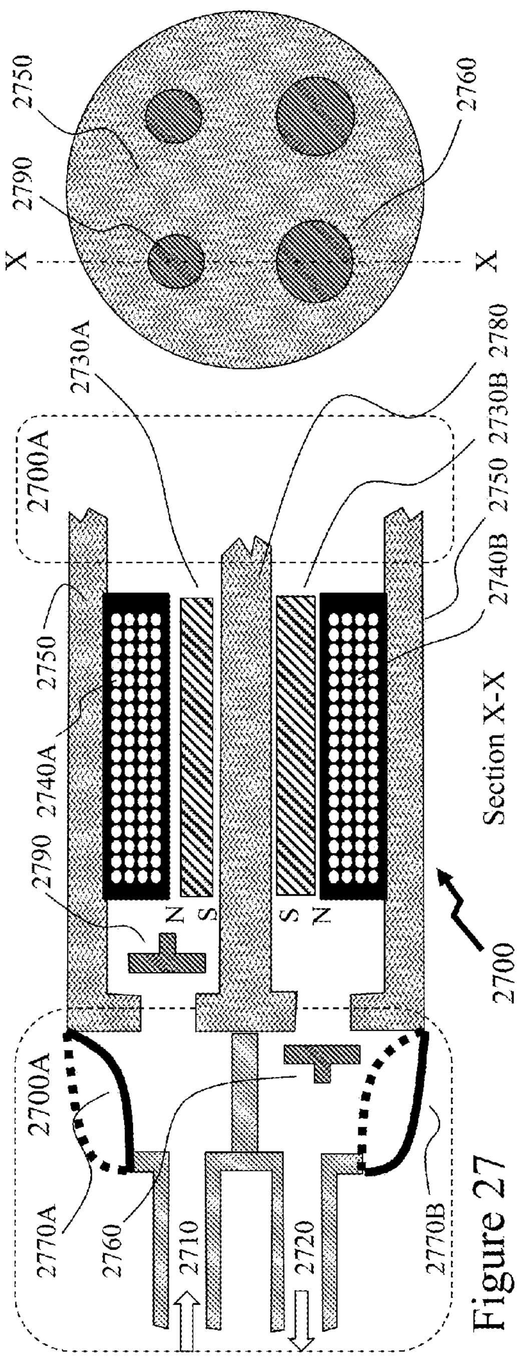
FIGS. 27 and 28 depict electronically controlled pumps for fluidic systems according to embodiments of the invention exploiting fluidic capacitors.

Referring to FIG. 27 there is depicted a cross-sectional view X-X of an electronically controlled pump (ECPUMP) 2700 for a fluidic system according to an embodiment of the invention wherein an outer body 2750 has disposed a fluidic assembly 2700A comprising a pair of inlets 2710 with one-way non-return inlet valves 2790 and a pair of outlets 2720 with one-way non-return outlet valves 2760. Each inlet 2710 and outlet 2720 also comprising a fluidic capacitor 2770. For simplicity only one fluidic assembly 2700A is depicted in FIG. 27. Internally the outer body 2750 has disposed on the upper side of central body element 2780 within the outer body 2750 a fluidic connection between an inlet valve 2710 at one end of ECPUMP 2700 and outlet valve 2720 at the other end of ECUMP 2700 a first coil 2740A and first magnet 2730A. Disposed to the lower side of central body element 2780 within the outer body 2750 a fluidic connection between an inlet valve 2710 at one end of ECPUMP 2700 and outlet valve 2720 at the other end of ECUMP 2700 second coil 2740B and second magnet 2730B. Accordingly activation of the first and second coils 2730A and 2730B results in the generation of magnetic fields within the regions defined by the outer body 2750 and central body element 2780 which drive the first and second magnets 2740A and 2740B thereby causing them to draw/push fluid within the ECPUMP 2700. It would be evident to one skilled in the art that the one-way non-return inlet valves 2790 and one-way non-return outlet valves 2760 facilitate the pumping by removing the return of fluid pumped in one direction when the ECPUMP 2700 cycles in the opposite direction under electromagnetic induced force from activation of the first and second coils 2740A and 2740B. It would also be evident to one skilled in the art that whilst the one-way non-return inlet and outlet valves 2790 and 2760 respectively are depicted in the end-view as being circular that the internal cross-sectional structure of the chambers within the outer body can be of multiple designs including, but not limited to, circular, square, rectangular, arcuate, and polygonal wherein accordingly the magnets and coils are designed to suit. Generally first and second coils 2730A and 2730B are the same coil and/or first and second magnets 2740A and 2740B are the same magnet.

The fluid drawn by the ECPUMP 2700 and pumped in each cycle can be small compared to the volume of fluid within the fluidic system before and after the ECPUMP 2700. Accordingly, the inventor has found that providing flexible elements between the ECPUMP 2700 and the fluidic systems either end, such as depicted by first and second capacitive elements 2770A and 2770B and as described in respect of previous Figures, provide for sufficient dynamic volume adjustment in the fluid on the inlet and outlet sides to facilitate operation of the ECPUMP 2700 and other pump embodiments described within this specification and act essentially as a fluidic capacitor in terms of providing a reservoir of fluid that can be drained/topped up by the ECPUMP 2700, hence the inventors use of the name to these elements.

Figure 28:
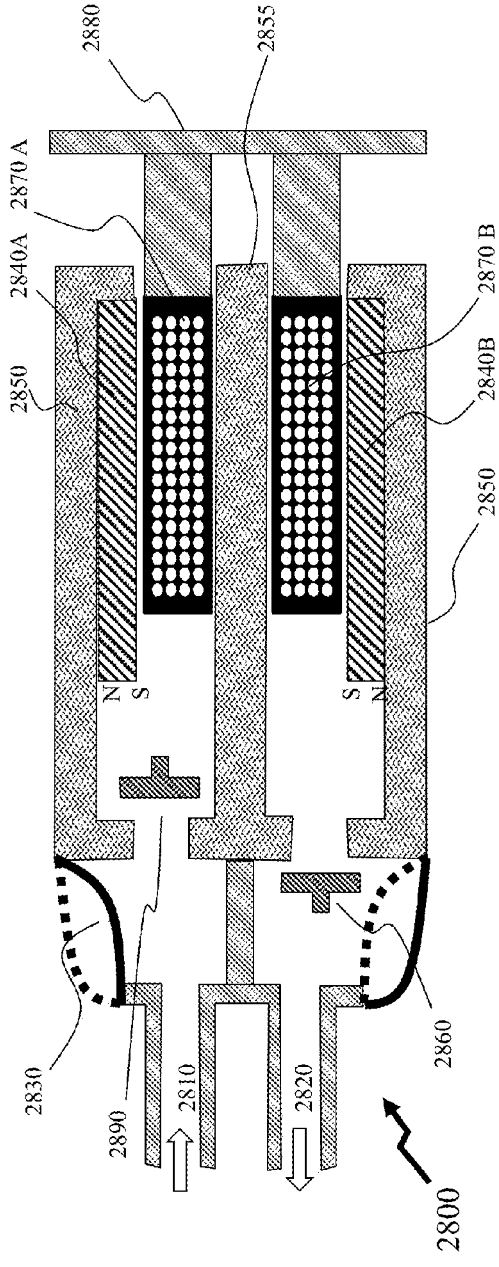

Referring to FIG. 28 there is depicted an electronically controlled pump (ECPUMP) 2800 for a fluidic system according to an embodiment of the invention wherein an outer body 2850 has disposed at one end an inlet 2810 with one-way non-return inlet valve 2890 and an outlet 2820 with one-way non-return outlet valve 2860. Each of the inlet 2810 and outlet 2820 also comprising a fluidic capacitor 2830. Internally the outer body 2850 has disposed on its inner surface on the upper side a first magnet 2840A and on the lower side a second magnet 2840B. Centrally disposed within the outer body 2850 is central body element 2855. Disposed between the first magnet 2840A and central body element 2855 is first coil 2870A attached to plunger 2880 and similarly disposed between the second magnet 2840B and central body element 2855 is second coil 2870B similarly attached to plunger 2880. Accordingly activation of the first and second coils 2870A and 2870B results in the generation of magnetic fields within the regions defined by the outer body 2850 and central body element 2855 which in combination with the magnetic fields of the first and second magnets 2840A and 2840B result in the plunger 2880 moving thereby causing fluid to be drawn/pushed within the ECPUMP 2800. It would be evident to one skilled in the art that the one-way non-return inlet valve 2890 and one-way non-return outlet valve 2860 facilitate the pumping by removing the return of fluid pumped in one direction when the ECPUMP 2800 cycles in the opposite direction. Generally first and second magnetics 2840A and 2840B are a single radial magnet or a pair of semi-circular magnets assembled to form a radial design.

Not depicted within the schematic cross-section of ECPUMP 2800 is the fluidic link between the upper and lower chambers. It would also be evident to one skilled in the art that in a similar manner to ECPUMP 2700 the internal cross-sectional structure of the chambers within the outer body 2850 of ECPUMP 2800 can be of multiple designs including, but not limited to, circular, square, rectangular, arcuate, and polygonal wherein accordingly the magnets and coils are designed to suit. According to another embodiment of the invention the first and second coils 2870A and 2870B can be fixed through plunger 2880 such that the remainder of ECPUMP 2800 moves relative to the plunger. Generally first and second coils 2870A and 2870B are a single coil.

Figure 29:
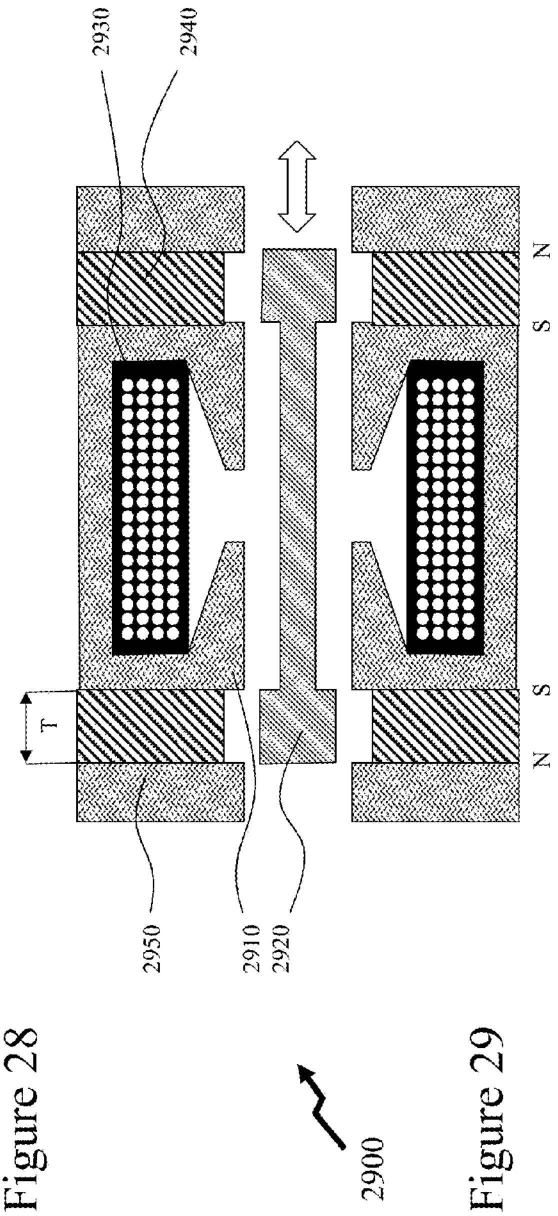
FIGS. 29 and 30 depict electronically controlled pumps for fluidic systems according to embodiments of the invention.

Now referring to FIG. 29 there is depicted an electronically controlled pump (ECPUMP) 2900 for a fluidic system according to an embodiment of the invention. As depicted in the cross-sectional view a central body 2910 has disposed within it a coil 2930 and surrounds piston 2920 comprised of a magnetic material. Disposed at each end of central body 2910 is a magnet 2940 and outer body portion 2950. In this instance each magnet 2940 has its N and S poles aligned along the axis of the ECPUMP 2900 rather than having the N and S poles radially disposed in each ECPUMP described supra in respect of FIGS. 26 through 28 respectively. Accordingly, activation of the coil 2930 in combination with the magnetic field within the piston 2920 and each magnet 2940 results in movement of the piston 2920 within the ECPUMP 2900. Accordingly, ECPUMP 2900 when combined with additional fluidic elements, omitted for clarity but discussed supra in respect of FIGS. 26 through 28 respectively, including but not limited to inlet, outlet, non-return valves, and fluidic capacitors provides for a fluidic pump of low complexity, good efficiency, good performance, lower power requirements and improved manufacturability. One aspect affecting this is the orientation of the magnetic poles relative to the body of magnet 2940 which are now the orientated along the axis of the ECPUMP 2900 rather than radially. The stroke of piston 2920 is related to the thickness of the magnet 2940 and the thickness of the piton tooth.

Figure 30:
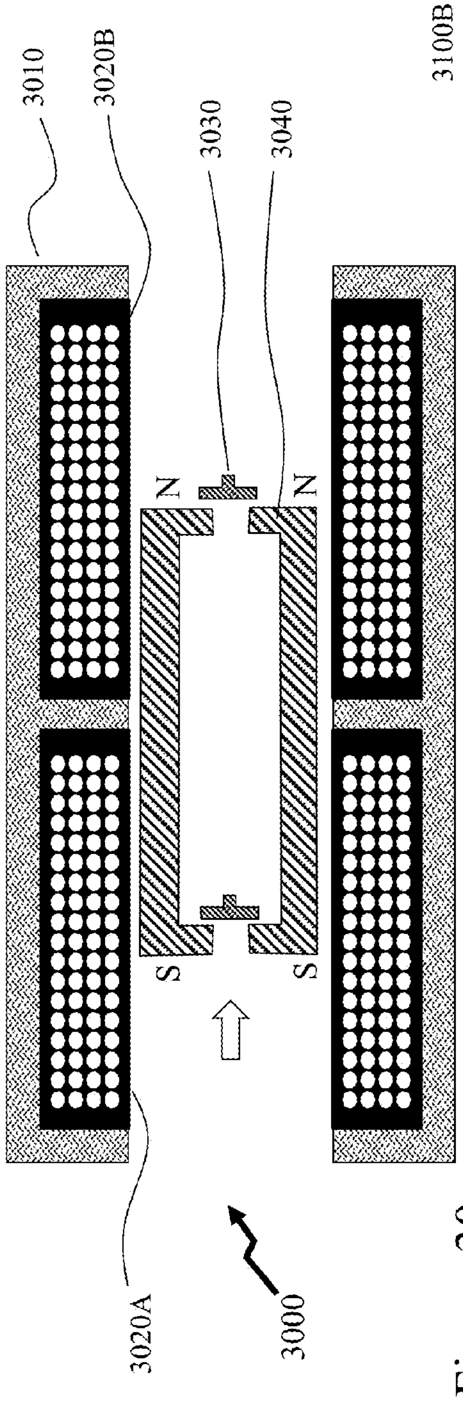

Referring to FIG. 30 there is depicted a cross-section of an electronically controlled pump (ECPUMP) 3000 for a fluidic system according to an embodiment of the invention. As depicted an outer body 3010 has disposed at each end first and second coils 3020A and 3020B respectively. Disposed within the outer body 3010 there is a pump body 3030 formed of a magnetic material, which is hollow and has disposed at either end non-return valves 3030. The pump body 3040 has its poles at either end along the axis of the ECPUMP 3000. Accordingly, in common with other embodiments of the invention activation of the first and second coils 3020A and 3020B in sequence results in movement of the pump body 3040 relative to the outer body 3010 and accordingly through the action of the non-return valves 3030 pumps fluid from left to right as depicted. ECPUMP 3000 when combined with additional fluidic elements, omitted for clarity but discussed supra in respect of FIGS. 26 through 28 respectively, including but not limited to inlet, outlet and fluidic capacitors provides for a fluidic pump of low complexity and improved manufacturability, particularly in respect of the orientation of the magnetic poles relative to the pump body 3040 formed from the magnetic material. As depicted ECPUMP 3000 has 2 non-return (check) valves 3030 within pump body 3040 and ECPUMP 3000 can be directly integrated into the fluidic system in-line. Additional non-return valves, not depicted for clarity, can be employed within the fluidic system either side of the ECPUMP 3000 to manage overall flow. Optionally, one of the non-return valve 3030 can be removed.

Figure 31:
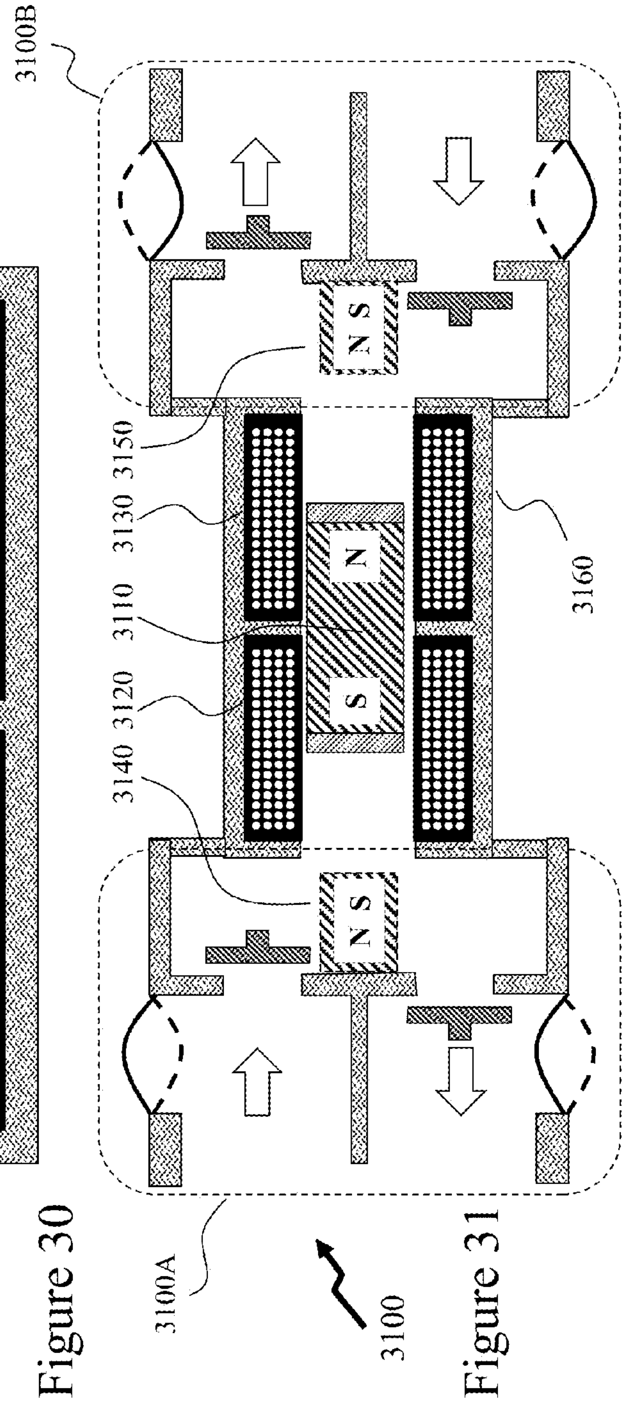
FIG. 31 depicts an electronically controlled pump for a fluidic system according to an embodiment of the invention exploiting fluidic capacitors.

Now referring to FIG. 31 there is depicted an electronically controlled pump (ECPUMP) 3100 for a fluidic system according to an embodiment of the invention. As depicted ECPUMP 3100 comprises first and second fluidic assemblies 3100A and 3100B respectively, which are essentially as described supra in respect of FIG. 27 and fluidic assemblies 2700, at either end of pump body 3160 which houses within, at either end, first and second coils 3120 and 3130 and disposed axially piston magnet 3110 having its poles disposed axially along the axis of the outer body 3160. Accordingly, activation of the first and second coils 3120 and 3130 results in electromagnetic force being applied to the piston magnet 3110 in a direction determined by the coil activated. Optionally within the first and second fluidic assemblies 3100A and 3100B respectively there are disposed first and second magnets 3140 and 3150 respectively having their poles facing towards the piston magnet 3110 matching to provide repulsive force as the piston magnet 3110 is driven under actuation of first and second coils 3120 and 3130 respectively to the respective ends of the pump body 3160. Alternatively first and second magnets 3140 and 3150 can be orientated in the reverse pole orientations to those shown such that rather than repulsive force as the piston magnet 3110 is driven attractive force is provided. In these optional configurations different electrical activation profiles of the first and second coils 3120 and 3130 respectively. Optionally, these magnets can be pieces of formed from a soft magnetic material such that they are magnetized based upon the excitation of the first and second coils 3120 and 3130 respectively. First and second magnets 3140 and 3150 also result in an increased magnetic flux confinement improving efficiency of the ECPUMP 3100.

Figure 32:
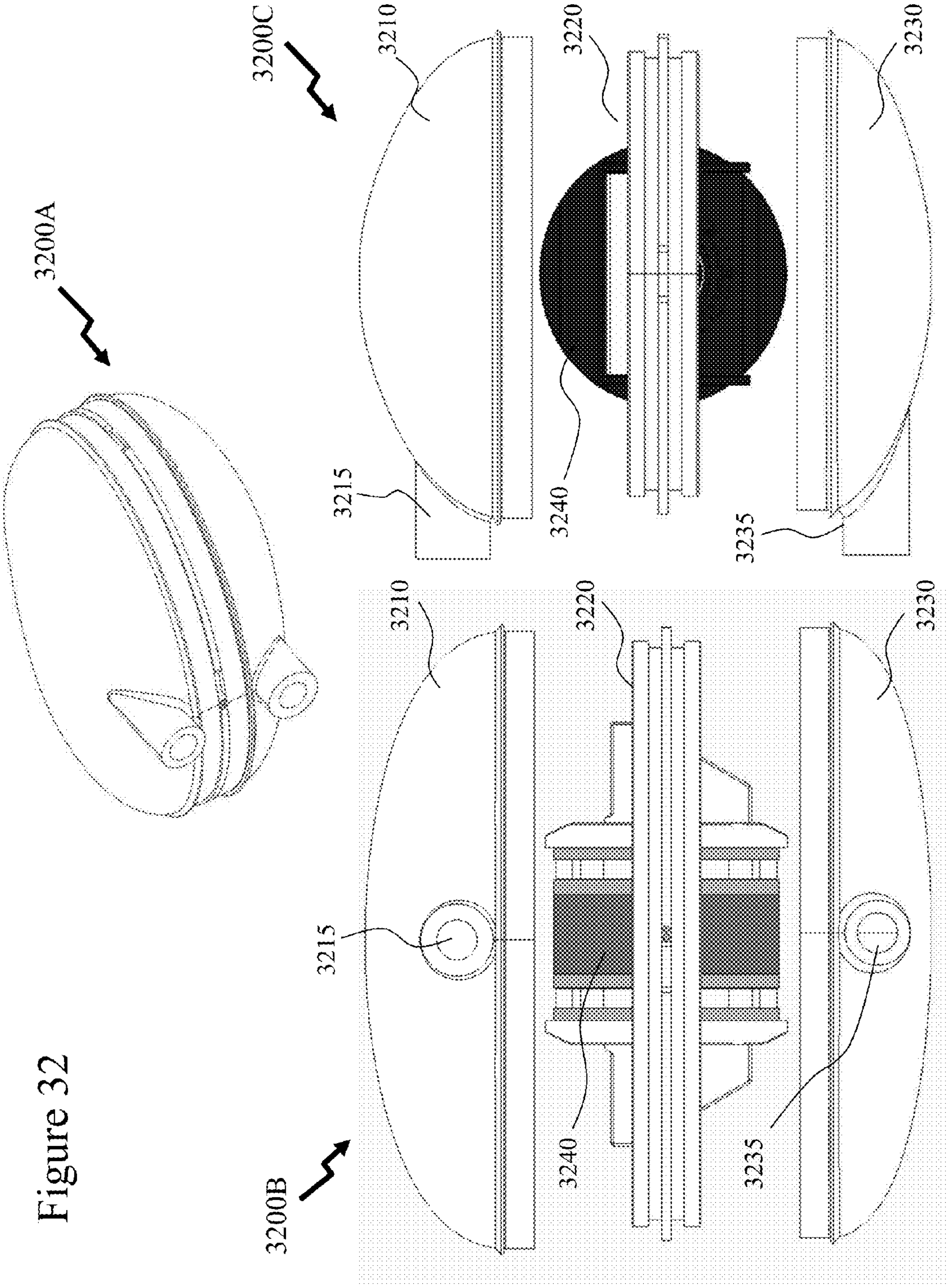
FIGS. 32 and 33 depict an electronically controlled pump (ECPUMP) according to an embodiment of the invention exploiting full cycle fluidic action.
Figure 33:
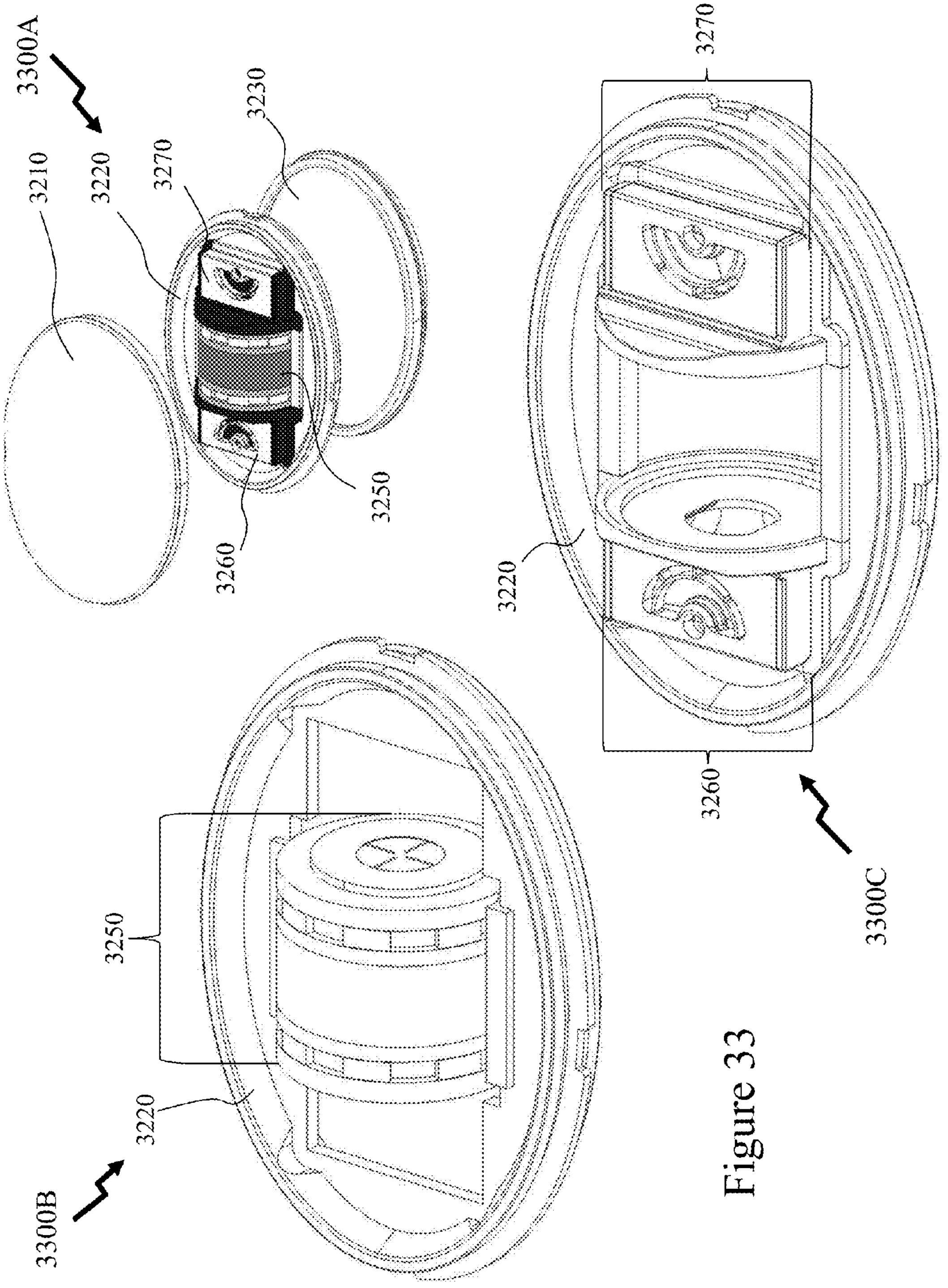

FIGS. 32 and 33 depict an electronically controlled pump assembly (ECPA) according to an embodiment of the invention exploiting full cycle fluidic action. Referring first to FIG. 32 first to third views 3200A to 3200C the ECPA is depicted in assembled, partially exploded end view, and partially exploded side views respectively. As shown ECPA comprises upper clam shell 3210, with inlet port 3215, and lower clam shell 3230 with outlet port 3235 which mount either side of motor frame 3220 upon which electronically controlled fluidic pump assembly (ECFPA) 3240 is mounted. As evident from first to third perspective views 3300A to 3300C in FIG. 33 ECFPA 3240 comprises first and second valve assemblies (VALVAS) 3260 and 3270 disposed at either end of electronically controlled magnetically actuated fluid pump (ECPUMP) 3250. Beneficially, the ECPA depicted in FIGS. 32 and 33 reduce the mass of water being driven by the pump close to a minimum amount as the outlet after the valve opens directly into the body of fluid within the ECPA.

Optionally, where upper clam shell 3210 and lower clam shell 3230 are implemented to provide elasticity under action of the ECPUMP then these act as fluidic capacitors as described within this specification. In other embodiments such fluidic actuators can have sufficient volume to act as the reservoir for the device rather than requiring the present of a separate reservoir. Alternatively, upper clam shell 3210 and lower clam shell 3230 are rigid such that no fluidic capacitor effect is present in which case these would vibrate at the pump frequency and the fluid leaving/entering the clam shell would be pulsating. Beneficially in both the flexible and stiff shell configurations the upper and lower clam shells 3210 and 3230 can provide directly vibratory excitation to the user. In fact, directly coupling the inlet port 3215 to outlet port 3235 provides a self-contained fluidically actuated device, i.e. a vibrator with flexible upper and lower clam shells 3210 and 3230 which is capable of providing users with vibrations at frequencies not attainable from prior art mechanical off-axis motors. Conversely, a rigid or stiff walled clam shell will not vibrate with much amplitude, but it will provide a pulsating water flow.

Figure 34A:
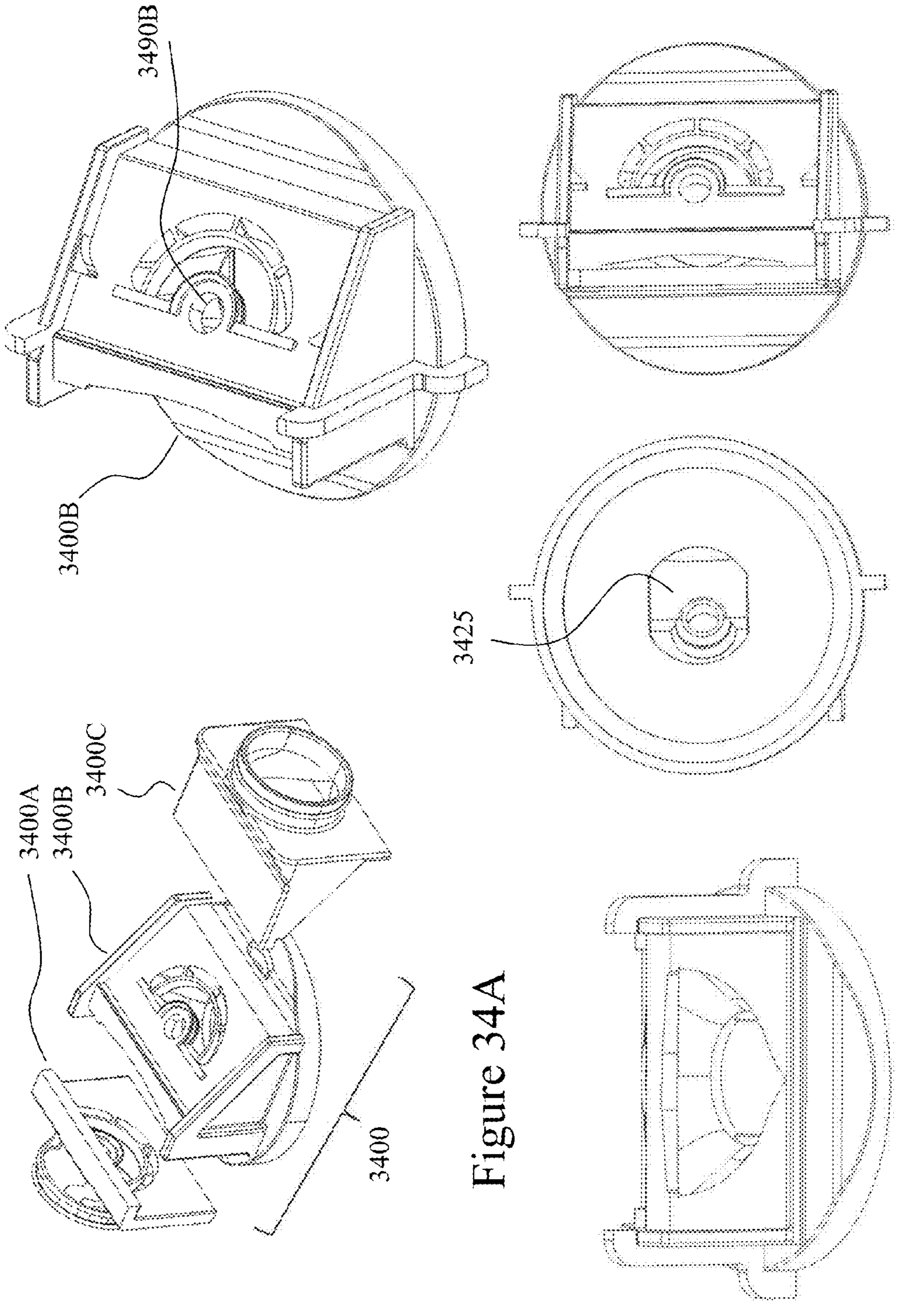
FIGS. 34A through 34C depict an assembly for mounting to an ECPUMP according to an embodiment of the invention to provide inlet and outlet ports with non-return valves.
Figure 34B:
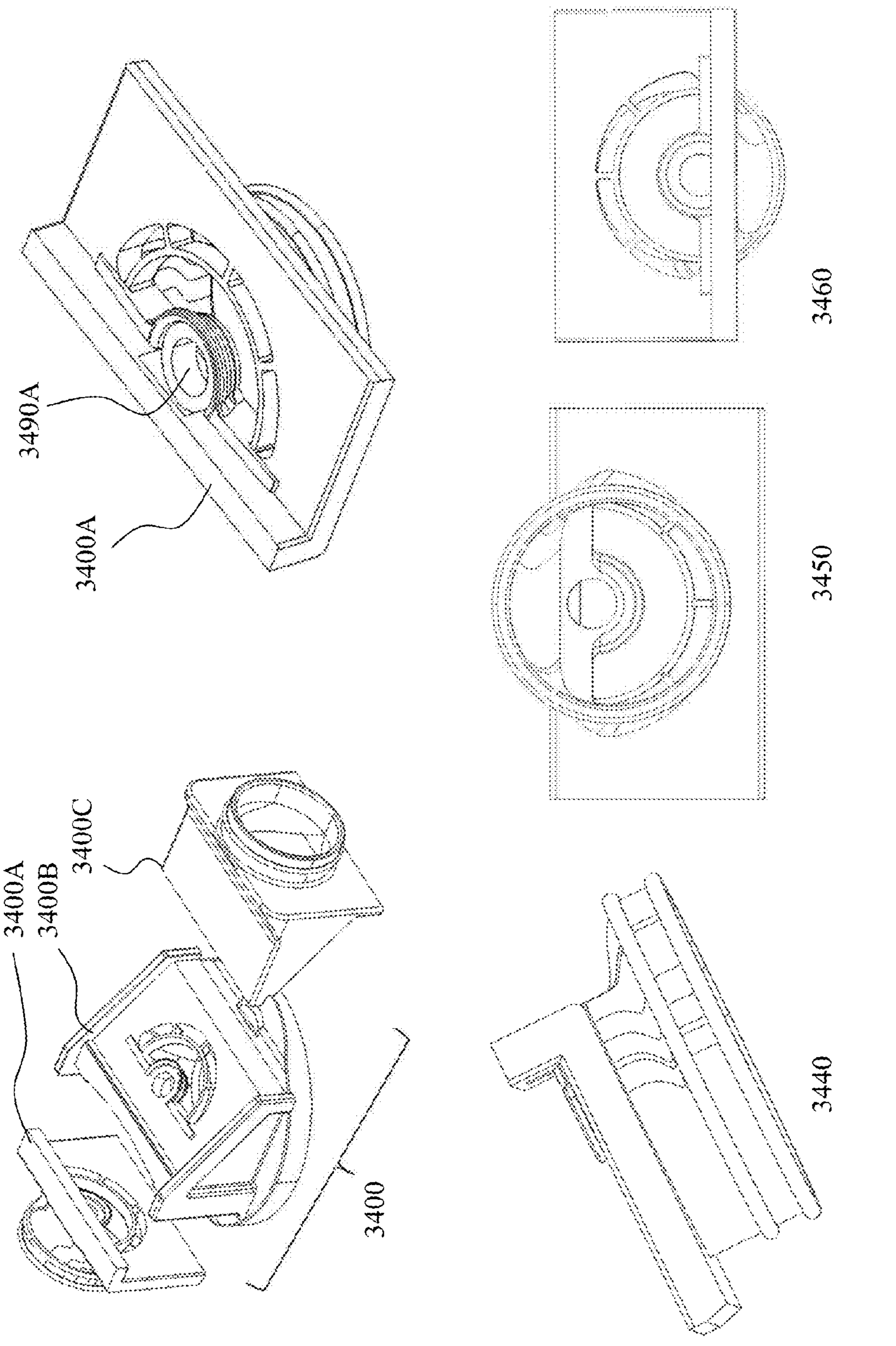
Figure 34C:
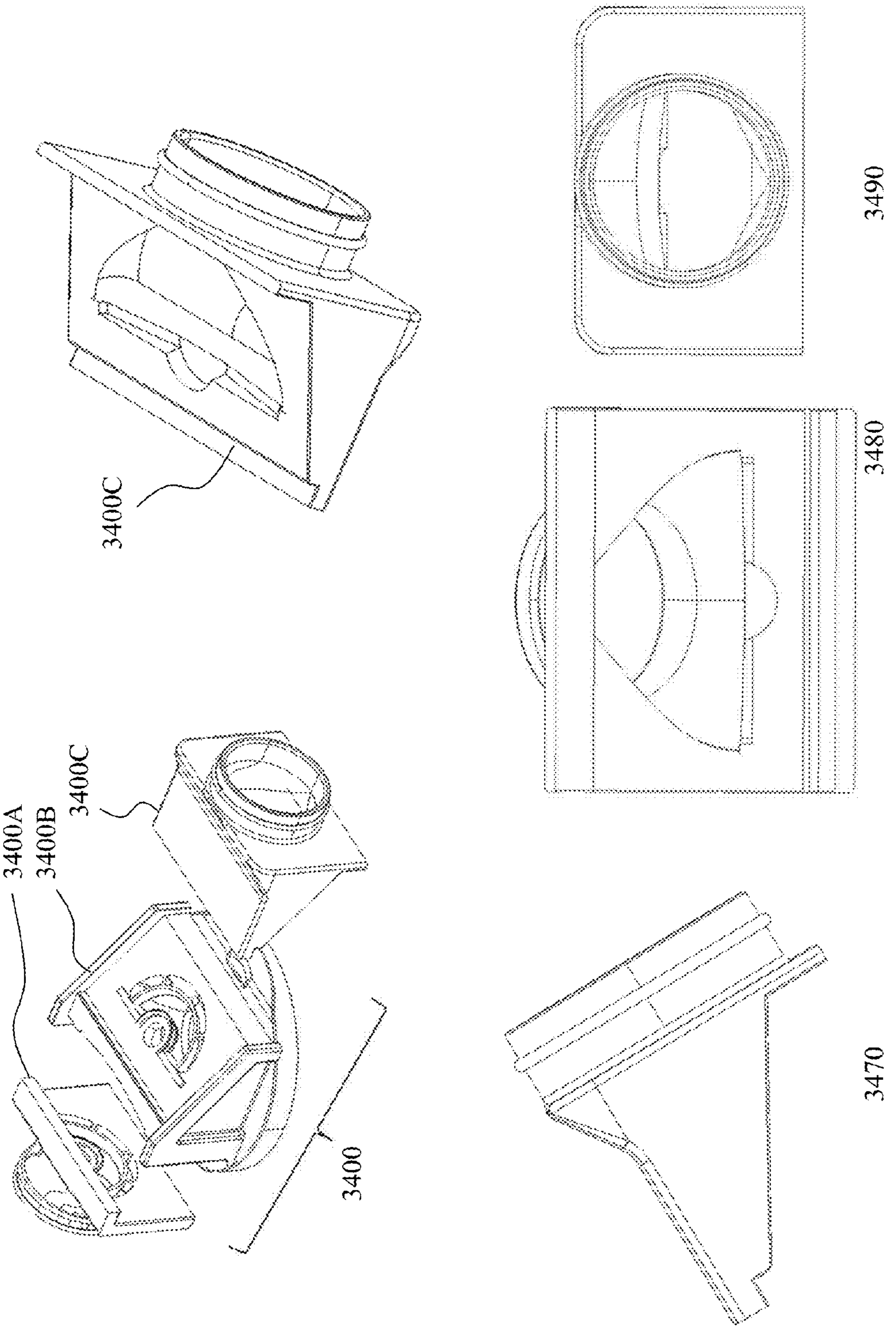

A VALVAS, such as VALVAS 3260 or 3270 in FIG. 32 according to an embodiment of the invention provide inlet and outlet ports with non-return valves such as depicted in FIGS. 34A through 34C for assembly to ECPUMP 3250. Referring initially to FIG. 34 an exploded view of the VALVAS 3400, such as providing the first and second VALVAS 3260 and 3270 in FIG. 32 is depicted. This comprises inlet manifold 3400A, valve body 3400B, and outlet manifold 3400C. Valve body 3400B is also depicted in perspective view in FIG. 34A as well as an end elevation 3410, bottom view 3420, and plan view 3430. Assembling to the valve body 3400B is inlet manifold 3400A as depicted in FIG. 34B in perspective view as well as a side elevation 3440, front view 3450, and rear view 3460. Mounted to the inlet manifold 3400A, via first mounting 3490A, is a valve (not shown for clarity), such as half valve 3900E in FIG. 39, which is disposed between inlet manifold 3400A and valve body 3400B. Accordingly, the motion of this valve is restrained in one direction by inlet manifold 3400A but unrestrained by valve body 3400B and accordingly fluid motion is towards the valve body 3400B. Also assembled to the valve body 3400B is outlet manifold 3400C as depicted in FIG. 34C in perspective view as well as a side elevation 3470, bottom view 3480, and front elevation 3490. Mounted to the valve body 3400B via second mounting 3490B, is a valve (not shown for clarity), such as half valve 3900E in FIG. 39, which is therefore disposed between outlet manifold 3400C and valve body 3400B. Accordingly, the motion of this valve is restrained in one direction by valve body 3400B but unrestrained by outlet manifold 3400C. Accordingly, fluid motion is away from valve body 3400B such that the overall combination of inlet manifold 3400A, valve body 3400B, outlet manifold 3400C and the two valves not shown function as inlet/outlet non-return valves coupled to a common port, this being the opening 3425 in the bottom of the valve body 3400B that is adjacent to the piston face.

Figure 35:
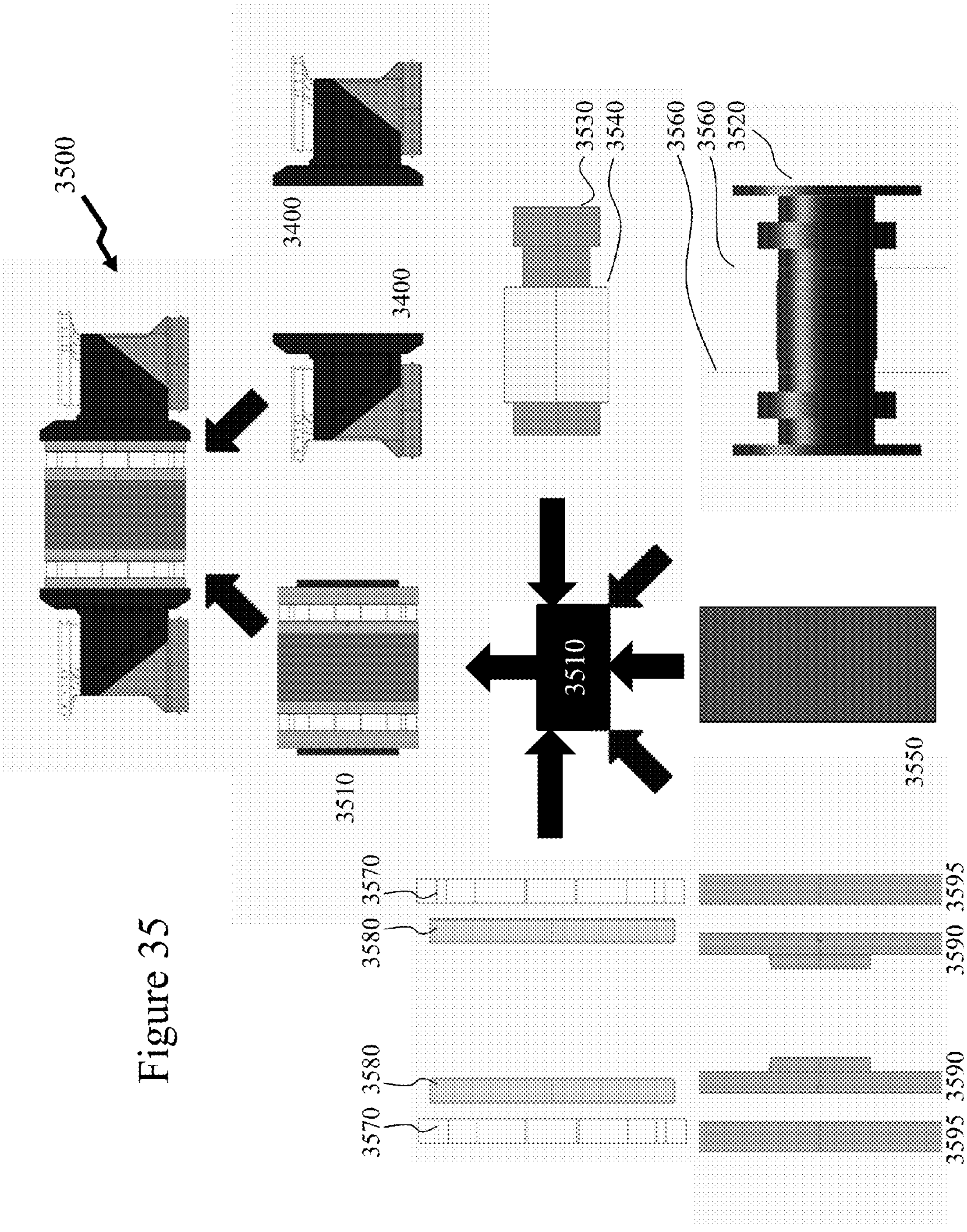
FIGS. 35 to 36D depict compact and mini ECPUMPs according to embodiments of the invention.
Figure 36A:
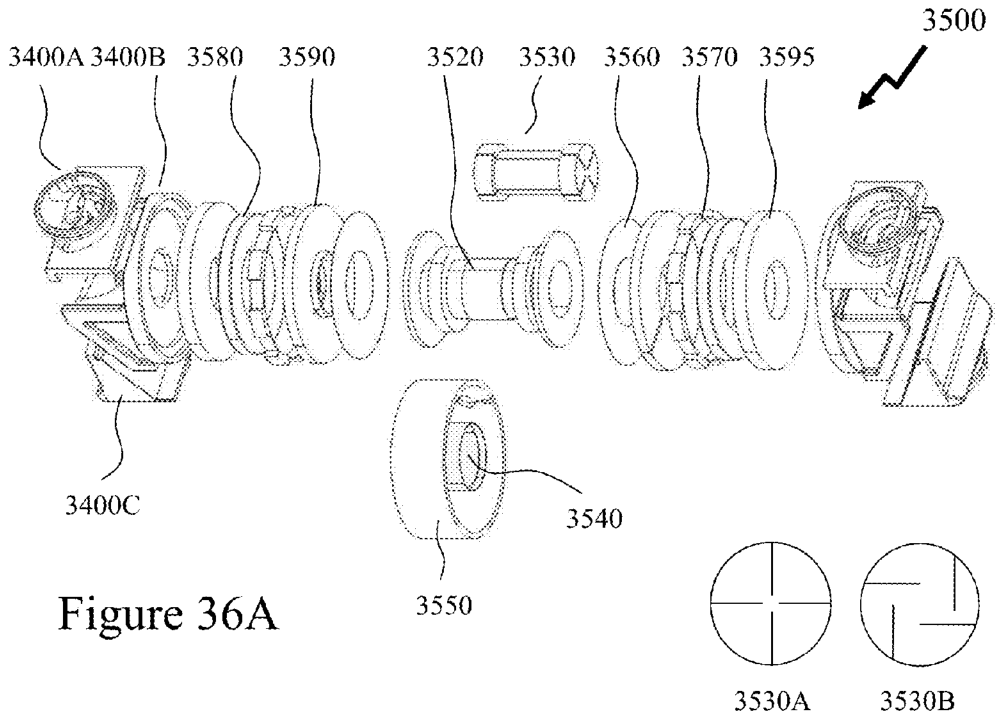
Figure 36B:
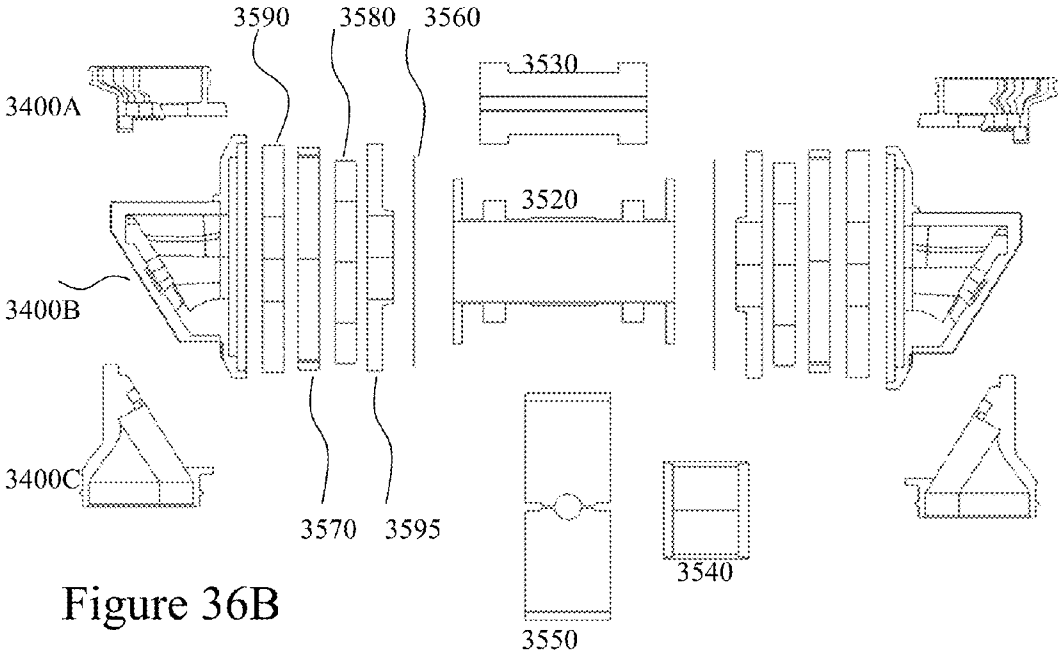
Figure 36C:
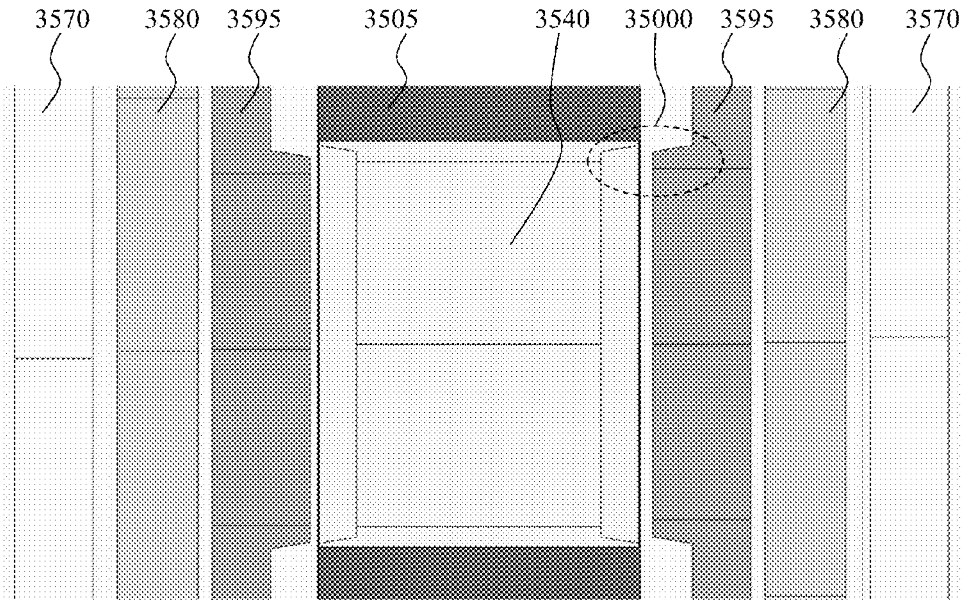

Now referring to FIGS. 35 to 36B there are depicted different views of a compact ECPUMP 3510 according to an embodiment of the invention, which together with inlet and outlet VALVAS 3400 provides ECFPA 3510 with full cycle fluidic action when combined with appropriate external connections. Referring to FIGS. 35, 36A, and 36B the ECPUMP 3510 is shown schematically exploded inside perspective, exploded in perspective and shown in cross-sectional exploded form. ECPUMP 3510 comprises piston 3530, bobbin core 3540, bobbin case 3550 and isolating washers 3560 together with outer washers 3595, inner washers 3590, magnets 3580 and magnet casings 3570. These are all supported and retained by body sleeve 3520 which can, for example, be injection molded once the remaining elements of ECPUMP 3510 have been assembled within an assembly jig. As depicted in FIG. 36C with exploded detail cross-section it can be seen that the inner washers 3590 self-align with the inner profile of the bobbin core 3540 as shown within region 35000. Isolation washers 3560 having been omitted for clarity. Accordingly, with subsequent positioning of magnets 3580 and magnet casings 3570 it would be evident that the resultant magnetic field profiles are appropriately aligned through the washers though the self-alignment from the bobbin core. Piston 3530 is also depicted in end-views 3530A and 3530B which show two different geometries of slots machined or formed within the piston 3530 which disrupt the formation of radial/circular Eddy currents, electrical currents, and/or radial/circular magnetic fields within the piston 3530.

Dimensions of an embodiment of ECPUMP 3510 are depicted and described below in respect of FIG. 44. However, it would be evident that other dimensioned ECPUMPs can be implanted according to the overall requirements of the fluidic system. For example, with a 1.4" (approximately 35.6 mm) diameter and 1.175" long (approximately 30 mm) ECPUMP with diameter 0.5" (approximately 12.7 mm) and 1" (approximately 25.4 mm) long piston the pump generates 7 psi at a flow rate of 3 l/minute. Accordingly, such a pump occupies approximately 2.7 cubic inches and weighs about 150 grams. Other variants have been built and tested by the inventors for ECPUMP with diameters 1.25" to 1.5" although other sized ECPUMPs can be built.

Figure 36D:
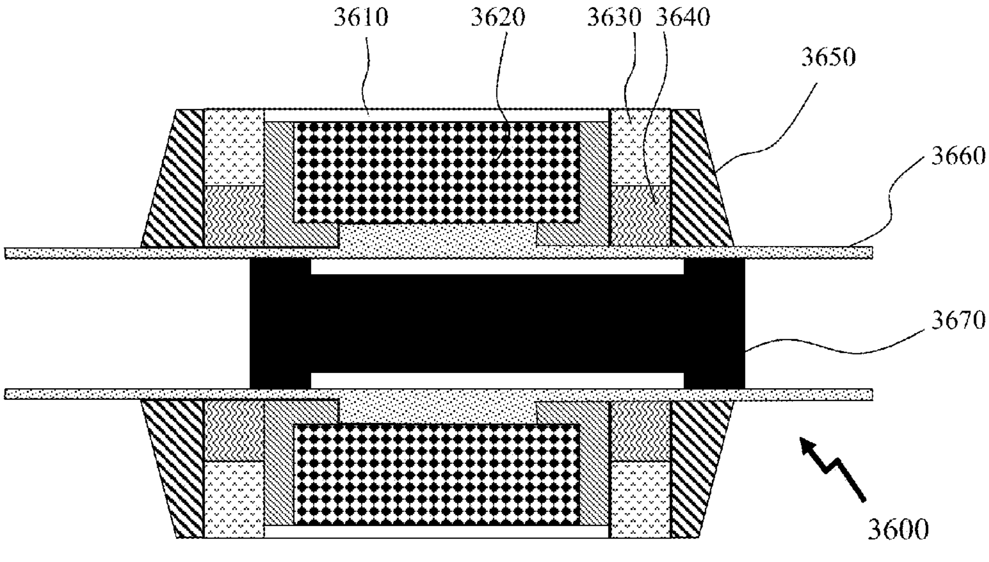

The VALVAS can, for example, mount over the ends of the bobbin core 3540. Alternatively, a multi-part bobbin core 3540 can be employed which assembles in stages along with the other elements of the ECPUMP 3510. In each scenario the design of ECPUMP 3510 is towards a low complexity, easily assembled design compatible with low cost manufacturing and assembly for commodity (high volume production) and niche (low volume production) type applications with low cost such as a device. A variant of the ECPUMP is depicted in FIG. 36D with Mini-ECPUMP 3600 which similarly comprises coil 3620, outer body 3610, magnet 3630, magnet support 3640, and outer washers 3650 which are all mounted and assembled around body sleeve 3660 within which piston 3670 moves. Embodiments of Mini-ECPUMP 3600 assembled and tested by the inventors have outer diameters between 0.5" (approximately 12.7 mm) and 0.625" (approximately 16 mm) with length 0.75" (approximately 19 mm) using a 0.25" (approximately 6 mm) diameter piston of length 0.5" (approximately 12.5 mm). Such Mini-ECPUMPs 3600 maintain a pressure of approximately 7 psi with a flow rate proportionally smaller and weigh approximately 20 grams. Optionally, magnetic support 3640 can be omitted.

Figure 37A:
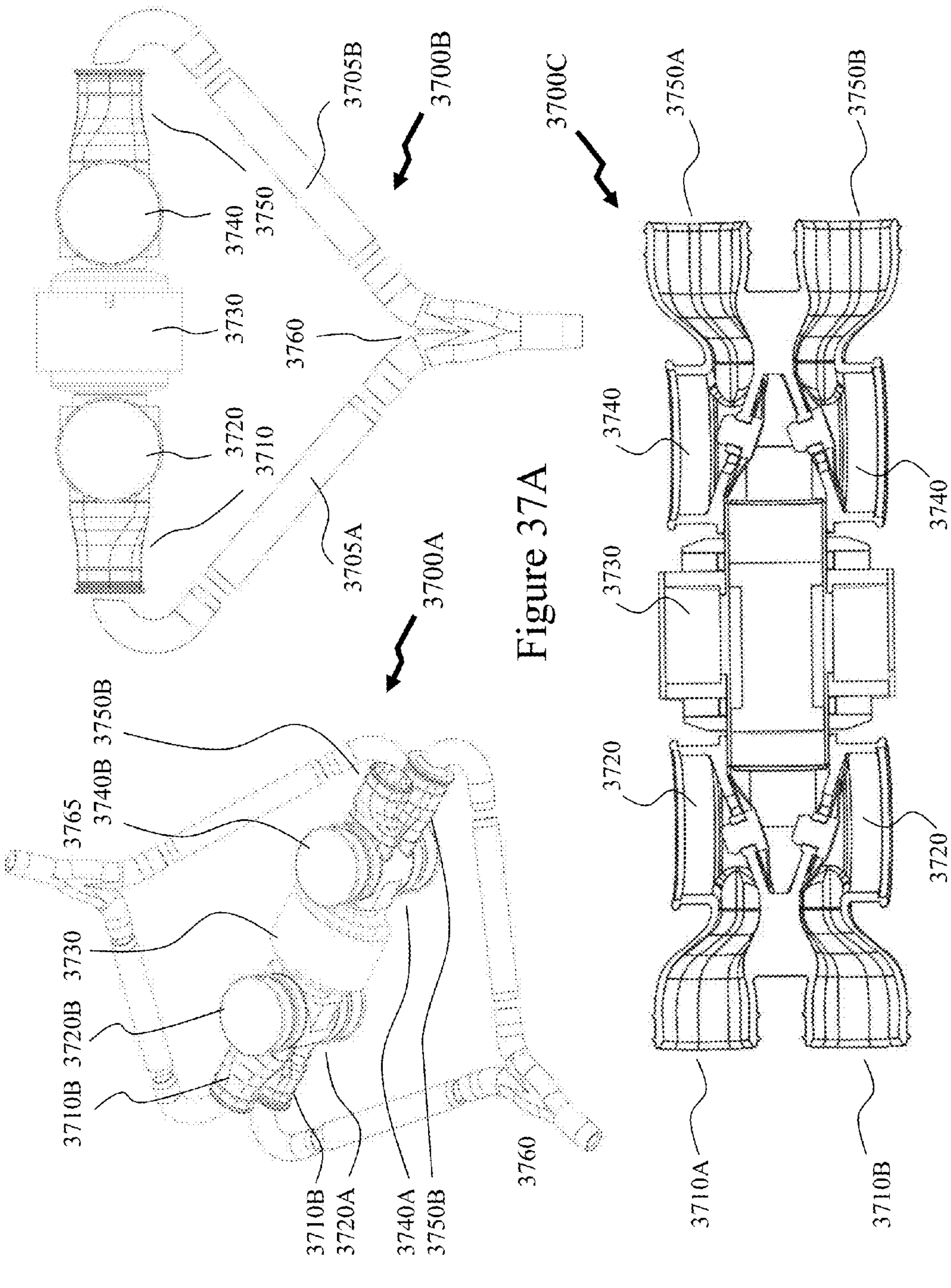
FIGS. 37A and 37B depict a compact ECPUMP according to an embodiment of the invention with dual inlet and outlet valve assemblies coupling to a fluidic system together with schematic representation of the performance of such ECPUMPs with and without fluidic capacitors.
Figure 37B:
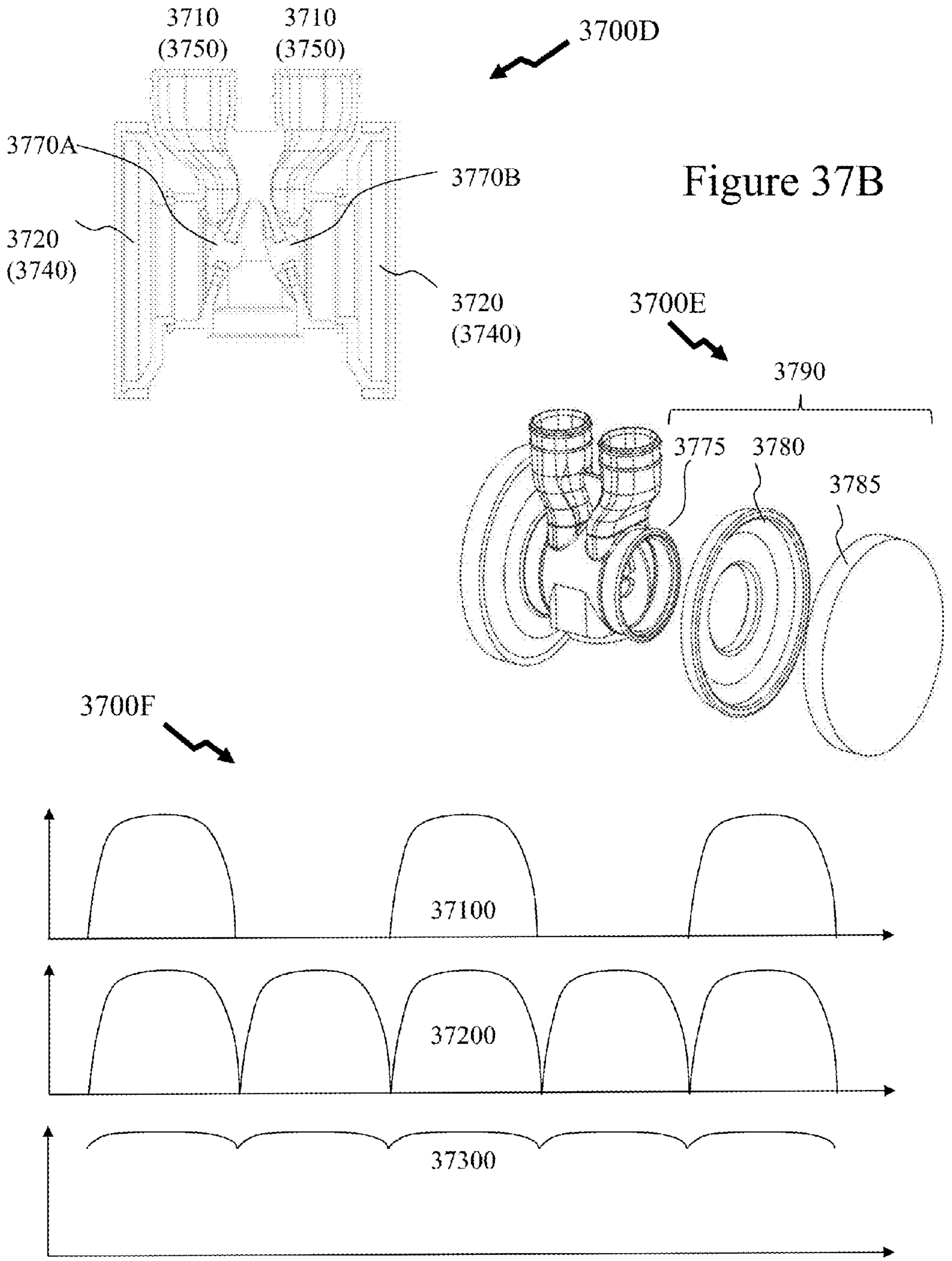

Now referring to FIGS. 37A and 37B there are depicted a compact ECPUMP according to an embodiment of the invention with dual inlet and outlet valve assemblies coupling to a fluidic system together with schematic representation of the performance of such ECPUMPs with and without fluidic capacitors. In FIG. 37A first to third views 3700A to 3700C respectively relate to an ECPUMP 3730 according to an embodiment of the invention supporting dual fluidic systems. As depicted in second view 3700B ECPUMP 3730 has to one side first VALVAS 3720 and first ports 3710 whilst at the other side it has second VALVAS 3740 and second ports 3750. As depicted in the perspective view of first view 3700A there are a pair of first ports 3710A/3710B connecting to dual first VALVAS 3720A/3720B on one side of ECPUMP 3730 whilst on the other side there are a pair of second ports 3720A/3720B connecting to dual second VALVAS 3720A/3720B. Accordingly as evident in cross-sectional view 3700C motion of the piston within ECPUMP 3730 towards the right results in fluid being drawn from first port 3710A through first VALVAS 3720 on the left hand side (LHS) and fluid being pushed out through second VALVAS 3740 into second port 3750B. In reverse as the piston moves to the left fluid is drawn from second port 3750A through second VALVAS 3740 whilst fluid is expelled through first VALVAS 3720 into first port 3710B. This cycle when repeated pulls fluid from second Y-port 3765 and pushes it through first Y-port 3760. Connection tubes 3705A and 3705B can in some embodiments of the invention be rigid whilst in others they can be "elastic" such that if the pressure rises above a predetermined value then these expand prior to a check valve, such as depicted in respect of FIG. 42, opens. Accordingly, a temporary over-pressuring of the fluidic system can be absorbed prior to the check valve opening. For example, connections tubes 3705A and 3750B can be designed to expand at pressures above 7 psi whilst the check valve triggers at 8 psi.

In FIG. 37B expanded and exploded views 3700D and 3700E depict the VALVAS/port configurations with first and second valve 3770A and 3770B which provide non-return inlet and outlet valves for each end of the assembled ECPUMP assembly. In exploded view 3700E a VALVAS is depicted wherein adjacent to the valve, e.g. second valve 3770B, a fluidic capacitor 3790 is provided formed from capacitor port 3775, expander flange 3780, and cap 3785. Accordingly, design of the cap 3785 through wall thickness, material selection, etc. provides for a flexible portion of the VALVAS acting as a fluidic capacitor or it can be rigid. Such a fluidic capacitor 3790 being a fluidic capacitor such as depicted and described supra in respect of FIGS. 27, 29, and 31 as well as described below in other variants and variations. Referring to first to third graphs 37100 through 37300 there are depicted schematic representations of the fluidic action from a pump under different configurations including, convention single ended action, what the inventors are referring to as full cyclic fluidic action without fluidic capacitors, and full cyclic fluidic action with fluidic capacitors. First graph 37100 depicts the operation of an ECPUMP wherein a single end of the ECPUMP is configured with inlet/outlet non-return valves such as described supra in respect of FIGS. 33 to 36B and 37A.

Accordingly, on each cycle the pump pushes fluid on only the second half of the cycle. In second graph 37200 an ECPUMP configuration such as described in FIG. 37A is depicted wherein the two ends of an ECPUMP are coupled together via common inlet/outlet ports, such as first and second Y-ports 3760 and 3765 respectively. Accordingly, on each half cycle fluid is pumped to the outlet Y-port such that the fluidic system sees and overall fluidic profile as depicted in second graph 37200 such that the "left" and "right" half cycles are combined. However, in many applications such as devices the resulting physical pulsations can be undesired (or alternatively very desired) as they occur at double the drive frequency of the drive signal to the ECPUMP. Accordingly, the inventors have established that fluidic capacitors disposed in close proximity to the valves act to suppress and smooth the sharp pressure drops within second graph 37200 by essentially making the fluidic time constant of the system longer than the frequency response of the ECPUMP. This results in a smoothed output curve from the ECPUMP providing enhanced performance of the ECPUMPs within the devices and other devices according to embodiments of the invention. According to embodiments of the invention fluidic capacitors can optionally be disposed before and/or after the dual fluidic paths meet and/or split. Further, by design in respect to geometry, wall thickness, material, etc. the properties of these fluidic capacitors can be varied to provide varying absorption/reduction of fluidic variations from the ECPUMPs and/or EAVs according to embodiments of the invention. In other embodiments of the invention the outputs from an ECPUMP, for example, can be coupled to a first set of fluidic actuators before being combined in conjunction with fluidic capacitors to provide the fluid activation of a second set of fluidics actuators. In this manner, a set of first fluidic actuators receive pulsed inputs and vibrate accordingly whilst the second set of fluidic actuators receive a constant input and provide extension/expansion for example. Optionally, prior to the set of first fluidic actuators another set of fluidic capacitors are employed which smooth the pulsed ECPUMP/EAV output to a more sinusoidal profile for the first set of fluidic actuators.

Now referring to FIG. 38 there is depicted a compact ECPFA in first view 3800A according to an embodiment of the invention exploiting an ECPUMP 3880 such as ECPUMP 3500 or ECPUMP 3600 as described and depicted in FIGS. 35 to 36D. As depicted ECPUMP 3880 is disposed between upper and lower VALVAS which are variants of VALVAS such as described supra in respect of FIG. 33 to FIG. 35. Accordingly upper VALVAS comprises a first body 3825A with first inlet 3840A with first valve 3830A and first outlet 3810A and second valve 3820A whilst lower VALVAS comprises a second body 3825B with second inlet 3840B with third valve 3830B and second outlet 3810B and fourth valve 3820B. The first and second inlets 3840A and 3840B respectively are coupled to Input Y-tube 3860 whilst first and second outlets 3810A and 3810B respectively are coupled to output Y-tube 3870. Second view 3800B depicts in detail the upper VALVAS.

It is evident that the inner profiles of the first inlet 3850A, first body 3825A, and first outlet 3810A have been profiled. These profiles together with the characteristics of first and second valves 3820A and 3840A are tailored according to the pressure and flow characteristics of the ECPUMP in order to minimize the losses during operation and therefore increasing overall efficiency of the ECPUMP and its associated toy. Additionally, the characteristics of output Y-tube 3870 can be varied in terms of resilience, elasticity, etc. to provide fluidic capacitors by deformation of the output Y-tube 3870 arms rather than the fluidic capacitors as depicted supra in respect of FIGS. 37A and 37B respectively. Optionally, Input Y-tube 3860 can be similarly implemented with predetermined elasticity etc. to provide fluidic capacitors on the input side of the ECPUMP.

Now referring to FIG. 39A there is depicted a compact ECPFA in first and second views 3900A and 3900B respectively exploiting an ECPUMP 3980 according to an embodiment of the invention such as ECPUMP 3500 or ECPUMP 3600 as described and depicted in FIGS. 35 to 36D. Disposed at either end of the ECPUMP 3980 are first and second VALVAS with inlet valves 3930A/3930B and outlet valves 3950A/3950B coupled to inlets 3920A/3920B and outlets 3960A/3960B respectively. In this ECPFA first and second Y-tubes 3910A and 3910B respectively couple the external physical system to the ECPUMP 3980 to exploit the full cyclic fluidic action principle. In contrast to other ECPUMPs described previously ECPUMP 3980 has first and second springs 3940A and 3940B respectively coupled to the piston from first and second housings 3990A and 3990B, respectively. Accordingly, the electromagnetic motion of the piston within ECPUMP 3980 results in alternating compression/expansion of the first and second springs 3940A and 3940B and accordingly their action to return the piston to central position. Accordingly, the drive signals to ECPUMP 3980 can be different to those in ECPUMPs 3500 and 3600 respectively in that a pulse to induce motion will be arrested through the action of the springs rather than combination of electrical control signals applied to the coil within the ECPUMP together with permanent or soft magnets.

FIG. 39B in first view 3900C depicts outer housing 3990 together with housing 3994 to which first and second springs 3940A and 3940B respectively are coupled. Within the pairs of inlets and outlets within housing 3994 each has a mounting 3992 for supporting insertion of the associated inlet or outlet valves 3930A/3950A respectively. Each inlet/outlet valve 3930A/3950A has a valve seat 3996 and fluidic sealing of outer housing 3990 to ECPUMP 3980 is achieved via O-ring 3905. It would be evident to one skilled in the art that other sealing techniques can be applied without departing from the scope of the invention. Within the housing 3994 there are four valves, two inlet valves 3930A and two outlet valves 3950A. This increases the area of valve presented on the inlet and outlet reducing fluid resistant. Optionally, outer housing 3990 can itself be rigid or flexible. When flexible the outer housing 3990 provides a fluidic capacitor which is very close to the inlet and outlet valves.

According to the design of the Y-tube combiners/splitters such as Input Y-tube 3870 and output Y-tube 3860 in FIG. 38 the behaviour of this element in the fluidic system can be made to resonate with the ECPUMP. Beneficially, a resonant Y-tube provides for a “push”/“suck” at the start of a “forward”/“reverse” stroke to help apply force to the piston near the ends of the stroke. This reduces the required magnetic actuation at the extremes of each stroke. As noted supra in respect of third image 3700F in FIG. 37B such a fluidic capacitor by providing a resonator with an overall time constant longer than the ECPUMP operation provides for a smooth running of the ECPUMP and fluidic assembly such that energy is not wasted stroking the mass/column of water upstream or downstream of the ECPUMP.

In addition to all the other design issues identified supra and subsequently for ECPUMPs and ECFPAs according to embodiments of the invention thermal expansion is an issue to address during the design phase based upon factors such as recommended ambient operating temperature range and actual temperature of ECPUMP during projected duration of use by the user. For example, the piston must be allowed to expand and the inner and outer washers 3590 and 3595 respectively in FIG. 35 are designed for larger inner diameter to allow for expansion during operation as ECPUMP heats up. It would be evident that as elements of ECPUMPs/EAVs according to embodiments of the invention can exploit multiple different materials, e.g. iron for piston and plastic for barrel core, that design analysis should include accommodation for thermal expansion of adjacent elements with close tolerances.

It would be evident that ECPUMPs such as described supra in respect of FIGS. 32 through 39B respectively and below in respect of FIGS. 44 to 63 can be implemented without non-return valves on either the input and output ports. It would be further evident that ECPUMPs such as described supra in respect of FIGS. 32 through 39B respectively and below in respect of FIGS. 44 to 63 can form the basis for variants of other electromagnetically driven fluidic pumps such as described supra in respect of FIGS. 26 through 31.

Figure 40:
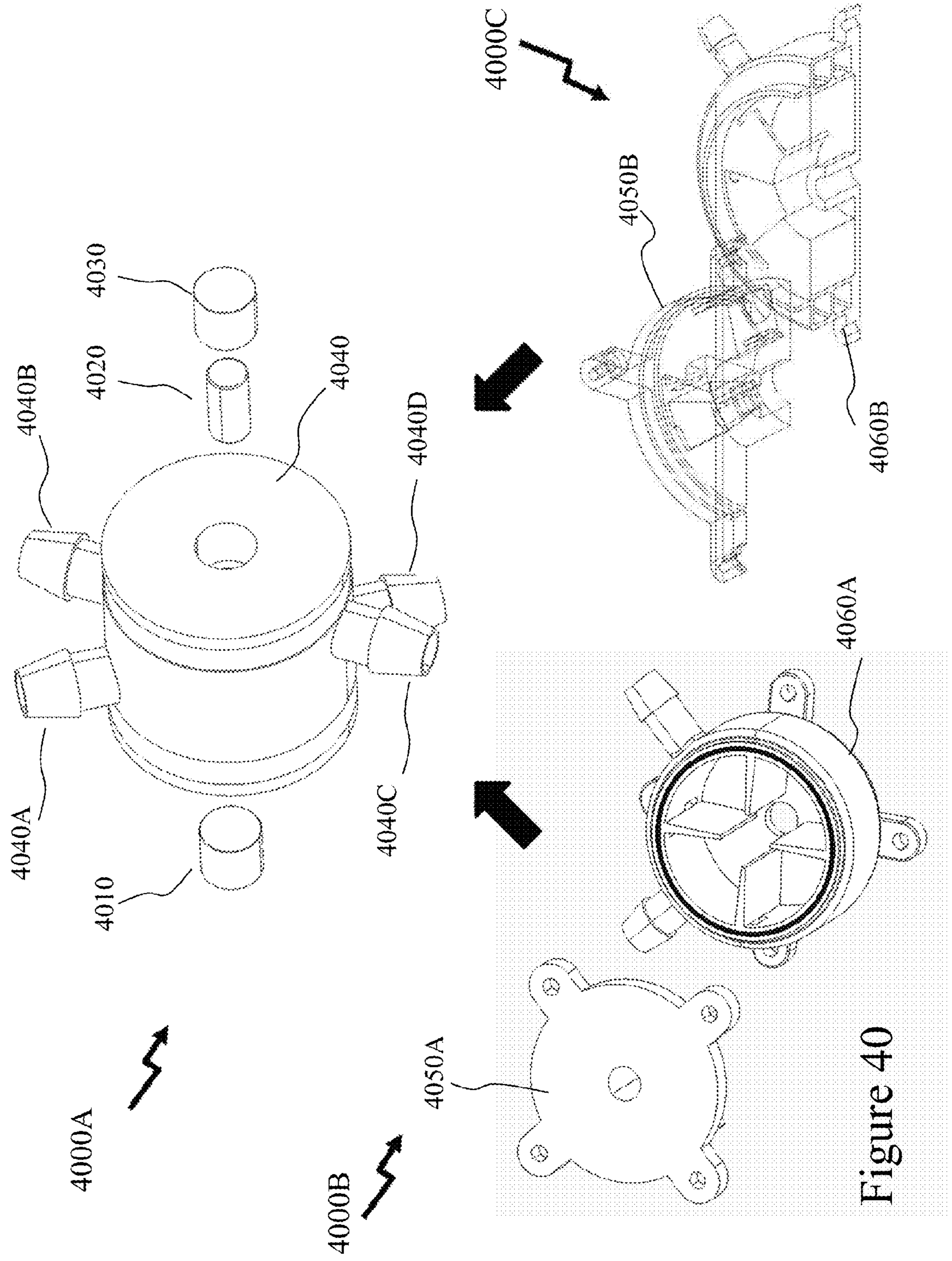
FIG. 40 depicts a compact rotary motion actuator according to an embodiment of the invention.

Now referring to FIG. 40 there are depicted first and second compact rotary motion actuators 4000B and 4000C according to embodiments of the invention. Each comprises an upper body 4050A and 4050B respectively operating in conjunction with a lower body 4060A and 4060B respectively. As depicted in third compact rotary motion actuator 4000A each comprises input ports 4040A/4040D and output port 4040B/4040C for coupling fluid into and out of the compact rotary motion actuator 4000A. Operation of the compact rotary motion actuator is controlled through movement of piston 4020 under electromagnetic actuation (coil etc. omitted for clarity) such that the piston opens/closes openings within lower body 4060A and 4060B respectively coupling fluid into these and rotating the upper body 4050A and 4050B respectively though the fluid impinging the vanes. Rotational motion is limited by vanes within the lower body 4060 and 4060B respectively as depicted. If these are removed free rotation of the upper body relative to the lower body can be provided.

Also depicted in third compact rotary motion actuator 4000A are upper and lower latching elements 4010 and 4030 respectively which allow for latching of the piston 4020 into one or other of the open/closed positions thereby reducing power consumption. Upper and lower latching elements 4010 and 4030 respectively maintain piston 4020 in position until another drive pulse is applied to a coil (not shown for clarity) which then transitions the compact rotary motion actuator between open/closed. Optionally, compact rotary motion actuator 4000A can have upper and lower latching magnets 4010 and 4030 respectively and piston 4020 removed so that the rotary motion is not enabled/disabled within the compact rotary motion actuator 4000A but externally via another valve or switch. Whilst the designs depicted depict four vane assemblies in each of first and second compact rotary motion actuators 4000B and 4000C it would be evident that more vanes can be added increasing the surface area the fluid impinges upon but reducing the angular range of motion.

Figure 41:
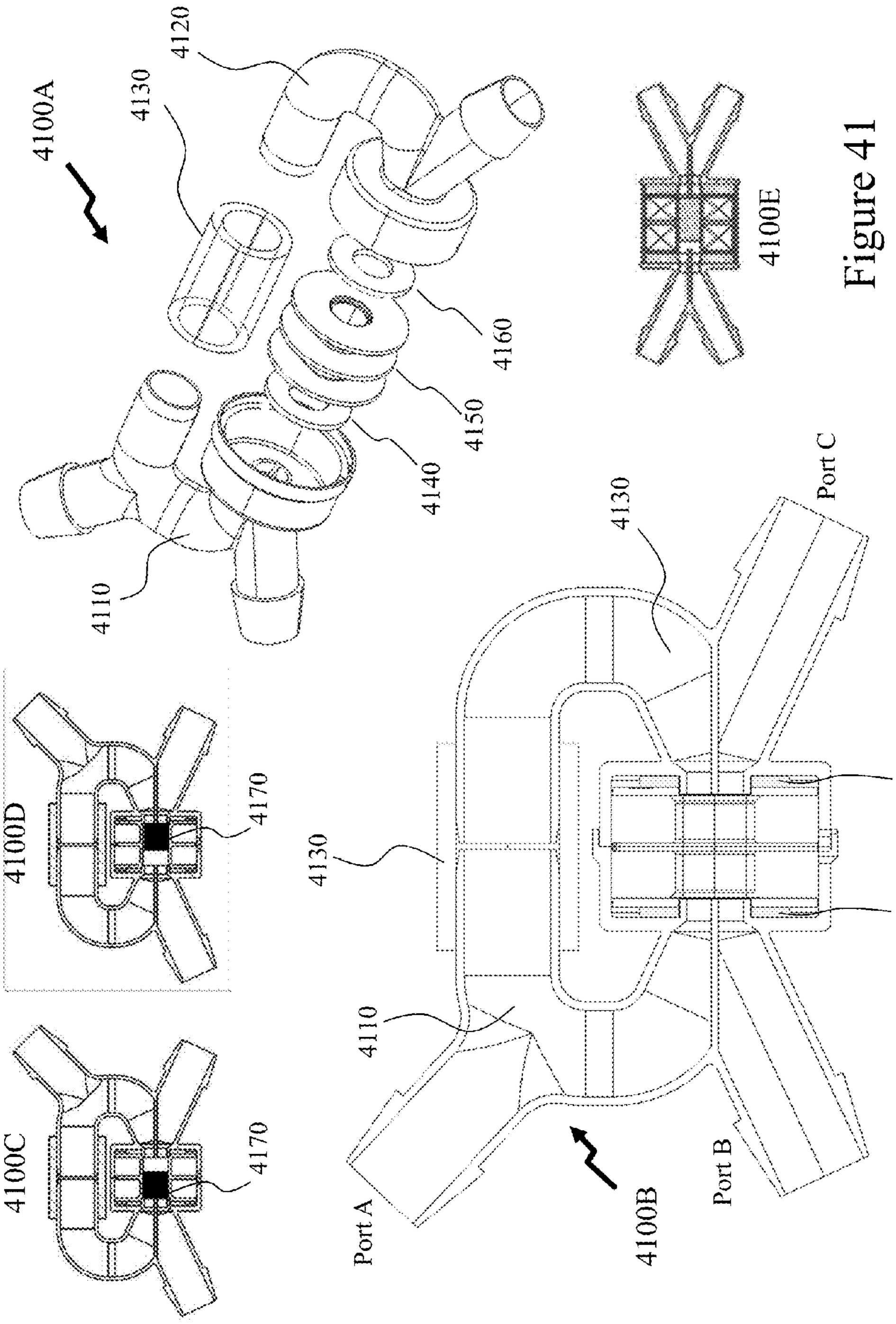
FIG. 41 depicts a compact electronically controlled fluidic valve/switch according to an embodiment of the invention.

Now referring to FIG. 41 there are depicted first to fourth views 4100A through 4100D respectively of a compact electronically controlled fluidic valve/switch (ECFVS) according to an embodiment of the invention. As depicted in first and second views 4100A and 4100B respectively the ECFVS comprises first and second bodies 4110 and 4120 respectively. Disposed between these are coupler 4130 for connecting two ports of these elements and an electronically controlled actuator (ECA) comprising magnetic washers 4140 and 4160. Additional aspects of ECA such as coil etc. have been omitted for clarity but would be evident to one of skill in the art. As evident in third and fourth views operation of the coils results in movement of magnet 4170 to either the left or right thereby blocking/opening either of the right and left routes within the second and first bodies 4130 and 4110 respectively. Magnetic washers 4140 and 4160 provide for latching operation of the ECA.

The ECFVS depicted in FIG. 41 can be considered as two valves coupled back to back where the ECFVS requires only one of Port B and Port C active at any one time. This being depicted in third and fourth views 4100C and 4100D respectively. One such implementation of ECFVS is that Port A is coupled to a fluidic actuator, Port B to the outlet of an ECPUMP, and Port C to an inlet of the (or another) ECPUMP. Accordingly, with Port C "closed" fluid is pumped from Port B to Port A driving the fluidic actuator and then with Port C "open" fluid is withdrawn from the fluidic actuator from Port A to Port C. In another configuration fluid input to Port A can be switched to either Port B or Port C and with suitable electronic control to adjust the position of the piston to both Ports B and C. Optionally, with variable pulse width modulation "PWM" of the control signal the ECFVS in the first configuration could be "dithered" so that even when all fluidic actuators are fully expanded a small amount of fluid is continuously inserted/extracted such that the fluid is always moving within the fluidic system. In the latter configuration variable PWM mode operation can allow to actuators to be simultaneously filled and/or driven with different fill or flow rates. Also depicted is fifth view 4100E of an alternate valve where only one or other of two independent flow paths are to be active. As noted variable pulse operation of the activation coil allows for variable opening ratios such that the valve can also as act a variable fluidic splitter. Embodiments of the invention have open/close times down to 5 milliseconds although typically 10-15 ms coil energizing cycles have been employed.

It would be evident to one skilled in the art that an efficient latching valve has a latching magnetic attraction, which is as small as possible to maintain the piston within the valve against the pressure head it is shutting off. For most devices it is desirable for a valve to be small, fast, have low power operation, and be simple to manufacture. The valve can be one of multiple valves integrated into a manifold. In some valves it can take more power to switch the valve off against a pressure than it is to open it when the pressure is now helping to push the piston. Any of the coil/magnetic driven motors described within this specification can be implemented in alternate designs latch and behave as a valve rather than a pump. A "switching valve" typically would not use one way valves such as a reciprocating pump would likely incorporate. Optionally, a switching valve could be partially powered in DC mode to reduce the latching piston holding force in a controlled manner and allow the closed valve to partially open or conversely the open valve to partially close. Alternatively, switching valves can incorporate closed loop feedback to influence the coil drive signal and therefore the piston's holding force.

Within an EAV such as depicted in FIG. 41 a perfect seal is not always required. In some applications, some leakage of the closed valve, e.g. 1%, can be accommodated as this does not affect materially the operation or the overall efficiency of the system. Consider the design of an EAV depicted in FIG. 41, or another valve/switch, then the gate which seals the switching valve can be formed from a softer conforming material to seat well with the piston face or the gate can be made of the same harder plastic as that the rest of the body is made of Optionally, the piston can be iron and the washers are magnets or the piston can be a magnet and the washers a soft magnetic material. Similarly, single coil, double coil, and a variety of other aspects of the ECPUMP designs can be employed in EAV designs. An EAV can optionally only latch at one end, or there can be alternate designs with gates/ports at one end of the EAV rather than both ends. By appropriate design cascaded EAV elements can form the basis of fluidic switching and regulating circuits.

Figure 42A:
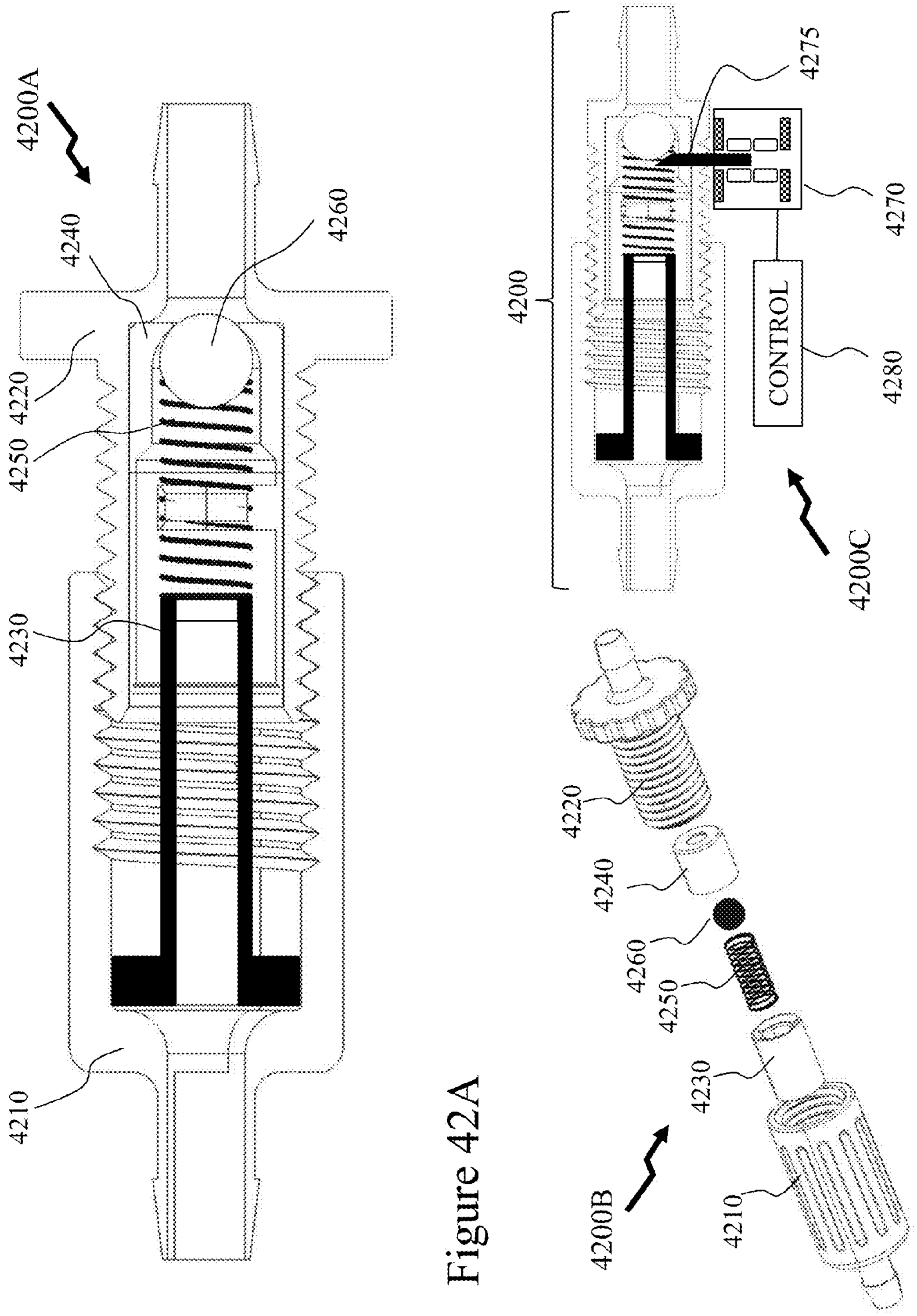
FIG. 42A depicts programmable and latching check fluidic valves according to an embodiment of the invention.

Referring to FIG. 42A there are depicted programmable and latching check fluidic valves according to embodiments of the invention. First view 4200A depicts a programmable check valve comprising body 4210, threaded valve body 4220, spring 4250, spring retainer 4230, bearing housing 4240, and ball bearing 4260. As threaded valve body 4220 is screwed into body 4210 then spring 4250 is compressed by the action of spring retainer 4230 and bearing housing 4240 such that the pressure required to overcome the spring pressure and open the programmable check valve by moving ball bearing 4260 increases. Second view 4200B depicts the programmable check valve in exploded view. Third view 4200C depicts a latching programmable check valve wherein a check value 4200 such as described supra in respect of first and second views 4200A and 4200B respectively has additionally mounted to the threaded valve body a pin 4275 which controlled by electromagnetic drive 4270 which is connected to driver circuit 4280. Accordingly, under direction of driver circuit 4280 the pin 4275 can be engaged behind the ball bearing via the electromagnetic drive 4270. When engaged the pin 4275 prevents the ball bearing moving and accordingly the check valve operating. Accordingly, it would be evident to one skilled in the art that such a latching programmable check valve or latching check valve can resolve hysteresis issues present within prior art pressure relief valves.

Figure 42B:
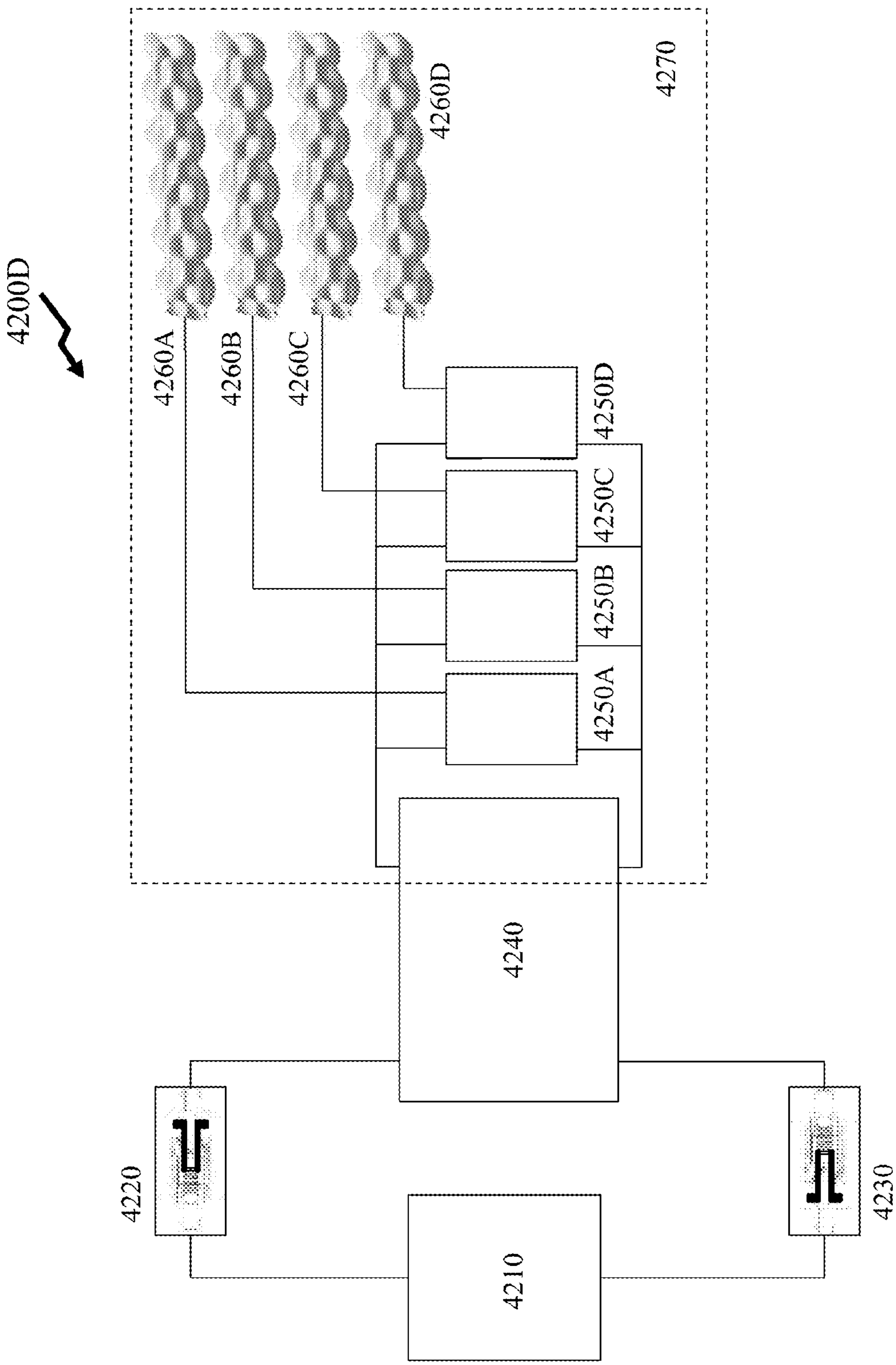
FIG. 42B depicts use of latching check fluidic valves within a fluidic system according to an embodiment of the invention within a device.

Referring to FIG. 42B first and second check valves 4220 and 4230 are employed within a fluidic system 4200D as pressure valves and are disposed between a reservoir 4210 and ECPUMP 4240. The ECPUMP 4240 is also connected to first to fourth valves 4250A through 4250D respectively, such as the ECFVS depicted in FIG. 41 for example. The first to fourth valves 4250A through 4250D respectively are also coupled to the return of the ECPUMP and first to fourth fluidic actuators 4260A through 4260D respectively. ECPUMP 4240 can for example have a structure that the fluidic capacity of the fluidic system 4200D operates under normal conditions without requiring fluid from the reservoir 4210. If that normal operation is that the pressure within the fluidic loop 4270 is 6 psi then first check valve 4220 can be set at 0.5 psi and second check valve 4230 at 6.5 psi. Accordingly if the pressure within loop 4270 increases above 6.5 psi second check valve 4230 opens releasing pressure via the reservoir 4210. If, in contrast, the pressure drops below 0.5 psi then first check valve 4220 opens adding fluid to the loop 4270 from the fluidic reservoir 4210. As typical prior art check valves require large surface areas of the pressure element, e.g. ball bearing 4260, in order to achieve accurate on/off pressure setting a compact check valve such as depicted in FIG. 42A with a small ball bearing will typically have poor accuracy.

However, as discussed in respect of FIG. 41 if the first and second check valves are latching check valves then the valves can be high accuracy as pin 4275 can force the check valve closed earlier than it would automatically and under-setting the check valve means that a rapid opening will be achieved at pressure with disengagement of pin 4275. Alternatively, a latching pressure release valve can be employed which is by default either open or closed and is controlled via a pressure sensor disposed within the fluidic system 4200D to determine when the pin 4275 is engaged or released. Whilst pin 4275 is shown perpendicular to latching programmable check valve in third view 4200C in FIG. 42A other embodiments can include, for example, a pin angled to axis of the latching programmable check valve or multiple pins. A check valve as described supra can also be considered as being a pressure relief valve or pressure regulator.

Figure 43:
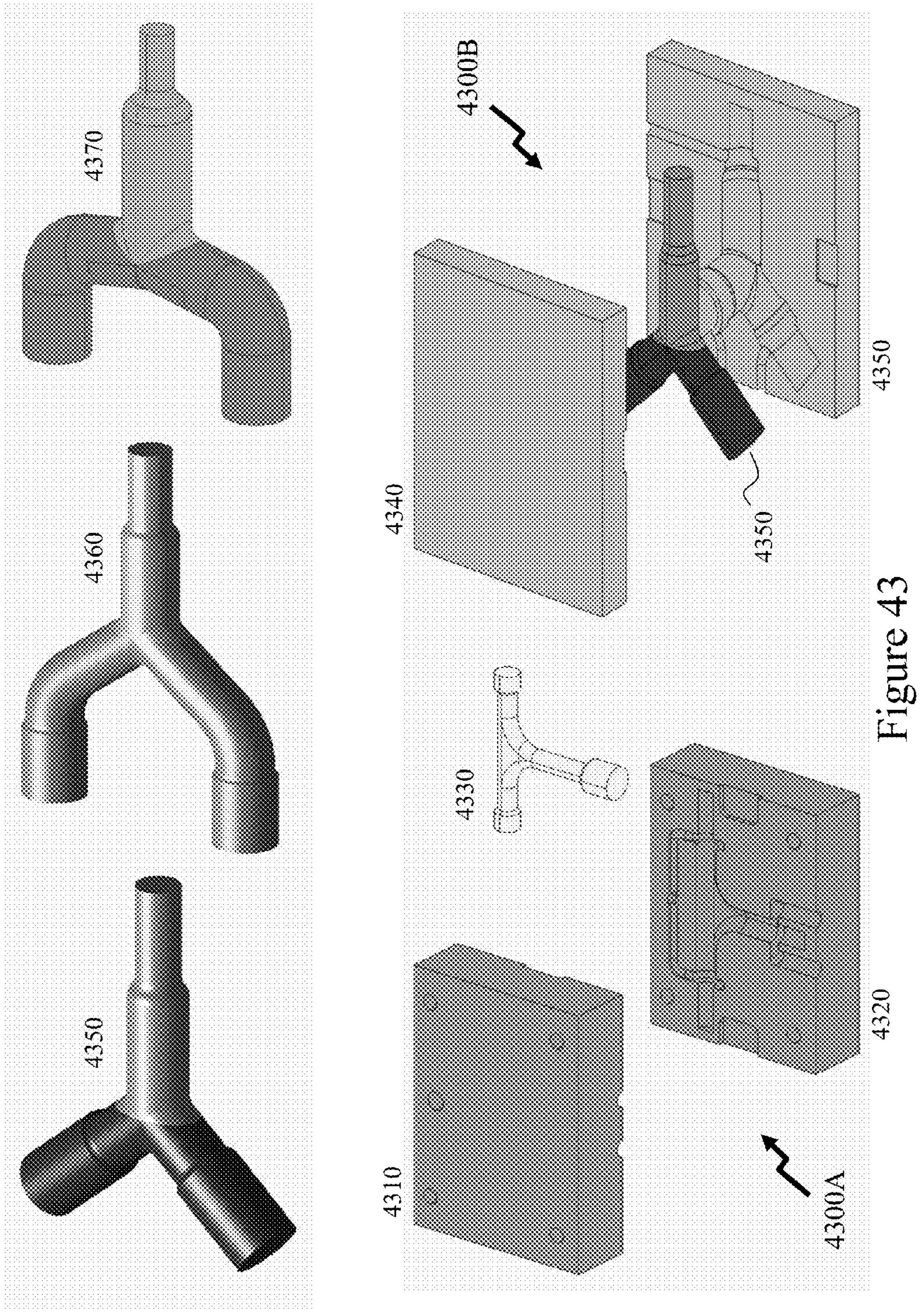
FIG. 43 depicts exemplary Y-tube configurations and molding configurations according to embodiments of the invention.

Referring to FIG. 43 there are depicted exemplary first to third Y-tube configurations 4350 to 4370 such as described supra in respect of Input Y-tube 3860 and output Y-tube 3870 in FIG. 38 and first and second Y-tubes 3910A and 3910B in FIG. 39A. As discussed the properties of these Y-tubes can be varied to provide varying resiliency/elasticity to provide fluidic capacitors to enhance operation of ECPFAs exploiting ECPUMPs according to embodiments of the invention. For example, in FIGS. 38 and 39 the Input Y-tube 3860 and first Y-tube 3910A can be low elasticity whilst the output Y-tube 3870 and second Y-tube 3910B can be highly elastic. The variable elasticity can be provided, for example through use of a different material and/or material composition during a molding process such as depicted in first and second molding configurations 4300A and 4300B respectively in FIG. 43. In each instance upper mold sections 4310/4340 and lower mold section 4320/4350 are aligned and joined before the liquid material for the fourth and fifth Y-tube configurations 4330 and 4360 is poured in, cured, and the fourth and fifth Y-tube configurations 4330 and 4360 removed. Within other manufacturing processes a variable elasticity can be provided by providing molds which allow for variable wall thickness or more complex molding processes exploiting two or more materials and material compositions can be configured.

In other embodiments of the invention alternate processes including, but not limited to, dip coating, casting, and machining can be employed. It would be evident that molding, casting, machining, laser cutting, laser ablation, sand blasting, consolidation etc. are all manufacturing processes that can be applied to the piece parts of the ECFPAs and ECPUMPs described. For example, the piston can be formed through compression of a powder through a predetermined process of temperature and pressure with or without the addition of a binder/matrix to support the iron particles. Within another embodiment of the invention a magnetically active material can be embedded within a matrix that is electrically non-conductive. In this manner a piston can be manufactured within the requirement for slots to be machined within it to reduce/disrupt electrical and magnetic currents flowing radially through the piston. The same issue arises with the inner and outer washers which the inventors has slotted to stop such radial currents/fields being established within these washers.

Referring to FIG. 44 there are depicted a cross-section view 4400A and dimensioned compact ECPUMP 4400B according to an embodiment of the invention exploiting the concepts described and depicted in respect of FIGS. 32 to 39A; Cross-section view 4300 provides reference to the dimensions employed by the inventors within simulations and modeling of ECPUMPs according to embodiments of the invention as well as nomenclature of variants in physical experiments and devices. Accordingly, reference to these dimensions is made below in respect to FIGS. 45 through 57 respectively. Dimensioned compact ECPUMP 4400B represents an embodiment of the invention as described in respect of FIGS. 32 to 36C and FIGS. 37 to 39A. Compact ECPUMP 4400B is 1.4" (approximately 35.6 mm) diameter and 1.175" long (approximately 30 mm) with a 0.5" (approximately 12.7 mm) by 1" (approximately 25.4 mm) long piston. Compact ECPUMP 4400B generates 7 psi at a flow rate of 3 l/minute occupying approximately 2.7 cubic inches and weighing about 150 grams.

Figure 45:
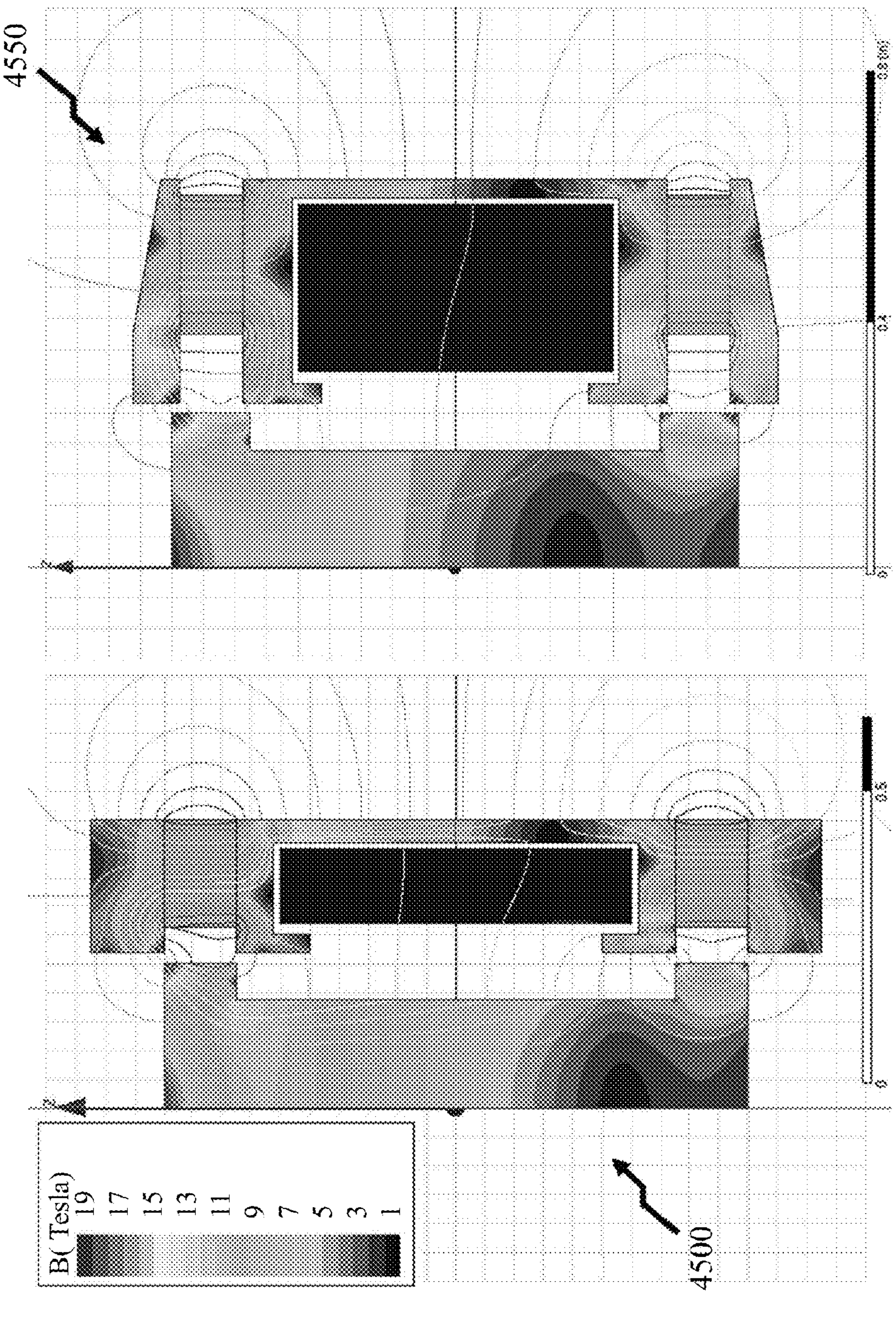
FIGS. 45 and 46 depict finite element modelling (FEM) results of magnetic flux distributions for compact ECPUMPs obtained during numerical simulation based design analysis.
Figure 46:
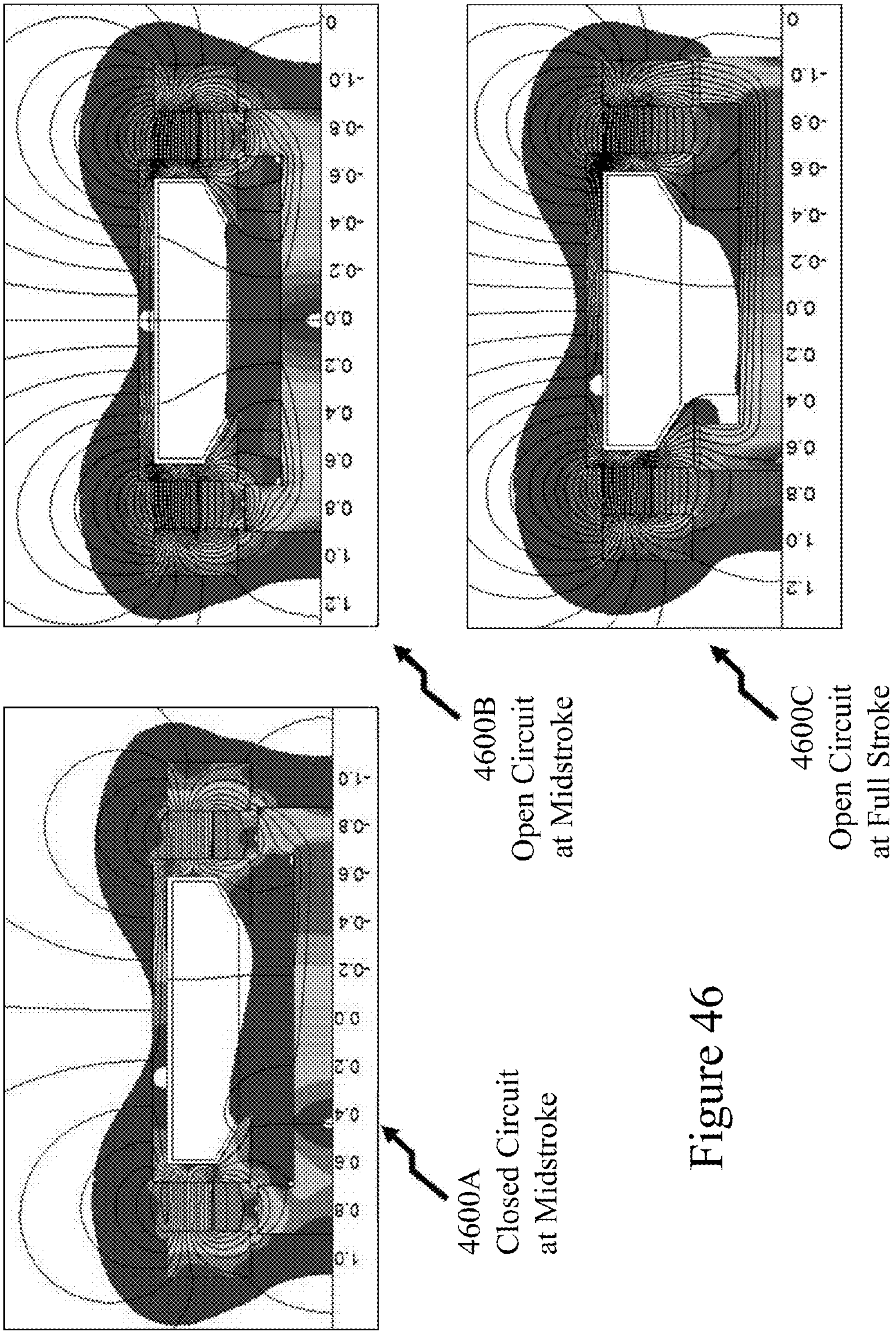

Now referring to FIGS. 45 and 46 there are depicted FEM modeling results of magnetic flux distributions for compact ECPUMPs obtained during numerical simulation based design analysis simulations run by the inventors. In FIG. 45 first FEM 4500 depicts a design, Design 6, according to an initial design with 0.625" outer diameter and length 0.75." The magnet thickness was Tm=0.075", stator length Ty=0.450", stator tooth tip Hst=0.025", slot opening b=0.250", and piston "tooth" length Trt=0.100" with an overall linear stroke Z=0.140". First FEM 4500 depicts the magnetic fluxplot at I=1.0 A for Z=0.000", i.e. midstroke. With an N42 NdFeB magnet, 192 turns of 28 AWG wire and a force constant of $K_f \approx 1.0$ lbf/A the RMS input power was approximately 0.5 W with sinusoidal drive. Second FEM 4550 depicts a subsequent design iteration, Design 21, according to an initial design with 0.625" outer diameter and length 1.025." The magnet thickness was Tm=0.100", stator length Ty=0.675", stator tooth tip Hst=0.030", slot opening b=0.425", and piston "tooth" length Trt=0.125" with an overall linear stroke Z=0.200". Second FEM 4550 depicts the magnetic fluxplot at I=1.0 A for Z=0.000", i.e. midstroke. With an N42M NdFeB magnet, 170 turns of 22 AWG wire and a force constant of Kf≈3.0 lbf/A the RMS input power of approximately 2.45 W with sinusoidal drive.

In contrast first to third FEM plots 4600A to 4600C respectively in FIG. 46 depict a baseline ECPUMP design in closed circuit and open circuit configurations at midstroke together with open circuit at full stroke. This baseline ECPUMP has a 0.75" outer diameter and length 2.150." The magnet thickness was Tm=0.200", stator length Ty=1.350", stator tooth tip Hst=0.025", slot opening b=0.800", and piston "tooth" length Trt=0.125" with an overall linear stroke Z=0.200". With an N42M NdFeB magnet the overall efficiency was approximately 40% with a force constant of Kf≈4.0 lbf/A with an RMS input power of approximately 6.9 W with sinusoidal drive. Accordingly, it is evident in comparing baseline design depicted in first to third FEM plots 4600A to 4600C with Design 21 in second FEM 4550 in FIG. 4 that the inventor have been able to establish substantial improvements in ECPUMP performance in maintaining output pump force whilst reducing the dimensions of the ECPUMP as well as reducing power consumption and improving efficiency.

Figure 47A:
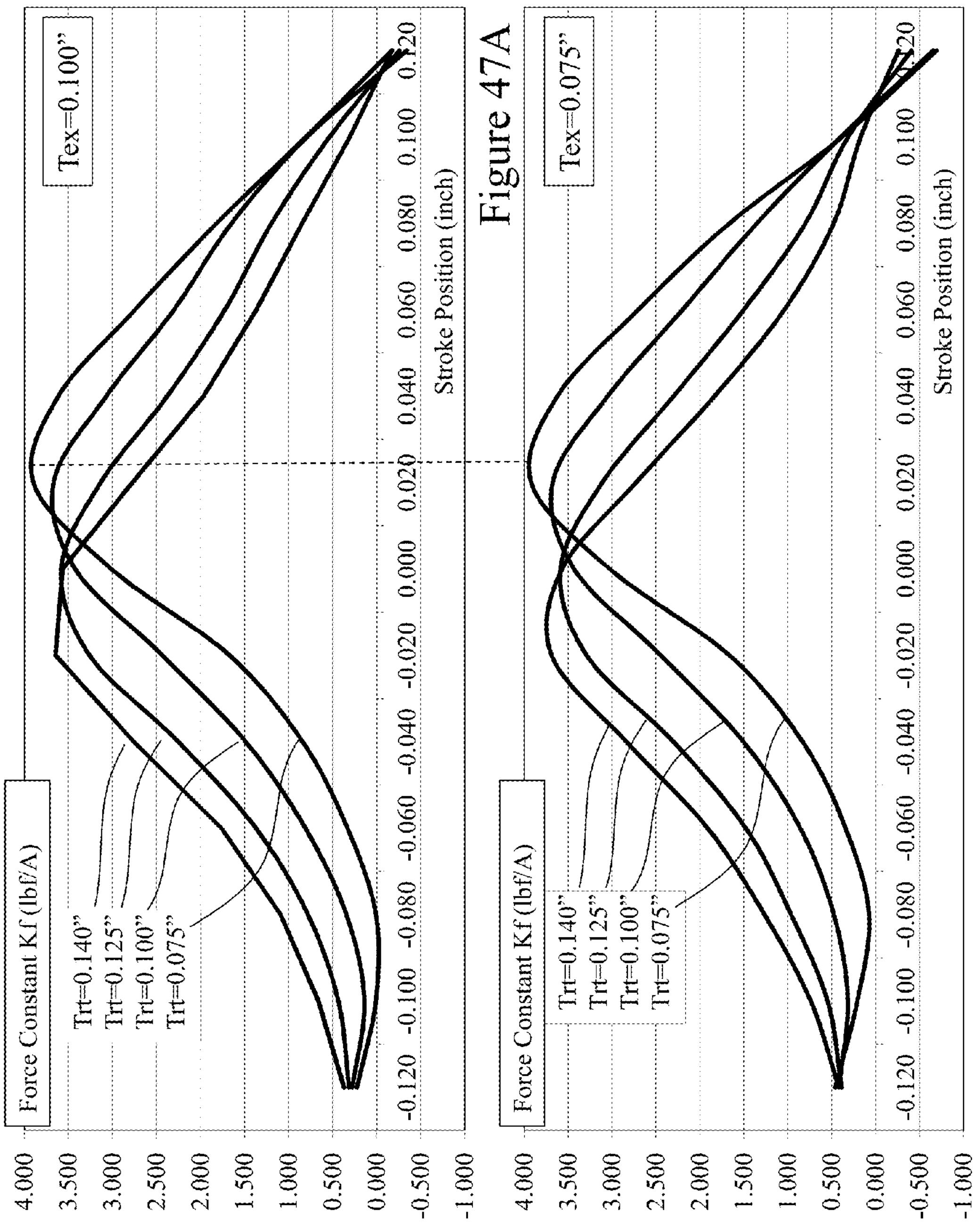
FIG. 47A depict numerical simulation results for compact ECPUMPs according to embodiments of the invention under parametric variation of piston tooth thickness and washer offset.

Examples of optimizations established by the inventors for fluidic ECPUMPs and fluidic devices are depicted in respect of FIG. 47A to 52. FIG. 47A depicts the variations in force constant Kf (lbf/A) for varying tooth width, Trt, at either end of the ECPUMP piston for varying stroke position over the range ±0.125" as this tooth width is varied from 0.075" to 0.140" showing an increasing offset in peak force constant and lower peak force constant values as the tooth width is increased. In the upper graph the magnet thickness, Tex, is 0.100" whilst in the lower graph the magnet thickness is reduced to 0.075".

Figure 47B:
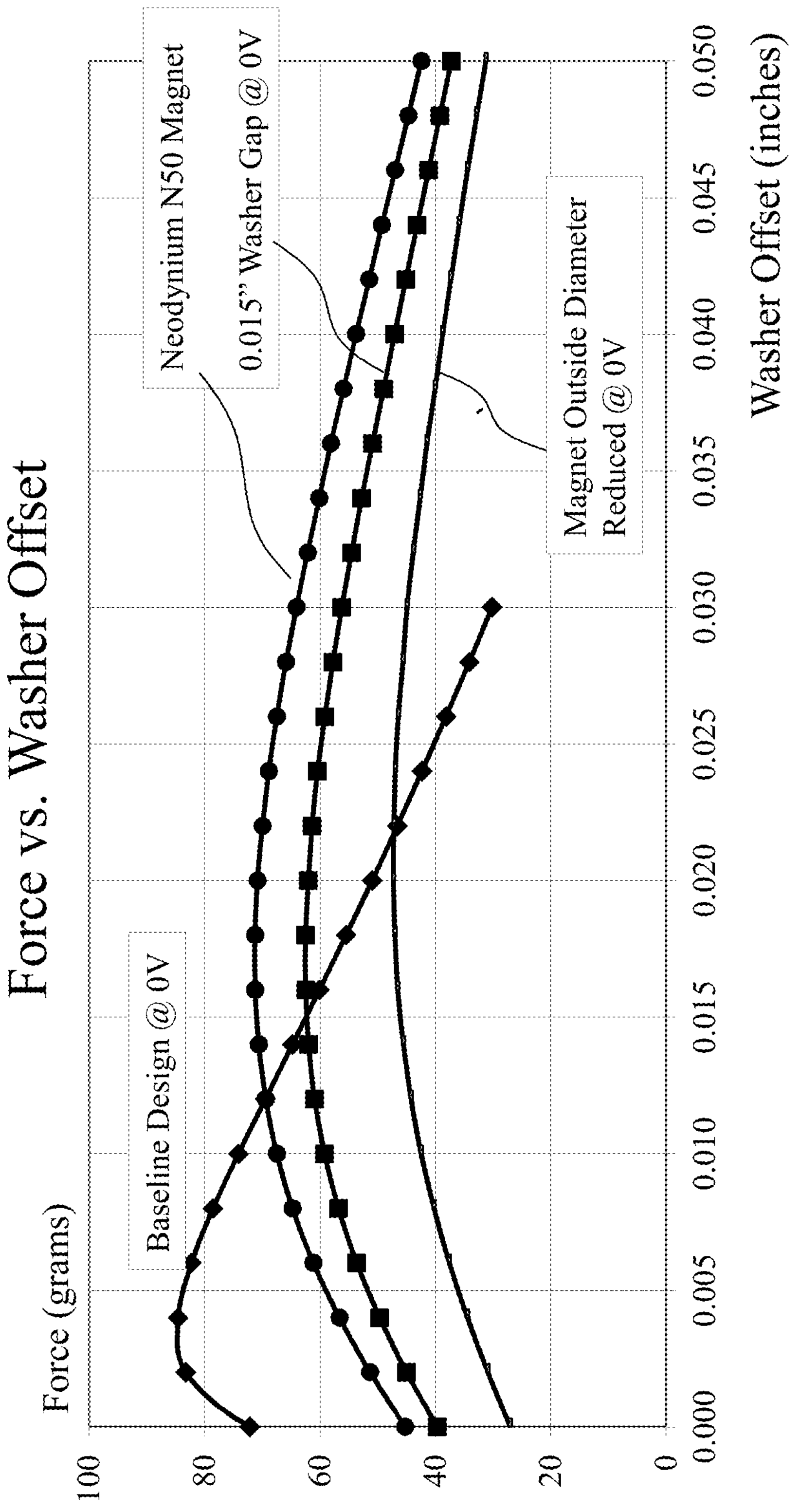
FIG. 47B depict numerical simulation results for compact EAVs according to embodiments of the invention under parametric variation of washer offset.

Referring to FIG. 47B shows the effects of washer offset for different EAV variations from an initial baseline design. The baseline design at 0V shows an initial rise in force but then linearly decreases with increasing washer offset. However, as evident a 0.015" washer gap whilst reducing the maximum force results in a significant flattening in the force versus washer offset graph. A similar effect is achieved with a reduction in the diameter of the magnet although the replacement of the N42 magnet with a N50 magnet with 0.015" washer gap results in sufficient force for keeping the magnetic valve closed against the fluidic pressure, which in these simulations was based upon design level provisioning of 7 psi and magnets. Accordingly, by modification of the washer, e.g. inner washers 3590/3595 in FIG. 35, and adjustment in magnet characteristics the manufacturing tolerances for offsets in assembly/manufacturing efficiency may be increased.

The force constant in FIG. 47B relates to a latching valve and is the holding latching force between the valve washer and latching magnet in the latching valve experienced as it is held closed when latched against an ECPUMP established 7 psi fluidic system pressure. Based upon these simulations a design target for the valve being to hold a pressure of 9 psi was established such that switching the valve requires low power and still maintains latching action.

Figure 48:
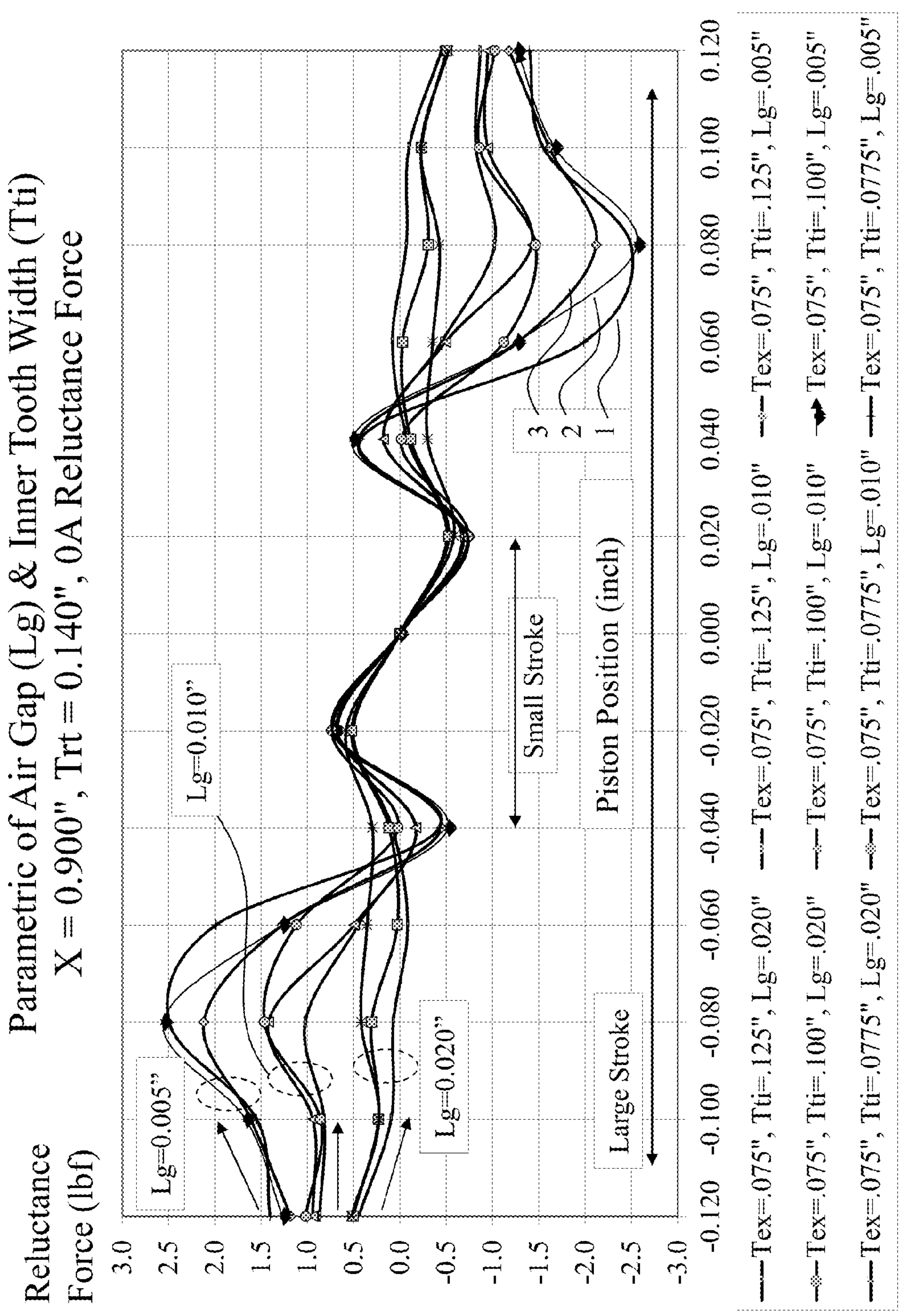
FIGS. 48 to 52 depict numerical simulation results for compact ECPUMPs according to embodiments of the invention under parametric variation showing the ability to tune long stroke characteristics.
Figure 49:
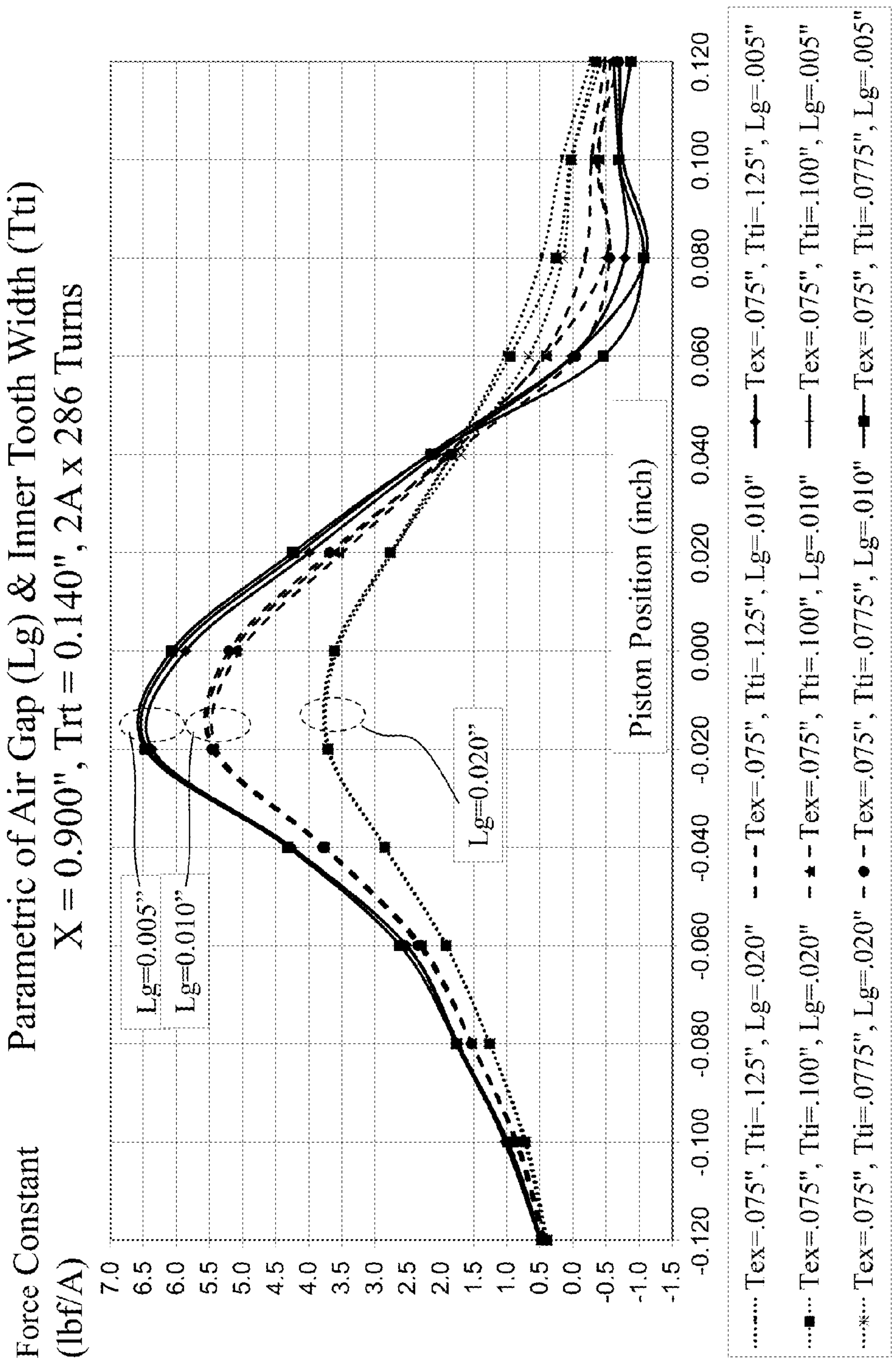

Referring to FIGS. 48 and 49 the force constant, Kf, for an ECPUMP variant similar to that described in dimensioned compact ECPUMP 4400B and Design 21 in respect of second FEM 4550 in FIG. 45 is depicted as a function of stroke offset over the range ±0.120" under 0A and 2A drive conditions. Accordingly there are curves for parametric variations in respect of air gap, Lg, and length of the inner tooth width of the inner washer, Tti, for constant outer washer thickness, Tex=0.075". Accordingly, it can be seen that in FIG. 49 at 2A the peak reluctance force reduces rapidly with air gap, Lg, but is relatively constant for varying inner tooth width, Tti. It is also evident that these curves are offset relative to the zero piston position and have significantly different behaviour from about ±0.040" from this peak position with the force constant becoming negative for positive offsets close to +0.120" with earlier force constant reversal at lower airgaps and yet remains positive for negative offsets to −0.120". Referring to FIG. 48 the 0A reluctance force can be seen to approximately constant in magnitude and profile over ±0.040" from the zero position for varying air gap and inner tooth width, Tti, and that at higher piston offsets from zero substantial variations in the reluctance magnitude are observed in addition to a cyclic behaviour.

Accordingly, considering Lg=0.005" (approximately 0.125 mm or 125 μm) then the reluctance force exhibits cyclic behaviour with earlier peaks in sequence 1, 2, 3 for inner tooth widths of 0.125", 0.100", and 0.075" respectively. At +0.080" the reluctance varies from −2.5 lbf for/Tti=0.125" down to approximately zero at Lg=0.020"/Tti=0.075" which follows the same shifts evident in the 2A current data in FIG. 49. Accordingly, the inventors have established ECPUMP designs that exploit large stroke lengths through initial electromagnetic excitation but that have large stroke characteristics determined by the combination of the reluctance force at 0A and the pressure of the fluid. Further as evident from FIG. 48 these zero current long stroke characteristics can be established through appropriate design of the ECPUMP.

Figure 50:
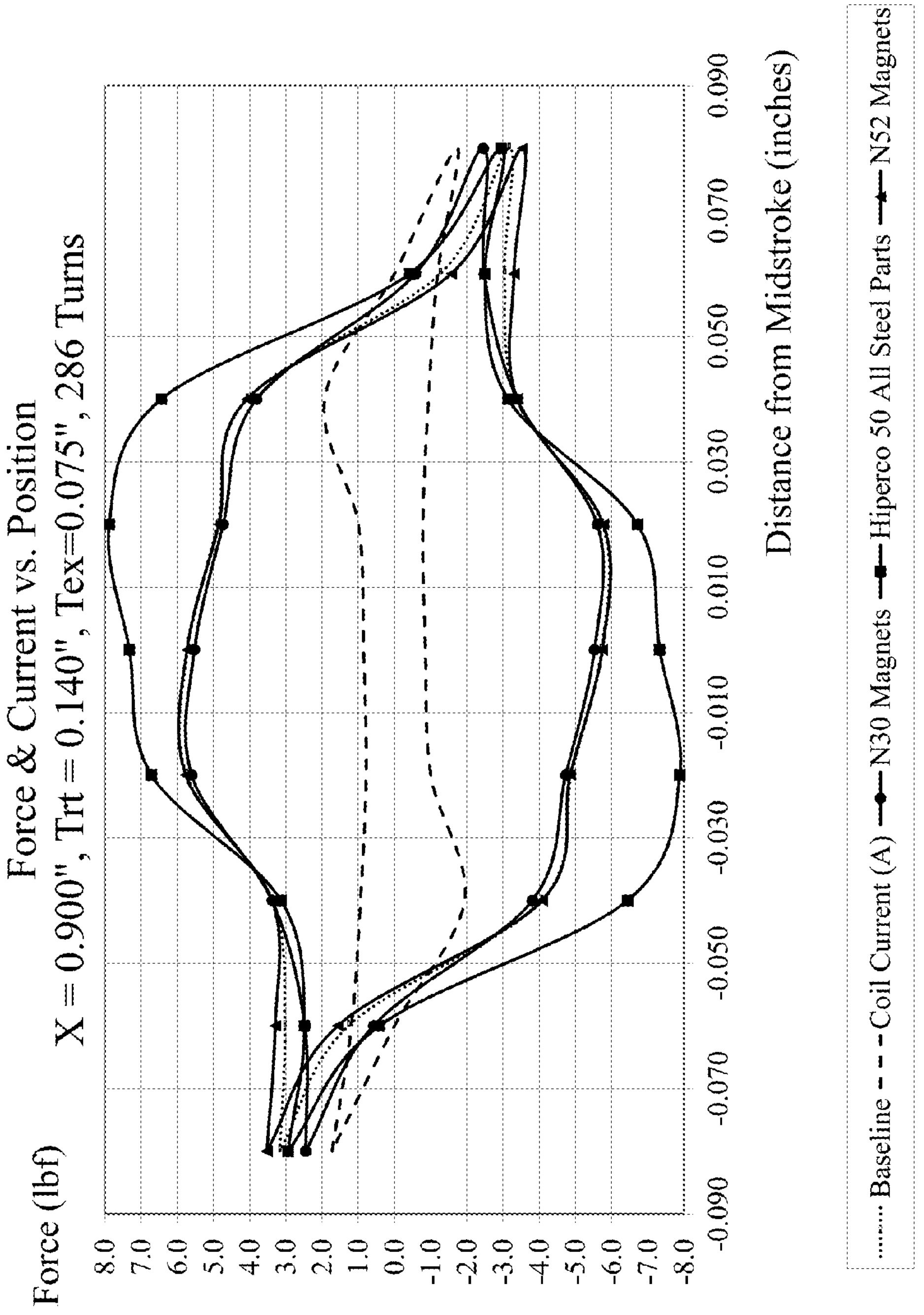
Figure 51:
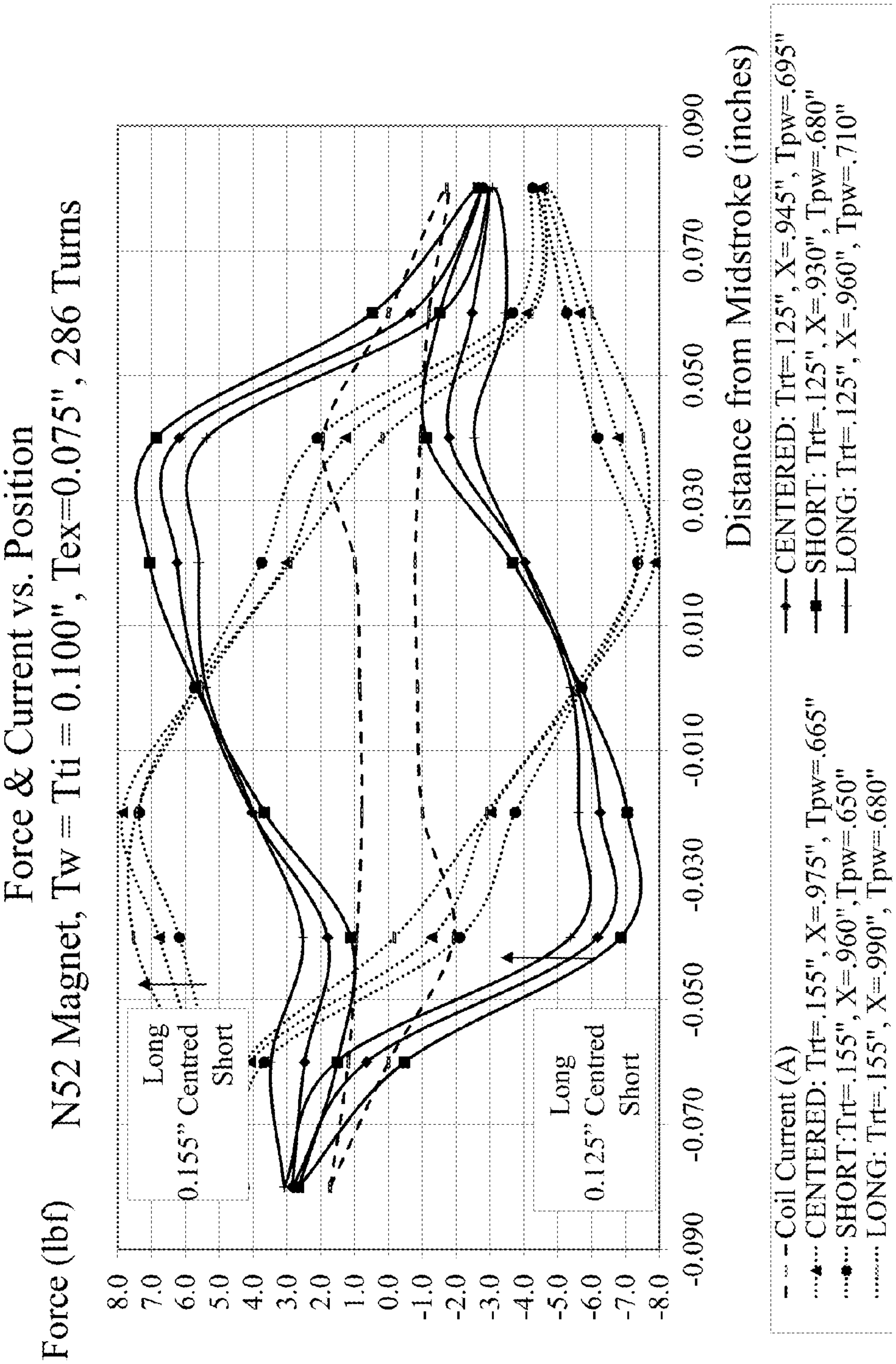

Referring to FIGS. 50 and 51, the effect of different magnetic materials for the magnets is presented for an ECPUMP variant similar to that described in dimensioned compact ECPUMP 4400B and Design 21 in respect of second FEM 4550 in FIG. 45 is depicted as a function of stroke offset under a pulsed drive condition. The current profile being represented by the dashed profile in the middle of the two graphs. In FIG. 50 the effect of changing from an N30 NdFeB magnet (10,800 Gauss) to an N52 NdFeB magnet (14,300 Gauss) is shown to be minor. More important is the change from standard soft magnetic steel to Hiperco® 50 iron-cobalt-vanadium soft magnetic alloy, which exhibits high magnetic saturation (24 kilogauss), high D.C. maximum permeability, low D.C. coercive force, and low A.C. core loss. Now referring to FIG. 51 the variations in force versus position for N52 magnets are depicted for two piston tooth widths, Trt, for three overall piston lengths where it can be seen that whilst the maximum force reduces the opposite piston position values increase as the piston length is varied from short to long. Accordingly, the overall force versus position profile can be modified according to the desired characteristics of the fluidic system such as for example improved overall force magnitude versus piston position.

Figure 52:
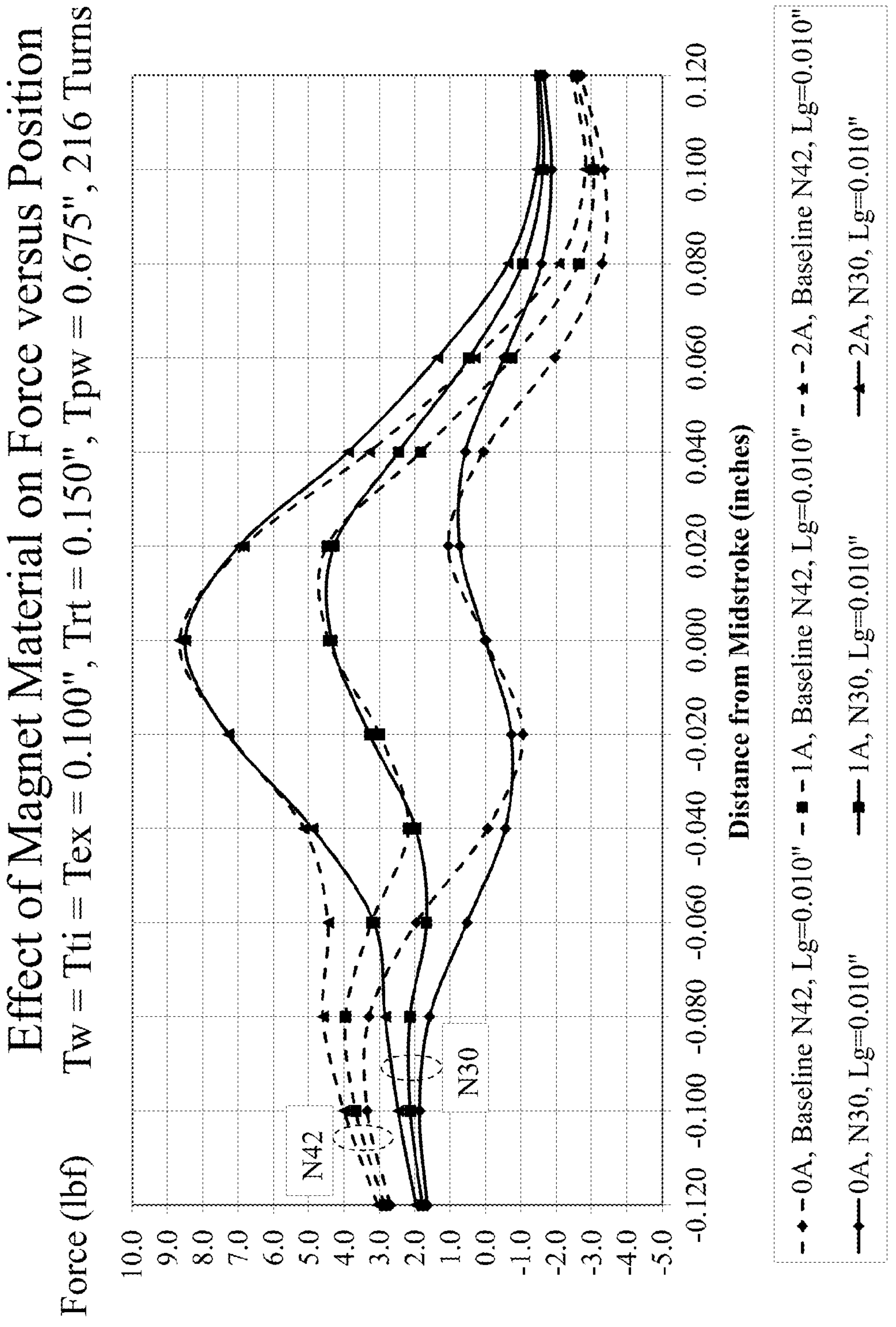

Similarly, referring to FIG. 52, numerical simulation results for compact ECPUMPs according to an ECPUMP variant similar to that described in dimensioned compact ECPUMP 4400B and Design 21 in respect of second FEM 4550 in FIG. 45 are depicted for two different magnetic materials, N30 and N42, at different currents with varying piston position. Accordingly, at zero current each passes through zero force at zero positional offset and has a periodic characteristic with piston position. With increasing current the long stroke characteristics of force change relatively slowly whilst the central short stroke characteristics vary relatively rapidly. Between 0A and 2A at 0" piston position (midstroke) the force goes from 0 lbf to approximately 8.5 lbf for either magnet whilst at −0.100" stroke distance the force goes from approximately 1.8 lbf to approximately 2.3 lbf for N30 magnet ECPUMPs and approximately 3.3 lbf to approximately 4.0 lbf for N30 magnet ECPUMPs.

As described supra linear displacement pumps, such as the ECPUMPs described and depicted in respect of FIGS. 32 to 37B, result in an area-averaged flow-rate fluctuation downstream from the pumping chamber due to the need for the pumping piston to reverse direction. These fluctuations in flow-rate result in increased instantaneous load on the pump motor with increased flow path length, due to the need to accelerate and decelerate all fluid along the flow-path. As described supra the inventors have established that an expandable elastic diaphragm may be employed immediately upstream and downstream from the pumping chamber. Within this section design space analysis against a target ECPUMP/device configuration is presented. The objectives of the inventors in performing the design space analysis were:

- minimize fluctuations of flow rate to an acceptable and/or desirable level based on product requirements;
- some velocity and pressure fluctuations are permissible and in fact desirable, but should be limited to not severely impact efficiency and end-user satisfaction;
- establish fluctuations of flow and/or pressure to maximize water column vibration energy available to the user;
- maximize mechanical energy efficiency by reducing work done on the fluid; and
- minimize or maximize fluid pressure on the pump piston while achieving a flow-rate of Q=3 L/min, and outlet pressure of 7 psi (gauge) depending upon intended purpose.

In order to assess the inventor's concept a mathematical model was developed for the dynamic behavior of the elastic capacitor coupled with the fluid response pressure. A sinusoidal piston velocity at a frequency ranging from 0 to 50 Hz was used as an input for the model and piston dynamics were not considered in this analysis. The model, to which the simulation results are presented and described in respect of FIGS. 53 to 55C respectively, is depicted in FIG. 55D and was discretized using an implicit finite volume scheme and solved numerically using a total variation diminishing solution scheme. Numerous simulations were performed where the flow path lengths $S_{45}$ and $S_{67}$, diaphragm radii $R_4$, $R_5$, $R_6$, and $R_7$, and elastic coefficients, k, of the different sections were varied independently. The dimensions of the elastic diaphragm and pumping system were selected to vary the damped cut-off frequency of the system, thereby filtering flow-rate and pressure fluctuations downstream from the elastic diaphragm.

The analysis of fluid dynamics is typically performed using the unsteady Euler equation and mass continuity equations, which are integrated along a streamline starting from the cylinder face, and ending downstream from the diaphragm. The elastic diaphragm is modelled as a thin-walled pressure vessel where stress-strain relationships are employed to obtain the diaphragm expansion and compression due to pressure variations. The instantaneous expansion rate of the diaphragm at a particular streamwise location is given by Equation (1) $k=(0.67)/(Et_0)$, and is the elastic stiffness coefficient related to the elastic modulus of silicone, E, and the thickness of the elastic diaphragm, $t_0$. The coefficient 0.67 is an analytically derived and experimentally verified correction factor to account for thinning of the elastic diaphragm thickness during strain.

$$\frac{d}{dt}(r) = kr^2\frac{d}{dt}(P) \tag{1}$$

From a general viewpoint then varying the geometric parameters k, S, and R has the following effects:

- increasing R and S increases the damping effect of the elastic diaphragm, leading to decreased frictional losses and decreased inertial pressure component;
- increasing R also decreases velocity magnitude minimizing the inertial component of pressure, and viscous losses;
- increasing S however directly increases the inertial pressure component;
- decreasing S decreases the inertial pressure component, but reduces the damping velocity effect at the same time; and
- increasing k increases the damping effect but decreases the critical pressure that the capacitor can operate at.

Figure 53:
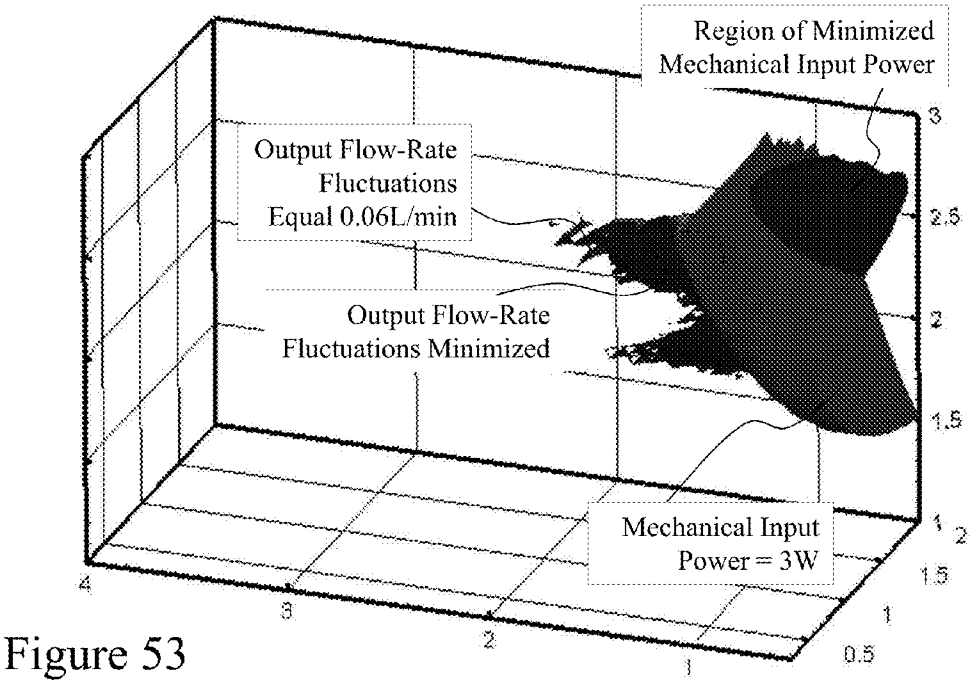
FIGS. 53 and 54 depict parametric space overlap between design parameters for compact ECPUMPs according to embodiments of the invention.
Figure 54:
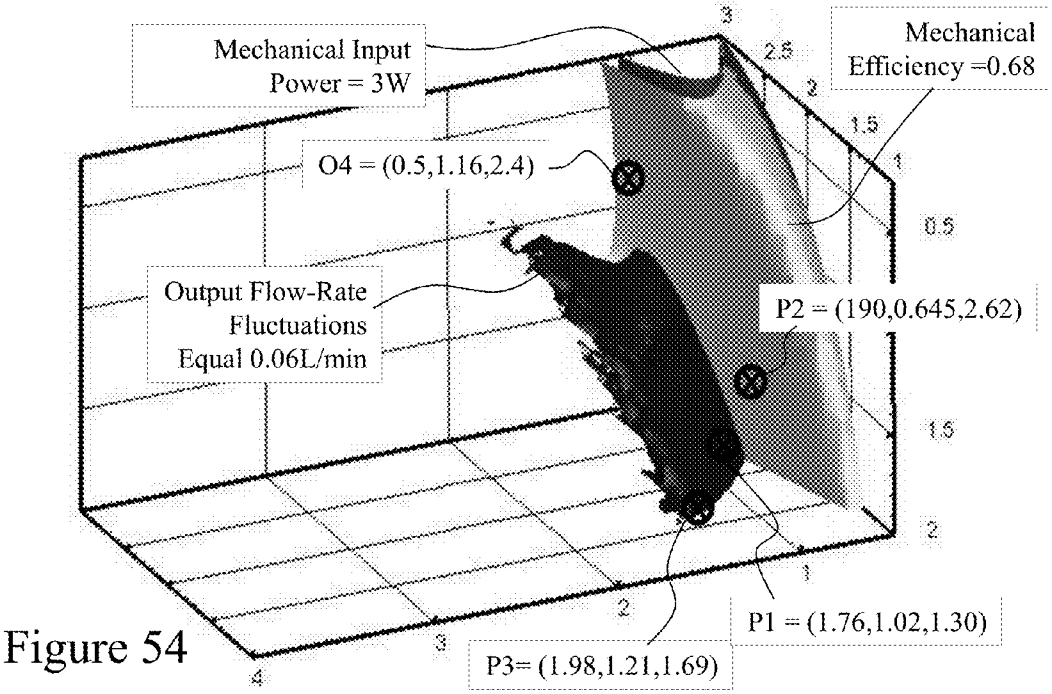

The length of the elastic diaphragm, $S_{45}$ and $S_{67}$, were uniformly scaled from a reference initial value by the ratio $S/S_0$; the radii of the diaphragm were uniformly scaled by the ratio $R/R_0$; and the stiffness coefficients, k, were likewise scaled by the ratio $k/k_0$. Simulations were performed in which $S/S_0$, $R/R_0$ and $k/_0$ were independently varied, a 3D parameter space was used to visualize the data as shown in FIGS. 53 and 54. FIG. 53 depicts the parameter space of the simulations wherein 31 different values of k were employed, $0.5\leq(k/k_0)\leq2.0$; 51 different values of S were employed, $1\leq(S/S_0)\leq4$; and 31 different values of R were employed, $1\leq(R/R_0)\leq3$, for a total of 49,011 simulations. FIG. 54 depicts the parameter space results of this analysis where isosurfaces of minimum velocity fluctuations, maximum efficiency, and minimum mechanical input power are plotted. Accordingly, each $(S/S_0, R/R_0, k/k_0)$ coordinate corresponds to a different pump configuration and therefore different efficiency characteristics. The isosurfaces show all coordinates where a certain parameter has specific level. For example the mechanical surface indicates all configurations that have a near optimal mechanical efficiency value of 68%. The intersection between the output flow-rate fluctuation isosurface and efficiency isosurface represents the optimum trade-off line between efficiency and velocity fluctuations $Q/\overline{Q}$. Several points are identified on the surfaces which yield different compromises, which are described in Table 1 below.

TABLE 1

Summary of design configuration points, key parameters, and design trade-offs

| | Configuration $(k/k_0, S/S_0, R/R_0)$ | $\eta$ | $\Delta Q/\overline{Q}$ Q/Q [%] | $P_{IN}$ [W] | $P_{BURST}$ [psi] | Design Trade-offs |
|---|---|---|---|---|---|---|
| $P_0$ | (1.00, 1.00, 1.00) | 0.39 | 310 | 3.94 | 114 | Initial configuration |
| $P_1$ | (1.76 1.02, 2.30) | 0.67 | 1.6 | 3.03 | 27 | Optimum trade-off between efficiency, input power best flow-rate damping Larger diaphragm size, low critical pressure |

TABLE 1-continued

Summary of design configuration points, key parameters, and design trade-offs

| | Configuration ($k/k_0$, $S/S_0$, $R/R_0$) | η | $\Delta Q/\overline{Q}$ Q/Q [%] | $P_{IN}$ [W] | $P_{BURST}$ [psi] | Design Trade-offs |
|---|---|---|---|---|---|---|
| $P_2$ | (1.90 0.645, 2.62) | 0.69 | 2.8 | 2.93 | 22 | Highest efficiency, lowest power required<br>Greater fluctuations, lowest burst pressure |
| $P_3$ | (1.98, 1.21, 1.69) | 0.62 | 3.0 | 3.26 | 34 | Smaller Radii and physical dimensions<br>Lower efficiency and higher input power |

Figure 55A:
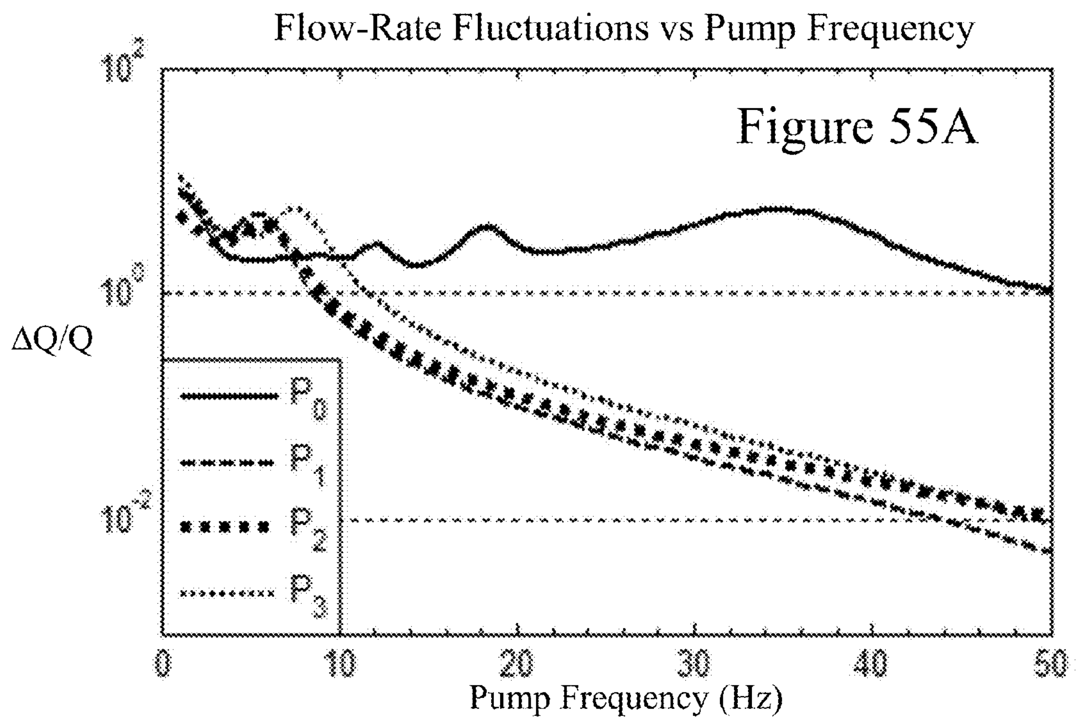
FIGS. 55A through 55C depict compact ECPUMP characteristics as a function of frequency according to embodiments of the invention.
Figure 55B:
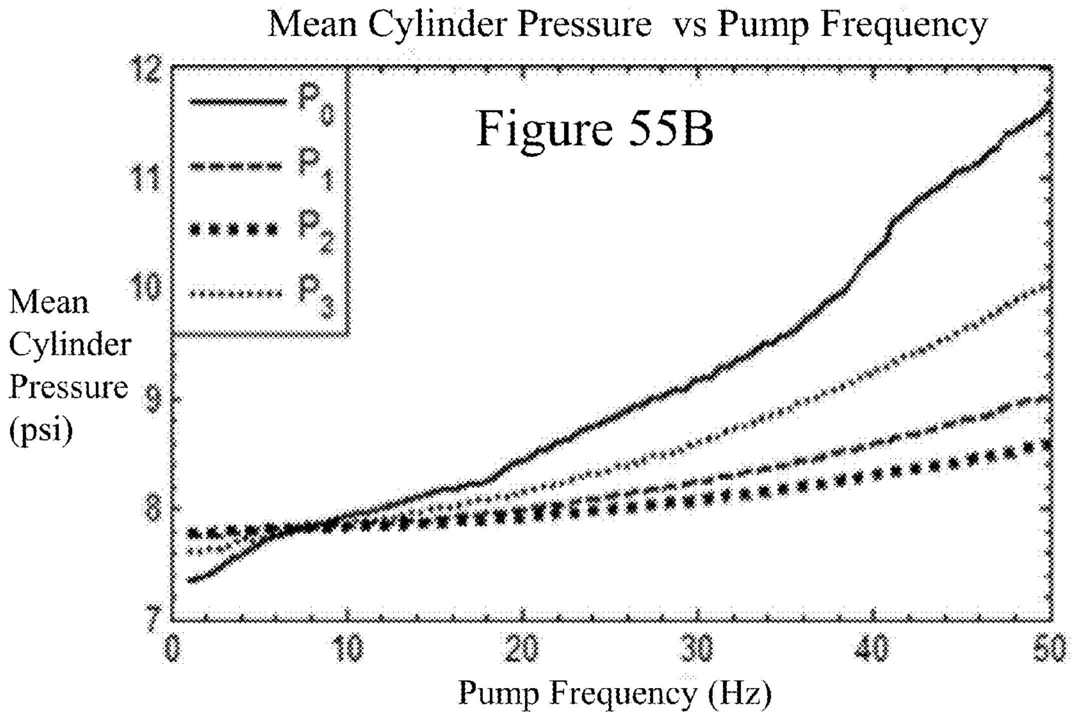
Figure 55C:
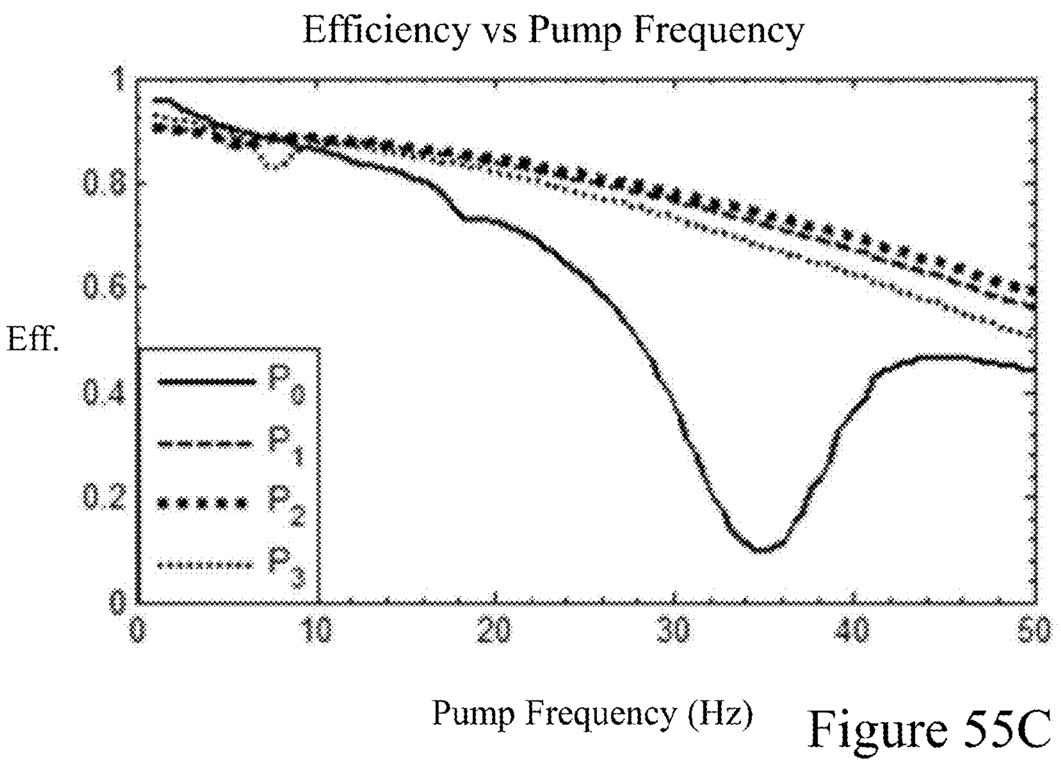
Figure 55D:
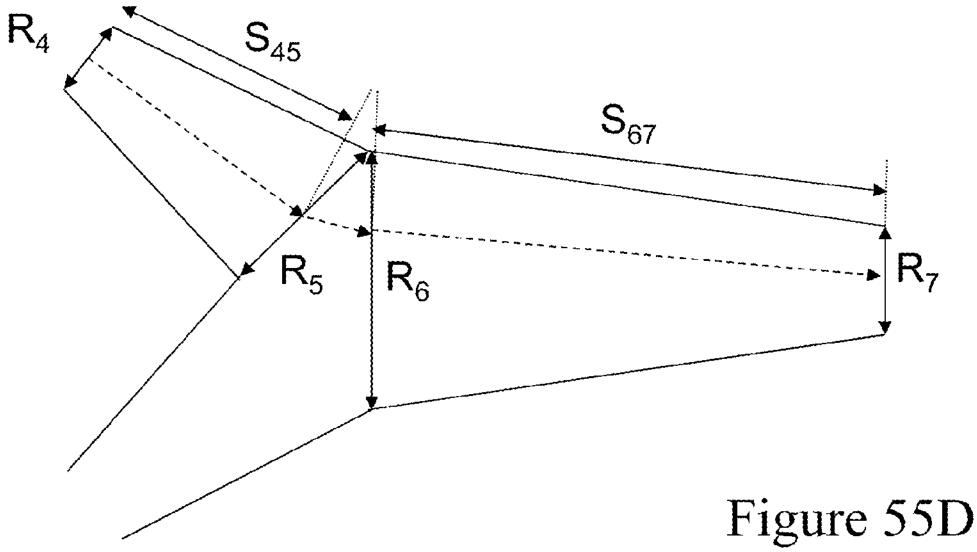
FIG. 55D depicts a Y-tube geometry employed in numerical analysis presented in respect of FIGS. 53 to 55C respectively.
Figure 55E:
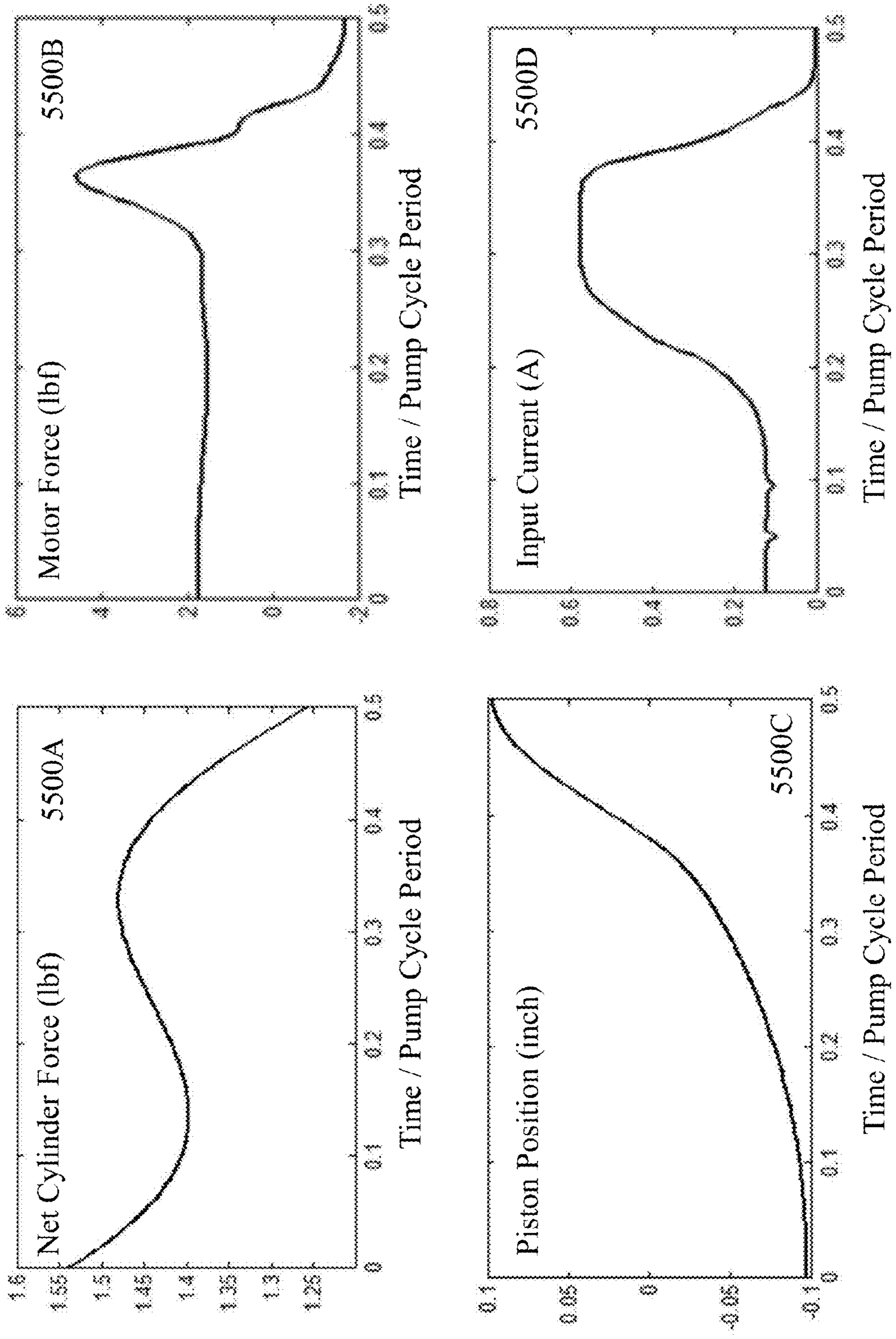
FIG. 55E depicts simulations with respect to generating a current drive profile to provide desired stroke characteristics within the design space for an ECPUMP according to an embodiment of the invention.
Figure 56:
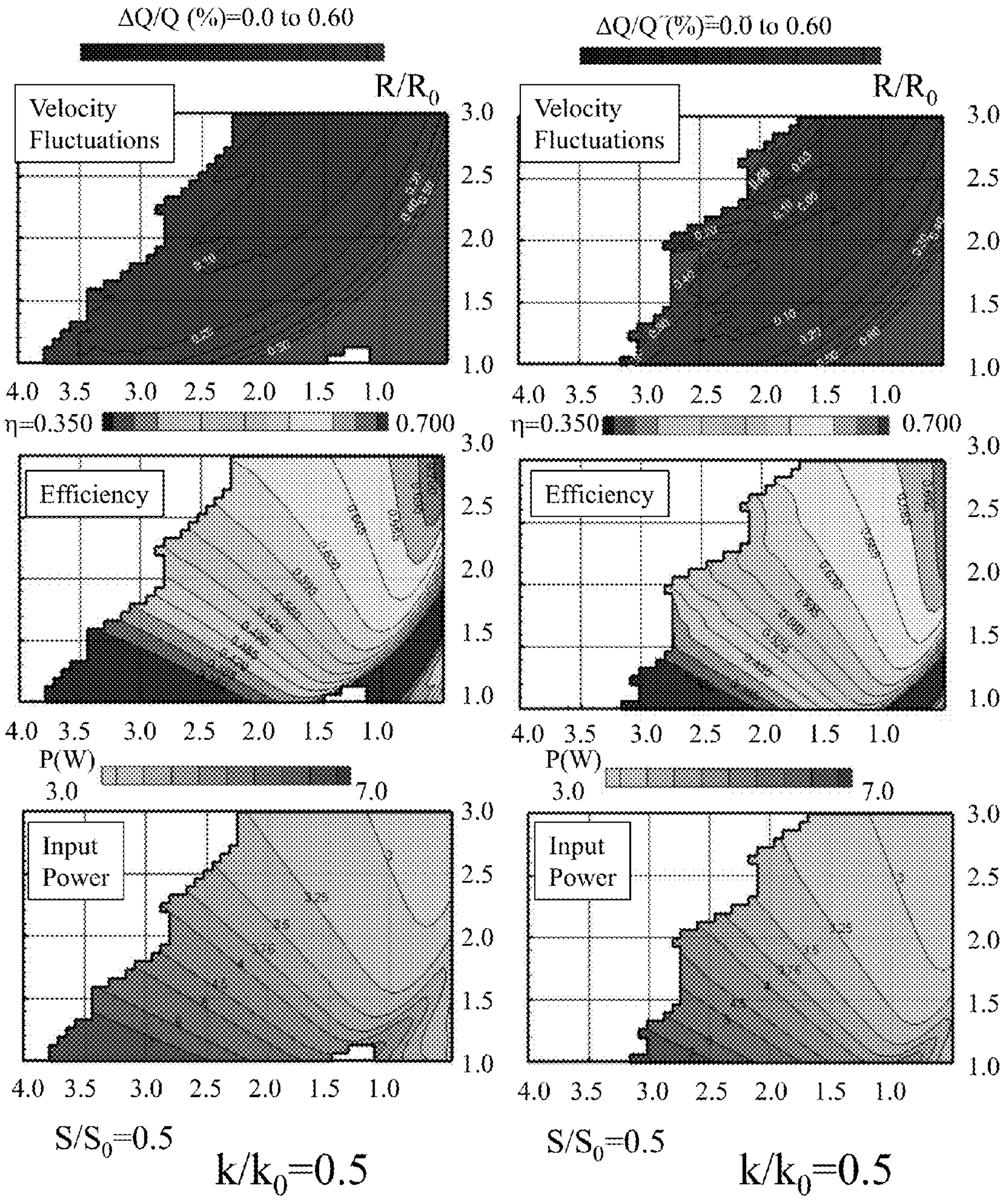
FIGS. 56 and 57 depict isocontour plots of performance characteristics of a compact ECPUMP system as a function of combining Y-tube design parameters.
Figure 57:
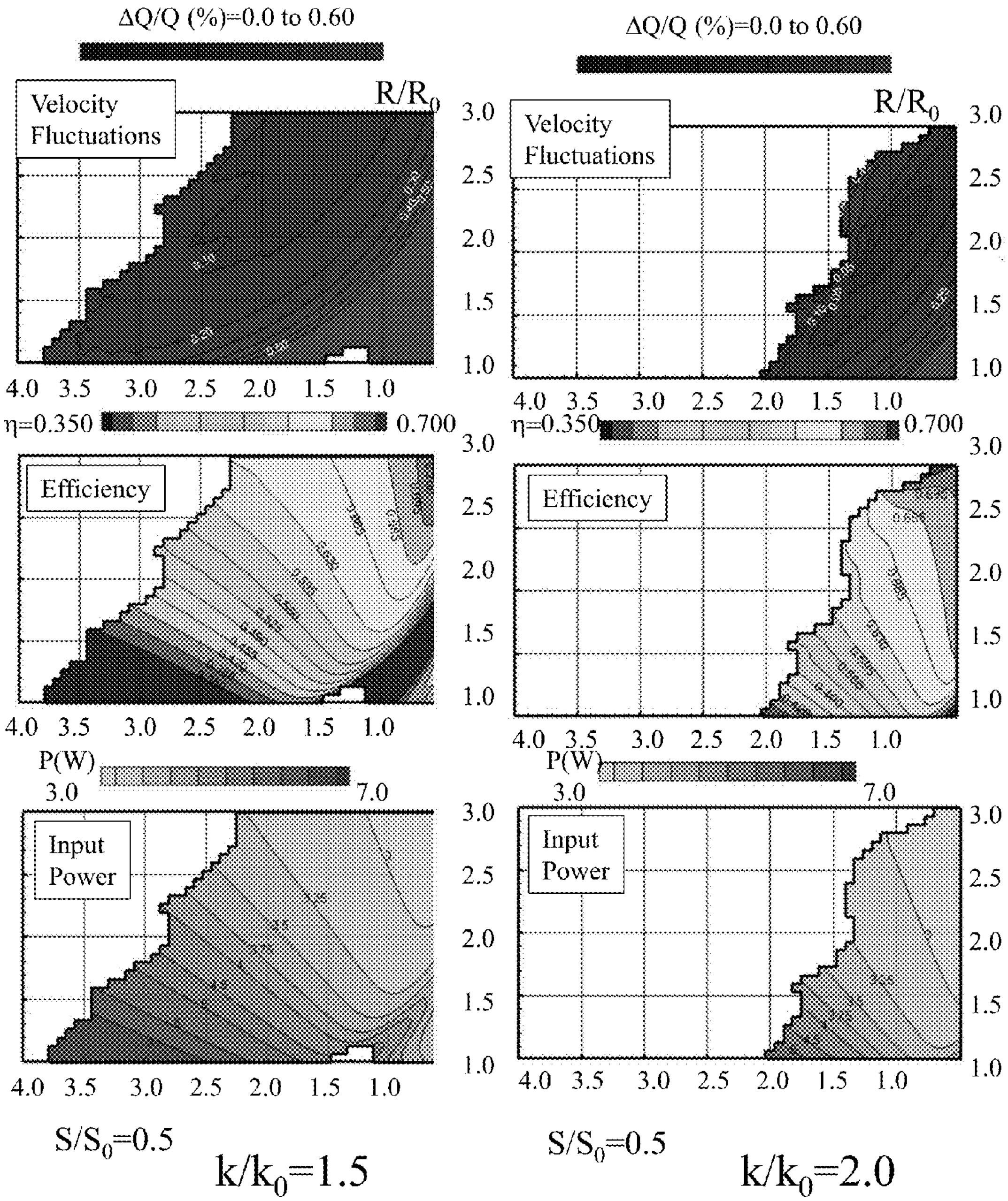

FIGS. 55A to 55C respectively show the decreased flow-rate fluctuations, decreased mean cylinder pressure, and correspondingly improved pump efficiency of the optimized configurations compared to the initial reference condition for these different designs. Further refinement is accomplished with more simulations where the radii of the pump are each individually varied and optimized, the flow path from the pump to capacitor is minimized, and losses from the umbrella valves are optimized. These result in further improvements to the theoretical mechanical efficiency of the compact ECPUMPs to 87%. FIGS. 56 and 57 depict iso-contour plots of the velocity fluctuations, efficiency, and mechanical input power in S-R planes for $k/k_0$=0.5, 1.0, 1.5, 2.0 from this analysis. Within each graph in FIGS. 56 and 57 the blank white region represents cases where the pressure within the diaphragm exceeds or is near the critical pressure and the diaphragm expands (balloons out) causing it to rupture. This instability occurs because the elastic diaphragm of the fluidic capacitor has insufficient stiffness rebound causing it to continually accumulate fluid.

When the bursting pressure ($P_{BURST}$), approaches the design pressure of 7 psi, diaphragm expansion and contraction is greater such that the diaphragm absorbs more energy from the fluid. The expansion and contraction cycles of the diaphragm are nearly 180° out of phase with the fluid pressure, and as a result the diaphragm can be used to reduce the pressure load on the pump during the beginning and end of the stroke.

Another design optimization performed by the inventors relates to addressing the motor force output. As evident from first graph 5500A in FIG. 55E the time variation of pressure on the pump piston requires consistently positive force throughout the pump cycle to allow the piston to traverse the entire 0.2" stroke and achieve a sinusoidal velocity profile. Hence, if insufficient force is applied at any time, the piston will decelerate prematurely, preventing the piston from reaching the opposite end and thus decreasing flow rate. However, the characteristics of the magnetic motor prevent or limit the positive force that can be applied at the end of the stroke. Furthermore, at either end of the stroke the motor efficiency is drastically decreased, whereas the motor has the greatest efficiency towards the center of the stroke.

Accordingly, it was an objective to find a force input signal to allow the piston to achieve its full stroke while meeting the output capabilities of the motor and specify a force signal that takes advantage of the current to force conversion efficiency curve of the electric motor, thus minimizing power requirements and maximizing electrical to mechanical energy conversion efficiency. In order to do this the piston dynamics were modelled and incorporated into the fluid system simulations, so that force was specified as an input and piston position was solved for in time along with fluid pressure and velocity. An arbitrarily shaped force signal which imparts an energy over the entire stroke that is equal to the energy imparted by the force curve is shown in first graph 5500A in FIG. 55E which will permit the piston to traverse the entire length of the stroke. The force signal is defined as an arbitrary curve, which is controlled such that it's integral over the length of the stroke yields an identical energy to the integral of the force curve shown in first graph 5500A of FIG. 55E. This force signal curve was then evolved using a cost minimizing optimization method where the mean current calculated from a particular force curve was minimized in simulations.

Based upon this optimization improved force and piston position curves were determined as shown in second and third graphs 5500B and 5500C in FIG. 55. First graph 5500A depicts the force signal optimized to achieve 0.2" stroke and use minimal input current, whilst third graph 5500C depicts the resulting piston position versus time curve. The force curve shown in the second graph 5500B of FIG. 55E redistributes energy imparted by the piston towards the center of the stroke, and allows for force to be negative at the end such that the pumping piston is decelerated by fluid pressure imparted by the elastic diaphragm and the zero-current magnetic reluctance force imparted by the motor magnetics. As a result the resulting piston position curve experiences substantially greater acceleration and deceleration towards the middle and end of the stroke cycle period. The corresponding velocity profile suffers from a slight decline in mechanical efficiency, which is more than compensated by the increase in electrical to mechanical energy conversion efficiency. The frequency that the piston oscillates at is determined by the force supplied throughout the stroke. As we wish to apply less current at the ends of the stroke, the zero-current magnetic reluctance force of the piston is tuned to the specific values (±1.75 lbf at 40 Hz), which are required to achieve a resonant frequency with minimal current. This force curve can then be converted to the required drive current which is depicted in fourth graph 5500D in FIG. 55, which it can be seen requires minimal current to be applied at the beginning and end of the cycle.

Figure 64:
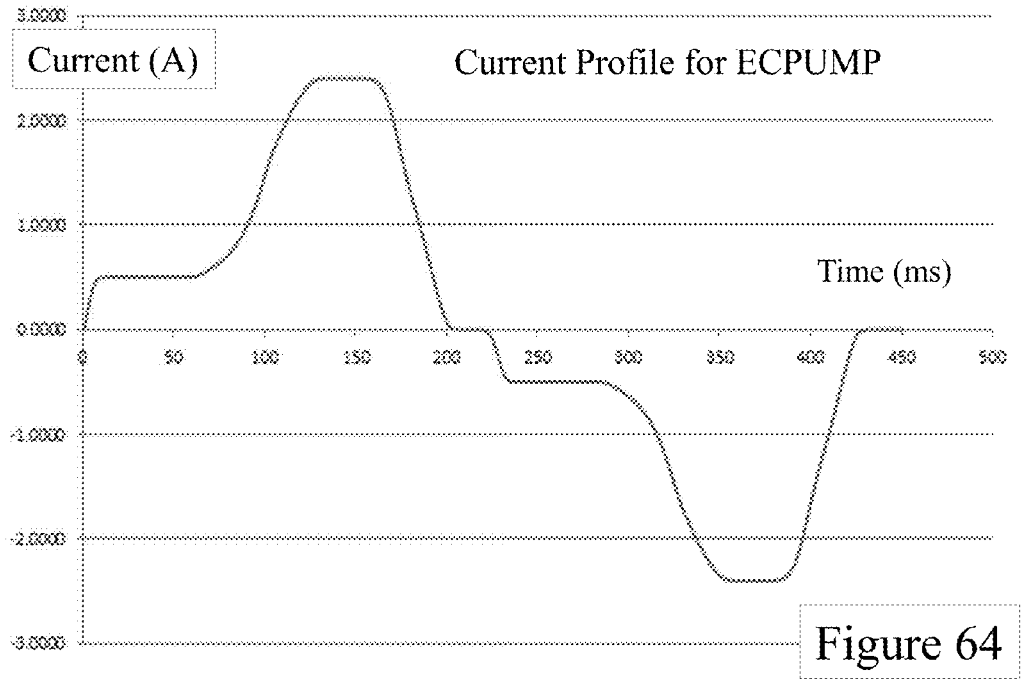
FIG. 64 depicts exemplary current drive performance of the electrical drive circuit of FIG. 63.
Figure 63:
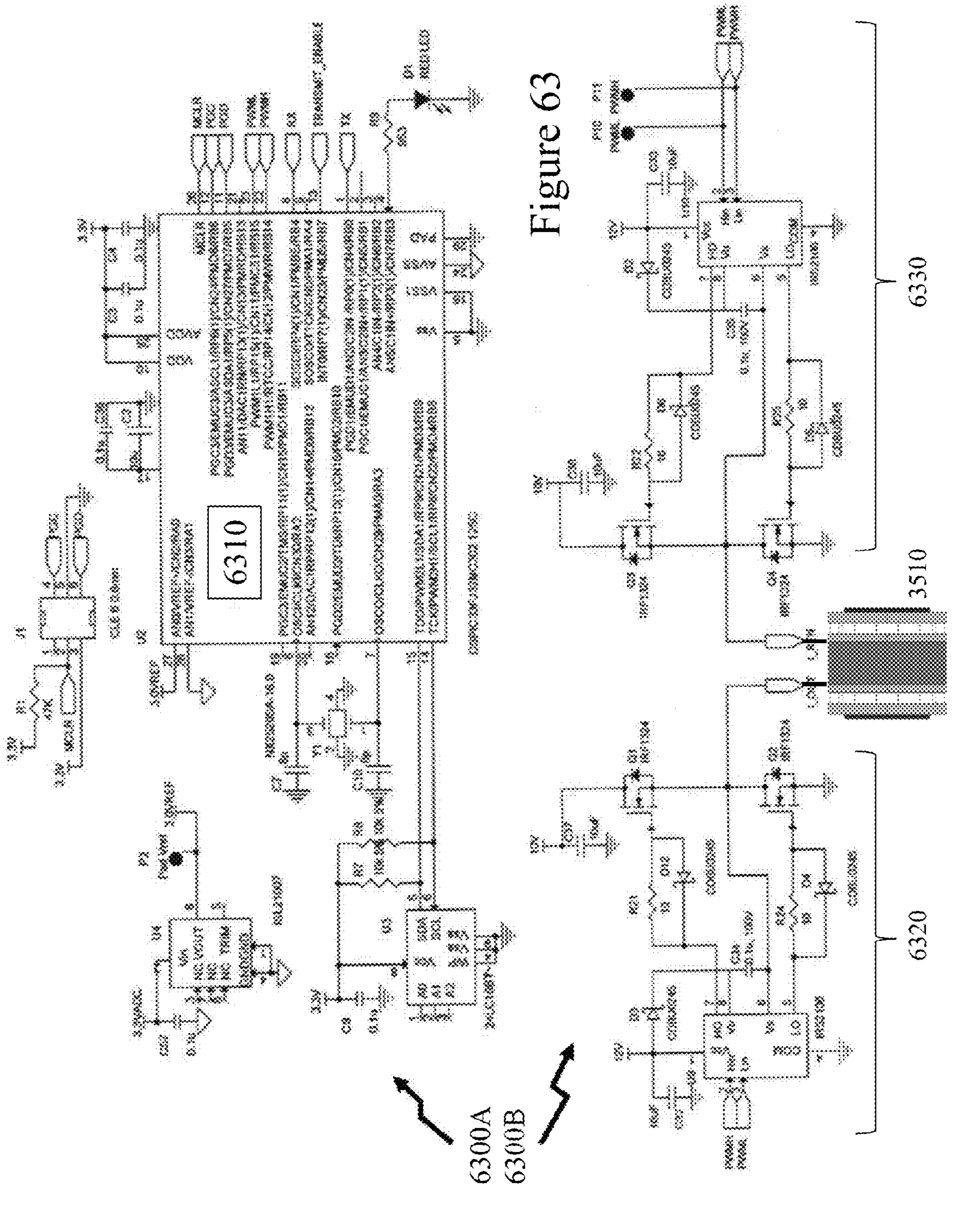
FIG. 63 depicts an exemplary electrical drive circuit for an ECPUMP according to an embodiment of the invention.

Referring to FIG. 63 there is depicted an example of a control circuit for an ECPUMP according to an embodiment of the invention. As depicted digital circuit 6300A comprises high performance digital signal controller, such as for example Microchip dsPIC33FJ128MC302 16-bit digital signal controller which generates output pulse width modulation (PWM) drive signals PWML and PWMH which are coupled to first and second driver circuits 6320 and 6330 which generate the current drive signals applied to the coil within the ECPUMP 3510. An example of the generated drive current applied to the coil of an ECPUMP is depicted in FIG. 64. Rather than a continuous signal the generated drive current according to an embodiment of the invention wherein the digital circuit 6310 generates amplitude varying pulses with an 18 kHz frequency. Accordingly, the 450 ms drive current signal depicted in FIG. 64 is composed of approximately 8000 discrete amplitude weighted cycles of this 18 kHz signal.

The operation of an ECPUMP using a drive signal such as depicted in FIG. 64 provides for continuous operation of the ECPUMP which via fluidic capacitors a constant fluid pressure/flow to the fluidic system and the valves. However, it would be evident that under the direction of a controller exploiting PWM techniques for driving an EAV that the EAV can be turned on and off quickly in order to keep a fluidic actuator, such as a balloon, at a predetermined fill level, e.g. 25%, 50%, and 100%. For example, with an EAV oscillating at 40 Hz then pulse width modulating the valve can be within the range 0.1 Hz to 40 Hz according to fill level desired. In this manner a single ECPUMP can fill and/or maintain the fill level of a plurality of balloons based upon the actuation of the valves, switches, etc. within the overall fluidic system. Similarly, the ECPUMP can be operated at different frequencies e.g. 10 Hz to 60 Hz. Additional frequency stimulation can be through the timing sequence of a series of valves. It would also be evident that a physical interaction, such as the pressure applied by a finger contacting a user's skin can be mimicked as the PWM based controller technique allows complex actuator expansion or effect profiles to be generated. Hence, a fluidic actuator can be inflated to provide a pressure profile mimicking another individual's finger touching them.

Figure 58:
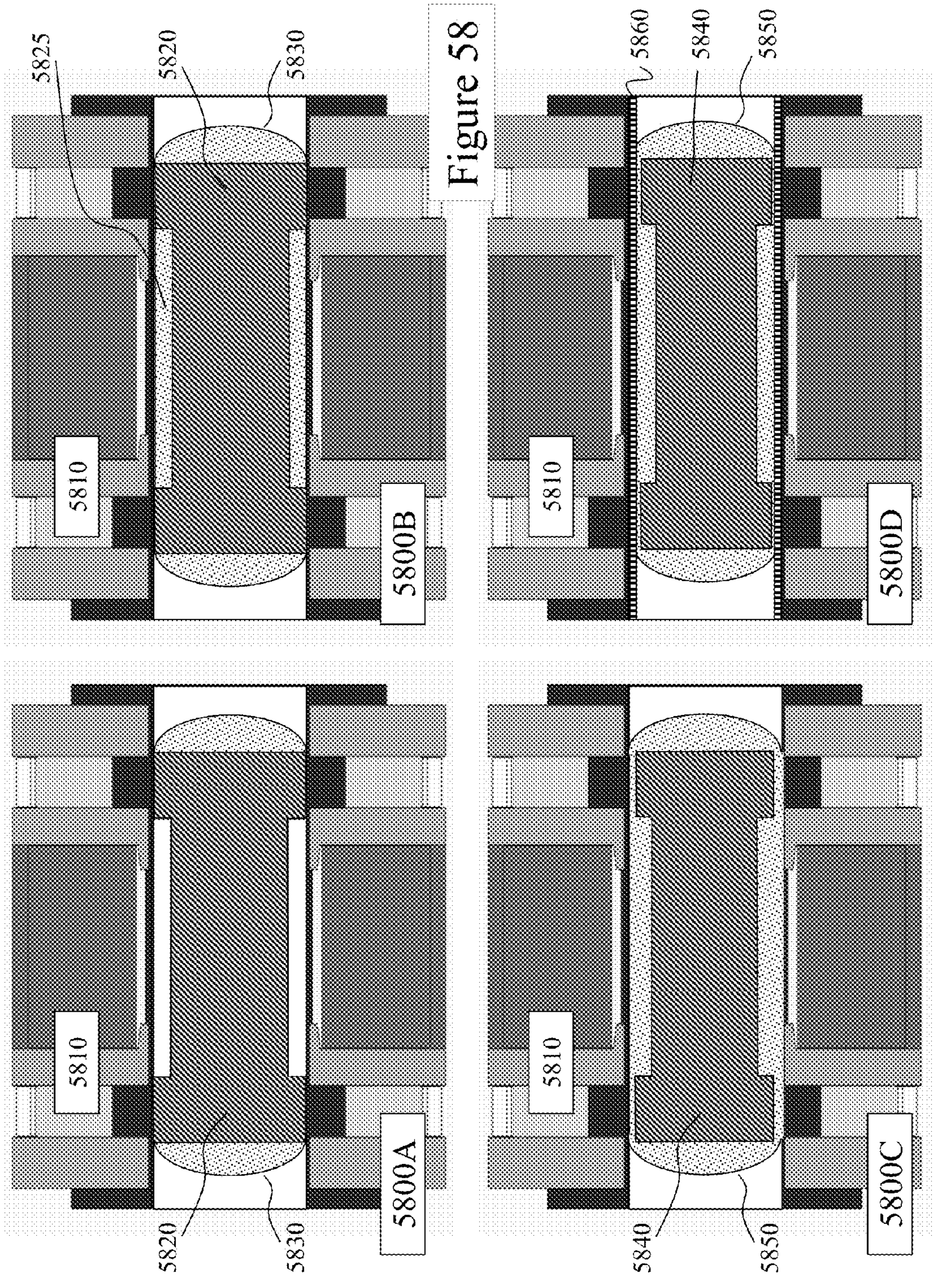
FIGS. 58 to 60 depict design variations for pump pistons within compact ECPUMPs according to embodiments of the invention.
Figure 59:
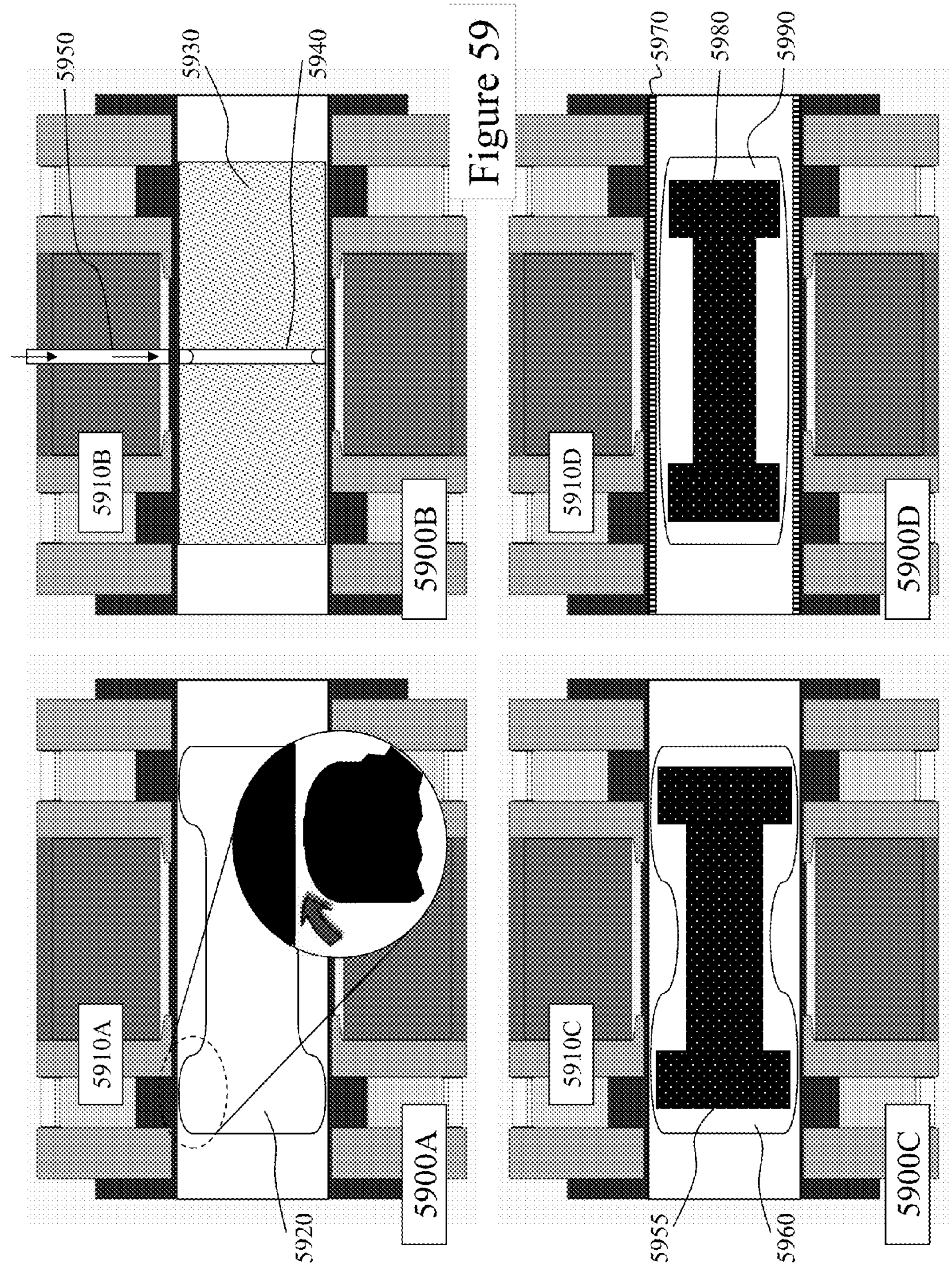
Figure 60:
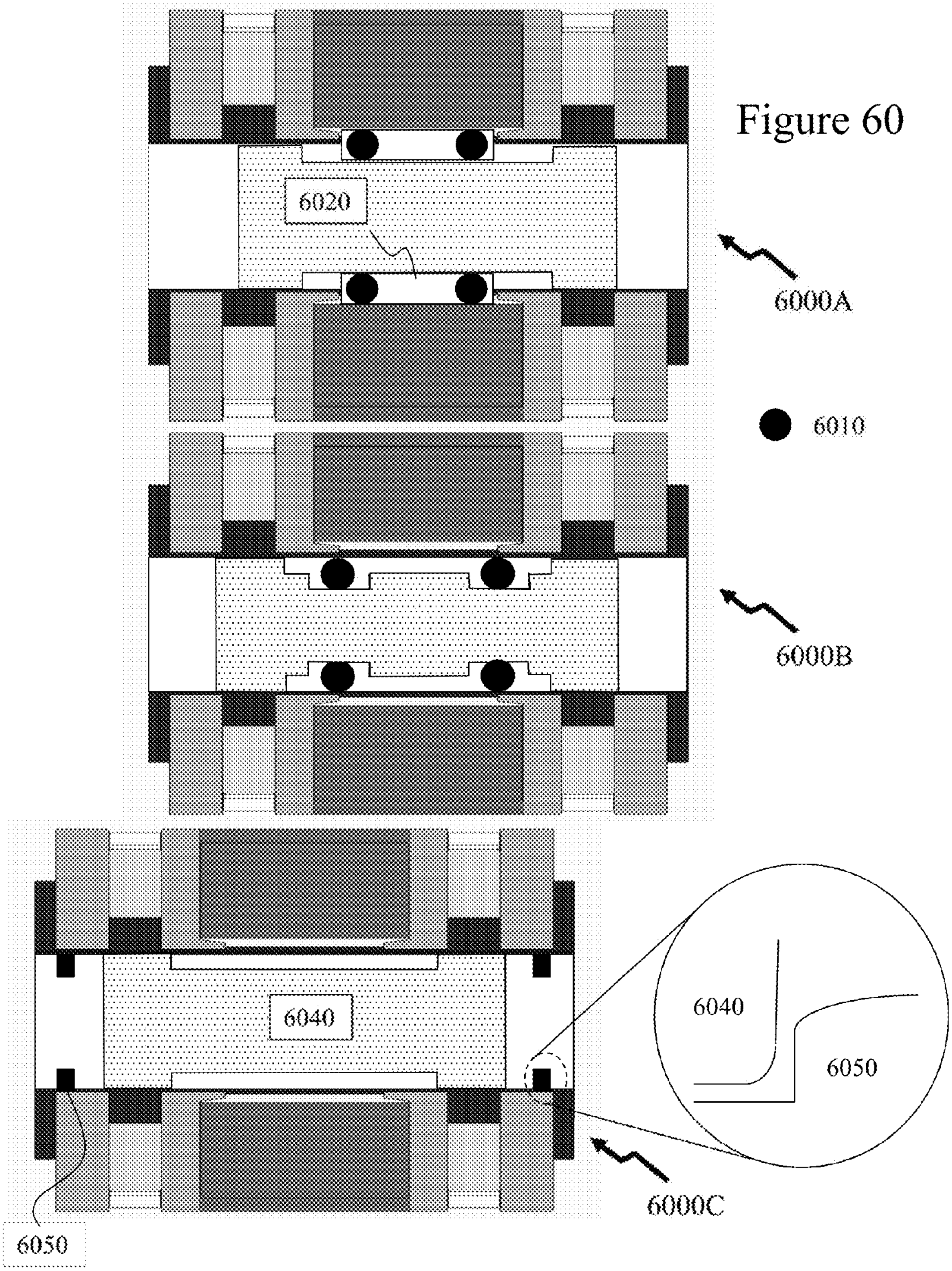
Figure 61:
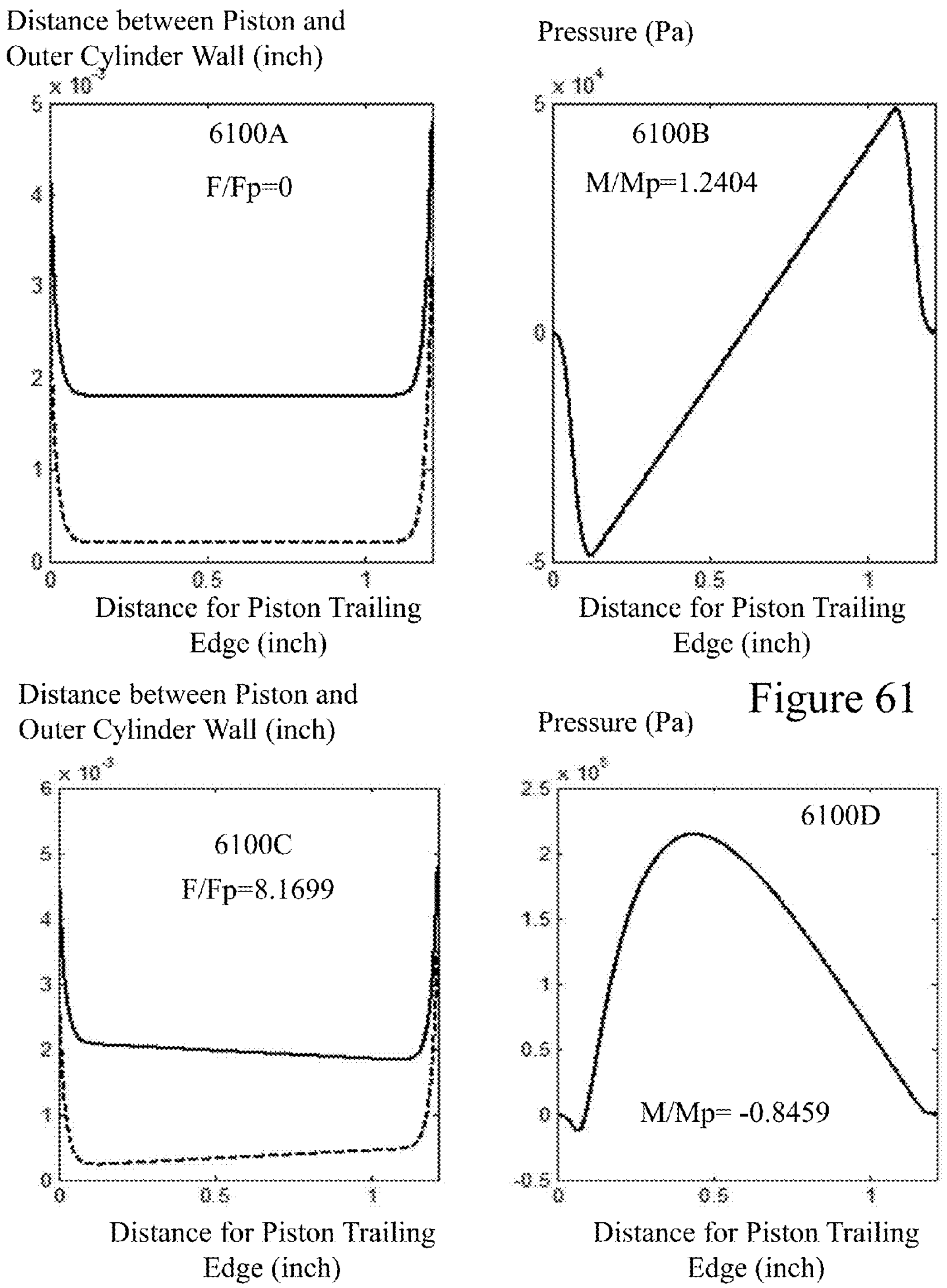
FIGS. 61 and 62 depict piston lubrication pressure profiles in respect of optimizing piston surface profile for reduced friction.

FIGS. 58 to 60 depict design variations for pump pistons within compact ECPUMPs according to embodiments of the invention. As evident from the simulations presented supra in respect of FIGS. 45 to 52 and other analysis the performance of an ECPUMP is sensitive to the gap such that lower gap, Lg, result in increased force etc. However, it would also evident that at such low gaps that friction between the piston and the barrel of the ECPUMP, e.g. barrel sleeve 3520 in FIG. 35, exists and increases. At the same time a sharp profile to the tooth of the piston results in improved performance but further increases issues of friction at the boundaries between the fluid, piston tooth, and barrel sleeve. Accordingly, first to fourth designs 5800A to 5800D within FIG. 58 represent options for design variants to address this issue. In each the ECPUMP 5810 has a design such as described in respect of FIG. 35. In first image 5800A the piston 5820 has profiled end caps 5830, for example of a plastic, which provide manipulation of the fluid boundary towards the narrow gap between teeth of the piston 5820 and inner surface of the barrel sleeve, not identified for clarity. Second image 5800B depicts a similar variant but now the piston body between the teeth has been similarly filled with a material, e.g. a plastic. This is further extended in third image 5800C where the outer diameter of the piston teeth has been reduced slightly allowing the piston 5840 to be embedded within the other material 3850, e.g. plastic, such that sharp edges of the piston teeth and manufacturing variations in the pistons are removed from direct contact with the inner surface of the barrel sleeve. Further, in fourth image 5800D the inner surface of the barrel sleeve has been coated with a thin film 5860, or thin layer of material, such that the piston 5840 embedded within the material 5850 runs within the thin film 5860 whose properties are design for low friction rather than mechanical strength etc. in respect of the barrel sleeve where this is molded to the other parts of the ECPUMP 5810.

First to fourth designs 5900A to 5900D within FIG. 59 represent further options for design variants to address the friction issue. In each the ECPUMP 5910 has a design such as described in respect of FIG. 35. In first image 5900A the piston 5920 has had the profile of the teeth modified such that rather than a sharp right angle corner there is a smooth tapered gap between the piston 5820 and inner surface of the barrel sleeve. Alternatively in second image 5900B a fluid is injected through the ECPUMP 5910 via lubrication path 5950 into a lubrication groove 5940 within the surface of the piston. Whilst depicted in the central portion of the piton 5940 it would be evident that these can also be implemented at the piston ends directly into lubricant grooves within the teeth of a piston such as 5820 in first image 5800A in FIG. 58. Such lubrication can be discretely employed or combined with other techniques described within this specification. The groove 5940 can be optimized to maximize bearing surface area but still provide adequate thick film lubrication to the surface of the piston. Where the lubricant is the same fluid within the overall fluidic system it would be evident that a portion of the fluid pumped by the ECPUMP can be "fed-back" to the lubrication path 5950. Reference is made to lubrication as being thick film as the fluid line between piston and barrel is approximately 0.001" although it would be evident if manufacturing tolerances can be established at desired cost/yield point to refine this then other embodiments of the invention can exploit thin-film lubrication, boundary layer, and or squeeze layer lubrication. It would be evident that in non-inline applications of the ECPUMP concepts that it is not necessary to provide a perfect seal around the piston.

Third image 5900C depict the scenario wherein the piston 5955 is embedded within a material 5960, e.g. a plastic, which is shaped in what the inventors call a double barrel shape. Fourth image 5900D depicts a variant wherein the piston 5980 is embedded within another material 5990, e.g. a plastic, and a thin film coating 5970 has been deposited upon the inner surface of the barrel sleeve. In other embodiments of the invention ball bearing races can be employed such as depicted for example in first and second images 6000A and 6000B in FIG. 60. In first image 6000A a single ball race 6020 is positioned with the slot opening of width. As such ball race 6020 can be the full width of the slot opening or smaller than it depending upon the piston length, slot opening, and piston stroke length in order to allow free longitudinal movement of the piston. In second image 6000B ball bearings 6010 are disposed within grooves within the piston. In this case issues over ball race length are removed as the ball bearings move with the piston. Ball bearings 6010 can, for example, be formed from one or more suitable plastic materials, a ceramic, a mineral, or a glass.

Also depicted in FIG. 60 is third image 6000C in respect of a zone formed between a piston 6040 and barrel end stops 6050 which projects inwardly from barrel inner surface (not marked for clarity). Accordingly, under operation within an embodiment of the invention the piston would move as normal within the barrel of the ECPUMP. However, as the barrel end stops are positioned at slightly longer than the normal operation maximum stroke length then if the piston passes maximum stroke then as it comes closer to the barrel end stops 6050 the fluid between the end of the piston 6040 and barrel end stops 6050 at that end of the ECPUMP begins to compress and apply pressure to the piston in the reverse direction slowing the piston and ultimately the piston 6040 stops before reversing direction. Within another embodiment of the invention the barrel end stops 6050 are placed close to the maximum stroke of the piston 6040 so that on every full length piston stroke this compressed fluid zone between the piston 6040 and barrel end stops 6050 directs fluid into the region between the piston 6040 perimeter and the barrel inner surface. This being beneficial in piston designs with very small clearance between piston 6040 and barrel inner surface with or without profile tapers on the piston teeth.

In addition to re-designing the piston and piston tooth geometry with hydrodynamic considerations of piston movement through the fluid to reduce friction, as described supra in respect of FIGS. 58 to 60 together with FIGS. 63 and 64, it would be evident that other factors can also be adjusted in order to seek to reduce the overall coefficient of friction between the moving piston and the stationary body of the ECPUMP. Accordingly, such factors can include, but are not limited to, piston steel selection, plastic selection for barrel, piston surface polish, mold surface polish for forming barrel, manufacturing tolerances for each element, and barrel surface finish. All of these must also additionally be considered in light of the design factors surrounding the ECPUMP itself including, but not limited to, viscosity, magnetic field side loading, non-uniformity of magnetic field generated by coil from assembly/manufacturing considerations, piston design, piston speed, fluid choice, operating temperature range, etc. It is also important to consider that whilst the piston during the stroke can be moving during the mid-stroke at rates of tens of centimeters per second to tens of meters per second that at the ends of each stroke the piston slows, stops and reverses. Accordingly, the fluid lubrication should also be capable of "supporting" the piston so that at rest the piston is surrounded by a film such that thick (or thin) film lubrication can be exploited during this phase of the ECPUMP operation before the piston speed is sufficient for the hydrodynamic effects described supra in respect of FIGS. 63 and 64 are operable, if exploited.

The ECPUMPs described and depicted according to embodiments of the invention exploit a strong electromagnet that surrounds the magnetic piston. The electromagnets are concentrically located surrounding the piston, and attract the piston in the radial direction as well as the axial direction. If the centroid of the piston is located at the centre of the magnetic flux field, then the piston experiences no net radial force. However, if the piston is displaced slightly from the centroid of the magnetic flux field, then it experiences outward radial force and is pressed against the outer casing side-wall. This contact results in metal-on-metal or metal-on-plastic contact, resulting in substantial frictional losses. Application of wet and/or dry lubrication such as described supra in respect of FIGS. 58 and 59 aim to address the friction by preventing or limiting the abrasive contact due the relatively high radial force applied in conjunction with the relatively small contact area.

Accordingly, the inventors have exploited hydrodynamic lubrication theory to determine the side-profile of the piston that will generate sufficient lift forces, offsetting the estimated magnetic attraction forces and preventing surface-surface contact. Hydrodynamic lubrication is sought for, typically, 80% of the stroke cycle and simulations exploit 30%-70% propylene glycol as the lubricant/pumping fluid in order to eliminate the need for repeated application of the lubricant. Analysis of curved end-caps fitted to the ends of a flat centre section which includes the piston to provide the necessary side profile to generate lift and prevent the need for further machining of the piston which would impact established magnetic motor configuration by removing magnetic material. Within the hydrodynamic analysis since pressure is directly proportional to velocity a constant velocity approximately 10% of the peak simulated piston velocity was employed to ensure that calculated lift forces are conservative and the piston remains in hydrodynamic lubrication mode.

A centered piston has a circumferentially uniform clearance, c, from cylinder (barrel) wall, and generates no net pressure profile. As the piston is displaced towards the outer cylinder wall, the difference wall clearance, generates a pressure distribution as illustrated in first and second images 6100A and 6100B in FIG. 61. The pressure distribution is symmetric if the piston is parallel to the outer cylinder wall, and generates no lift, but a pitching moment tends to lift the leading edge closest to the wall away from the wall. The pitched up piston now develops a very slight angle relative to the wall, which via the wedge effect causes a pressure field to develop underneath the piston, as shown in third and fourth images 6100C and 6100D in FIG. 61. The pressure field causes the piston to lift up, and be repelled from the wall. The forces and moments generated by the hydrodynamic lubrication effects are normalized by Fp, and Mp, which denote the magnetic perturbation force attracting the piston to the side wall, and the corresponding moment applied if the magnetic force is applied through the leading tooth of the magnetic iron.

Figure 62:
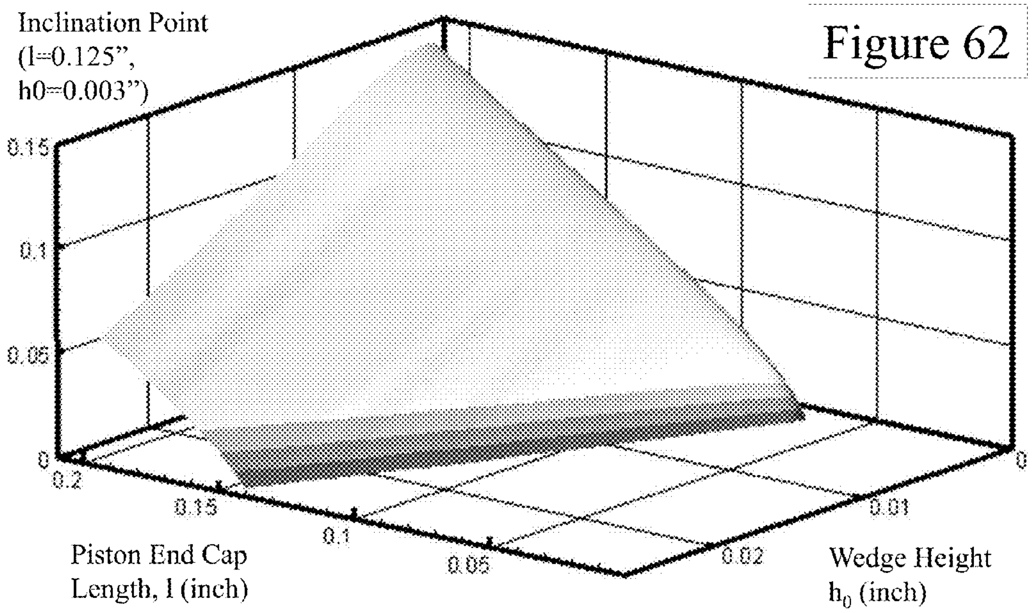

A force of $F/F_p>1$ ensures that the piston is able to be deflect the approximately 2 lbf magnetic side force, and a moment of $M/M_p>1$ indicates that sufficient moment is generated to tilt the piston upwards to develop the required lift force. While lift force increases when the piston is pitched up, the pitching moment decreases. Thus at a certain angle, the hydrodynamically generated pitching moment will balance the magnetic pitch-down moment, which will govern the maximum lift-force that can be developed. Accordingly, to establish an appropriate configuration pitching moments and forces were calculated at a variety of leading edge inclination heights while independently varying the length, l, and height, $h_0$, of the end-cap wedge profile. FIG. 62 depicts an isosurface showing all configurations where $M/M_p=1.1$, and which is shaded with grayscale isocontour lines showing the lift-force developed. At zero inclination height, zero lift force is developed for all configurations, so a point must be selected in the light-shaded region of the surface. Lift force, and pitching moment increase linearly with l, but decrease inversely with increased height, $h_0$. Selecting a small height is increasingly complicated to machine, whereas selecting a longer end-cap length will extend the length of the motor. Thus a compromise is sought between these two factors, such as for example (l=0.125", $h_0$=0.003").

It would be evident that the design principles described supra in respect of the ECPUMP with respect to the many different factors including, but not limited to, hydrodynamic fluidic effects, design of piston, barrel design, manufacturing, and assembly may also be applied to other electronically controlled magnetically activated devices such as valves and switches for example. Optionally, the piston within any of the embodiments of the invention described supra in respect of profiling to support formation of a thick/thin film layer between the piston and the barrel as well as hydrodynamic correction of piston offsets within the barrel may be modified to provide an asymmetric piston that has a different profile at one end to the other either over the entire length and/or over the piston teeth such that during operation the fluid circulates from outside the piston to the region along the piston and out the other end of the piston. In this manner degradation of the fluid locally to the piston due to elevated operating temperatures may be reduced.

It would be evident to one skilled in the art that the depictions of ECPUMPs and ECFPAs in respect to embodiments of the invention within the descriptions and drawings have not shown or described the construction or presence of the excitation coil. The design and winding of such coils is known within the art and their omission has been for clarity of depiction of the remaining elements of the ECPUMPs and/or ECFPAs. For example, in FIGS. 35, 36A and 36B the coil would be wound or formed upon bobbin core 3540 and housed within bobbin case 3550 which includes an opening(s) for feeding the electrical wires in/out for connection to the external electrical drive and control circuit. Examples of such coils include, for example, 170/22, 209/

23, 216/24, 320/24, 352/24, 192/28 (e.g. 8 layers of 24 turns per layer), 234/28, 468/32, and 574/33. Each pair of numbers representing the number of windings and American wire gauge (AWG) of the wire employed.

It would be evident to one skilled in the art that other structures comprising elastic elements, resilient members, and fluidic actuators can be implemented wherein one or more aspects of the motion, dimensions, etc. of elements of the device and the device itself change according to the sequence of actuation of the same subset of fluidic actuators within the element of the device and/or device itself. Further, it would be evident that one or more active elements such as the fluidic pump(s) and fluidic valve(s) can be designed as a single module rather than multiple modules.

It would be evident to one skilled in the art that by suitable design of the ECPUMPs depicted supra in respect of FIGS. 26 through 31 that in addition to providing pump action, and acting as primary pumps such as described in respect of FIGS. 12 and 13 that these can also act as second pumps as depicted in these Figures as well as providing vibrator type functionality. Further, within the embodiments of the invention described supra in respect of electronically controlled pumps in FIGS. 26 through 31 it would evident to one skilled in the art that whilst these have been described with the provisioning of fluidic capacitors these can be omitted according to the design of the overall device in terms of aspects including, but not limited to, the tubing employed to connect the various elements of the fluidic system together or those portions of the fluidic system proximate the fluidic pump(s). In some instances the fluidic capacitor removal can result in a cyclic/periodic pressure profile being applied to the overall profile established by the electronic controller wherein the cyclic/periodic pressure profile provides additional stimulation to the user of the device. It would be evident that in other embodiments of the invention a fluidic capacitor can act as a high pass filter dampening low frequency pressure variations but passing higher frequency pressure variations. In other embodiments of the invention an ECPUMP can form the basis of a compact RAM/Hammer pump.

Within other embodiments of the invention a fluidic actuator can act as a fluidic capacitor and can in some instances be disposed such that any other fluidic actuators are coupled from this fluidic actuator rather than directly from the pump or from the pump via a valve. Within other embodiments of the invention a fluidic capacitor can be provided on one side of the pump such as for example, the inlet.

Optionally, the inlet fluidic capacitor can be designed to provide minimal impact to the device movement or designed to impact the device movement, such as for example by not adjusting dimensions in response to pump action. In this instance the when the pump piston seeks to draw fluid and one or more fluidic actuators have their control valves open such that there is an active fluidic connection between the pump and fluidic actuator(s) then fluid will be drawn from the fluidic actuator(s) towards the piston. However, if one or more valves is not open or the fluidic actuators are all collapsed, then the "vacuum" at the pump piston inlet would increase and accordingly a pressure relief valve can allow fluid to flow from a high pressure inlet fluidic capacitor or directly from the valve and allow the fluid to circulate when the fluidic actuators are not changing in volume. In this manner the pump can continue to run, such as for example providing, a vibration, even when the device is in a state that there is no adjustment in the volume of the fluidic actuators.

Within devices according to embodiments of the invention the fluid within the device can be heated or cooled to provide additional sensations to the user during their use of the device. Optionally, by varying the thermal conductivity of the body of the device in different regions and/or by varying the thickness of the external device skin etc. between the fluid and user's skin the degree of hot or cold applied to the user's skin can be varied across the surface of the device. In other embodiments dual fluidic circuits can provide hot and cold within the same device. Whilst heating the fluid is relatively straight-forward cooling, such as for example through the use of a thermoelectric cooler to cool a metallic element against or around which the fluid flows, requires that heat be extracted from the fluid. In some embodiments of the invention this can through use of a heatsink and/or forced air cooling or through the skin/exterior of the device. In another embodiment the thermoelectric cooler on one side cools a first fluidic loop's fluid whilst on the other side it heats a second fluidic loop's fluid.

In some embodiments of the invention the fluidic capacitor function can be removed such that the fluidic system directs all pressure possible, i.e., all that the pump piston can exert, through rigid pipes and control valves to the fluidic actuator such that the motion of the pump piston, is translated into fluid movement into/out of the fluidic actuator. This can be employed where the distance between fluidic actuator and pump is relatively short and the volume/weight of fluid being driven by the pump piston is not too large. Accordingly, depending upon the fluidic circuit design if more than one valve is open the fluid flow would be shared, and if no valves were open or valves were open but the fluidic actuator cannot expand or contract more, through some pressure/vacuum limits controlled through design of the fluidic actuator and surrounding materials, then the back pressure/vacuum on the pump piston would go up/down until the pressure relief valve opens and allows the fluid to recirculate from the pump outlet to the pump inlet. Accordingly, the pump piston can keep running without the device undergoing any movement. It would be evident that in such embodiments of the invention that the fluidic system with capacitors can contain only a small reservoir or no reservoir.

Fluidic systems such as described above in respect of embodiments of the invention with reservoirs and/or fluidic capacitors can still employ a pressure relieve valve or optionally have the pressure monitored to shut the pump down under circumstances such as being stalled against closed valves or fluidic actuators that will not move for example or where the pressure exceeds a predetermined threshold. For example, squeezing the device hard can prevent it from expanding when desired thereby leading to stalling the pump but the pressure monitoring can shut the pump down already. Optionally a thermal cut-off can be also employed within the overall control circuit. Optionally, the pump frequency might be adjusted or valves triggered to put the ECPUMP into a closed loop isolated from the actuators for either a predetermined period of time or until pressure has reduced to an acceptable level. It would be evident that more complex decisions could be made such as assessing whether the pressure is periodic/aperiodic and indicative of an intense vaginal orgasm for example rather than an individual squeezing the device. It would be evident that with ECPUMPS we can vary the pump frequency, pump stroke length, pump pulse profile, etc. to vary effective pressure, flow rate, and pulse frequencies of fluid motion within the device and accordingly actions from the fluidic actuators to which these fluidic motions are coupled by valves, switches, splitters, etc. In other embodiments of the invention the ECPUMP can be allowed to stall and through appropriate design not overheat.

Where a pressure sensor is embedded then this can itself establish the desired pressure that the user wishes to experience and then determine the pump drive signals required to achieve this desired result under variations of other pump parameters such as if the user adjusts the frequency at which operating in the user configuration stage the pressure profile is maintained. It would be evident that ECPUMP performance can be monitored. For example, the back electromagnetic field (EMF) generated can be measured to determine the position of the piston within the ECPUMP and compared relative to expected position as well as deriving position—time profile to establish whether adjustments are required to the control signals to achieve the desired device and/or ECPUMP performance. Alternatively capacitive or other sensors can derive piston position, acceleration etc. as well as fluidic flow and pressure at the ECPUMP head could also be monitored to verify performance.

Alternatively, the fluidic system can be designed such that the pump always runs and is varied in revolutions per minute (RPM) according to some desired pattern including the stimulation vibration pattern and the valves are opening and closing so that the device is always moving in one aspect or another and therefore the pump would not need to be shut off in the design scenarios wherein there was no fluidic capacitor or an inadequate fluidic capacitor, reservoir or pressure relief bypass valve.

Materials

Within the fluidic assemblies, actuators, devices, fluidic valves and fluidic pumps described above in respect of FIGS. 1 through 31, the fluid can be a gas or liquid. Such fluids can be non-toxic to the user in the event of physical failure of the device releasing the fluid as well as being non-corrosive to the materials employed within the device for the different elements in contact with the fluid. Within other embodiments of the invention the fluid can be adjusted in temperature, such as heated for example. For example, the fluid can be a 50% propylene glycol and 50% water mixture although other ratios can be employed according to the desired viscosity of the liquid. A range of other materials can be employed based upon desired properties of the fluid, which can include, but are not limited to, it being anti-fungal, a lubricant, a lubricant additive, anti-freeze over storage and/or operating range, anti-bacterial, anti-foaming, inhibiting corrosion, non-toxic, and long lifetime within sealed fluidic systems. Examples of such fluids can include, but are not limited to, vegetable oils, mineral oils, silicones, water, and synthetic oils.

In terms of materials for the fabrication of the device a variety of materials can be employed in conjunction with the fluidic actuators including for example closed-cell foam, open-celled foam, polystyrene, expanded polystyrene, extruded polystyrene foam, polyurethane foam, phenolic foams, rubber, latex, jelly-rubber, silicone rubber, elastomers, stainless steel, Cyberskin and glass. The fluidic actuator in many embodiments of the invention is designed to expand under an increase in pressure (or injection of fluid) and collapse under a decrease in pressure (or extraction of fluid). Accordingly, the fluidic actuator will typically be formed from an elastic material examples of which include rubber, latex, silicone rubber and an elastomer. In some embodiments of the invention the fluidic connections between the fluidic actuator(s) and the fluidic pump and/or valve can be formed from the same material as the fluidic actuator rather than another material. In such instances the fluidic actuator can be formed by reducing the wall thickness of the material. Examples of manufacturing processes include, but are not limited to, dip-coating, blow molding, vacuum molding, thermoforming and injection molding. It would also be evident that multiple actuators can be formed simultaneously within a single process step as a single piece-part. Alternatively multiple discrete actuators can be coupled together directly or via intermediate tubing through processes such as thermal bonding, ultrasonic bonding, mechanical features, adhesives, etc. Similar processes can then be applied to attach the fluidic actuators to the valves, switches, ECPUMP, ECFPA, EAVs etc.

Device Configuration

Whilst emphasis has been made to self-contained discrete devices it would be evident that according to other embodiments of the invention that the device can be separated into multiple units, such as for example a pump assembly with device coupled to the pump assembly via a flexible tube which can be tens of centimeters, a meter or a few meters long. In other embodiments a very short tube can be employed to isolate the pump assembly from the remainder of the device or as part of a flexible portion of the body allowing user adjustment such as arc of a vaginal penetrative portion of a device. It would also be evident that devices according to embodiments of the invention can be configured to be held during use; fitted to a harness; fitted via an attachment to a part of the user's body or another user's body, e.g., hand, thigh, or foot; or fitted via a suction cup or other mounting means to a physical object such as a wall, floor, or table.

Within embodiments of the invention with respect to devices and the electronic control the descriptions supra in respect of the Figures have described electrical power as being derived from batteries, either standard replaceable (consumable) designs such as alkaline, zinc-carbon, and lithium iron sulphide ($LiFeS_2$) types, or rechargeable designs such as nickel cadmium (NiCd or Nicad), nickel zinc, and nickel-metal hydride (NiMH). Typically, such batteries are AAA or AA although other battery formats including, but not limited to, C, D, and PP3. Accordingly, such devices would be self-contained with electrical power source, controller, pump(s), valve(s) and actuator(s) all formed within the same body. It would be evident that fluidic pumps, electronic controller, and fluidic valves are preferably low power, high efficiency designs when considering battery driven operation although electrical main connections can ease such design limits. For example, considering a device where the operating pressure for fluidic actuators is approximately 2-6 psi with flow rates of approximately for typical geometries and efficiencies then power consumption is approximately 3 W. Considering 4 AA rechargeable 1.3V DC batteries then these offer approximately power provisioning such that overall these can provide approximately at approximately for about an hour, i.e. approximately such that multiple pumps can be implemented within the device.

However, alternate embodiments of devices can be configured in so-called wand type constructions, see for example Hitachi Magic Wand within the prior art for example, wherein increased dimensions are typical but additionally the device includes a power cord and is powered directly from the electrical mains via a transformer. Optionally, a device can be configured with battery and electrical mains connections via a small electrical connector with a cord to a remote transformer and therein a power plug. However, it would also be evident that other embodiments of the invention can be configured to house a predetermined portion of the pump(s), valve(s), power supply, and control electronics within a separate module to that containing the fluidic actuators.

Within embodiments of the invention to devices and the electronic control the descriptions supra in respect of the Figures the electrical control has been described as being within the device. However, optionally the controller can be remote to the device either connected via an electrical cable or communicating via an indirect means such as wireless communications for example. Additionally, the electronic controller has been primarily described as providing control signals to the fluidic pumps and valves, as well as other active elements, of the device. However, in some embodiments of the invention the electronic controller can receive inputs from sensors embedded within the device or external to the device. For example, a sensor can provide an output in dependence upon pressure applied to that portion of the device the user, for example from vaginal contractions, wherein the controller can adjust one or more aspects of the device actions in terms of maximum pressure, speed, slew rate, and extension for example. Optionally, other sensors can be internally deployed within the device to monitor the performance of the device, including for example, linear transducers to monitor length extension, pressure sensors to monitor fluid pressure at predetermined points within the device.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above and/or a combination thereof.

Also, it is noted that the embodiments can be described as a process, which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be rearranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

The foregoing disclosure of the embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A sexual stimulation device comprising:

an electromagnetically driven pump for pumping a fluid from an inlet port to an outlet port; and a fluidic capacitor coupled at one end to the electromagnetically driven pump and coupled at its other end to a self-contained fluidic system; wherein the fluidic capacitor comprises a first predetermined portion having a first predetermined elasticity and a second predetermined portion having a second predetermined elasticity lower than the first predetermined elasticity wherein the second predetermined portion deforms under activation of the electromagnetically driven pump in a manner such that the electromagnetically driven pump is not at least one of drawing upon or pumping into the complete fluidic system according to whether the fluidic capacitor is on the inlet side or the outlet side port of the electromagnetically driven pump; and fluid within the self-contained fluidic system when pumped by the electromagnetically driven pump drives a fluidic actuated element forming part of the sexual stimulation device to provide physical stimulation to a predetermined region of an individual.

2. The sexual stimulation device according to claim 1, wherein at least one of:

the first and second predetermined portions of the fluidic capacitor form predetermined portions of the electromagnetically driven pump between the inlet port and an inlet non-return valve when the fluidic capacitor is on the inlet side of the electromagnetically driven pump and between the outlet port and an output non-return valve when the fluidic capacitor is on the output side of the electromagnetically driven pump; and the electromagnetically driven pump has the inlet and outlet ports at least one of on the same end and opposite ends of the electromagnetic driven pump.

3. A sexual stimulation device comprising:

an electromagnetically driven pump comprising a piston for pumping a fluid upon both forward and backward piston strokes within a self-contained fluidic system;

first and second valve assemblies coupled to each end of the electromagnetically driven pump, each valve assembly comprising an inlet non-return valve, an outlet non-return valve, and a valve body having a port fluidically coupled to the electromagnetically driven pump, a port coupled to the inlet non-return valve, and a port coupled to the output non-return valve; and a first fluidic capacitor disposed at least one of prior to an inlet non-return valve and after an outlet non-return valve; wherein the first fluidic capacitor comprises a first predetermined portion having a first predetermined elasticity and a second predetermined portion having a second predetermined elasticity lower than the first predetermined elasticity wherein the second predetermined portion deforms under activation of the electromagnetically driven pump in a manner such that the electromagnetically driven pump is not at least one of drawing upon or pumping into s fluidic system to which the electromagnetically driven pump is connected according to whether the fluidic capacitor is on the inlet side or the outlet side port of the electromagnetically driven pump; and fluid within the self-contained fluidic system when pumped by the electromagnetically driven pump drives a fluidic actuated element forming part of the sexual stimulation device to provide physical stimulation to a predetermined region of an individual.

4. The sexual stimulation device according to claim 3, further comprising; at least one of:

a second fluidic capacitor disposed on the other one of the pair of inlet and outlet non-return valves when the first fluidic capacitor is coupled to the one of the inlet return valve or the outlet non-return valve; and second to fourth fluidic capacitors are disposed on the remaining inlet and output inlet return valves.

5. The sexual stimulation device according to claim 4, wherein at least one of:

the fluidic capacitors coupled to either the pair of inlet non-return valves are the same fluidic capacitor;

the fluidic capacitors coupled to the pair of inlet non-return valves form a first part of a clamshell surrounding the electromagnetically driven pump;

the fluidic capacitors coupled to the pair of outlet non-return valves form a second part of a clamshell surrounding the electromagnetically driven pump;

the fluidic capacitors coupled to inlet and outlet non-return valves on the same end of the electromagnetically driven pump are part of a single housing coupled to that end of the electromagnetically driven piston;

the fluidic capacitors coupled to either the pair of outlet non-return valves or the inlet non-return valves form part of Y-tube coupler joining respect pair of inlets or outlets to a common port of a fluidic system.

6. The sexual stimulation device according to claim 3 further comprising;

a second fluidic capacitor coupled to the other outlet non-return valve when the first fluidic capacitor is coupled to an outlet non-return valve;

Y-tube coupler coupled to the first and second fluidic capacitors for coupling fluid from the first and second fluidic capacitors to a common port of a fluidic system; and a fluidic switch disposed between one of the first and second fluidic capacitors and its respective Y-tube port, the fluidic switch in a first configuration coupling the one of the first and second fluidic capacitors to its respective Y-tube port and in a second configuration coupling the one of the first and second fluidic capacitors at least one of back to the electromagnetically driven pump and to another part of the fluidic system; wherein in the first configuration fluid is continuously pumped on both directions of piston stroke to the fluidic system with a pressure fluctuation across each piston stroke determined in dependence upon the magnitude of the fluidic capacitance provided by the first and second fluidic capacitors and in the second configuration is pumped upon only a single direction of pump stroke with a pressure fluctuation determined in dependence upon the magnitude of the fluidic capacitance of the one of the first and second fluidic capacitances.

7. The sexual stimulation device according to claim 3 further comprising;

a second fluidic capacitor coupled to the other outlet non-return valve when the first fluidic capacitor is coupled to an outlet non-return valve or to the other input non-return valve when the first fluidic capacitor is coupled to an inlet non-return valve; and a Y-tube coupler coupled to the first and second fluidic capacitors for coupling fluid from the first and second fluidic capacitors to a common port of a fluidic system when they are coupled to the outlet non-return valves and to the first and second fluidic capacitors from a common port of a fluidic system when they are coupled to the inlet non-return valves; wherein each of the two arms of the Y-tube comprise first and second portions, each first portion having predetermined elasticity and forming the first and second fluidic capacitors.

8. A sexual stimulation device comprising:

an electromagnetically driven device;

a fluidic capacitor which acts as a low pass fluidic filter in combination with self-contained fluidic system to smooth pressure fluctuations arising from the operation of the electromagnetically driven device over a first predetermined frequency range; and a control circuit providing a first signal for driving the electromagnetically driven device at a frequency within the first predetermined frequency range and a second signal for driving the electromagnetically driven device with an oscillatory signal above a low pass cut-off frequency of the low pass fluidic filter; wherein the pulsed fluidic output generated by the second signal is coupled to the self-contained fluidic system but the pulsed fluidic output generated by the first signal is filtered to provide a constant fluidic flow from the electromagnetically driven device with predetermined ripple; and fluid within the self-contained fluidic system when pumped by the electromagnetically driven pump drives a fluidic actuated element forming part of the sexual stimulation device to provide physical stimulation to a predetermined region of an individual.

9. A method of configuring a sexual stimulation device comprising:

a) providing the sexual stimulation device comprising an electromagnetically driven pump for pumping a fluid from an inlet port to an outlet port and a fluidic capacitor coupled at one end to the electromagnetically driven pump and coupled at its other end to a self-contained fluidic system, wherein fluid within the self-contained fluidic system when pumped by the electromagnetically driven pump drives a fluidic actuated functional element forming part of the sexual stimulation device to provide physical stimulation to a predetermined region of an individual;

b) executing a set-up procedure for an action relating to the functional element of the sexual stimulation device to be personalized to an individual;

c) automatically varying an aspect of the action relating to the functional element of the sexual stimulation device between a first predetermined value and a second predetermined value in a predetermined number of steps whilst the individual applies the sexual stimulation device to the predetermined region of their body until an input is received from the individual; and d) terminating step (c) upon receiving the individual's input and storing the value relating to the aspect of the action when the individual provided the input within a profile of a plurality of profiles associated with the sexual stimulation device.

10. The method of configuring a sexual stimulation device according to claim 9, further comprising; at least one of e) repeating steps (c) and (d) for at least one of all other aspects relating to the action of the functional device, for all other actions of the functional element, and for any other functional element of the sexual stimulation device;

f) transmitting at least one of the stored value and the profile of the plurality of profiles to a remote device for at least one of subsequent transmittal to the sexual stimulation device, execution by a remote device to control the sexual stimulation device; transmittal to another sexual stimulation device associated with the individual, and transmittal to another sexual stimulation device associated with another individual.

11. The method of configuring a sexual stimulation device according to claim 9, further comprising at least one of:

e) executing steps (b) to (d) during use of the device at least one of by and on the individual; and f) executing steps (b) to (d) whilst the sexual stimulation device is inserted into an orifice of the individual.

12. The method of configuring a sexual stimulation device according to claim 9, further comprising:

e) operating the sexual stimulation device in response to received control data wherein the control data is mapped onto the sexual stimulation device in dependence upon the profile of the plurality of profiles and the control data is at least one of purchased by the individual, provided from another individual, and provided in association with an item of multimedia content.

* * * * *